US005219879A

United States Patent [19]

Ko et al.

[11] Patent Number: 5,219,879

[45] Date of Patent: Jun. 15, 1993

[54] HETEROCYCLIC STEROID COMPOUNDS

[75] Inventors: Soo S. Ko, Wilmington, Del.; James M. Trzaskos, Boothwyn, Pa.

[73] Assignee: Du Pont Merck Pharmaceutical Company, Wilmington, Del.

[21] Appl. No.: 664,988

[22] Filed: Mar. 1, 1991

Related U.S. Application Data

[63] Continuation-in-part of Ser. No. 489,093, Mar. 5, 1990, abandoned.

[51] Int. Cl.[5] ........................ C07J 73/00; C07J 75/00; A61K 31/34; A61K 31/38

[52] U.S. Cl. .................................... 514/438; 514/461; 546/77; 544/23; 544/42; 544/83; 544/384; 544/461; 552/540; 548/426

[58] Field of Search ..................... 549/42, 384, 83, 23, 549/457; 514/443, 438, 46; 552/540; 546/77

[56] References Cited

U.S. PATENT DOCUMENTS

| | | | |
|---|---|---|---|
| 3,872,076 | 3/1975 | Rosen | 549/457 |
| 3,947,453 | 3/1976 | Jones | 546/77 |
| 3,972,884 | 8/1976 | Jones | 546/77 |
| 4,001,246 | 1/1977 | Jones | 546/77 |
| 4,008,238 | 2/1977 | Jones | 546/77 |
| 4,039,547 | 8/1977 | Chamberlin | 546/77 |
| 4,053,487 | 10/1977 | Rosen | 549/457 |
| 4,202,891 | 5/1980 | Schroepfer, Jr. et al. | 424/242 |
| 4,230,626 | 10/1980 | Chorvat | 260/397.2 |
| 5,034,548 | 7/1991 | Gaylor et al. | 552/540 |

OTHER PUBLICATIONS

Grynkiewicz, Carbohydrate Res. 128 (1984) C9–C10.
Chang, et al., Journal of Biological Chemistry, vol. 255, pp. 7787–7794, (1980).
Gibbons, et al., Journal of Biological Chemistry, vol. 255, pp. 395–400, (1980).
Kandutsch, et al., Journal of Biological Chemistry, vol. 252, pp. 409–415, (1977).
Journal of Chronic Disease, vol. 31, pp. 201–306 (1978).
Cavenee, et al., Journal of Biological Chemistry, vol. 256, pp. 2675–2681 (1981).
Breslow, et al., Biochem. Biophysica Acta, vol. 398, 10–17, (1975).
Rodwell, et al., "Advances in Lipid Research" vol. 14, pp. 2–74, (1976).
Bresike, et al., Circulation, vol. 69, pp. 313–324, (1984).
Kannel, et al., Annals of Internal Medicine, vol. 90, pp. 85–91, (1979).
Kandutsch, et al., Science, vol. 21, pp. 498–501 (1978).
Schroepfer, et al., Proc. Natl. Acad. Sci. USA, vol. 81, pp. 6861–6865, (1984).
Schriner, et al, J. Org. Chem., vol. 10, pp. 228, (1945).
Dolle, et al., J. Org. Chem., vol. 51, pp. 4047, (1986).
Brown, et al., J. Lipid Res., vol. 21, pp. 505–517, (1980).
Leonard, et al., J. Biol. Chem., vol. 262, pp. 7914–1719, (1987).
Tanaka, et al., J. Biol. Chem., vol. 258, pp. 13331–13339, (1983).
Havel, et al., J. Biol. Chem., vol. 254, pp. 9573–9582, (1979).
Chen, et al., J. Biol. Chem., vol. 254, pp. 714–720, (1979).
Kandutsch, et al., J. Biol. Chem., vol. 255, pp. 10813–10821, (1980).
Levy, Circulation, vol. 69, pp. 325–336, (1984).
Trzaskos, et al., Fed. Proc., vol. 44, p. 656, Abstract No. 1437 (1985).

*Primary Examiner*—Robert T. Bond
*Assistant Examiner*—Ward E. C.
*Attorney, Agent, or Firm*—Gerald J. Boudreaux

[57] ABSTRACT

The present invention relates to novel substituted 15-oxa-, 15-thia-, and 15-aza- dihydrolanosterols, to pharmaceutical compositions containing such compounds, and to methods of using these compounds to suppress the activity of 3-hydroxy-3- methylglutaryl coenzyme A reductase (HMGR), an enzyme which is important in cholesterol biosynthesis. The overall effect of these heterocyclic lanosterol analogs is to decrease cholesterol formation, thereby resulting in lower serum cholesterol levels in mammals, and impaired ergosterol synthesis in fungi.

58 Claims, No Drawings

HETEROCYCLIC STEROID COMPOUNDS

CROSS-REFERENCE TO RELATED APPLICATIONS

The present application is a continuation-in-part of our copending application U.S. Ser. No. 07/489,093, filed 5 March 1990 now abandoned, the disclosure of which is hereby incorporated herein by reference.

FIELD OF THE INVENTION

The present invention relates to novel substituted 15-oxa-, 15-thia-, and 15-aza- dihydrolanosterols, to pharmaceutical compositions containing such compounds, and to methods of using these compounds to suppress the activity of 3-hydroxy-3- methylglutaryl coenzyme A reductase (HMGR), an enzyme which is important in sterol biosynthesis. The overall effect of these heterocyclic lanosterol analogs is to decrease sterol formation, thereby resulting in lower serum cholesterol levels in mammals, and impaired ergosterol synthesis in fungi.

STATE OF THE ART

Clinical studies have demonstrated that elevated concentrations of serum cholesterol are a major contributing factor in the development and progression of atherosclerosis, a disease characterized by the formation of cholesterol-containing plaques in the aorta and lesser arteries. These plaques tend to clog the arterial passageways, making it difficult, if not impossible, for blood to flow from the heart to various tissues in the body. This pathobiological condition can ultimately lead to Coronary Heart Disease (CHD). See, e.g., Kannel et al., *Ann. Intern. Med.*, 90: 85–91 (1979); Final Report of the Pooling Project, *J. Chron. Dis.*, 31: 201–306 (1978). By maintaining low cholesterol levels in the blood, arterial plaque formation and CHD can potentially be avoided. See, e.g., Brensike et al., *Circulation*, 69: 313–324 (1984) and Levy et al., *Circulation*, 69: 325–336 (1984).

In mammals, serum cholesterol is derived from exogenous dietary sources as well as through endogenous de novo synthesis. Endogenous synthesis of cholesterol involves a complex set of enzyme-catalyzed reactions and regulatory mechanisms which to date are only partially understood. As Rodwell et al., *Adv. Lipid Res.*, 14: 1074 (1976) indicate, HMGR is generally accepted as the rate-limiting enzyme which controls cholesterol biosynthesis from acetyl-CoA in all organisms.

Brown et al., *J. Lipid Res.*, 21: 505–517 (1980) have shown that regulation of HMGR is a complex process which is under a feedback control mechanism involving both steroidal as well as nonsteroidal isoprenoid metabolites. These authors point out that under normal conditions, the ability of cholesterol to regulate its own biosynthesis when associated with lipoprotein particles is one aspect of this feedback control mechanism.

Moreover, it has been demonstrated that various oxygenated sterols, when used in a highly purified state, are even more effective than cholesterol in attenuating the amount of HMGR activity, see Breslow et al., *Biochem. Biophys. Acta*, 398: 10–17 (1975), Kandutsch et al., *J. Biol. Chem.*, 252: 409–415 (1977), and Chen et al., *J. Biol. Chem.*, 254: 714–720 (1979), leading to the hypothesis that oxysterols may also be endogenous mediators which regulate HMGR activity and cholesterol synthesis in situ. See, Kandutsch et al., *Science*, 201: 498–501 (1978).

This proposition stimulated considerable research activity. See, e.g., Chen et al., *J. Biol. Chem.*, 254: 715–720 (1979); Havel et al., *J. Biol. Chem.*, 254: 9573–9582 (1979); Chang et al., *J. Biol. Chem.*, 255: 7787–7795 (1980); Chorvat, U.S. Pat. No. 4,230,626 (1980); Gibbons et al., *J. Biol. Chem.*, 255: 395:400, (1980); Kandutsch et al., *J. Biol. Chem.*, 255: 10814–10821 (1980); Cavenee et al., *J. Biol. Chem.*, 256: 2675–2681 (1981); Tanaka et al., *J. Biol. Chem.*, 258: 13331–13339 (1983) and Trzaskos et al., *Fed. Proc.*, 44: 656, (1985). As a result, a number of inhibitors of HMGR activity have been found.

Gibbons et al., *J. Biol. Chem.*, 255: 395–400 (1980), for example, have shown that certain synthetic oxygenated lanosterol derivatives are active inhibitors of HMGR activity. Trzaskos et al., *Fed. Proc.*, 44: 656 (1985) have established that in situ generation of the Gibbons compounds leads to attenuated HMGR activity and decreased cholesterol biosynthesis.

In addition, Schroepfer et al., U. S. Patent No. 4,202,891 and Schroepfer et al., *Proc. Natl. Acad. Sci. USA*. 81: 6861–6865 (1984) have revealed that other oxygenated lanosterol derivatives may be successfully employed to lower serum cholesterol levels in animals.

INFORMATION DISCLOSURE

Heterocyclic steroid compounds have been prepared in the past. For example, U.S. Pat. Nos. 3,845,203 (Williams et al.); 3,887,433 (Williams et al.); 3,887,564 (Williams et al.); 3,947,453 (Jones); 3,987,055 (Berlin et al.); 3,972,884 (Jones); 4,001,246 (Jones); 4,008,238 (Jones); and 4,039,547 (Chamberlin) are directed to various aza steroid compounds. Oxa steroid derivatives are disclosed in U.S. Pat. Nos. 3,872,076 and 4,053,487 (Rosen), and in Ferland and Lefebfre, *Can. J. Chem.*, 62: 315–319 (1984). Thia steroids are disclosed in Tolstikov et al., *Zhurnal Organicheskoi Khimi*, 22: 121–132 (1986).

None of the aforementioned heterocyclic steroid compounds are described as having utility against cholesterol biosynthesis. Thus, additional compounds which affect HMGR and/or other enzymes critical to serum cholesterol biosynthesis are needed. The present invention is directed to this end.

SUMMARY OF THE INVENTION

The present invention provides novel substituted 15-oxa-, 15-thia-, and 15-aza-dihydrolanosterol compounds of the formula:

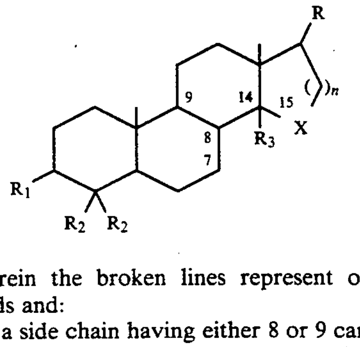

Formula 1 wherein the broken lines represent optional double bonds and:

R is a side chain having either 8 or 9 carbon atoms and from 15 to 20 hydrogen atoms, optionally with one site of unsaturation;

$R_1$ is $=O$, $OR_7$ or $OCOR_7$;

$R_2$ is H, $C_1$–$C_6$ alkyl, $C_2$–$C_6$ alkenyl, $C_2$–$C_6$ alkynyl, arylalkyl;

$R_3$ is H, $C_1$–$C_6$ alkyl, $C_2$–$C_6$ alkenyl, $C_2$–$C_6$ alkynyl, arylalkyl, $C(R_4)_2R_5$, $COR_4$, $CSR_4$, $C(=NR_4)R_4$, $COR_5$, $CSR_5$, $C(R_4)_2C(R_4)_2R_5$, $C(R_4)_2COR_4$, $C(R_4)_2CSR_4$, $C(R_4)_2C(=NR_4)R_4$, $C(R_4)_4COR_5$, $C(R_4)_2CSR_5$, $C(R_4)_2Z$, $C(R_4)_2C(R_4)_2Z$, CN, $CR_4NOR_4$, $CR_4NOR_6$, $CR_4NN(R_4)_2$, $CR_4NNR_4R_6$, $CHR_4NHOR_4$, $CHR_4NHOR_6$, $CHR_4NHN(R_4)_2$, $CHR_4NHNR_4N_6$, $CHR_4CR_4NOR_4$, $CHR_4CR_4NOR_6$ $CHR_4CR_4NN(R_4)_2$, $CHR_4CR_4NNR_4R_6$ $CHR_4CHR_4NHOR_4$, $CHR_4CHR_4NHOR_6$, $CHR_4CHR_4NHN(R_4)_2$, $C(O)NR_4OR_4$, $C(O)NR_4OR_6$, $C(S)NR_4OR_4$, $C(S)NR_4OR_6$, $CR_4=CR_4R_6$, $C\equiv CR_6$, $CR_4=CR_4C(R_4)_2Z$, $C\equiv CC(R_4)_2Z$, $CR_4=CR_4C(R_4)_2OR_6$, $C\equiv CC(R_4)_2OR_6$, poly-($OR_4$, $OR_6$, epoxy)-$C_1$–$C_6$ alkyl;

$R_4$ is H, $C_1$–$C_6$ alkyl, $C_2$–$C_6$ alkenyl, $C_2$–$C_6$ alkynyl, aryl, arylalkyl;

$R_5$ is $OR_4$, $SR_4$, $N(R_4)_2$, $NR_4R_6$;

$R_6$ is $COR_4$, $CSR_4$, $C(=NR_4)R_4$;

$R_7$ is H, $C_1$–$C_{20}$ alkyl, $C_2$–$C_{20}$ alkenyl, $C_2$–$C_{20}$ alkynyl, aryl, arylalkyl;

X is O, S, SO, $SO_2$, N, $NR_4$, $NR_6$, $N(O)R_4$;

Z is halogen; and n is 1 or 2;

and their physiologically acceptable salts.

The compounds of Formula I are effective suppressants of 3-hydroxy-3- methylglutaryl coenzyme A reductase (HMGR) activity. By interfering with this enzyme, which is essential in the cholesterol biosynthetic pathway, cholesterol formation is decreased and serum cholesterol levels lowered. Thus, the present invention also includes therapeutic pharmaceutical compositions for suppressing HMGR activity, decreasing cholesterol formation and lowering serum cholesterol levels.

The pharmaceutical compositions comprises (i) an effective amount of a compound of the formula:

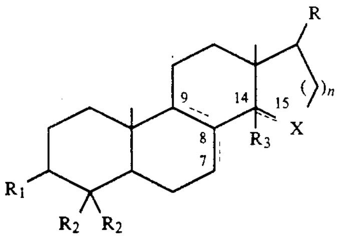

Formula 1 wherein the broken lines represent optional double bonds and:

R is a side chain having either 8 or 9 carbon atoms and from 15 to 20 hydrogen atoms, optionally with one site of unsaturation;

$R_1$ is $=O$, $OR_7$ or $OCOR_7$;

$R_2$ is H, $C_1$–$C_6$ alkyl, $C_2$–$C_6$ alkenyl, $C_2$–$C_6$ alkynyl, arylalkyl;

$R_3$ is H, $C_1$–$C_6$ alkyl, $C_2$–$C_6$ alkenyl, $C_2$–$C_6$ alkynyl, arylalkyl, $C(R_4)_2R_5$, $COR_4$, $CSR_4$, $C(=NR_4)R_4$, $COR_5$, $CSR_5$, $C(R_4)_2C(R_4)_2R_5$, $C(R_4)_2COR_4$, $C(R_4)_2CSR_4$, $C(R_4)_2C(=NR_4)R_4$, $C(R_4)_4COR_5$, $C(R_4)_2CRS_5$, $C(R_4)_2Z$, $C(R_4)_2C(R_4)_2Z$, CN, $CR_4NOR_4$, $CR_4NOR_6$, $CR_4NN(R_4)_2$, $CR_4NNR_4R_6$, $CHR_4NHOR_4$, $CHR_4NHOR_6$, $CHR_4NHN(R_4)_2$, $CHR_4NHNR_4N_6$, $CHR_4CR_4NOR_4$, $CHR_4CR_4NOR_6$ $CHR_4CR_4NN(R_4)_2$, $CHR_4CR_4NNR_4R_6$ $CHR_4CHR_4NHOR_4$, $CHR_4CHR_4NHOR_6$, $CHR_4CHR_4NHN(R_4)_2$, $C(O)NR_4OR_4$, $C(O)NR_4OR_6$, $C(S)NR_4OR_4$, $C(S)NR_4OR_6$, $CR_4=CR_4R_6$, $C\equiv CR_6$, $CR_4=CR_4C(R_4)_2Z$, $C\equiv CC(R_4)_2Z$, $CR_4=CR_4C(R_4)_2OR_6$, $C\equiv CC(R_4)_2OR_6$, poly-($OR_4$, $OR_6$, epoxy)-$C_1$–$C_6$ alkyl;

$R_4$ is H, $C_1$–$C_6$ alkyl, $C_2$–$C_6$ alkenyl, $C_2$–$C_6$ alkynyl, aryl, arylalkyl;

$R_5$ is $OR_4$, $SR_4$, $N(R_4)_2$, $NR_4R_6$;

$R_6$ is $COR_4$, $CSR_4$, $C(=NR_4)R_4$;

$R_7$ is H, $C_1$–$C_{20}$ alkyl, $C_2$–$C_{20}$ alkenyl, $C_2$–$C_{20}$ alkynyl, aryl, arylalkyl;

X is O, S, SO, $SO_2$, N, $NR_4$, $NR_6$ $N(O)R_4$;

Z is halogen; and n is 1 or 2;

and (ii) a pharmaceutically acceptable carrier or diluent.

In addition, the present invention encompasses methods for suppressing HMGR activity, decreasing cholesterol formation and lowering serum cholesterol levels comprising administering to a host an effective amount of a compound of the formula:

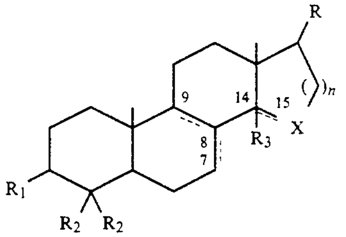

Formula 1 wherein the broken lines represent optional double bonds and:

R is a side chain having either 8 or 9 carbon atoms and from 15 to 20 hydrogen atoms, optionally with one site of unsaturation;

$R_1$ is $=O$, $OR_7$ or $OCOR_7$;

$R_2$ is H, $C_1$–$C_6$ alkyl, $C_2$–$C_6$ alkenyl, $C_2$–$C_6$ alkynyl, benzyl;

$R_3$ is H, $C_1$–$C_6$ alkyl, $C_2$–$C_6$ alkenyl, $C_2$–$C_6$ alkynyl, benzyl, $C(R_4)_2R_5$, $COR_4$, $CSR_4$, $C(=NR_4)R_4$, $COR_5$, $CSR_5$, $C(R_4)_2C(R_4)_2R_5$, $C(R_4)_2COR_4$, $C(R_4)_2CSR_4$, $C(R_4)_2C(=NR_4)R_4$, $C(R_4)_4COR_5$, $C(R_4)_2CRS_5$, $C(R_4)_2Z$, $C(R_4)_2C(R_4)_2Z$, CN, $CR_4NOR_4$, $CR_4NOR_6$, $CR_4NN(R_4)_2$, $CR_4NNR_4R_6$, $CHR_4NHOR_4$, $CHR_4NHOR_6$, $CHR_4NHN(R_4)_2$, $CHR_4NHNR_4N_6$, $CHR_4CR_4NOR_4$, $CHR_4CR_4NOR_6$ $CHR_4CR_4NN(R_4)_2$, $CHR_4CR_4NNR_4R_6$ $CHR_4CHR_4NHOR_4$, $CHR_4CHR_4NHOR_6$, $CHR_4CHR_4NHN(R_4)_2$, $C(O)NR_4OR_4$, $C(O)NR_4OR_6$, $C(S)NR_4OR_4$, $C(S)NR_4OR_6$, $CR_4=CR_4R_6$, $C\equiv CR_6$, $CR_4=CR_4C(R_4)_2Z$, $C\equiv CC(R_4)_2Z$, $CR_4=CR_4C(R_4)_2OR_6$, $C\equiv CC(R_4)_2OR_6$, poly-($OR_4$, $OR_6$, epoxy)-$C_1$–$C_6$ alkyl;

$R_4$ is H, $C_1$–$C_6$ alkyl, $C_2$–$C_6$ alkenyl, $C_2$–$C_6$ alkynyl, aryl, benzyl;

$R_5$ is $OR_4$, $SR_4$, $N(R_4)_2$, $NR_4R_6$;

$R_6$ is $COR_4$, $CSR_4$, $C(=NR_4)R_4$;

$R_7$ is H, $C_1$–$C_{20}$ alkyl, $C_2$–$C_{20}$ alkenyl, $C_2$–$C_{20}$ alkynyl, aryl, benzyl;

X is O, S, SO, $SO_2$, N, $NR_4$, $NR_6$, $N(O)R_4$;

Z is halogen; and n is 1 or 2.

In the above formulae, the R side chain is preferably selected from the cholesterol side chain ($C_8H_{17}$) and the ergosterol side chain ($C_9H_{17}$). These are generically represented by the formula:

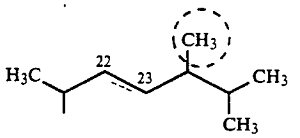

where the dashed line represents an optional double bond and the circled alpha-methyl group is likewise optional. However, when the D ring is piperidine or the N-oxide thereof, the R side chain is not an ergosterol side chain.

Likewise, in the above formulae, the ring structure may be unsaturated between carbons 7 and 8 or 8 and 9. When X is N the structure has an additional double bond between C-14 and N and C-14 does not have $R_3$ substitution.

As used herein, the substituent designated as "poly-($OR_4$, $OR_5$, epoxy) $C_1$–$C_6$ alkyl" shall be taken to mean a $C_1$ to $C_6$ alkyl chain substituted with one or more of any combination of $OR_4$, $OR_5$ and epoxy.

As used herein, the term "alkyl" employed either alone or in combination with other terms such as "poly-($OR_4$, $OR_5$, epoxy) $C_1$–$C_6$ alkyl" or "arylalkyl", denotes straight chain or branched alkyl, e.g., methyl, ethyl, n-propyl, isopropyl, and the different butyl, pentyl or hexyl isomers.

As used herein, the term "alkynyl", employed either alone or in combination with other terms, denotes straight chain or branched mono- or poly- unsaturated alkyl, e.g., ethynyl, propynyl (propargyl), 2-butynyl isomers, and the different pentynyl, hexadiynyl and hexynyl isomers.

As used herein, the term "acyl", employed either alone or in combination with other terms, denotes a carbonyl group attached to an alkyl, alkenyl, alkynyl, arylalkyl or aryl group e.g. acetate, butyrate, benzoate, and different alkyl, alkenyl, alkynyl, or aryl isomers.

As used herein, the term "halogen" denotes fluorine, chlorine, bromine and iodine.

As used herein the term "physiologically acceptable salts" refers to salts prepared from pharmaceutically acceptable non-toxic acids and/or bases, including inorganic acids/bases and organic acids/bases.

DETAILED DESCRIPTION OF THE INVENTION

The compounds of Formula I can be employed to suppress HMGR activity, decrease cholesterol formation and lower serum cholesterol levels in mammals. These compounds can be administered alone, or in combination with pharmaceutically acceptable carriers or diluents appropriate to the indicated route of administration. Administration can be oral, sublingual, buccal, topical and parenteral such as intravenous, subcutaneous or intramuscular.

Acceptable carriers and diluents are well-known in the pharmaceutical art, and are described, for example, in Remington's Pharmaceutical Sciences, Gennaro, A. R., ed., Mack Publishing Co., Easton, Pa. (1985). The useful dosage to be administered and the mode of administration will vary depending upon the age, weight and species of mammal treated.

While not wishing to be bound to theory or conjecture, a brief description of the mechanism by which the active 15-oxa-, 15-thia-, and 15-aza-dihydro-lanosterol compounds of the present invention are believed to function is as follows.

The observed decrease in HMGR activity is thought to occur as a result of a decreased synthesis of HMGR protein and/or an enhanced rate of HMGR degradation (collectively termed herein as "suppression").

General Procedures for the Preparation of Heterocyclic Lanosterol Derivatives The compounds of the present invention accommodate the necessary requirements for suppression of HMGR activity. To allow the introduction of various functional groups at 14-position, a strategy, which involves an opening and a reclosing of the D ring of the steroidal structure, was developed. In the schemes and tables which follow, for simplicity, only the cholesterol side chain ($C_8H_{17}$) is shown. It is to be understood that the ergosterol side chain ($C_9H_{17}$) or modifications of either side chain may be present instead of the illustrated cholesterol side chain.

15-Oxa-Lanosterols

The common intermediate for 15-oxa-, thia- and aza-dihydrolanosterols, the enone-aldehyde 4, has been obtained by an osmium tetroxide hydroxylation on the 8,14-diene (Compound 2) followed by an oxidative cleavage of the resulting diol, Compound 3 (See, Scheme I).

SCHEME I

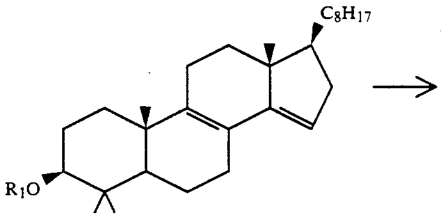

2a $R_1$ = H
2b $R_1$ = p-$CH_3OC_6H_4CH_2$(pMBn)

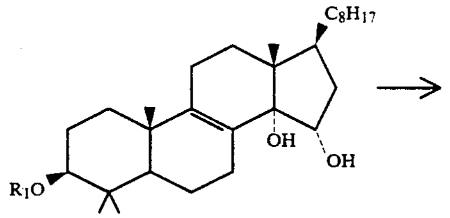

3a $R_1$ = H
3b $R_1$ = pMBn

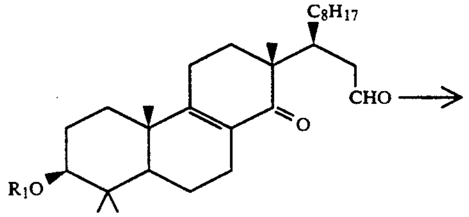

4a $R_1$ = H
4b $R_1$ = pMBn

-continued

SCHEME I

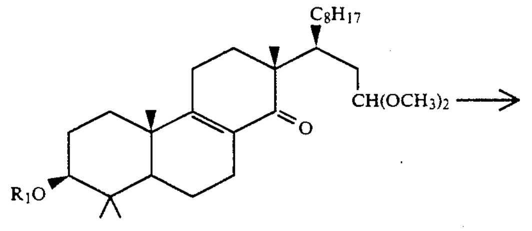

5a $R_1 = H$
5b $R_1$ = pMBn

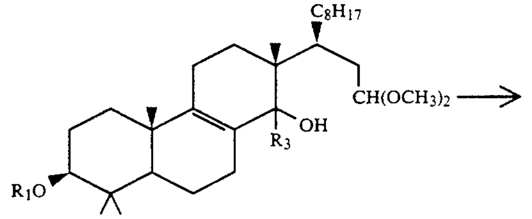

6a $R_1 = H$, $R_3 = CH_3$
6b $R_1$ = pMBn, $R_3 = CH_3$
12a $R_1 = R_3 = H$
12b $R_1$ = pMBn, $R_3 = H$
18a $R_1 = H$, $R_3 = CH{=}CH_2$
18b $R_1$ = pMBn, $R_3 = CH{=}CH_2$

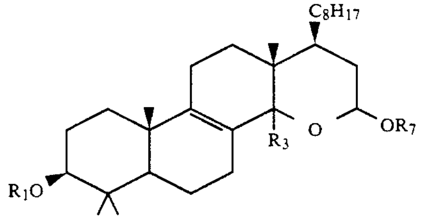

7a $R_1 = H$, $R_3 = R_7 = CH_3$
7b $R_1$ = pMBn, $R_3 = CH_3$, $R_7 = H$
7c $R_1$ = pMBn, $R_3 = R_7 = CH_3$
13a $R_1 = R_3 = H$, $R_7 = CH_3$
13b $R_1$ = pMBn, $R_3 = R_7 = H$
13c $R_1$ = pMBn, $R_3 = H$, $R_7 = CH_3$
19a $R_1 = H$, $R_3 = CH{=}CH_2$, $R_7 = CH_3$
19b $R_1$ = pMBn, $R_3 = CH{=}CH_2$, $R_7 = H$
19c $R_1$ = pMBn, $R_3 = CH{=}CH_2$, $R_7 = CH_3$

The starting species, Compound 2a, 4-dimethyl-5a-cholesta-8,14-dien-3b-ol, was prepared from 7-dehydrocholesterol (Sigma Chemical Co., P.O. Box 14508, St. Louis, Mo. 63178) by the method described by Bloch and Gautschi in *J. Chem. Soc.*, 223 (6), 1343 (1958). Treatment of the 8,14-dien-3b-ol (2a) with sodium hydride (Alfa Products, P.O. Box 299, Danvers, Mass. 01923) and 4-methoxybenzyl chloride [prepared by the method described by R. L. Schriner and C. J. Hull in *J. Org. Chem.*, 10, 228 (1945)] in 4 parts of tetrahydrofuran and 1 part of N,N-dimethylformamide at 70° C. afforded the corresponding p-methoxybenzyl ether 2b in near quantitative yield. Hydroxylation of the diene 2b with stoichiometric amount of osmium tetroxide (Alfa) in the presence of 10 equivalents of anhydrous pyridine (Aldrich Chemical Co., Inc., 940 West St., Paul Ave., Milwaukee, Wis. 53233) in benzene provided the 14,15-diol in 82% yield. Opening of the steroid D-ring was achieved by reacting the diol 3b with lead tetraacetate (Aldrich, recrystallized from acetic acid) in benzene to give the corresponding tricyclic enone-aldehyde 4b in quantitative yield. Selective conversion of the enone-aldehyde 4b to a dimethyl acetal 5b by with trimethyl orthoformate (Aldrich) and camphorsulfonic acid (Aldrich) in methanol (>95% yield) ensured the functionalization at C-14 without complication at C-15. The necessary functional groups at 14-position were introduced at this stage by adding various nucleophiles to the carbonyl. Diisobutyl aluminum hydride (Aldrich, 1 molar solution in hexane) reduction of the enone 5b in methyl chloride afforded the alcohol 12b in 85% yield.

A methyl group was introduced by a Grignard reaction with methyl magnesium bromide (Aldrich, 3 molar solution in diethyl ether) in diethyl ether to give the tertiary alcohol 6b in above 90% yield.

Similarly a vinyl group was introduced by treating the enone acetal 5b with vinyl magnesium bromide (Alfa, 1.6 molar solution in tetrahydrofuran) in refluxing dry tetrahydrofuran to give the doubly allylic alcohol 18b in near 90% yield.

The steroid D-ring was reclosed to form a six-membered ring with introduction of an oxygen at 14 -position by treating the tertiary alcohol 6b in 80% aqueous acetic acid to provide a 3.3:1 mixture of cyclic hemiacetal 7b and cyclic acetal 7c. The acetal 7c was easily separated form the hemiacetal 7b by column chromatography on silica gel (Kieselgel 60), EM Science, 111 Woodcrest Road, Cherry Hill, N.J. 08034-0395) with elution by 15:85 ethyl acetate-hexane followed by 3:7 ethyl acetate - hexane. The acetal 7c was further hydrolyzed to the hemiacetal 7b by exposing to 80% aqueous acetic acid containing a catalytic amount of 1M - hydrochloric acid (78% overall yield for the hemiacetal from the diene 2b).

For the extrusion of the extra carbon atom to form the five-membered heterocyclic D-ring the hemiacetal 7b was converted to the corresponding glycal 8b by reacting with methanesulfonyl chloride (Aldrich, filtered freshly through basic alumina) in the presence of excess triethylamine (Aldrich, distilled from calcium hydride) in methylene chloride (See, Scheme II).

The intermediate methanesulfonyl ester was eliminated to form the glycal 8b under conventional reaction conditions. Osmium tetroxide hydroxylation of the glycal 8b in benzene containing 10 equivalents of pyridine afforded a diasteromeric mixture of diols 9b. This unstable mixture of diols 9b was reacted with sodium periodate (Aldrich) in 4 parts of diethyl ether, 4 parts of methanol and 1 part of water in the presence of camphorsulfonic acid to give a mixture of p-methoxybenzyl ether of 16-methoxy-15-oxa-dihydrolanosterol 10b and p-methoxybenzyl ether of 16-hydroxy-15-oxa-dihydrolanosterol 10c in about 7:1 ratio. The mixture was then treated with excess triethylsilane (Aldrich) and then redistilled boron trifluoride etherate (Aldrich) in methylene chloride to give the desired 15-oxa-dihydrolanosterol (11a) in 40% overall yield from the compound 7b. The p-methoxy benzyl protecting group at C-3 was conveniently cleaved during this process to afford the free hydroxy compound.

In the same manner the C-14 hydride compound 12b and the C-14 vinyl compound 18b have also been transformed successfully into the corresponding 4,4-dimethyl-15-oxa-5a-cholest-8-en-3b-ol (17a) and 4,4-dimethyl-15-oxa-14a-vinyl-5a-cholest-8-en-3b-ol (23a) in 36% and 50% overall yields respectively. The compounds 17a, 11a, and 23a constitute three examples of 15-oxa-lanosterols within the scope of the present invention.

Exposing the 14a-vinyl-oxa-sterol (23a) to acetic anhydride (Fischer Scientific, Fair Lawn, N.J. 07440) in anhydrous pyridine gave 3b-acetoxy-4,4-dimethyl-15-oxavinyl-lanost-8-ene (23c), a compound within the scope of the present invention, in 81% yield. Esters of other lanosterol derivatives within the scope of the invention may be prepared in this or a similar manner.

SCHEME II

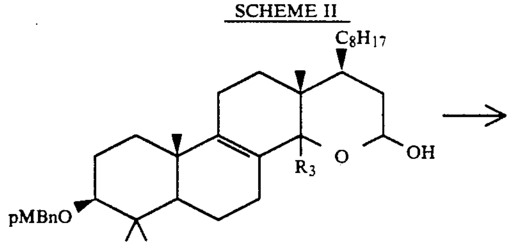

7b $R_3 = CH_3$
13b $R_3 = H$
19b $R_3 = CH{=}CH_2$

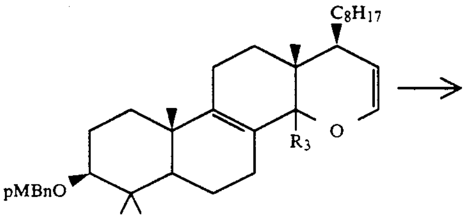

8b $R_3 = CH_3$
14b $R_3 = H$
20b $R_3 = CH{=}CH_2$

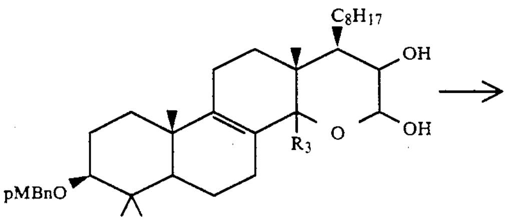

9b $R_3 = CH_3$
15b $R_3 = H$
21b $R_3 = CH{=}CH_2$

-continued
SCHEME II

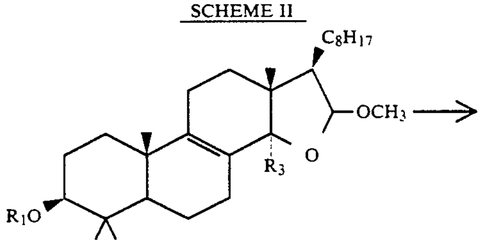

10b $R_3 = CH_3$
16b $R_3 = H$
22b $R_3 = CH{=}CH_2$

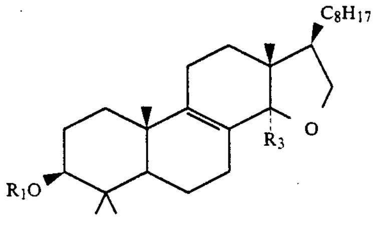

11 $R_1 = H$, $R_3 = CH_3$
17 $R_1 = H$, $R_3 = H$
23a $R_1 = H$, $R_3 = CH{=}CH_2$
23c $R_1 = CH_3CO$, $R_3 = CH{=}CH_2$

Further elaboration at the 14-position was achieved by treating the vinyl compound 23c with osmium tetroxide in pyridine to afford a diastereomeric mixture of diols 24c and 25c (2.84:1) in 45% yield (Scheme III).

The mixture of diols 24c and 25c was reacted with sodium metaperiodate in 4 parts of ethanol and 1 part of water to give 3b-acetoxy-15-oxa-lanost-8-en-32-al (26c) in near quantitative yield. Hydrolysis of the acetate-aldehyde 26c by 3 molar potassium hydroxide afforded the corresponding free hydroxy-aldehyde 26a in near quantitative yield. Reduction of the aldehyde 26a with sodium borohydride (Fischer Scientific) in ethanol afforded 15-oxa-lanost-8-ene-3b, 32-diol (27) in near quantitative yield.

The same chemistry is also applicable to the free hydroxy-vinyl compound 23a to provide 24a, 25a, and 26a directly. Compounds 24a, 24c, 25a, 25c, 26a, 26c and 27 are seven additional examples of 15-oxa-lanosterols within the scope of the present invention.

SCHEME III

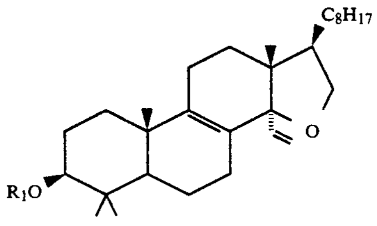

23c $R_1 = CH_3CO$

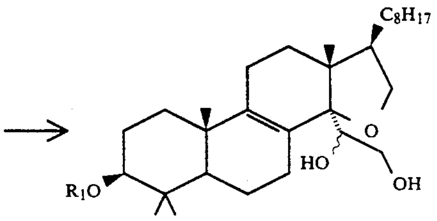

24c, 25c $R_1 = CH_3CO$

-continued

SCHEME III

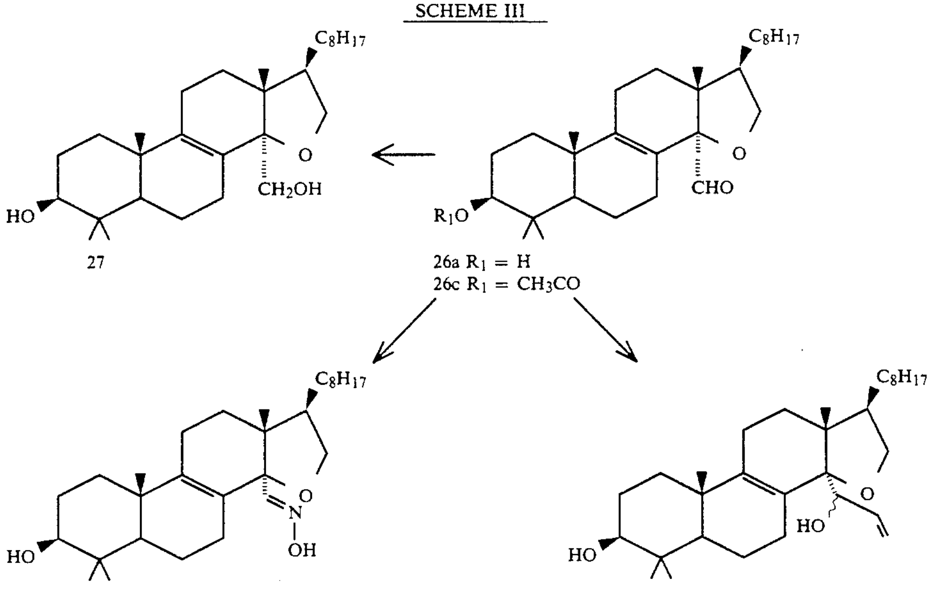

27

26a $R_1 = H$

26c $R_1 = CH_3CO$

30

28, 29

The aldehyde functional group of the Compound 26 allows further functionalization at the 32-position of lanosterol. A Grignard addition to the aldehyde 26c with vinyl magnesium bromide (Alfa, 1.6 molar solution in tetrahydrofuran) in refluxing tetrahydrofuran provided a diasteromeric mixture of allylic alcohols 28 and 29 (1.4:1) in >95% combined yield. Upon exposing the aldehyde 26a to hydroxylamine hydrochloride (Aldrich) in pyridine at 80°, the corresponding oxime 30 was obtained in quantitative yield. Compounds 28, 29, and 30 constitute three additional examples of 15-oxa- lanosterols within the scope of the present invention. Table 1 sets forth various oxasterols of the present invention.

TABLE 1

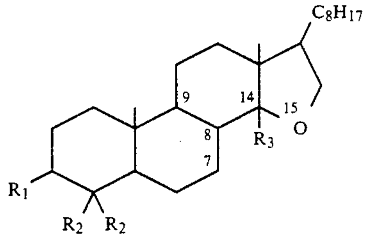

| Ex. No. | $R_1$ | $R_2$ | $R_3$ | D | No. | M.P. |
|---|---|---|---|---|---|---|
| 1 | OH | $CH_3$ | $CH_3$ | 8 | 11 | amorphous* |
| 2 | OH | $CH_3$ | H | 8 | 17 | amorphous* |
| 3 | OH | $CH_3$ | $CH{=}CH_2$ | 8 | 23a | amorphous* |
| 3a | $CH_3$ | $CH_3$ | $CH{=}CH_2$ | 8 | 23c | |
| 4 | OH | $CH_3$ | $CHOHCH_2OH$—(R) | 8 | 24c | |
| 5 | OH | $CH_3$ | $CHOHCH_3OH$—(S) | 8 | 25c | |
| 6 | $CH_3CO$ | $CH_3$ | CHO | 8 | 26c | amorphous* |
| 7 | OH | $CH_3$ | CHO | 8 | 2a | amorphous* |
| 8 | OH | $CH_3$ | $CH_2OH$ | 8 | 27 | |
| 9 | OH | $CH_3$ | $CO_2CH_3$ | 8 | | |
| 10 | OH | $CH_3$ | CH=NOH | 8 | 30 | amorphous* |
| 11 | OH | $CH_3$ | $CHOHCH{=}CH_2$—(R) | 8 | 28 | amorphous* |
| 12 | OH | $CH_3$ | $CHOHCH{=}CH_2$—(S) | 8 | 29 | amorphous* |
| 13 | OH | H | $CH_3$ | 8 | 47 | |
| 14 | OH | H | H | 8 | | |
| 15 | OH | H | $CH{=}CH_2$ | 8 | | |
| 16 | OH | H | $CHOHCH_2OH$—(R) | 8 | | |
| 17 | OH | H | $CHOHCH_2OH$—(S) | 8 | | |
| 18 | OH | H | CHO | 8 | | |
| 19 | OH | H | $CH_2OH$ | 8 | | |
| 20 | OH | H | $CO_2H$ | 8 | | |
| 21 | OH | H | $CO_2CH_3$ | 8 | | |
| 22 | OH | H | CH=NOH | 8 | | |
| 23 | OH | H | $CHOHCH{=}CH_2$—(R) | 8 | | |
| 24 | OH | H | $CHOHCH{=}CH_2$—(S) | 8 | | |
| 25 | OH | $CH_3$ | $C_3H_5$ | 8 | | |
| 26 | OH | $CH_3$ | $C_3H_7$ | 8 | | |
| 27 | OH | $CH_3$ | i-$C_3H_9$ | 8 | | |
| 28 | OH | $CH_3$ | $C_6H_{13}$ | 8 | | |

TABLE 1-continued

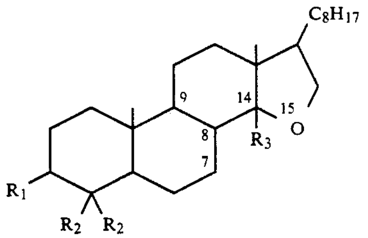

| Ex. No. | $R_1$ | $R_2$ | $R_3$ | D | No. | M.P. |
|---|---|---|---|---|---|---|
| 29 | OH | $CH_3$ | $C_6H_{13}$ | 8 | | |
| 30 | OH | $CH_3$ | $C_6H_{13}$ | 8 | | |
| 31 | OH | $CH_3$ | $CH_2CH{=}CH_2$ | 8 | | |
| 32 | OH | $CH_3$ | $C{\equiv}CH$ | 8 | | |
| 33 | OH | $CH_3$ | $CH_2C{\equiv}CH$ | 8 | | |
| 34 | OH | $CH_3$ | $CH_2Ph$ | 8 | | |
| 35 | OH | $CH_3$ | $CHOHCH_3$ | 8 | | |
| 36 | OH | $CH_3$ | $CHOHC{\equiv}CH$ | 8 | | |
| 37 | OH | $CH_3$ | $CH_2OCH_3$ | 8 | | |
| 38 | OH | $CH_3$ | $CH_2OC_2H_5$ | 8 | | |
| 39 | OH | $CH_3$ | $CH_2OC_3H_7$ | 8 | | |
| 40 | OH | $CH_3$ | $CH_2OCH_2CH{=}CH_2$ | 8 | | |
| 41 | OH | $CH_3$ | $CH_2OPh$ | 8 | | |
| 42 | OH | $CH_3$ | $CH_2OCOCH_3$ | 8 | | |
| 43 | OH | $CH_3$ | $CH_2SH$ | 8 | | |
| 44 | OH | $CH_3$ | $CH_2SCH_3$ | 8 | | |
| 45 | OH | $CH_3$ | $CH_2SC_2H_5$ | 8 | | |
| 46 | OH | $CH_3$ | $CH_2SPr$ | 8 | | |
| 47 | OH | $CH_3$ | $CH_2SCH_2CH{=}CH_2$ | 8 | | |
| 48 | OH | $CH_3$ | $CH_2SPh$ | 8 | | |
| 49 | OH | $CH_3$ | $CH_2SCOH_3$ | 8 | | |
| 50 | OH | $CH_3$ | $CH_2NH_2$ | 8 | | |
| 51 | OH | $CH_3$ | $CH_2NHCH_3$ | 8 | | |
| 52 | OH | $CH_3$ | $CH_2NHC_2H_5$ | 8 | | |
| 53 | OH | $CH_3$ | $CH_2NHC_3H_7$ | 8 | | |
| 54 | OH | $CH_3$ | $CH_2NHi\text{-}Pr$ | 8 | | |
| 55 | OH | $CH_3$ | $CH_2NHC_6H_{13}$ | 8 | | |
| 56 | OH | $CH_3$ | $CH_2NHPh$ | 8 | | |
| 57 | OH | $CH_3$ | $CH_2NMe_2$ | 8 | | |
| 58 | OH | $CH_3$ | $CH_2NEt_2$ | 8 | | |
| 59 | OH | $CH_3$ | $CH_2NHCHO$ | 8 | | |
| 60 | OH | $CH_3$ | $CH_2NHCOCH_3$ | 8 | | |
| 61 | OH | $CH_3$ | $CH_2NHCSCH_3$ | 8 | | |
| 62 | OH | $CH_3$ | $CH_2NH(C{=}NH)CH_3$ | 8 | | |
| 63 | OH | $CH_3$ | $COCH_3$ | 8 | | |
| 64 | OH | $CH_3$ | $COC_2H_5$ | 8 | | |
| 65 | OH | $CH_3$ | $COC_3H_7$ | 8 | | |
| 66 | OH | $CH_3$ | $COi\text{-}C_3H_7$ | 8 | | |
| 67 | OH | $CH_3$ | $COC_6H_{13}$ | 8 | | |
| 68 | OH | $CH_3$ | $COCH{=}CH_2$ | 8 | | |
| 69 | OH | $CH_3$ | $COCH_2CH{=}CH_2$ | 8 | | |
| 70 | OH | $CH_3$ | $COCH{=}CHCH_3$ | 8 | | |
| 71 | OH | $CH_3$ | $COC{\equiv}CH$ | 8 | | |
| 72 | OH | $CH_3$ | $COCH_2C{=}CH$ | 8 | | |
| 73 | OH | $CH_3$ | $COC{=}CCH_3$ | 8 | | |
| 74 | OH | $CH_3$ | $COPh$ | 8 | | |
| 75 | OH | $CH_3$ | $CSCH_3$ | 8 | | |
| 76 | OH | $CH_3$ | $CSC_2H_5$ | 8 | | |
| 77 | OH | $CH_3$ | $CSC_3H_7$ | 8 | | |
| 78 | OH | $CH_3$ | $CSC_3H_7$ (i) | 8 | | |
| 79 | OH | $CH_3$ | $CSC_6H_{13}$ | 8 | | |
| 80 | OH | $CH_3$ | $CSCH{=}CH_2$ | 8 | | |
| 81 | OH | $CH_3$ | $CSCH_2CH{=}CH_2$ | 8 | | |
| 82 | OH | $CH_3$ | $CSCH{=}CHCH_3$ | 8 | | |
| 83 | OH | $CH_3$ | $CSC{\equiv}CH$ | 8 | | |
| 84 | OH | $CH_3$ | $CSCH_2CH$ | 8 | | |
| 85 | OH | $CH_3$ | $CSC{=}CCH_3$ | 8 | | |
| 86 | OH | $CH_3$ | $CSPh$ | 8 | | |
| 87 | OH | $CH_3$ | $C({=}NH)CH_3$ | 8 | | |
| 88 | OH | $CH_3$ | $C({=}NH)C_3H_7$ | 8 | | |
| 89 | OH | $CH_3$ | $C({=}NH)C_3H_7$ | 8 | | |
| 90 | OH | $CH_3$ | $C({=}NH)Ph$ | 8 | | |
| 91 | OH | $CH_3$ | $C({=}NH)CH_3$ | 8 | | |
| 92 | OH | $CH_3$ | $C({=}NCH_3)C_2H_5$ | 8 | | |
| 93 | OH | $CH_3$ | $C({=}NCH_3)C_3H_7$ | 8 | | |
| 94 | OH | $CH_3$ | $CO_2C_2H_5$ | 8 | | |
| 95 | OH | $CH_3$ | $CO_2C_3H_7$ | 8 | | |
| 96 | OH | $CH_3$ | $CO_2i\text{-}C_3H_7$ | 8 | | |
| 97 | OH | $CH_3$ | $CO_2C_4H_9$ | 8 | | |

TABLE 1-continued

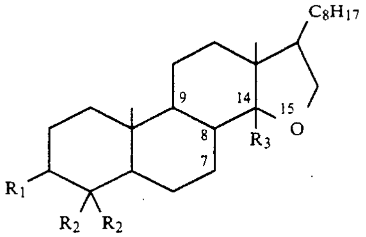

| Ex. No. | $R_1$ | $R_2$ | $R_3$ | D | No. | M.P. |
|---|---|---|---|---|---|---|
| 98 | OH | $CH_3$ | $CO_2C_6H_{13}$ | 8 | | |
| 99 | OH | $CH_3$ | $CO_2CH_2CH{=}CH_2$ | 8 | | |
| 100 | OH | $CH_3$ | $CO_2Ph$ | 8 | | |
| 101 | OH | $CH_3$ | $COSCH_3$ | 8 | | |
| 102 | OH | $CH_3$ | $COSC_2H_5$ | 8 | | |
| 103 | OH | $CH_3$ | $COSC_3H_7$ | 8 | | |
| 104 | OH | $CH_3$ | COSPh | 8 | | |
| 105 | OH | $CH_3$ | $CONH_2$ | 8 | | |
| 106 | OH | $CH_3$ | $CONHCH_3$ | 8 | | |
| 107 | OH | $CH_3$ | $CONHC_2H_5$ | 8 | | |
| 108 | OH | $CH_3$ | $CONHC_3H_7$ | 8 | | |
| 109 | OH | $CH_3$ | $CONHi\text{-}C_3H_7$ | 8 | | |
| 110 | OH | $CH_3$ | $CONHC_6H_{13}$ | 8 | | |
| 111 | OH | $CH_3$ | CONHPh | 8 | | |
| 112 | OH | $CH_3$ | $CONMe_2$ | 8 | | |
| 113 | OH | $CH_3$ | CONEt2 | 8 | | |
| 114 | OH | $CH_3$ | CONPr2 | 8 | | |
| 115 | OH | $CH_3$ | $CONHCOCH_3$ | 8 | | |
| 116 | OH | $CH_3$ | $CONHCOC_2H_5$ | 8 | | |
| 117 | OH | $CH_3$ | $CSNH_2$ | 8 | | |
| 118 | OH | $CH_3$ | $CSNHCH_3$ | 8 | | |
| 119 | OH | $CH_3$ | $CSNHC_2H_5$ | 8 | | |
| 120 | OH | $CH_3$ | $CSNHC_3H_7$ | 8 | | |
| 121 | OH | $CH_3$ | $CSNHi\text{-}C_3H_7$ | 8 | | |
| 122 | OH | $CH_3$ | $CSNHC_6H_{13}$ | 8 | | |
| 123 | OH | $CH_3$ | CSNHPh | 8 | | |
| 124 | OH | $CH_3$ | $CSNMe_2$ | 8 | | |
| 125 | OH | $CH_3$ | $CSNEt_2$ | 8 | | |
| 126 | OH | $CH_3$ | CSNPr2 | 8 | | |
| 127 | OH | $CH_3$ | $SCNHCOCH_3$ | 8 | | |
| 128 | OH | $CH_3$ | $CSNHCOC_2H_5$ | 8 | | |
| 129 | OH | $CH_3$ | $CH_2CH_2OH$ | 8 | | |
| 130 | OH | $CH_3$ | $CH_2CH(CH_3)OH$ | 8 | | |
| 131 | OH | $CH_3$ | $CH_2CH_2OCH_3$ | 8 | | |
| 132 | OH | $CH_3$ | $CH_2CH_2OC_2H_5$ | 8 | | |
| 133 | OH | $CH_3$ | $CH_2CH_2OPh$ | 8 | | |
| 134 | OH | $CH_3$ | $CH_2CH(CH_3)OCH_3$ | 8 | | |
| 135 | OH | $CH_3$ | $CH_2CH_2OCOCH_3$ | 8 | | |
| 136 | OH | $CH_3$ | $CH_2CH_2SH$ | 8 | | |
| 137 | OH | $CH_3$ | $CH_2CH(CH_3)SH$ | 8 | | |
| 138 | OH | $CH_3$ | $CH_2CH_2SCH_3$ | 8 | | |
| 139 | OH | $CH_3$ | $CH_2CH_2SC_2H_5$ | 8 | | |
| 140 | OH | $CH_3$ | $CH_2CH_2SPh$ | 8 | | |
| 141 | OH | $CH_3$ | $CH_2CH(CH_3)SCH_3$ | 8 | | |
| 142 | OH | $CH_3$ | $CH_2CH_2SCOCH_3$ | 8 | | |
| 143 | OH | $CH_3$ | $CH_2CH_2NH_2$ | 8 | | |
| 144 | OH | $CH_3$ | $CH_2CH(CH_3)NH_2$ | 8 | | |
| 145 | OH | $CH_3$ | $CH_2CH_2NHCH_3$ | 8 | | |
| 146 | OH | $CH_3$ | $CH_2CH_2NHC_2H_5$ | 8 | | |
| 147 | OH | $CH_3$ | $CH_2CH_2NHPh$ | 8 | | |
| 148 | OH | $CH_3$ | $CH_2CH(CH_3)NHCH_3$ | 8 | | |
| 149 | OH | $CH_3$ | $CH_2CH_2NMe_2$ | 8 | | |
| 150 | OH | $CH_3$ | $CH_2CH_2NHCOCH_3$ | 8 | | |
| 151 | OH | $CH_3$ | $CH_2CH(CH_3)NHCOCH_3$ | 8 | | |
| 152 | OH | $CH_3$ | $CH_2CH_2NHCSCH_3$ | 8 | | |
| 153 | OH | $CH_3$ | $CH_2CH(CH_3)NHCSCH_3$ | 8 | | |
| 154 | OH | $CH_3$ | $CH_2CH_2NHC({=}NH)CH_3$ | 8 | | |
| 155 | OH | $CH_3$ | $CH_2CH(CH_3)NHC({=}NH)CH_3$ | 8 | | |
| 156 | OH | $CH_3$ | $CH_2CHO$ | 8 | | |
| 157 | OH | $CH_3$ | $CH_2COCH_3$ | 8 | | |
| 158 | OH | $CH_3$ | $CH_2COC_2H_5$ | 8 | | |
| 159 | OH | $CH_3$ | $CH_2COCH{=}CH_2$ | 8 | | |
| 160 | OH | $CH_3$ | $CH_2COCH_2CH{=}CH_2$ | 8 | | |
| 161 | OH | $CH_3$ | $CH_2COCH{=}CHCH_3$ | 8 | | |
| 162 | OH | $CH_3$ | $CH_2COC{\equiv}CH$ | 8 | | |
| 163 | OH | $CH_3$ | $CH_2COPh$ | 8 | | |
| 164 | OH | $CH_3$ | $CH_2CSCH_3$ | 8 | | |
| 165 | OH | $CH_3$ | $CH_2CSC_2H_5$ | 8 | | |
| 166 | OH | $CH_3$ | $CH_2CSCH{=}CH_2$ | 8 | | |

TABLE 1-continued

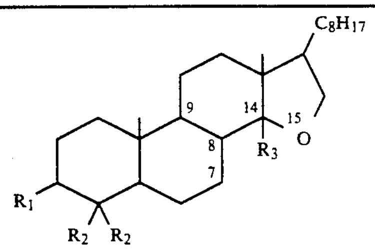

| Ex. No. | $R_1$ | $R_2$ | $R_3$ | D | No. | M.P. |
|---|---|---|---|---|---|---|
| 167 | OH | $CH_3$ | $CH_2CSCH_2CH{=}CH_2$ | 8 | | |
| 168 | OH | $CH_3$ | $CH_2CSCH{=}CHCH_3$ | 8 | | |
| 169 | OH | $CH_3$ | $CH_2CSC{\equiv}CH$ | 8 | | |
| 170 | OH | $CH_3$ | $CH_2CSPh$ | 8 | | |
| 171 | OH | $CH_3$ | $CH_2C({=}NH)CH_3$ | 8 | | |
| 172 | OH | $CH_3$ | $CH_2C({=}NH)C_2H_5$ | 8 | | |
| 173 | OH | $CH_3$ | $CH_2C({=}NCH_3)CH_3$ | 8 | | |
| 174 | OH | $CH_3$ | $CH_2C({=}NCH_3)C_2H_5$ | 8 | | |
| 175 | OH | $CH_3$ | $CH_2C({=}NH)Ph$ | 8 | | |
| 176 | OH | $CH_3$ | $CH_2CO_2CH_3$ | 8 | | |
| 177 | OH | $CH_3$ | $CH_2CO_2C_2H_5$ | 8 | | |
| 178 | OH | $CH_3$ | $CH_2CO_2CH_2CH{=}CH_2$ | 8 | | |
| 179 | OH | $CH_3$ | $CH_2CO_2Ph$ | 8 | | |
| 180 | OH | $CH_3$ | $CH_2COSCH_3$ | 8 | | |
| 181 | OH | $CH_3$ | $CH_2COSCH_3$ | 8 | | |
| 181 | OH | $CH_3$ | $CH_2COSC_2H5$ | 8 | | |
| 182 | OH | $CH_3$ | $CH_2COSPh$ | 8 | | |
| 183 | OH | $CH_3$ | $CH_2CONH_2$ | 8 | | |
| 184 | OH | $CH_3$ | $CH_2CONHCH_3$ | 8 | | |
| 185 | OH | $CH_3$ | $CH_2CONHC_2H_5$ | 8 | | |
| 186 | OH | $CH_3$ | $CH_2CONHPh$ | 8 | | |
| 187 | OH | $CH_3$ | $CH_2CONMe_2$ | 8 | | |
| 188 | OH | $CH_3$ | $CH_2CONHCOCH_3$ | 8 | | |
| 189 | OH | $CH_3$ | $CH_2CSNH_2$ | 8 | | |
| 190 | OH | $CH_3$ | $CH_2C({=}NH)NH_2$ | 8 | | |
| 191 | OH | $CH_3$ | $CH_2Cl$ | 8 | | |
| 192 | OH | $CH_3$ | $CH_2Br$ | 8 | | |
| 193 | OH | $CH_3$ | $CH_2CH_2Cl$ | 8 | | |
| 194 | OH | $CH_3$ | $CH_2CH_2Br$ | 8 | | |
| 195 | OH | $CH_3$ | CN | 8 | | |
| 196 | OH | $CH_3$ | $C(CH_3){=}NOH$ | 8 | | |
| 197 | OH | $CH_3$ | $CH{=}NOCH_3$ | 8 | | |
| 198 | OH | $CH_3$ | $CH{=}NOC_2H_5$ | 8 | | |
| 199 | OH | $CH_3$ | $CH{=}NOCOCH_3$ | 8 | | |
| 200 | OH | $CH_3$ | $CH{=}NNH_2$ | 8 | | |
| 201 | OH | $CH_3$ | $CN{=}NNHCH_3$ | 8 | | |
| 202 | OH | $CH_3$ | $CH{=}NNHCOCH_3$ | 8 | | |
| 203 | OH | $CH_3$ | $CH{=}NNHCSCH_3$ | 8 | | |
| 204 | OH | $CH_3$ | $CH_2NHOH$ | 8 | | |
| 205 | OH | $CH_3$ | $CH_2NHOCH_3$ | 8 | | |
| 206 | OH | $CH_3$ | $CH_2NHOCOCH_3$ | 8 | | |
| 207 | OH | $CH_3$ | $CH_2NHNH_2$ | 8 | | |
| 208 | OH | $CH_3$ | $CH_2NHNHCH_3$ | 8 | | |
| 209 | OH | $CH_3$ | $CH_2NHNHCOCH_3$ | 8 | | |
| 210 | OH | $CH_3$ | $CH_2NHNHCSCH_3$ | 8 | | |
| 211 | OH | $CH_3$ | $CH_2CN$ | 8 | | |
| 212 | OH | $CH_3$ | $CH_2CH{=}NOH$ | 8 | | |
| 213 | OH | $CH_3$ | $CH_2C(CH_3){=}NOH$ | 8 | | |
| 214 | OH | $CH_3$ | $CH_2CH{=}NOCH_3$ | 8 | | |
| 215 | OH | $CH_3$ | $CH_2CH{=}NOC_2H_5$ | 8 | | |
| 216 | OH | $CH_3$ | $CH_2CH{=}NOCOCH_3$ | 8 | | |
| 217 | OH | $CH_3$ | $CH_2CH{=}NNH_2$ | 8 | | |
| 218 | OH | $CH_3$ | $CH_2CH{=}NNHCH_3$ | 8 | | |
| 219 | OH | $CH_3$ | $CH_2CH{=}NNHCOCH_3$ | 8 | | |
| 220 | OH | $CH_3$ | $CH_2CH{=}NNHCSCH_3$ | 8 | | |
| 221 | OH | $CH_3$ | $CH_2CH_2NHOH$ | 8 | | |
| 222 | OH | $CH_3$ | $CH_2CH_2NHOCH_3$ | 8 | | |
| 223 | OH | $CH_3$ | $CH_2CH_2NHOCOCH_3$ | 8 | | |
| 224 | OH | $CH_3$ | $CH_2CH_2NHNH_2$ | 8 | | |
| 225 | OH | $CH_3$ | $CH_2CH_2NHNHCH_3$ | 8 | | |
| 226 | OH | $CH_3$ | $CH_2CH_2NHNHCOCH_3$ | 8 | | |
| 227 | OH | $CH_3$ | $CH_2CH_2NHNHCSCH_3$ | 8 | | |
| 228 | OH | $CH_3$ | CONHOH | 8 | | |
| 229 | OH | $CH_3$ | $CONHOCH_3$ | 8 | | |
| 230 | OH | $CH_3$ | $CONHOC_2H_5$ | 8 | | |
| 231 | OH | $CH_3$ | CONHOPh | 8 | | |
| 232 | OH | $CH_3$ | $CONHOCOCH_3$ | 8 | | |
| 233 | OH | $CH_3$ | CSNHOH | 8 | | |
| 234 | OH | $CH_3$ | $CSNHOCH_3$ | 8 | | |

TABLE 1-continued

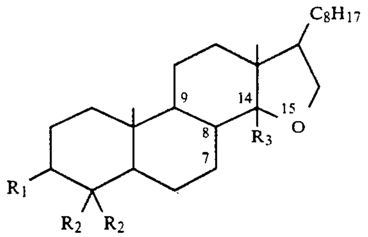

| Ex. No. | $R_1$ | $R_2$ | $R_3$ | D No. | M.P. |
|---|---|---|---|---|---|
| 235 | OH | $CH_3$ | $CSNHOCOCH_3$ | 8 | |
| 236 | OH | $CH_3$ | $CH=CHCHO$ | 8 | |
| 237 | OH | $CH_3$ | $CH=CHCOCH_3$ | 8 | |
| 238 | OH | $CH_3$ | $CH=CHCOC_2H_5$ | 8 | |
| 239 | OH | $CH_3$ | $CH=CHCSCH_3$ | 8 | |
| 240 | OH | $CH_3$ | $CH=CHCSC_2H_5$ | 8 | |
| 241 | OH | $CH_3$ | $CH=CHCH=NH$ | 8 | |
| 242 | OH | $CH_3$ | $CH=CHC(=NH)CH_3$ | 8 | |
| 243 | OH | $CH_3$ | $C\equiv CCHO$ | 8 | |
| 244 | OH | $CH_3$ | $C\equiv CCOCH_3$ | 8 | |
| 245 | OH | $CH_3$ | $C\equiv CCOC_2H_5$ | 8 | |
| 246 | OH | $CH_3$ | $C\equiv CCSCH_3$ | 8 | |
| 247 | OH | $CH_3$ | $C\equiv CCSC_2H_5$ | 8 | |
| 248 | OH | $CH_3$ | $C\equiv CCH=NH$ | 8 | |
| 249 | OH | $CH_3$ | $C\equiv CC(=NH)CH_3$ | 8 | |
| 250 | OH | $CH_3$ | $CH=CHCH_2Cl$ | 8 | |
| 251 | OH | $CH_3$ | $CH=CHCH_2Br$ | 8 | |
| 252 | OH | $CH_3$ | $C\equiv CCH_2Cl$ | 8 | |
| 253 | OH | $CH_3$ | $C\equiv CCH_2Br$ | 8 | |
| 254 | OH | $CH_3$ | $CH=CHCH_2OCOCH_3$ | 8 | |
| 255 | OH | $CH_3$ | $CH=CHCH_2OCOC_2H_5$ | 8 | |
| 256 | OH | $CH_3$ | $C\equiv CCH_2OCOCH_3$ | 8 | |
| 257 | OH | $CH_3$ | $C\equiv CCH_2OCOC_2H_5$ | 8 | |
| 258 | OH | $CH_3$ | $CH_2CHOHCH_2OH$ | 8 | |
| 259 | OH | $CH_3$ | $CHOHCHOHCH_2OH$ | 8 | |
| 260 | OH | $CH_3$ | 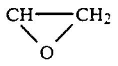 | 8 | |
| 261 | OH | $CH_3$ | 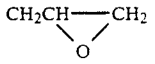 | 8 | |
| 262 | OH | $CH_3$ | 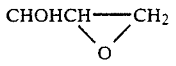 | 8 | |
| 263 | OH | H | $C_2H_5$ | 8 | |
| 264 | OH | H | $CH_2CH=CH_2$ | 8 | |
| 265 | OH | H | $C\equiv CH$ | 8 | |
| 266 | OH | H | $CH_2Ph$ | 8 | |
| 267 | OH | H | $CH_2OCH_3$ | 8 | |
| 268 | OH | H | $CH_2OCOCH_3$ | 8 | |
| 269 | OH | H | $CH_2SH$ | 8 | |
| 270 | OH | H | $CH_2SCH_3$ | 8 | |
| 271 | OH | H | $CH_2SCOCH_3$ | 8 | |
| 272 | OH | H | $CH_2NH_2$ | 8 | |
| 273 | OH | H | $CH_2NHCH_3$ | 8 | |
| 274 | OH | H | $CH_2N2(CH_3)_2$ | 8 | |
| 275 | OH | H | $CH_2NHCOCH_3$ | 8 | |
| 276 | OH | H | $CH_2NHCSCH_3$ | 8 | |
| 277 | OH | H | $CH_2NHC(=NH)CH_3$ | 8 | |
| 278 | OH | H | $COCH_3$ | 8 | |
| 279 | OH | H | $COCH=CH_2$ | 8 | |
| 280 | OH | H | $CSCH_3$ | 8 | |
| 281 | OH | H | $CSCH=CH_2$ | 8 | |
| 282 | OH | H | $C(=NH)CH_3$ | 8 | |
| 283 | OH | H | $C(=NCH_3)CH_3$ | 8 | |
| 284 | OH | H | $CO_2C_2H_5$ | 8 | |
| 285 | OH | H | $COSCH_3$ | 8 | |
| 286 | OH | H | $CONH_2$ | 8 | |
| 287 | OH | H | $CONHCH_3$ | 8 | |
| 288 | OH | H | $CON2(CH_3)_2$ | 8 | |
| 289 | OH | H | $CONHCOCH_3$ | 8 | |
| 290 | OH | H | $CSNH_2$ | 8 | |
| 291 | OH | H | $CSNHCH_3$ | 8 | |
| 292 | OH | H | $CSNMe_2$ | 8 | |

TABLE 1-continued

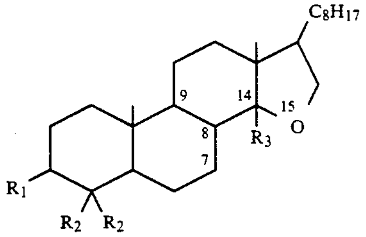

| Ex. No. | $R_1$ | $R_2$ | $R_3$ | D | No. | M.P. |
|---|---|---|---|---|---|---|
| 293 | OH | H | $CSNHCOCH_3$ | 8 | | |
| 294 | OH | H | $CH_2CH_2OH$ | 8 | | |
| 295 | OH | H | $CH_2CH_2OCH_3$ | 8 | | |
| 296 | OH | H | $CH_2CH_2OCOCH_3$ | 8 | | |
| 297 | OH | H | $CH_2CH_2SH$ | 8 | | |
| 298 | OH | H | $CH_2CH_2SCH_3$ | 8 | | |
| 299 | OH | H | $CH_2CH_2SCOCH_3$ | 8 | | |
| 300 | OH | H | $CH_2CH_2NH_2$ | 8 | | |
| 301 | OH | H | $CH_2CH_2NHCH_3$ | 8 | | |
| 302 | OH | H | $CH_3CH_2NMe_2$ | 8 | | |
| 303 | OH | H | $CH_2CH_2NHCOCH_3$ | 8 | | |
| 304 | OH | H | $CH_2CH_2NHCSCH_3$ | 8 | | |
| 305 | OH | H | $CH_2CH_2NHC(=NH)CH_3$ | 8 | | |
| 306 | OH | H | $CH_2CHO$ | 8 | | |
| 307 | OH | H | $CH_2COCH_3$ | 8 | | |
| 308 | OH | H | $CH_2COCH=CH_2$ | 8 | | |
| 309 | OH | H | $CH_2CSCH_3$ | 8 | | |
| 310 | OH | H | $CH_2CSCH=CH_2$ | 8 | | |
| 311 | OH | H | $CH_2C(=NH)CH_3$ | 8 | | |
| 312 | OH | H | $CH_2C(=NCH_3)CH_3$ | 8 | | |
| 313 | OH | H | $CH_2CO_2CH_3$ | 8 | | |
| 314 | OH | H | $CH_2COSCH_3$ | 8 | | |
| 315 | OH | H | $CH_2CONH_2$ | 8 | | |
| 316 | OH | H | $CH_2CONHCH_3$ | 8 | | |
| 317 | OH | H | $CH_2CONMe2$ | 8 | | |
| 318 | OH | H | $CH_2CONHCOCH_3$ | 8 | | |
| 319 | OH | H | $CH_2CSNH_2$ | 8 | | |
| 320 | OH | H | $CH_2C(=NH)CH_3$ | 8 | | |
| 321 | OH | H | $CH_2Cl$ | 8 | | |
| 322 | OH | H | $CH_2Br$ | 8 | | |
| 323 | OH | H | $CH_2CH_2Cl$ | 8 | | |
| 324 | OH | H | $CH_2CH_2Br$ | 8 | | |
| 325 | OH | H | CN | 8 | | |
| 326 | OH | H | $CH=NOCH_3$ | 8 | | |
| 327 | OH | H | $CH=NOCOCH_3$ | 8 | | |
| 328 | OH | H | $CH=NNH_2$ | 8 | | |
| 329 | OH | H | $CH=NNHCH_3$ | 8 | | |
| 330 | OH | H | $CH=NNHCOCH_3$ | 8 | | |
| 331 | OH | H | $CH=NNHCSCH_3$ | 8 | | |
| 332 | OH | H | $CH_2NHOH$ | 8 | | |
| 333 | OH | H | $CH_2NHOCH_3$ | 8 | | |
| 334 | OH | H | $CH_2NHOCOCH_3$ | 8 | | |
| 335 | OH | H | $CH_2NHNH_2$ | 8 | | |
| 336 | OH | H | $CH_2NHNHCH_3$ | 8 | | |
| 337 | OH | H | $CH_2NHNHCOCH_3$ | 8 | | |
| 338 | OH | H | $CH_2NHNHCSCH_3$ | 8 | | |
| 339 | OH | H | $CH_2CN$ | 8 | | |
| 340 | OH | H | $CH_2CH=NOH$ | 8 | | |
| 341 | OH | H | $CH_2CH=NOCH_3$ | 8 | | |
| 342 | OH | H | $CH_2CH=NOCOCH_3$ | 8 | | |
| 343 | OH | H | $CH_2CH=NNH_2$ | 8 | | |
| 344 | OH | H | $CH_2CH=NNHCH_3$ | 8 | | |
| 345 | OH | H | $CH_2CH=NNHCOCH_3$ | 8 | | |
| 346 | OH | H | $CH_2CH=NNHCSCH_3$ | 8 | | |
| 347 | OH | H | $CH_2CH_2NHOH$ | 8 | | |
| 348 | OH | H | $CH_2CH_2NHOCH_3$ | 8 | | |
| 349 | OH | H | $CH_2CH_2NHOCOCH_3$ | 8 | | |
| 350 | OH | H | $CH_2CH_2NHNH_2$ | 8 | | |
| 351 | OH | H | $CH_2CH_2NHNHCH_3$ | 8 | | |
| 352 | OH | H | $CH_2CH_2NHNHCOCH_3$ | 8 | | |
| 353 | OH | H | $CH_2CH_2NHNHCSCH_3$ | 8 | | |
| 354 | OH | H | CONHOH | 8 | | |
| 355 | OH | H | $CONHOCH_3$ | 8 | | |
| 356 | OH | H | $CONHOCOCH_3$ | 8 | | |
| 357 | OH | H | CSNHOH | 8 | | |
| 358 | OH | H | $CSNHOCH_3$ | 8 | | |
| 359 | OH | H | $CSNHOCOCH_3$ | 8 | | |
| 360 | OH | H | $CH=CHCHO$ | 8 | | |
| 361 | OH | H | $CH=CHCOCH_3$ | 8 | | |

TABLE 1-continued

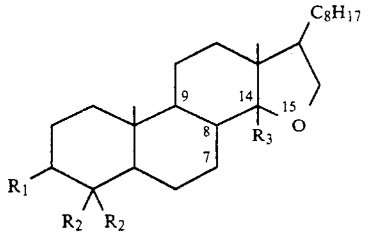

| Ex. No. | $R_1$ | $R_2$ | $R_3$ | D | No. | M.P. |
|---|---|---|---|---|---|---|
| 362 | OH | H | $CH{=}CHCSCH_3$ | 8 | | |
| 363 | OH | H | $CH{=}CHCH{=}NH$ | 8 | | |
| 364 | OH | H | $CH{=}CHC({=}NH)CH_3$ | 8 | | |
| 365 | OH | H | $CH{\equiv}CCHO$ | 8 | | |
| 366 | OH | H | $C{\equiv}CCOCH_3$ | 8 | | |
| 367 | OH | H | $C{\equiv}CCSCH_3$ | 8 | | |
| 368 | OH | H | $C{\equiv}CCH{=}NH$ | | | |
| 369 | OH | H | $C{\equiv}CC({=}NH)CH_3$ | 8 | | |
| 370 | OH | H | $CH{=}CHCH_2Cl$ | 8 | | |
| 371 | OH | H | $CH{=}CHCH_2Br$ | 8 | | |
| 372 | OH | H | $C{\equiv}CCH_2Cl$ | 8 | | |
| 373 | OH | H | $C{\equiv}CCH_2Br$ | 8 | | |
| 374 | OH | H | $CH{=}CHCH_2OCOCH_3$ | 8 | | |
| 375 | OH | H | $C{\equiv}CCH_2OCOCH_3$ | 8 | | |
| 376 | OH | H | $CH_2CHOHCH_2OH$ | 8 | | |
| 377 | OH | H | $CHOHCHOHCH_2OH$ | 8 | | |
| 378 | OH | H | 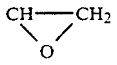 | 8 | | |
| 379 | OH | H | 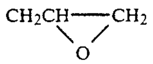 | 8 | | |
| 380 | OH | H | 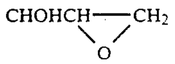 | 8 | | |
| 381 | =O | $CH_3$ | $CH_3$ | 8 | | |
| 382 | =O | $CH_3$ | H | 8 | | |
| 383 | =O | $CH_3$ | $CH{=}CH_2$ | 8 | | |
| 384 | =O | $CH_3$ | $CHOHCH_2OH$—(R) | 8 | | |
| 385 | =O | $CH_3$ | $CHOHCH_2OH$—O(S) | 8 | | |
| 386 | =O | $CH_3$ | CHO | 8 | | |
| 387 | =O | $CH_3$ | $CH_2OH$ | 8 | | |
| 388 | =O | $CH_3$ | $CO_2H$ | 8 | | |
| 389 | =O | $CH_3$ | $CO_2CH_3$ | 8 | | |
| 390 | =O | $CH_3$ | $CH{=}NOH$ | 8 | | |
| 391 | =O | $CH_3$ | $CHOHCH{=}CH_2$—(R) | 8 | | |
| 392 | =O | $CH_3$ | $CHOHCH{=}CH_2$—(S) | 8 | | |
| 393 | =O | $CH_3$ | $CH_2SH$ | 8 | | |
| 394 | =O | $CH_3$ | $CH_2NH_2$ | 8 | | |
| 395 | =O | $CH_3$ | $COCH_3$ | 8 | | |
| 396 | =O | $CH_3$ | $CONH_2$ | 8 | | |
| 397 | =O | $CH_3$ | $CSNH_2$ | 8 | | |
| 398 | =O | $CH_3$ | $CH_2CH_2OH$ | 8 | | |
| 399 | =O | $CH_3$ | $CH_2CHO$ | 8 | | |
| 400 | =O | $CH_3$ | $CH_2COCH_3$ | 8 | | |
| 401 | =O | $CH_3$ | $CH_2CO_2CH_3$ | 8 | | |
| 402 | =O | $CH_3$ | $CH_2CONH_2$ | 8 | | |
| 403 | =O | $CH_3$ | $CH_2Cl$ | 8 | | |
| 404 | =O | $CH_3$ | $CH_2CH_2Cl$ | 8 | | |
| 405 | =O | $CH_3$ | CN | 8 | | |
| 406 | =O | $CH_3$ | $CH{=}NNH_2$ | 8 | | |
| 407 | =O | $CH_3$ | $CH_2NHOH$ | 8 | | |
| 408 | =O | $CH_3$ | $CH_2NHNH_2$ | 8 | | |
| 409 | =O | $CH_3$ | $CH_2CN$ | 8 | | |
| 410 | =O | $CH_3$ | $CH_2CH{=}NOH$ | 8 | | |
| 411 | =O | $CH_3$ | $CH_2CH{=}NNH_2$ | 8 | | |
| 412 | =O | $CH_3$ | $CH_2CH_2NHOH$ | 8 | | |
| 413 | =O | $CH_3$ | $CH_2CH_2NHNH_2$ | 8 | | |
| 414 | =O | $CH_3$ | CONHOH | 8 | | |
| 415 | =O | $CH_3$ | $CH{=}CHCHO$ | 8 | | |
| 416 | =O | $CH_3$ | $CH{=}CHCOCH_3$ | 8 | | |
| 417 | =O | $CH_3$ | $CH{=}CHCH_2Cl$ | 8 | | |
| 418 | =O | $CH_3$ | $CH_2CHOHCH_2OH$ | 8 | | |

TABLE 1-continued

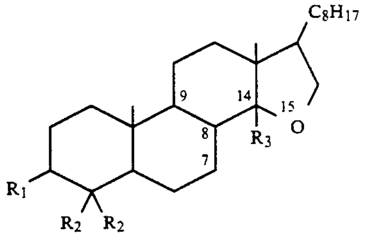

| Ex. No. | $R_1$ | $R_2$ | $R_3$ | D No. | M.P. |
|---|---|---|---|---|---|
| 419 | =O | $CH_3$ | 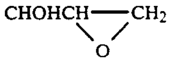 | 8 | |
| 420 | =O | H | $CH_3$ | 8 | |
| 421 | =O | H | H | 8 | |
| 422 | =O | H | $CH{=}CH_2$ | 8 | |
| 423 | =O | H | $CHOHCH_2OH$—(R) | 8 | |
| 424 | =O | H | $CHOHCH_2OH$—(S) | 8 | |
| 425 | =O | H | CHO | 8 | |
| 426 | =O | H | $CH_2OH$ | 8 | |
| 427 | =O | H | $CO_2H$ | 8 | |
| 428 | =O | H | $CO_2CH_3$ | 8 | |
| 429 | =O | H | CH=NOH | 8 | |
| 430 | =O | H | $CHOHCH{=}CH_2$—(R) | 8 | |
| 431 | =O | H | $CHOHCH{=}CH_2$—(S) | 8 | |
| 432 | $OCH_3$ | $CH_3$ | $CH_3$ | 8 | |
| 433 | $OCH_3$ | $CH_3$ | H | 8 | |
| 434 | $OCH_3$ | $CH_3$ | $CH{=}CH_2$ | 8 | |
| 435 | $OCH_3$ | $CH_3$ | $CHOHCH_2OH$—(R) | 8 | |
| 436 | $OCH_3$ | $CH_3$ | $CHOHCH_2OH$—(S) | 8 | |
| 437 | $OCH_3$ | $CH_3$ | CHO | 8 | |
| 438 | $OCH_3$ | $CH_3$ | $CH_2OH$ | 8 | |
| 439 | $OCH_3$ | $CH_3$ | $CO_3H$ | 8 | |
| 440 | $OCH_3$ | $CH_3$ | $CO_2CH_3$ | 8 | |
| 441 | $OCH_3$ | $CH_3$ | CH=NOH | 8 | |
| 442 | $OCH_3$ | $CH_3$ | $CHOHCH{=}CH_2$—(R) | 8 | |
| 443 | $OCH_3$ | $CH_3$ | $CHOHCH{=}CH_2$—(S) | 8 | |
| 444 | $OCH_3$ | $CH_3$ | $CH_2SH$ | 8 | |
| 445 | $OCH_3$ | $CH_3$ | $CH_2NH_2$ | 8 | |
| 446 | $OCH_3$ | $CH_3$ | $COCH_3$ | 8 | |
| 447 | $OCH_3$ | $CH_3$ | $CONH_2$ | 8 | |
| 448 | $OCH_3$ | $CH_3$ | $CSNH_2$ | 8 | |
| 449 | $OCH_3$ | $CH_3$ | $CH_2CH_2OH$ | 8 | |
| 450 | $OCH_3$ | $CH_3$ | $CH_2CHO$ | 8 | |
| 451 | $OCH_3$ | $CH_3$ | $CH_2COCH_3$ | 8 | |
| 452 | $OCH_3$ | $CH_3$ | $CH_2CO_2CH_3$ | 8 | |
| 453 | $OCH_3$ | $CH_3$ | $CH_2CONH_2$ | 8 | |
| 454 | $OCH_3$ | $CH_3$ | $CH_2Cl$ | 8 | |
| 455 | $OCH_3$ | $CH_3$ | $CH_2CH_2Cl$ | 8 | |
| 456 | $OCH_2$ | $CH_3$ | CN | 8 | |
| 457 | $OCH_3$ | $CH_3$ | $CH{=}NNH_2$ | 8 | |
| 458 | $OCH_3$ | $CH_3$ | $CH_2NHOH$ | 8 | |
| 459 | $OCH_3$ | $CH_3$ | $CH_2NHNH_2$ | 8 | |
| 460 | $OCH_3$ | $CH_3$ | $CH_2CN$ | 8 | |
| 461 | $OCH_3$ | $CH_3$ | $CH_2CH{=}NOH$ | 8 | |
| 462 | $OCH_3$ | $CH_3$ | $CH_2CH{=}NNH_2$ | 8 | |
| 463 | $OCH_3$ | $CH_3$ | $CH_2CH_2NHOH$ | 8 | |
| 464 | $OCH_3$ | $CH_3$ | $CH_2CH_2NHNH_2$ | 8 | |
| 465 | $OCH_3$ | $CH_3$ | CONHOH | 8 | |
| 466 | $OCH_3$ | $CH_3$ | CH=CHCHO | 8 | |
| 467 | $OCH_2$ | $CH_3$ | $CH{=}COCH_3$ | 8 | |
| 468 | $OCH_3$ | $CH_3$ | $CH{=}CHCH_2Cl$ | 8 | |
| 469 | $OCH_3$ | $CH_3$ | $CH_2CHOHCH_2OH$ | 8 | |
| 470 | $OCH_3$ | $CH_3$ | 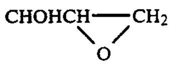 | 8 | |
| 471 | $OCH_3$ | H | $CH_3$ | 8 | |
| 472 | $OCH_3$ | H | H | 8 | |
| 473 | $OCH_3$ | H | $CH{=}CH_2$ | 8 | |
| 474 | $OCH_3$ | H | $CHOHCH_2OH$—(R) | 8 | |
| 475 | $OCH_3$ | H | $CHOHCH_2OH$—(S) | 8 | |
| 476 | $OCH_3$ | H | CHO | 8 | |
| 477 | $OCH_3$ | H | $CH_2OH$ | 8 | |
| 478 | $OCH_3$ | H | $CO_2H$ | 8 | |
| 479 | $OCH_3$ | H | $CO_2CH_3$ | 8 | |
| 480 | $OCH_3$ | H | CH=NOH | 8 | |

TABLE 1-continued

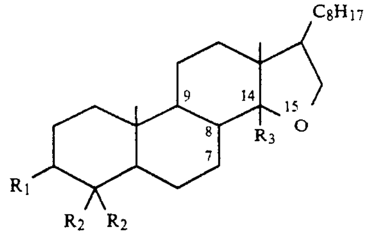

| Ex. No. | $R_1$ | $R_2$ | $R_3$ | D | No. | M.P. |
|---|---|---|---|---|---|---|
| 481 | $OCH_3$ | H | $CHOHCH{=}CH_2$—(R) | 8 | | |
| 482 | $OCH_3$ | H | $CHOHCH{=}CH_2$—(S) | 8 | | |
| 483 | $OC_2H_5$ | $CH_3$ | $CH_3$ | 8 | | |
| 484 | $OC_2H_5$ | $CH_3$ | CHO | 8 | | |
| 485 | $OC_2H_5$ | $CH_3$ | $CH_2OH$ | 8 | | |
| 486 | $OC_3H_7$ | $CH_3$ | $CH_3$ | 8 | | |
| 487 | $OC_3H_7$ | $CH_3$ | CHO | 8 | | |
| 488 | $OC_3H_7$ | $CH_3$ | $CH_2OH$ | 8 | | |
| 489 | Oi-$C_3H_7$ | $CH_3$ | $CH_3$ | 8 | | |
| 490 | $OC_4H_9$ | $CH_3$ | $CH_3$ | 8 | | |
| 491 | $OC_4H_9$ | $CH_3$ | CHO | 8 | | |
| 492 | $OC_4H_9$ | $CH_3$ | $CH_2OH$ | 8 | | |
| 493 | Oi-$C_4H_9$ | $CH_3$ | $CH_3$ | 8 | | |
| 494 | Ot-$C_4H_9$ | $CH_3$ | $CH_3$ | 8 | | |
| 495 | OPh | $CH_3$ | $CH_3$ | 8 | | |
| 496 | OPh | $CH_3$ | CHO | 8 | | |
| 497 | OPh | $CH_3$ | $CH_2OH$ | 8 | | |
| 498 | $OCH_2Ph$ | $CH_3$ | $CH_3$ | 8 | | |
| 499 | $OCH_2Ph$ | $CH_3$ | CHO | 8 | | |
| 500 | $OCH_2Ph$ | $CH_3$ | $CH_2OH$ | 8 | | |
| 501 | $OCOCH_3$ | $CH_3$ | $CH_3$ | 8 | | |
| 502 | $OCOCH_3$ | $CH_3$ | H | 8 | | |
| 503 | $OCOCH_3$ | $CH_3$ | $CH{=}CH_2$ | 8 | 23c | amorphous* |
| 504 | $OCOCH_3$ | $CH_3$ | $CHOHCH_2OH$—(R) | 8 | 24c | amorphous* |
| 505 | $OCOCH_3$ | $CH_3$ | $CHOHCH_2OH$—(S) | 8 | 25c | amorphous* |
| 506 | $OCOCH_3$ | $CH_3$ | CHO | 8 | 26c | amorphous* |
| 507 | $OCOCH_3$ | $CH_3$ | $CH_2OH$ | 8 | | |
| 508 | $OCOCH_3$ | $CH_3$ | $CO_2H$ | 8 | | |
| 509 | $OCOCH_3$ | $CH_3$ | $CO_2CH_3$ | 8 | | |
| 510 | $OCOCH_3$ | $CH_3$ | $CH{=}NOH$ | 8 | | |
| 511 | $OCOCH_3$ | $CH_3$ | $CHOHCH{=}CH_2$—(R) | 8 | | |
| 512 | $OCOCH_3$ | $CH_3$ | $CHOHCH{=}CH_2$—(S) | 8 | | |
| 513 | $OCOCH_3$ | $CH_3$ | $CH_2SH$ | 8 | | |
| 514 | $OCOCH_3$ | $CH_3$ | $CH_2NH_2$ | 8 | | |
| 515 | $OCOCH_3$ | $CH_3$ | $COCH_3$ | 8 | | |
| 516 | $OCOCH_3$ | $CH_3$ | $CONH_2$ | 8 | | |
| 517 | $OCOCH_3$ | $CH_3$ | $CSNH_2$ | 8 | | |
| 518 | $OCOCH_3$ | $CH_3$ | $CH_2CH_2OH$ | 8 | | |
| 519 | $OCOCH_3$ | $CH_3$ | $CH_2CHO$ | 8 | | |
| 520 | $OCOCH_3$ | $CH_3$ | $CH_2COCH_3$ | 8 | | |
| 521 | $OCOCH_3$ | $CH_3$ | $CH_2CO_2CH_3$ | 8 | | |
| 522 | $OCOCH_3$ | $CH_3$ | $CH_2CONH_2$ | 8 | | |
| 523 | $OCOCH_3$ | $CH_3$ | $CH_2Cl$ | 8 | | |
| 524 | $OCOCH_3$ | $CH_3$ | $CH_2CH_2Cl$ | 8 | | |
| 525 | $OCOCH_3$ | $CH_3$ | CN | 8 | | |
| 526 | $OCOCH_3$ | $CH_3$ | $CH{=}NNH_2$ | 8 | | |
| 527 | $OCOCH_3$ | $CH_3$ | $CH_2NHOH$ | 8 | | |
| 528 | $OCOCH_3$ | $CH_3$ | $CH_2NHNH_2$ | 8 | | |
| 529 | $OCOCH_3$ | $CH_3$ | $CH_2CN$ | 8 | | |
| 530 | $OCOCH_3$ | $CH_3$ | $CH_2CH{=}NOH$ | 8 | | |
| 531 | $OCOCH_3$ | $CH_3$ | $CH_2CH{=}NNH_2$ | 8 | | |
| 532 | $OCOCH_3$ | $CH_3$ | $CH_2CH_2NHOH$ | 8 | | |
| 533 | $OCOCH_3$ | $CH_3$ | $CH_2CH_2NHNH_2$ | 8 | | |
| 534 | $OCOCH_3$ | $CH_3$ | CONHOH | 8 | | |
| 535 | $OCOCH_3$ | $CH_3$ | $CH{=}CHCHO$ | 8 | | |
| 536 | $OCOCH_3$ | $CH_3$ | $CH{=}CHCOCH_3$ | 8 | | |
| 537 | $OCOCH_3$ | $CH_3$ | $CH{=}CHCH_2Cl$ | 8 | | |
| 538 | $OCOCH_3$ | $CH_3$ | $CH_2CHOHCH_2OH$ | 8 | | |
| 539 | $OCOCH_3$ | $CH_3$ | 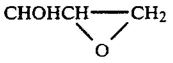 | 8 | | |
| 540 | $OCOCH_3$ | H | $CH_3$ | 8 | | |
| 541 | $OCOCH_3$ | H | H | 8 | | |
| 542 | $OCOCH_3$ | H | $CH{=}CH_2$ | 8 | | |
| 543 | $OCOCH_3$ | H | $CHOHCH_2OH$—(R) | 8 | | |
| 544 | $OCOCH_3$ | H | $CHOHCH_2OH$—(S) | 8 | | |
| 545 | $OCOCH_3$ | H | CHO | 8 | | |

TABLE 1-continued

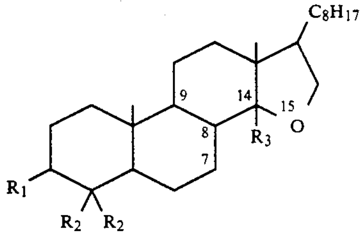

| Ex. No. | $R_1$ | $R_2$ | $R_3$ | D · No. | M.P. |
|---|---|---|---|---|---|
| 546 | $OCOCH_3$ | H | $CH_2OH$ | 8 | |
| 547 | $OCOCH_3$ | H | $CO_2H$ | 8 | |
| 548 | $OCOCH_3$ | H | $CO_2CH_3$ | 8 | |
| 549 | $OCOCH_3$ | H | CH=NOH | 8 | |
| 550 | $OCOCH_3$ | H | $CHOHCH{=}CH_2$—(R) | 8 | |
| 551 | $OCOCH_3$ | H | $CHOHCH{=}CH_2$—(S) | 8 | |
| 552 | $OCOCH_2H_5$ | $CH_3$ | $CH_3$ | 8 | |
| 553 | $OCOC_2H_5$ | $CH_3$ | CHO | 8 | |
| 554 | $OCOC_2H_5$ | $CH_3$ | $CH_2OH$ | 8 | |
| 555 | $OCOC_3H_7$ | $CH_3$ | $CH_3$ | 8 | |
| 556 | $OCOC_3H_7$ | $CH_3$ | CHO | 8 | |
| 557 | $OCOC_3H_7$ | $CH_3$ | $CH_2OH$ | 8 | |
| 558 | OCOi-$C_3H_7$ | $CH_3$ | $CH_3$ | 8 | |
| 559 | $OCOC_4H_9$ | $CH_3$ | $CH_3$ | 8 | |
| 560 | $OCOC_4H_9$ | $CH_3$ | CHO | 8 | |
| 561 | $OCOC_4H_9$ | $CH_3$ | $CH_2OH$ | 8 | |
| 562 | OCOi-$C_4H_9$ | $CH_3$ | $CH_3$ | 8 | |
| 563 | OCOt-$C_4H_9$ | $CH_3$ | $CH_3$ | 8 | |
| 564 | $OCOC15H_{31}$ | $CH_3$ | $CH_3$ | 8 | |
| 565 | $OCOC15H_{31}$ | $CH_3$ | CHO | 8 | |
| 566 | $OCOC15H_{31}$ | $CH_3$ | $CH_2OH$ | 8 | |
| 567 | $OCOC15H_{29}$ | $CH_3$ | $CH_3$ | 8 | |
| 568 | $OCOC17H_{35}$ | $CH_3$ | $CH_3$ | 8 | |
| 569 | $OCOC17H_{33}$ | $CH_3$ | $CH_3$ | 8 | |
| 570 | $OCOC17H_{31}$ | $CH_3$ | $CH_3$ | 8 | |
| 571 | $OCOC17H_{29}$ | $CH_3$ | $CH_3$ | 8 | |
| 572 | $OCOC19H_{31}$ | $CH_3$ | $CH_3$ | 8 | |
| 573 | OCOPh | $CH_3$ | $CH_3$ | 8 | |
| 574 | OCOPh | $CH_3$ | CHO | 8 | |
| 575 | OCOPh | $CH_3$ | $CH_2OH$ | 8 | |
| 576 | OH | $CH_3$ | $CH_3$ | 7 | |
| 577 | OH | $CH_3$ | H | 7 | |
| 578 | OH | $CH_3$ | $CH{=}CH_2$ | 7 | |
| 579 | OH | $CH_3$ | $CHOHCH_2OH$—(R) | 7 | |
| 580 | OH | $CH_3$ | $CHOHCH_2OH$—(S) | 7 | |
| 581 | OH | $CH_3$ | CHO | 7 | |
| 582 | OH | $CH_3$ | $CH_2OH$ | 7 | |
| 583 | OH | $CH_3$ | $CO_2H$ | 7 | |
| 584 | OH | $CH_3$ | $CO_2CH_3$ | 7 | |
| 585 | OH | $CH_3$ | CH=NOH | 7 | |
| 586 | OH | $CH_3$ | $CHOHCH{=}CH_2$—(R) | 7 | |
| 587 | OH | $CH_3$ | $CHOHCH{=}CH_2$—(S) | 7 | |
| 588 | OH | H | $CH_3$ | 7 | |
| 589 | OH | H | H | 7 | |
| 590 | OH | H | $CH{=}CH_2$ | 7 | |
| 591 | OH | H | $CHOHCH_2OH$—(R) | 7 | |
| 592 | OH | H | $CHOHCH_2OH$—(S) | 7 | |
| 593 | OH | H | CHO | 7 | |
| 594 | OH | H | $CH_2OH$ | 7 | |
| 595 | OH | H | $CO_2H$ | 7 | |
| 596 | OH | H | $CO_2CH_3$ | 7 | |
| 597 | OH | H | CH=NOH | 7 | |
| 598 | OH | H | $CHOHCH{=}CH_2$—(R) | 7 | |
| 599 | OH | H | $CHOHCH{=}CH_2$—(S) | 7 | |
| 600 | =O | $CH_3$ | $CH_3$ | 7 | |
| 601 | =O | $CH_3$ | H | 7 | |
| 602 | =O | $CH_3$ | $CH{=}CH_2$ | 7 | |
| 603 | =O | $CH_3$ | $CHOHCH_2OH$—(R) | 7 | |
| 604 | =O | $CH_3$ | $CHOHCH_2OH$—(S) | 7 | |
| 605 | =O | $CH_3$ | CHO | 7 | |
| 606 | =O | $CH_3$ | $CH_2OH$ | 7 | |
| 607 | =O | $CH_3$ | $CO_2H$ | 7 | |
| 608 | =O | $CH_3$ | $CO_2CH_3$ | 7 | |
| 609 | =O | $CH_3$ | CH=NOH | 7 | |
| 610 | =O | $CH_3$ | $CHOHCH{=}CH_2$—(R) | 7 | |
| 611 | =O | $CH_3$ | $CHOHCH{=}CH_2$—(S) | 7 | |
| 612 | =O | H | $CH_3$ | 7 | |
| 613 | =O | H | H | 7 | |
| 614 | =O | H | $CH{=}CH_2$ | 7 | |

TABLE 1-continued

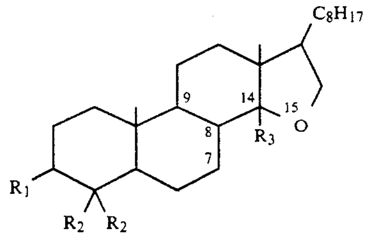

| Ex. No. | $R_1$ | $R_2$ | $R_3$ | D | No. | M.P. |
|---|---|---|---|---|---|---|
| 615 | =O | H | $CHOHCH_2OH$—(R) | 7 | | |
| 616 | =O | H | $CHOHCH_2OH$—(S) | 7 | | |
| 617 | =O | H | CHO | 7 | | |
| 618 | =O | H | $CH_2OH$ | 7 | | |
| 619 | =O | H | $CO_2H$ | 7 | | |
| 620 | =O | H | $CO_2CH_3$ | 7 | | |
| 621 | =O | H | CH=NOH | 7 | | |
| 622 | =O | H | $CHOHCH=CH_2$—(R) | 7 | | |
| 623 | =O | H | $CHOHCH=CH_2$—(S) | 7 | | |
| 624 | $OCH_3$ | $CH_3$ | $CH_3$ | 7 | | |
| 625 | $OCH_3$ | $CH_3$ | H | 7 | | |
| 626 | $OCH_3$ | $CH_3$ | $CH=CH_2$ | 7 | | |
| 627 | $OCH_3$ | $CH_3$ | $CHOHCH_2OH$—(R) | 7 | | |
| 628 | $OCH_3$ | $CH_3$ | $CHOHCH_2OH$—(S) | 7 | | |
| 629 | $OCH_3$ | $CH_3$ | CHO | 7 | | |
| 630 | $OCH_3$ | $CH_3$ | $CH_2OH$ | 7 | | |
| 631 | $OCH_3$ | $CH_3$ | $CO_2H$ | 7 | | |
| 632 | $OCH_3$ | $CH_3$ | $CO_2CH_3$ | 7 | | |
| 633 | $OCH_3$ | $CH_3$ | CH=NOH | 7 | | |
| 634 | $OCH_3$ | $CH_3$ | $CHOHCH=CH_2$—(R) | 7 | | |
| 635 | $OCH_3$ | $CH_3$ | $CHOHCH=CH_2$—(S) | 7 | | |
| 636 | $OCH_3$ | H | $CH_3$ | 7 | | |
| 637 | $OCH_3$ | H | H | 7 | | |
| 638 | $OCH_3$ | H | $CH=CH_2$ | 7 | | |
| 639 | $OCH_3$ | H | $CHOHCH_2OH$—(R) | 7 | | |
| 640 | $OCH_3$ | H | $CHOHCH_2OH$—(S) | 7 | | |
| 641 | $OCH_3$ | H | CHO | 7 | | |
| 642 | $OCH_3$ | H | $CH_2OH$ | 7 | | |
| 643 | $OCH_3$ | H | $CO_2H$ | 7 | | |
| 644 | $OCH_3$ | H | $CO_2CH_3$ | 7 | | |
| 645 | $OCH_3$ | H | CH=NOH | 7 | | |
| 646 | $OCH_3$ | H | $CHOHCH=CH_2$—(R) | 7 | | |
| 647 | $OCH_3$ | H | $CHOHCH=CH_2$—(S) | 7 | | |
| 648 | $OCOCH_3$ | $CH_3$ | $CH_3$ | 7 | | |
| 649 | $OCOCH_3$ | $CH_3$ | H | 7 | | |
| 650 | $OCOCH_3$ | $CH_3$ | $CH=CH_2$ | 7 | | |
| 651 | $OCOCH_3$ | $CH_3$ | $CHOHCH_2OH$—(R) | 7 | | |
| 652 | $OCOCH_3$ | $CH_3$ | $CHOHCH_2OH$—(S) | 7 | | |
| 653 | $OCOCH_3$ | $CH_3$ | CHO | 7 | | |
| 654 | $OCOCH_3$ | $CH_3$ | $CH_2OH$ | 7 | | |
| 655 | $OCOCH_3$ | $CH_3$ | $CO_2H$ | 7 | | |
| 656 | $OCOCH_3$ | $CH_3$ | $CO_2CH_3$ | 7 | | |
| 657 | $OCOCH_3$ | $CH_3$ | CH=NOH | 7 | | |
| 658 | $OCOCH_3$ | $CH_3$ | $CHOHCH=CH_2$—(R) | 7 | | |
| 659 | $OCOCH_3$ | $CH_3$ | $CHOHCH=CH_2$—(S) | 7 | | |
| 660 | $OCOCH_3$ | H | $CH_3$ | 7 | | |
| 661 | $OCOCH_3$ | H | H | 7 | | |
| 662 | $OCOCH_3$ | H | $CH=CH_2$ | 7 | | |
| 663 | $OCOCH_3$ | H | $CHOHCH_2OH$—(R) | 7 | | |
| 664 | $OCOCH_3$ | H | $CHOHCH_2OH$—(S) | 7 | | |
| 665 | $OCOCH_3$ | H | CHO | 7 | | |
| 666 | $OCOCH_3$ | H | $CH_2OH$ | 7 | | |
| 667 | $OCOCH_3$ | H | $CO_2H$ | 7 | | |
| 668 | $OCOCH_3$ | H | $CO_2CH_3$ | 7 | | |
| 669 | $OCOCH_3$ | H | CH=NOH | 7 | | |
| 670 | $OCOCH_3$ | H | $CHOHCH=CH_2$—(R) | 7 | | |
| 671 | $OCOCH_3$ | H | $CHOHCH=CH_2$—(S) | 7 | | |

*Further analytical data are available in the examples section

The six-membered 15-oxa-D-homo-lanosterol derivatives are synthesized by reducing the six-membered cyclic acetals and hemiacetals under conditions similar as those used for the five-membered 15-oxalanosterols. However, the entire sequence was carried out more conveniently in higher overall yield without the protecting group at the 3-position. Thus the unprotected 8,14-diene 2a was converted to a mixture of six-membered cyclic acetal 7a in the same manner as described earlier for p-methoxybenzyl protected intermediates (Scheme I). The cyclic hemiacetal 7a was treated with triethylsilane and redistilled boron trifluoride etherate in methylene chloride to afford 15-oxa-D-homo-dihydrolanosterol (31) in 92% yield (See, Scheme IV). The corresponding cyclic acetal 7d is also converted to the compound 31 in slightly lower yield than the acetal 7a.

4,4-Dimethyl-15-oxa-D-homo-5a-cholest-8-en-3b-ol (32) and 4,4-dimethyl-15-oxa- 14a-vinyl-5a-cholest-8-en-3b-ol (33) have also been prepared in the same manner through the secondary alcohol 6a and the doubly allylic alcohol 8a respectively in comparable yields. Compounds 31, 32, and 33 are all within the scope of the present invention.

SCHEME IV

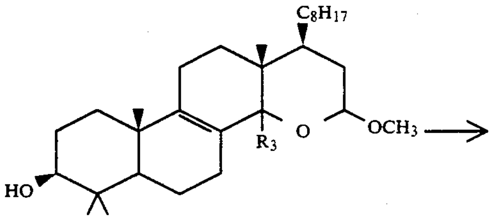

7a $R_3$ = $CH_3$
13a $R_3$ = H
19a $R_3$ = $CH{=}CH_2$

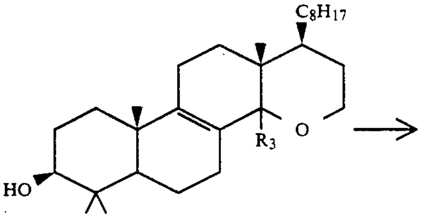

31 $R_3$ = $CH_3$
32 $R_3$ = H
33 $R_3$ = $CH{=}CH_2$

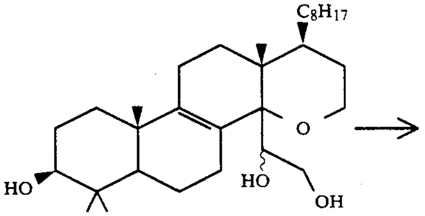

34, 35

-continued
SCHEME IV

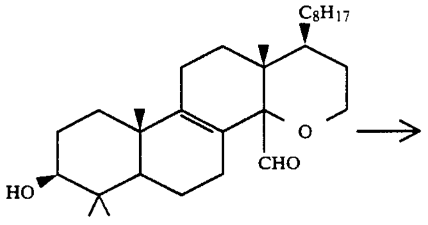

36

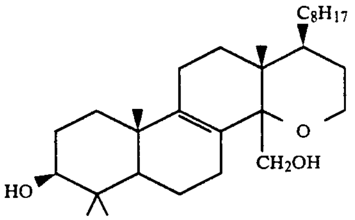

37

For further functionalization at the 14-position, the vinyl compound 33 was converted to a 1:1 mixture of diasteromeric diols 34 and 35 in 84% combined yield by reacting with osmium tetroxide as described earlier for five-membered 15-oxa-lanosterols. The mixture of diols 34 and 35 was treated with sodium metaperiodate in 4 parts of ethanol and 1 part of water to give 15-oxa-32-oxo-D-homo-dihydrolanosterol (36) in near quantitative yield. Reduction of the aldehyde 36 with sodium borohydride in ethanol provided 15-oxa-D-homo-lanost-8-ene-3b-32-diol (37) in near quantitative yield. Compounds 34, 35, 36 and 37 also constitute four additional examples of 15-oxa-lanosterols within the scope of the present invention.

Elaborations of the aldehyde 36 may yield the corresponding oxime, allylic alcohol, etc., which are within the scope of the present invention, as described in the synthesis of five-membered 15-oxa-lanosterols.

Table 2 sets forth additional oxasterols of the present invention.

TABLE 2

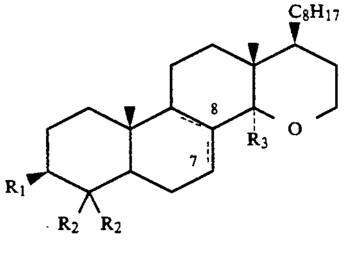

| Ex. No. | $R_1$ | $R_2$ | $R_3$ | D | No. | M.P. |
|---|---|---|---|---|---|---|
| 672 | OH | $CH_3$ | $CH_3$ | 8 | 31 | amorphous* |
| 673 | OH | $CH_3$ | H | 8 | 32 | amorphous* |
| 674 | OH | $CH_3$ | $CH{=}CH_2$ | 8 | 32 | amorphous* |
| 675 | OH | $CH_3$ | $CHOHCH_2OH$—(R) | 8 | 34 | amorphous* |
| 676 | OH | $CH_3$ | $CHOHCH_2OH$—(S) | 8 | 35 | amorphous* |
| 677 | OH | $CH_3$ | CHO | 8 | 36 | amorphous* |
| 678 | OH | $CH_3$ | $CH_2OH$ | 8 | 37 | amorphous* |
| 679 | OH | $CH_3$ | $CO_2H$ | 8 | | |
| 680 | OH | $CH_3$ | $CO_2CH_3$ | 8 | | |
| 681 | OH | $CH_3$ | $CH{=}NOH$ | 8 | | |
| 682 | OH | $CH_3$ | $CHOHCH{=}CH_2$—(R) | 8 | | |
| 683 | OH | $CH_3$ | $CHOHCH{=}CH_2$—(S) | 8 | | |

TABLE 2-continued

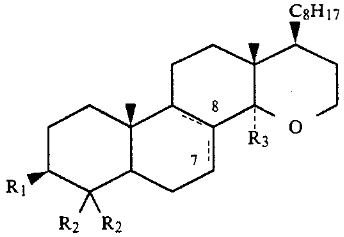

| Ex. No. | $R_1$ | $R_2$ | $R_3$ | D | No. | M.P. |
|---|---|---|---|---|---|---|
| 684 | OH | H | $CH_3$ | 8 | | |
| 685 | OH | H | H | 8 | | |
| 686 | OH | H | $CH{=}CH_2$ | 8 | | |
| 687 | OH | H | $CHOHCH_2OH$—(R) | 8 | | |
| 689 | OH | H | $CHOHCH_2OH$—(S) | 8 | | |
| 690 | OH | H | CHO | 8 | | |
| 691 | OH | H | $CH_2OH$ | 8 | | |
| 692 | OH | H | $CO_2H$ | 8 | | |
| 693 | OH | H | $CO_2CH_3$ | 8 | | |
| 694 | OH | H | CH=NOH | 8 | | |
| 695 | OH | H | $CHOHCH{=}CH_2$—(R) | 8 | | |
| 696 | OH | H | $CHOHCH{=}CH_2$—(S) | 8 | | |
| 697 | OH | $CH_3$ | $CH_2SH$ | 8 | | |
| 698 | OH | $CH_3$ | $CH_2NH_2$ | 8 | | |
| 699 | OH | $CH_3$ | $COCH_3$ | 8 | | |
| 700 | OH | $CH_3$ | $CONH_2$ | 8 | | |
| 701 | OH | $CH_3$ | $CSNH_2$ | 8 | | |
| 702 | OH | $CH_3$ | $CH_2CH_2OH$ | 8 | | |
| 703 | OH | $CH_3$ | $CH_2CHO$ | 8 | | |
| 704 | OH | $CH_3$ | $CH_2COCH_3$ | 8 | | |
| 705 | OH | $CH_3$ | $CH_2CO_2CH_3$ | 8 | | |
| 706 | OH | $CH_3$ | $CH_2CONH_2$ | 8 | | |
| 707 | OH | $CH_3$ | $CH_2Cl$ | 8 | | |
| 708 | OH | $CH_3$ | $CH_2CH_2Cl$ | 8 | | |
| 709 | OH | $CH_3$ | CN | 8 | | |
| 710 | OH | $CH_3$ | $CH{=}NNH_2$ | 8 | | |
| 711 | OH | $CH_3$ | $CH_2NHOH$ | 8 | | |
| 712 | OH | $CH_3$ | $CH_2NHNH_2$ | 8 | | |
| 713 | OH | $CH_3$ | $CH_2CN$ | 8 | | |
| 714 | OH | $CH_3$ | $CH_2CH{=}NOH$ | 8 | | |
| 715 | OH | $CH_3$ | $CH_2CH$—$NNH_2$ | 8 | | |
| 716 | OH | $CH_3$ | $CH_2CH_2NHOH$ | 8 | | |
| 717 | OH | $CH_3$ | $CH_2CH_2NHNH_2$ | 8 | | |
| 718 | OH | $CH_3$ | CONHOH | 8 | | |
| 719 | OH | $CH_3$ | CH=CHCHO | 8 | | |
| 720 | OH | $CH_3$ | $CH{=}CHCOCH_3$ | 8 | | |
| 721 | OH | $CH_3$ | $CH{=}CHCH_2Cl$ | 8 | | |
| 722 | OH | $CH_3$ | $CH_2CHOHCH_2OH$ | 8 | | |
| 723 | OH | $CH_3$ | 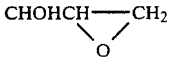 | 8 | | |
| 724 | =O | $CH_3$ | $CH_3$ | 8 | | |
| 725 | =O | $CH_3$ | H | 8 | | |
| 726 | =O | $CH_3$ | $CH{=}CH_2$ | 8 | | |
| 727 | =O | $CH_3$ | $CHOHCH_2OH$—(R) | 8 | | |
| 728 | =O | $CH_3$ | $CHOHCH_2OH$—(S) | 8 | | |
| 729 | =O | $CH_3$ | CHO | 8 | | |
| 730 | =O | $CH_3$ | $CH_2OH$ | 8 | | |
| 731 | =O | $CH_3$ | $CO_2H$ | 8 | | |
| 732 | =O | $CH_3$ | $CO_2CH_3$ | 8 | | |
| 733 | =O | $CH_3$ | CH=NOH | 8 | | |
| 734 | =O | $CH_3$ | $CHOHCH{=}CH_2O(R)$ | 8 | | |
| 735 | =O | $CH_3$ | $CHOHCH{=}CH_2$—(S) | 8 | | |
| 736 | =O | H | $CH_3$ | 8 | | |
| 737 | =O | H | H | 8 | | |
| 738 | =O | H | $CH{=}CH_2$ | 8 | | |
| 739 | =O | H | $CHOHCH_2OH$—(R) | 8 | | |
| 740 | =O | H | $CHOHCH_2OH$—(S) | 8 | | |
| 741 | =O | H | CHO | 8 | | |
| 742 | =O | H | $CH_2OH$ | 8 | | |
| 743 | =O | H | $CO_2H$ | 8 | | |
| 744 | =O | H | $CO_2CH_3$ | 8 | | |
| 745 | =O | H | CH=NOH | 8 | | |
| 746 | =O | H | $CHOHCH{=}CH_2$—(R) | 8 | | |
| 747 | =O | H | $CHOHCH{=}CH_2$—(S) | 8 | | |
| 748 | $OCH_3$ | $CH_3$ | $CH_3$ | 8 | | |

TABLE 2-continued

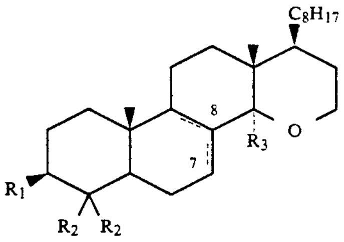

| Ex. No. | $R_1$ | $R_2$ | $R_3$ | D | No. | M.P. |
|---|---|---|---|---|---|---|
| 749 | $OCH_3$ | $CH_3$ | H | 8 | | |
| 750 | $OCH_3$ | $CH_3$ | $CH=CH_2$ | 8 | | |
| 751 | $OCH_3$ | $CH_3$ | $CHOHCH_2OH$—(R) | 8 | | |
| 752 | $OCH_3$ | $CH_3$ | $CHOHCH_2OH$—(S) | 8 | | |
| 753 | $OCH_3$ | $CH_3$ | CHO | 8 | | |
| 754 | $OCH_3$ | $CH_3$ | $CH_2OH$ | 8 | | |
| 755 | $OCH_3$ | $CH_3$ | $CO_2H$ | 8 | | |
| 756 | $OCH_3$ | $CH_3$ | $CO_2CH_3$ | 8 | | |
| 757 | $OCH_3$ | $CH_3$ | CH=NOH | 8 | | |
| 758 | $OCH_3$ | $CH_3$ | $CHOHCH=CH_2$=(R) | 8 | | |
| 759 | $OCH_3$ | $CH_3$ | $CHOHCH=CH_2$—(S) | 8 | | |
| 760 | $OCH_3$ | H | $CH_3$ | 8 | | |
| 761 | $OCH_3$ | H | H | 8 | | |
| 762 | $OCH_3$ | H | $CH=CH_2$ | 8 | | |
| 763 | $OCH_3$ | H | $CHOHCH_2OH$—(R) | 8 | | |
| 764 | $OCH_3$ | H | $CHOHCH_2OH$—(S) | 8 | | |
| 765 | $OCH_3$ | H | CHO | 8 | | |
| 766 | $OCH_3$ | H | $CH_2OH$ | 8 | | |
| 767 | $OCH_3$ | H | $CO_2H$ | 8 | | |
| 768 | $OCH_3$ | H | $CO_2CH_3$ | 8 | | |
| 769 | $OCH_3$ | H | CH=NOH | 8 | | |
| 770 | $OCH_3$ | H | $CHOHCH=CH_2$—(R) | 8 | | |
| 771 | $OCH_3$ | H | $CHOHCH=CH_2$—(S) | 8 | | |
| 772 | $OC_2H_5$ | $CH_3$ | $CH_3$ | 8 | | |
| 773 | $OC_2H_5$ | $CH_3$ | CHO | 8 | | |
| 774 | $OC_2H_5$ | $CH_3$ | $CH_2OH$ | 8 | | |
| 775 | $OC_3H_7$ | $CH_3$ | $CH_3$ | 8 | | |
| 776 | $OC_3H_7$ | $CH_3$ | CHO | 8 | | |
| 777 | $OC_3H_7$ | $CH_3$ | $CH_2OH$ | 8 | | |
| 778 | $OC_4H_9$ | $CH_3$ | $CH_3$ | 8 | | |
| 779 | $OC_4H_9$ | $CH_3$ | CHO | 8 | | |
| 780 | $OC_4H_9$ | $CH_3$ | $CH_2OH$ | 8 | | |
| 781 | OPh | $CH_3$ | $CH_3$ | 8 | | |
| 782 | OPh | $CH_3$ | CHO | 8 | | |
| 783 | OPh | $CH_3$ | $CH_3OH$ | 8 | | |
| 784 | $OCH_2Ph$ | $CH_3$ | $CH_3$ | 8 | | |
| 785 | $OCH_2Ph$ | $CH_3$ | CHO | 8 | | |
| 786 | $OCH_2Ph$ | $CH_3$ | $CH_2OH$ | 8 | | |
| 787 | $OCOCH_3$ | $CH_3$ | $CH_3$ | 8 | | |
| 788 | $OCOCH_3$ | $CH_3$ | H | 8 | | |
| 789 | $OCOCH_3$ | $CH_3$ | $CH=CH_2$ | 8 | | |
| 790 | $OCOCH_3$ | $CH_3$ | $CHOHCH_2OH$—(R) | 8 | | |
| 791 | $OCOCH_3$ | $CH_3$ | $CHOHCH_2OH$—(S) | 8 | | |
| 792 | $OCOCH_3$ | $CH_3$ | CHO | 8 | | |
| 793 | $OCOCH_3$ | $CH_3$ | $CH_2OH$ | 8 | | |
| 794 | $OCOCH_3$ | $CH_3$ | $CO_2H$ | 8 | | |
| 795 | $OCOCH_3$ | $CH_3$ | $CO_2CH_3$ | 8 | | |
| 796 | $OCOCH_3$ | $CH_3$ | CH=NOH | 8 | | |
| 797 | $OCOCH_3$ | $CH_3$ | $CHOHCH=CH_2$—(R) | 8 | | |
| 798 | $OCOCH_3$ | $CH_3$ | $CHOHCH=CH_2$—(S) | 8 | | |
| 799 | $OCOCH_3$ | H | $CH_3$ | 8 | | |
| 800 | $OCOCH_3$ | H | H | 8 | | |
| 801 | $OCOCH_3$ | H | $CH=CH_2$ | 8 | | |
| 802 | $OCOCH_3$ | H | $CHOHCH_2OH$—(R) | 8 | | |
| 803 | $OCOCH_3$ | H | $CHOHCH_2OH$—(S) | 8 | | |
| 804 | $OCOCH_3$ | H | CHO | 8 | | |
| 805 | $OCOCH_3$ | H | $CH_2OH$ | 8 | | |
| 806 | $OCOCH_3$ | H | $CO_2H$ | 8 | | |
| 807 | $OCOCH_3$ | H | $CO_2CH_3$ | 8 | | |
| 808 | $OCOCH_3$ | H | CH=NOH | 8 | | |
| 809 | $OCOCH_3$ | H | $CHOHCH=CH_2$—(R) | 8 | | |
| 810 | $OCOCH_3$ | H | $CHOHCH=CH_2$—(S) | 8 | | |
| 811 | $OCOCO_2H_5$ | $CH_3$ | $CH_3$ | 8 | | |
| 812 | $OCOC_2H_5$ | $CH_3$ | CHO | 8 | | |
| 813 | $OCOC_2H_5$ | $CH_3$ | $CH_2OH$ | 8 | | |
| 814 | $OCOC_3H_7$ | $CH_3$ | $CH_3$ | 8 | | |
| 815 | $OCOC_3H_7$ | $CH_3$ | CHO | 8 | | |
| 816 | $OCOC_3H_7$ | $CH_3$ | $CH_2OH$ | 8 | | |
| 817 | $OCOC_4H_7$ | $CH_3$ | $CH_3$ | 8 | | |

TABLE 2-continued

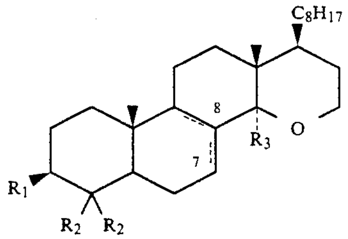

| Ex. No. | $R_1$ | $R_2$ | $R_3$ | D | No. | M.P. |
|---|---|---|---|---|---|---|
| 818 | $OCOC_4H_9$ | $CH_3$ | CHO | 8 | | |
| 819 | $OCOC_4H_9$ | $CH_3$ | $CH_2OH$ | 8 | | |
| 820 | $OCOC_{15}H_{31}$ | $CH_3$ | $CH_3$ | 8 | | |
| 821 | $OCOC_{15}H_{31}$ | $CH_3$ | CHO | 8 | | |
| 822 | $OCOC_{15}H_{31}$ | $CH_3$ | $CH_2OH$ | 8 | | |
| 823 | $OCOC_{15}H_{29}$ | $CH_3$ | $CH_3$ | 8 | | |
| 824 | $OCOC_{17}H_{35}$ | $CH_3$ | $CH_3$ | 8 | | |
| 825 | $OCOC_{17}H_{33}$ | $CH_3$ | $CH_3$ | 8 | | |
| 826 | $OCOC_{17}H_{31}$ | $CH_3$ | $CH_3$ | 8 | | |
| 827 | $OCOC_{17}H_{29}$ | $CH_3$ | $CH_3$ | 8 | | |
| 828 | $OCOC_{19}H_{31}$ | $CH_3$ | $CH_3$ | 8 | | |
| 829 | OCOPh | $CH_3$ | $CH_3$ | 8 | | |
| 830 | OCOCPh | $CH_3$ | $CH_3$ | 8 | | |
| 831 | OCOCPh | $CH_3$ | $CH_3$ | 8 | | |
| 832 | OH | $CH_3$ | $CH_3$ | 7 | | |
| 833 | OH | $CH_3$ | CHO | 7 | | |
| 834 | OH | $CH_3$ | $CH_2OH$ | 7 | | |
| 835 | OH | $CH_3$ | $CO_2H$ | 7 | | |
| 836 | OH | H | $CH_3$ | 7 | | |
| 837 | OH | H | CHO | 7 | | |
| 838 | OH | H | $CH_2OH$ | 7 | | |
| 839 | =O | $CH_3$ | $CH_3$ | 7 | | |
| 840 | =O | $CH_3$ | CHO | 7 | | |
| 841 | =O | $CH_3$ | $CH_2OH$ | 7 | | |
| 842 | =O | H | $CH_3$ | 7 | | |
| 843 | =O | H | CHO | 7 | | |
| 844 | =O | H | $CH_2OH$ | 7 | | |
| 845 | $OCH_3$ | $CH_3$ | $CH_3$ | 7 | | |
| 846 | $OCH_3$ | $CH_3$ | CHO | 7 | | |
| 847 | $OCH_3$ | $CH_3$ | $CH_2OH$ | 7 | | |
| 848 | $OCH_3$ | H | $CH_3$ | 7 | | |
| 849 | $OCH_3$ | H | CHO | 7 | | |
| 850 | $OCH_3$ | H | $CH_2OH$ | 7 | | |
| 851 | $OCOCH_3$ | $CH_3$ | $CH_3$ | 7 | | |
| 852 | $OCOCH_3$ | $CH_3$ | CHO | 7 | | |
| 853 | $OCOCH_3$ | $CH_3$ | $CH_2OH$ | 7 | | |
| 854 | $OCOCH_3$ | H | $CH_3$ | 7 | | |
| 855 | $OCOCH_3$ | H | CHO | 7 | | |
| 856 | $OCOCH_3$ | H | $CH_2OH$ | 7 | | |

*Further analytical data are available in the examples section.

A 4,4-bis-normethyl 15-oxasterol ($R_2$ of the general structure 1 is H), 14α-methyl-15-oxa-5α-cholest-8-en-3b-ol (47), has also been synthesized from 5 -cholesta-8,14-diene-3b-ol by following the sequence of the reaction steps depicted in the synthesis of 15-oxa-dihydrolansterol (11a). Conversion of the normethyl 8,14-diene 38a to the corresponding p-methoxybenzyl ether 38b followed by an osmium tetroxide hydroxylation, an acetalization, a Grignard reaction with methyl magnesium bromide and hydrolysis in 80% aqueous acetic acid provided the six-membered cyclic hemiacetal 43a in 50% overall yield (See, Scheme V).

The compound 43a was subsequently transformed into the desired 14α-methyl-15-oxa-5α-cholest-8-en-3b-ol (47) by glycal formation, osmium tetroxide hydroxylation, oxidative cleavage by sodium metaperiodate, and reduction with triethylsilane and boron trifluoride etherate in 34.5% overall yield from the cyclic hemiacetal 43a. Compound 47 is another example within the scope of the present invention and its synthesis is an example, which demonstrates that preparative methods for compounds with dimethyl at C-4 in the scope (Formula I, with $R_2$=$CH_3$) are applicable to di-bis-normethyl compounds in the scope (Formula I, with $R_2$=H).

SCHEME V

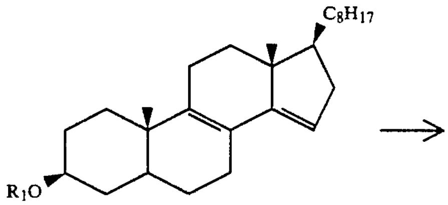

2a $R_1$ = H

2b $R_1$ = $p\text{-}CH_3OC_5H_4CH_2$(pMBn)

-continued
SCHEME V

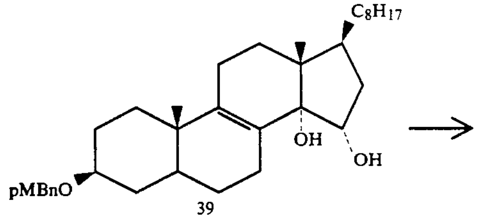
39

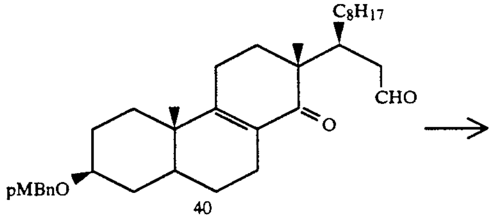
40

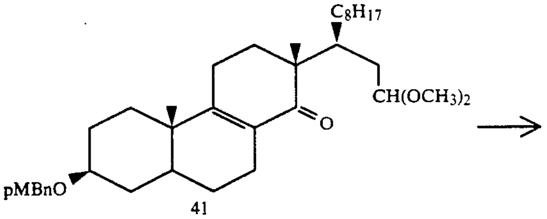
41

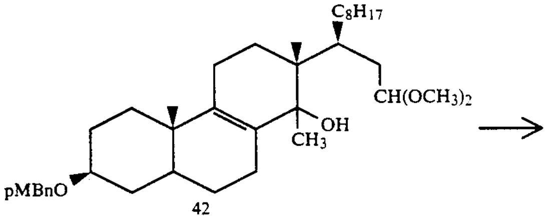
42

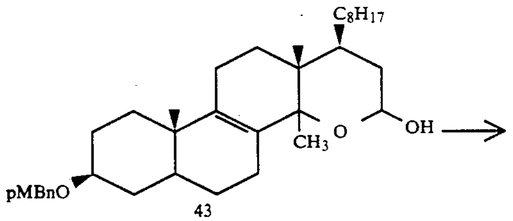
43

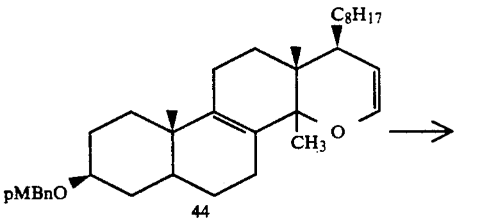
44

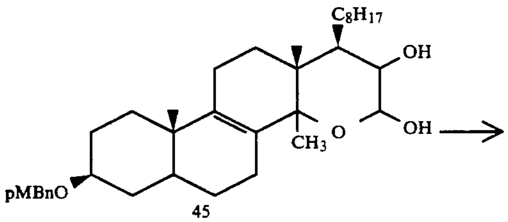
45

-continued
SCHEME V

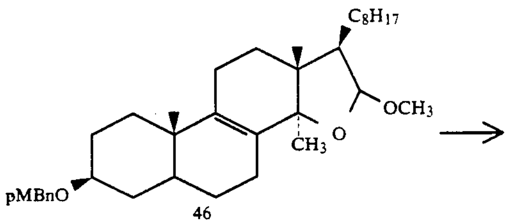
46

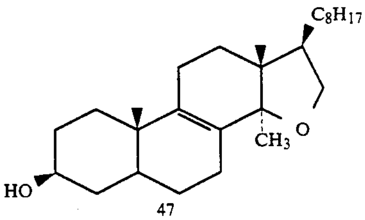
47

15-Thia-lanosterols

For the synthesis of 15-thia-lanosterols, a novel class of compounds, a convenient and novel process has been developed.

Traditionally cyclic sulfides are prepared by displacing a halide, a sulfonate or an equivalent leaving group by an internal thiol.

Taking advantage of the ability to form a stable carbonium ion at the 14-position, a mixture of the cyclic hemiacetal 10b, and cyclic hemiacetal 10c, the intermediates for 15-oxa-dihydrolanosterol, was treated with gaseous hydrogen sulfide (Union Carbide Corp., Linde Division, Danbury, Conn. 06817) and boron trifluoride etherate in methylene chloride followed by triethylsilane to obtain the desired 15-thia-dihydrolanosterol (50) in 60% yield (43% overall yield from the six-membered cyclic hemiacetal 7b) (See, Scheme VI).

The one pot cyclic sulfide formation reaction presumably occurs via cyclic thioacetal 48 and the intermediate 48 is reduced by triethylsilane in the presence of boron trifluoride etherate. The p-methoxybenzyl protecting group at the 3-position was conveniently cleaved during the hydrogen sulfide and boron trifluoride treatment to carry out three operations in a single reaction vessel. This novel cyclic sulfide preparation method may also be operable when a stable carbonium ion formation is possible at the latent alcoholic center by other functional groups such as alkynyl, aryl and other alkenyl. 4,4-Dimethyl-15-thia-5a-cholest-8-en-3b-ol (49) and 4,4-dimethyl-15-thia-14a-vinyl-5a-cholest-8-en-3b-ol (51) have also been synthesized from the compounds 16b and 22b in 26% and 27% overall yields from the compounds 13b and 19b respectively.

Compounds 49, 50, and 52 constitute three examples of 15-thia-lanosterols within the scope of the present invention.

SCHEME VI

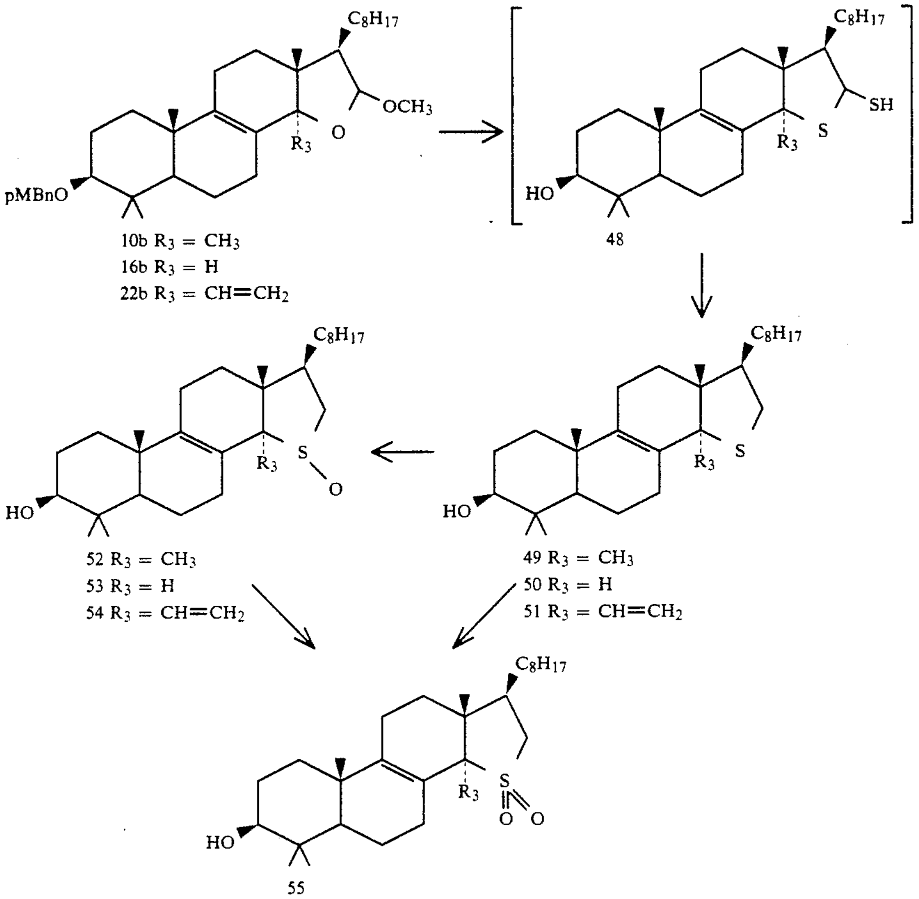

10b $R_3 = CH_3$
16b $R_3 = H$
22b $R_3 = CH{=}CH_2$

48

52 $R_3 = CH_3$
53 $R_3 = H$
54 $R_3 = CH{=}CH_2$

49 $R_3 = CH_3$
50 $R_3 = H$
51 $R_3 = CH{=}CH_2$

55

Sulfides are easily converted to sulfoxides with various oxidizing agents including sodium metaperiodate. Exposing the cyclic sulfide 50 to sodium metaperiodate in 5 parts of ethanol and 1 part of water produced the corresponding sulfoxide 53 in 67% yield. In the same manner C-14 hydride analog 52 and vinyl analog 54 may also be synthesized from the compounds 49 and 51 respectively. Compounds 52, 53, and 54 are three additional examples within the scope of the present invention.

Using more powerful oxidizing agents such as hydrogen peroxide or potassium permanganate (see S. R. Sandler, and W. Karo, *Organic Functional Group Preparations*, Vol. I pp. 610–618, Academic Press, 1983) sulfides or sulfoxides may be converted to the corresponding sulfones represented by the general structure 55, which are within the scope of the present invention.

For syntheses of other examples of compounds within the scope of this invention, further functionalization at the 14-position may also be achieved by converting the vinyl group of the compound 51 to an aldehyde and carrying out other necessary chemistry as discussed in the 15-oxa-lanosterols section, vide supra.

Tables 3, 4, and 5 set forth various thiasterols of the present invention.

TABLE 3

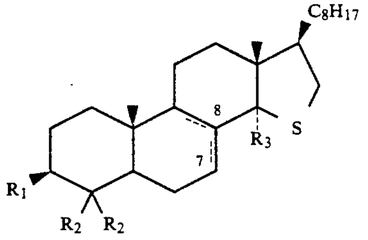

| Ex. No. | $R_1$ | $R_2$ | $R_3$ | D | No. | M.P. |
|---|---|---|---|---|---|---|
| 857 | OH | $CH_3$ | $CH_3$ | 8 | 49 | amorphous* |
| 858 | OH | $CH_3$ | H | 8 | 50 | amorphous* |
| 859 | OH | $CH_3$ | $CH{=}CH_2$ | 8 | 51 | amorphous* |
| 860 | OH | $CH_3$ | $CHOHCH_2OH$—(R) | 8 | | |
| 861 | OH | $CH_3$ | $CHOHCH_2OH$—(S) | 8 | | |
| 862 | OH | $CH_3$ | CHO | 8 | | |

TABLE 3-continued

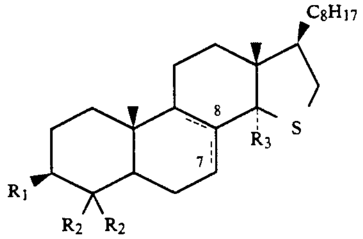

| Ex. No. | $R_1$ | $R_2$ | $R_3$ | D | No. | M.P. |
|---|---|---|---|---|---|---|
| 863 | OH | $CH_3$ | $CH_2OH$ | 8 | | |
| 864 | OH | $CH_3$ | $CO_2H$ | 8 | | |
| 865 | OH | $CH_3$ | $CO_2CH_3$ | 8 | | |
| 866 | OH | $CH_3$ | $CH{=}NOH$ | 8 | | |
| 867 | OH | $CH_3$ | $CHOHCH{=}CH_2$—(R) | 8 | | |
| 868 | OH | $CH_3$ | $CHOHCH{=}CH_2$—(S) | 8 | | |
| 869 | OH | H | $CH_3$ | 8 | | |
| 870 | OH | H | H | 8 | | |
| 871 | OH | H | $CH{=}CH_2$ | 8 | | |
| 872 | OH | H | $CHOHCH_2OH$—(R) | 8 | | |
| 873 | OH | H | $CHOHCH_2OH$—(S) | 8 | | |
| 874 | OH | H | CHO | 8 | | |
| 875 | OH | H | $CH_2OH$ | 8 | | |
| 876 | OH | H | $CO_2H$ | 8 | | |
| 877 | OH | H | $CO_2CH_3$ | 8 | | |
| 878 | OH | H | $CH{=}NOH$ | 8 | | |
| 879 | OH | H | $CHOHCH-CH_2$—(R) | 8 | | |
| 880 | OH | H | $CHOHCH{=}CH_2$—(S) | 8 | | |
| 881 | OH | $CH_3$ | $C_2H_5$ | 8 | | |
| 882 | OH | $CH_3$ | $CH_2CH{=}CH_2$ | 8 | | |
| 883 | OH | $CH_3$ | $C{=}CH$ | 8 | | |
| 884 | OH | $CH_3$ | $CH_2Ph$ | 8 | | |
| 885 | OH | $CH_3$ | $CH_2OCH_3$ | 8 | | |
| 886 | OH | $CH_3$ | $CH_2OCOCH_3$ | 8 | | |
| 887 | OH | $CH_3$ | $CH_2SH$ | 8 | | |
| 888 | OH | $CH_3$ | $CH_2SCH_3$ | 8 | | |
| 889 | OH | $CH_3$ | $CH_2SCOCH_3$ | 8 | | |
| 890 | OH | $CH_3$ | $CH_2NH_2$ | 8 | | |
| 891 | OH | $CH_3$ | $CH_2NHCH_3$ | 8 | | |
| 892 | OH | $CH_3$ | $CH_2NHCOCH_3$ | 8 | | |
| 893 | OH | $CH_3$ | $CH_2NHCSCH_3$ | 8 | | |
| 894 | OH | $CH_3$ | $CH_2NHC({=}NH)CH_3$ | 8 | | |
| 895 | OH | $CH_3$ | $COCH_3$ | 8 | | |
| 896 | OH | $CH_3$ | $COCH{=}CH_2$ | 8 | | |
| 897 | OH | $CH_3$ | $CSCH_3$ | 8 | | |
| 898 | OH | $CH_3$ | $CSCH{=}CH_2$ | 8 | | |
| 899 | OH | $CH_3$ | $C({=}NH)CH_3$ | 8 | | |
| 900 | OH | $CH_3$ | $CO_2C_2H_5$ | 8 | | |
| 901 | OH | $CH_3$ | $COSCH_3$ | 8 | | |
| 902 | OH | $CH_3$ | $CONH_2$ | 8 | | |
| 903 | OH | $CH_3$ | $CONHCH_3$ | 8 | | |
| 904 | OH | $CH_3$ | $CONHCOCH_3$ | 8 | | |
| 905 | OH | $CH_3$ | $CSNH_2$ | 8 | | |
| 906 | OH | $CH_3$ | $CSNHCH_3$ | 8 | | |
| 907 | OH | $CH_3$ | $CSNHCOCH_3$ | 8 | | |
| 908 | OH | $CH_3$ | $CH_2CH_2OH$ | 8 | | |
| 909 | OH | $CH_3$ | $CH_2CH_2OCH_3$ | 8 | | |
| 910 | OH | $CH_3$ | $CH_2CH_2OCOCH_3$ | 8 | | |
| 911 | OH | $CH_3$ | $CH_2CH_2SH$ | 8 | | |
| 912 | OH | $CH_3$ | $CH_2CH_2SCH_3$ | 8 | | |
| 913 | OH | $CH_3$ | $CH_2CH_2SCOCH_3$ | 8 | | |
| 914 | OH | $CH_3$ | $CH_2CH_2NH_2$ | 8 | | |
| 915 | OH | $CH_3$ | $CH_2CH_2NHCH_3$ | 8 | | |
| 916 | OH | $CH_3$ | $CH_2CH_2NHCOCH_3$ | 8 | | |
| 917 | OH | $CH_3$ | $CH_2CHO$ | 8 | | |
| 918 | OH | $CH_3$ | $CH_2COCH_3$ | 8 | | |
| 919 | OH | $CH_3$ | $CH_2COCH{=}CH_2$ | 8 | | |
| 920 | OH | $CH_3$ | $CH_2CSCH_3$ | 8 | | |
| 921 | OH | $CH_3$ | $CH_2CSCH{=}CH_2$ | 8 | | |
| 922 | OH | $CH_3$ | $CH_2({=}NH)CH_3$ | 8 | | |
| 923 | OH | $CH_3$ | $CH_2CO_2CH_3$ | 8 | | |
| 924 | OH | $CH_3$ | $CH_2COSCH_3$ | 8 | | |
| 925 | OH | $CH_3$ | $CH_2CONH_2$ | 8 | | |
| 926 | OH | $CH_3$ | $CH_2CONHCH_3$ | 8 | | |
| 927 | OH | $CH_3$ | $CH_2CONHCOCH_3$ | 8 | | |
| 928 | OH | $CH_3$ | $CH_2CSNH_2$ | 8 | | |
| 929 | OH | $CH_3$ | $CH_2C({=}NH)CH_3$ | 8 | | |
| 930 | OH | $CH_3$ | $CH_2Cl$ | 8 | | |
| 931 | OH | $CH_3$ | $CH_2CH_2Cl$ | 8 | | |

TABLE 3-continued

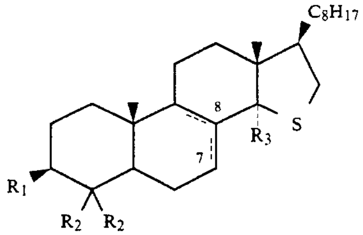

| Ex. No. | $R_1$ | $R_2$ | $R_3$ | D | No. | M.P. |
|---|---|---|---|---|---|---|
| 932 | OH | $CH_3$ | CN | 8 | | |
| 933 | OH | $CH_3$ | $CH=NOCH_3$ | 8 | | |
| 934 | OH | $CH_3$ | $CH=NOCOCH_3$ | 8 | | |
| 935 | OH | $CH_3$ | $CH=NNH_2$ | 8 | | |
| 936 | OH | $CH_3$ | $CH=NNHCH_3$ | 8 | | |
| 937 | OH | $CH_3$ | $CH=NNHCOCH_3$ | 8 | | |
| 938 | OH | $CH_3$ | $CH=NNHCSCH_3$ | 8 | | |
| 939 | OH | $CH_3$ | $CH_2NHOH$ | 8 | | |
| 940 | OH | $CH_3$ | $CH_2NHOCH_3$ | 8 | | |
| 941 | OH | $CH_3$ | $CH_2NHOCOCH_3$ | 8 | | |
| 942 | OH | $CH_3$ | $CH_2NHNH_2$ | 8 | | |
| 943 | OH | $CH_3$ | $CH_2NHNHCH_3$ | 8 | | |
| 944 | OH | $CH_3$ | $CH_2NHNHCOCH_3$ | 8 | | |
| 945 | OH | $CH_3$ | $CH_2NHNHCSCH_3$ | 8 | | |
| 946 | OH | $CH_3$ | $CH_2CN$ | 8 | | |
| 947 | OH | $CH_3$ | $CH_2CH=NOH$ | 8 | | |
| 948 | OH | $CH_3$ | $CH_2CH=NOCH_3$ | 8 | | |
| 949 | OH | $CH_3$ | $CH_2CH=NOCOCH_3$ | 8 | | |
| 950 | OH | $CH_3$ | $CH_2CH=NNH_2$ | 8 | | |
| 951 | OH | $CH_3$ | $CH_2CH=NNHCH_3$ | 8 | | |
| 952 | OH | $CH_3$ | $CH_2CH=NNHCOCH_3$ | 8 | | |
| 953 | OH | $CH_3$ | $CH_2CH=NNHCSCH_3$ | 8 | | |
| 954 | OH | $CH_3$ | $CH_2CH_2NHOH$ | 8 | | |
| 955 | OH | $CH_3$ | $CH_2CH_2NHOCH_3$ | 8 | | |
| 956 | OH | $CH_3$ | $CH_2CH_2NHOCOCH_3$ | 8 | | |
| 957 | OH | $CH_3$ | $CH_2CH_2NHNH_2$ | 8 | | |
| 958 | OH | $CH_3$ | $CH_2CH_2NHNHCH_3$ | 8 | | |
| 959 | OH | $CH_3$ | $CH_2CH_2NHNHCOCH_3$ | 8 | | |
| 960 | OH | $CH_3$ | $CH_2CH_2NHNHCSCH_3$ | 8 | | |
| 961 | OH | $CH_3$ | CONHOH | 8 | | |
| 962 | OH | $CH_3$ | $CONHOCH_3$ | 8 | | |
| 963 | OH | $CH_3$ | $CONHOCOCH_3$ | 8 | | |
| 964 | OH | $CH_3$ | CSNHOH | 8 | | |
| 965 | OH | $CH_3$ | $CSNHOCH_3$ | 8 | | |
| 966 | OH | $CH_3$ | $CSNHOCOCH_3$ | 8 | | |
| 967 | OH | $CH_3$ | $CH=CHCHO$ | 8 | | |
| 968 | OH | $CH_3$ | $CH=CHCOCH_3$ | 8 | | |
| 969 | OH | $CH_3$ | $CH=CHCSCH_3$ | 8 | | |
| 970 | OH | $CH_3$ | $CH=CHCH-NH$ | 8 | | |
| 971 | OH | $CH_3$ | $CH=CHC(=NH)CH_3$ | 8 | | |
| 972 | OH | $CH_3$ | $C=CCHO$ | 8 | | |
| 973 | OH | $CH_3$ | $C=CCOCH_3$ | 8 | | |
| 974 | OH | $CH_3$ | $C=CCSCH_3$ | 8 | | |
| 975 | OH | $CH_3$ | $C=CCH=NH$ | 8 | | |
| 976 | OH | $CH_3$ | $C=CC(=NH)CH_3$ | 8 | | |
| 977 | OH | $CH_3$ | $CH=CHCH_2Cl$ | 8 | | |
| 978 | OH | $CH_3$ | $C=CCH_2Cl$ | 8 | | |
| 979 | OH | $CH_3$ | $CH=CHCH_2OCOCH_3$ | 8 | | |
| 980 | OH | $CH_3$ | $C=CCH_2OCOCH_3$ | 8 | | |
| 981 | OH | $CH_3$ | $CH_2CHOHCH_2OH$ | 8 | | |
| 982 | OH | $CH_3$ | $CHOHCHOHCH_2OH$ | 8 | | |
| 983 | OH | $CH_3$ | 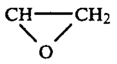 | 8 | | |
| 984 | OH | $CH_3$ | 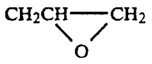 | 8 | | |
| 985 | OH | $CH_3$ | 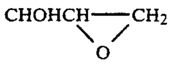 | 8 | | |
| 986 | OH | H | $CH_2SH$ | 8 | | |
| 987 | OH | H | $CH_2NH_2$ | 8 | | |
| 988 | OH | H | $COCH_3$ | 8 | | |
| 989 | OH | H | $CONH_2$ | 8 | | |

TABLE 3-continued

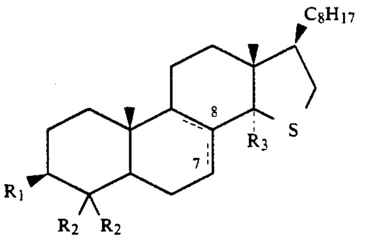

| Ex. No. | $R_1$ | $R_2$ | $R_3$ | D | No. | M.P. |
|---|---|---|---|---|---|---|
| 990 | OH | H | $CSNH_2$ | 8 | | |
| 991 | OH | H | $CH_2CH_2OH$ | 8 | | |
| 992 | OH | H | $CH_2CHO$ | 8 | | |
| 993 | OH | H | $CH_2COCH_3$ | 8 | | |
| 994 | OH | H | $CH_2CO_2CH_3$ | 8 | | |
| 995 | OH | H | $CH_2CONH_2$ | 8 | | |
| 996 | OH | H | $CH_2Cl$ | 8 | | |
| 997 | OH | H | $CH_2CH_2Cl$ | 8 | | |
| 998 | OH | H | CN | 8 | | |
| 999 | OH | H | $CH{=}NNH_2$ | 8 | | |
| 1000 | OH | H | $CH_2NHOH$ | 8 | | |
| 1001 | OH | H | $CH_2NHNH_2$ | 8 | | |
| 1002 | OH | H | $CH_2CN$ | 8 | | |
| 1003 | OH | H | $CH_2CH{=}NOH$ | 8 | | |
| 1004 | OH | H | $CH_2CH{=}NNH_2$ | 8 | | |
| 1005 | OH | H | $CH_2CH_2NHOH$ | 8 | | |
| 1006 | OH | H | $CH_2CH_2NHNH_2$ | 8 | | |
| 1007 | OH | H | CONHOH | 8 | | |
| 1008 | OH | H | $CH{=}CHCHO$ | 8 | | |
| 1009 | OH | H | $CH{=}CHCOCH_3$ | 8 | | |
| 1010 | OH | H | $CH{=}CHCH_2Cl$ | 8 | | |
| 1011 | OH | H | $CH_2CHOHCH_2OH$ | 8 | | |
| 1012 | OH | H | 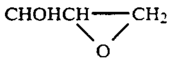 | 8 | | |
| 1013 | =O | $CH_3$ | $CH_3$ | 8 | | |
| 1014 | =O | $CH_3$ | H | 8 | | |
| 1015 | =O | $CH_3$ | $CH{=}CH_2$ | 8 | | |
| 1016 | =O | $CH_3$ | $CHOHCH_2OH$—(R) | 8 | | |
| 1017 | =O | $CH_3$ | $CHOHCH_2OH$—(S) | 8 | | |
| 1018 | =O | $CH_3$ | CHO | 8 | | |
| 1019 | =O | $CH_3$ | $CH_2OH$ | 8 | | |
| 1020 | =O | $CH_3$ | $CO_2H$ | 8 | | |
| 1021 | =O | $CH_3$ | $CO_2CH_3$ | 8 | | |
| 1022 | =O | $CH_3$ | $CH{=}NOH$ | 8 | | |
| 1023 | =O | $CH_3$ | $CHOHCH{=}CH_2$—(R) | 8 | | |
| 1024 | =O | $CH_3$ | $CHOHCH{=}CH_2$—(S) | 8 | | |
| 1025 | =O | $CH_3$ | $CH_2SH$ | 8 | | |
| 1026 | =O | $CH_3$ | $CH_2NH_2$ | 8 | | |
| 1027 | =O | $CH_3$ | $COCH_3$ | 8 | | |
| 1028 | =O | $CH_3$ | $CONH_2$ | 8 | | |
| 1029 | =O | $CH_3$ | $CSNH_2$ | 8 | | |
| 1030 | =O | $CH_3$ | $CH_2CH_2OH$ | 8 | | |
| 1031 | =O | $CH_3$ | $CH_2CHO$ | 8 | | |
| 1032 | =O | $CH_3$ | $CH_2COCH_3$ | 8 | | |
| 1033 | =O | $CH_3$ | $CH_2CO_2CH_3$ | 8 | | |
| 1034 | =O | $CH_3$ | $CH_2CONH_2$ | 8 | | |
| 1035 | =O | $CH_3$ | $CH_2Cl$ | 8 | | |
| 1036 | =O | $CH_3$ | $CH_2CH_2Cl$ | 8 | | |
| 1037 | =O | $CH_3$ | CN | 8 | | |
| 1038 | =O | $CH_3$ | $CH{=}NNCH_2$ | 8 | | |
| 1039 | =O | $CH_3$ | $CH_2NHOH$ | 8 | | |
| 1040 | =O | $CH_3$ | $CH_2NHNH_2$ | 8 | | |
| 1041 | =O | $CH_3$ | $CH_2CN$ | 8 | | |
| 1042 | =O | $CH_3$ | $CH_2CH{=}NOH$ | 8 | | |
| 1043 | =O | $CH_3$ | $CH_2CH{=}NNH_2$ | 8 | | |
| 1044 | =O | $CH_3$ | $CH_2CH_2NHOH$ | 8 | | |
| 1045 | =O | $CH_3$ | $CH_2CH_2NHNH_2$ | 8 | | |
| 1046 | =O | $CH_3$ | CONHOH | 8 | | |
| 1047 | =O | $CH_3$ | $CH{=}CHCHO$ | 8 | | |
| 1048 | =O | $CH_3$ | $CH{=}CHCOCH_3$ | 8 | | |
| 1049 | =O | $CH_3$ | $CH{=}CHCH_2Cl$ | 8 | | |
| 10[illegible] | =O | $CH_3$ | $CH_2CHOHCH_2OH$ | 8 | | |

TABLE 3-continued

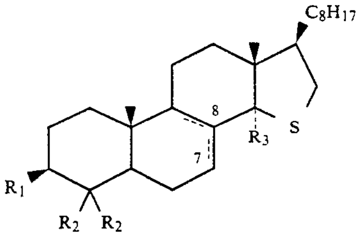

| Ex. No. | $R_1$ | $R_2$ | $R_3$ | D No. | M.P. |
|---|---|---|---|---|---|
| 1051 | =O | $CH_3$ | 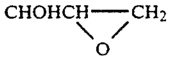 | 8 | |
| 1052 | =O | H | $CH_3$ | 8 | |
| 1053 | =O | H | H | 8 | |
| 1054 | =O | H | $CH{=}CH_2$ | 8 | |
| 1055 | =O | H | $CHOHCH_2OH$—(R) | 8 | |
| 1056 | =O | H | $CHOHCH_2OH$—(S) | 8 | |
| 1057 | =O | H | CHO | 8 | |
| 1058 | =O | H | $CH_2OH$ | 8 | |
| 1059 | =O | H | $CO_2H$ | 8 | |
| 1060 | =O | H | $CO_2CH_3$ | 8 | |
| 1061 | =O | H | CH=NOH | 8 | |
| 1062 | =O | H | $CHOHCH{=}CH_2$—(R) | 8 | |
| 1063 | =O | H | $CHOHCH{=}CH_2$—(S) | 8 | |
| 1064 | $OCH_3$ | $CH_3$ | $CH_3$ | 8 | |
| 1065 | $OCH_3$ | $CH_3$ | H | 8 | |
| 1066 | $OCH_3$ | $CH_3$ | $CH{=}CH_2$ | 8 | |
| 1067 | $OCH_3$ | $CH_3$ | $CHOHCH_2OH$—(R) | 8 | |
| 1068 | $OCH_3$ | $CH_3$ | $CHOHCH_2OH$—(S) | 8 | |
| 1069 | $OCH_3$ | $CH_3$ | CHO | 8 | |
| 1070 | $OCH_3$ | $CH_3$ | $CH_2OH$ | 8 | |
| 1071 | $OCH_3$ | $CH_3$ | $CO_2H$ | 8 | |
| 1072 | $OCH_3$ | $CH_3$ | $CO_2CH_3$ | 8 | |
| 1073 | $OCH_3$ | $CH_3$ | CH=NOH | 8 | |
| 1074 | $OCH_3$ | $CH_3$ | $CHOHCH{=}CH_2$—(R) | 8 | |
| 1075 | $OCH_3$ | $CH_3$ | $CHOHCH{=}CH_2$—(S) | 8 | |
| 1076 | $OCH_3$ | $CH_3$ | $CH_2SH$ | 8 | |
| 1077 | $OCH_3$ | $CH_3$ | $CH_2NH_2$ | 8 | |
| 1078 | $OCH_3$ | $CH_3$ | $COCH_3$ | 8 | |
| 1079 | $OCH_3$ | $CH_3$ | $CONH_2$ | 8 | |
| 1080 | $OCH_3$ | $CH_3$ | $CSNH_2$ | 8 | |
| 1081 | $OCH_3$ | $CH_3$ | $CH_2CH_2OH$ | 8 | |
| 1082 | $OCH_3$ | $CH_3$ | $CH_2CHO$ | 8 | |
| 1083 | $OCH_3$ | $CH_3$ | $CH_2COCH_3$ | 8 | |
| 1084 | $OCH_3$ | $CH_3$ | $CH_2CO_2CH_3$ | 8 | |
| 1085 | $OCH_3$ | $CH_3$ | $CH_2CONH_2$ | 8 | |
| 1086 | $OCH_3$ | $CH_3$ | $CH_2Cl$ | 8 | |
| 1087 | $OCH_3$ | $CH_3$ | $CH_2CH_2Cl$ | 8 | |
| 1088 | $OCH_3$ | $CH_3$ | CN | 8 | |
| 1089 | $OCH_3$ | $CH_3$ | $CH{=}NNH_2$ | 8 | |
| 1090 | $OCH_3$ | $CH_3$ | $CH_2NHOH$ | 8 | |
| 1091 | $OCH_3$ | $CH_3$ | $CH_2NHNH_2$ | 8 | |
| 1092 | $OCH_3$ | $CH_3$ | $CH_2CN$ | 8 | |
| 1093 | $OCH_3$ | $CH_3$ | $CH_2CH{=}NOH$ | 8 | |
| 1094 | $OCH_3$ | $CH_3$ | $CH_2CH{=}NNH_2$ | 8 | |
| 1095 | $OCH_3$ | $CH_3$ | $CH_2CH_2NHOH$ | 8 | |
| 1096 | $OCH_3$ | $CH_3$ | $CH_2CH_2NHNH_2$ | 8 | |
| 1097 | $OCH_3$ | $CH_3$ | CONHOH | 8 | |
| 1098 | $OCH_3$ | $CH_3$ | CH=CHCHO | 8 | |
| 1099 | $OCH_3$ | $CH_3$ | $CH{=}CHCOCH_3$ | 8 | |
| 1100 | $OCH_3$ | $CH_3$ | $CH{=}CHCH_2Cl$ | 8 | |
| 1101 | $OCH_3$ | $CH_3$ | $CH_2CHOHCH_2OH$ | 8 | |
| 1102 | $OCH_2$ | $CH_3$ | 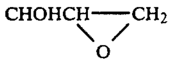 | 8 | |
| 1103 | $OCH_3$ | H | $CH_3$ | 8 | |
| 1104 | $OCH_3$ | H | H | 8 | |
| 1105 | $OCH_3$ | H | $CH{=}CH_2$ | 8 | |
| 1106 | $OCH_3$ | H | $CHOHCH_2OH$—(R) | 8 | |
| 1107 | $OCH_3$ | H | $CHOHCH_2OH$—(S) | 8 | |
| 1108 | $OCH_3$ | H | CHO | 8 | |
| 1109 | $OCH_3$ | H | $CH_2OH$ | 8 | |
| 1110 | $OCH_3$ | H | $CO_2H$ | 8 | |
| 1111 | $OCH_3$ | H | $CO_2CH_3$ | 8 | |

TABLE 3-continued

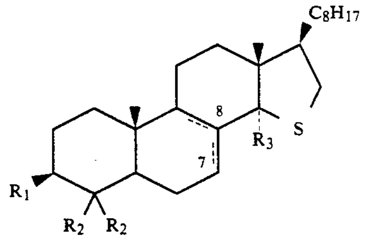

| Ex. No. | $R_1$ | $R_2$ | $R_3$ | D No. | M.P. |
|---|---|---|---|---|---|
| 1112 | $OCH_3$ | H | $CHOHCH{=}CH_2-(R)$ | 8 | |
| 1114 | $OCH_3$ | H | $CHOHCH{=}CH_2-(S)$ | 8 | |
| 1115 | $OC_2H_5$ | $CH_3$ | $CH_3$ | 8 | |
| 1116 | $OC_2H_5$ | $CH_3$ | CHO | 8 | |
| 1117 | $OC_2H_5$ | $CH_3$ | $CH_2OH$ | 8 | |
| 1118 | $OC_3H_7$ | $CH_3$ | $CH_3$ | 8 | |
| 1119 | $OC_3H_7$ | $CH_3$ | CHO | 8 | |
| 1120 | $OC_3H_7$ | $CH_3$ | $CH_2OH$ | 8 | |
| 1121 | $Oi\text{-}C_3H_7$ | $CH_3$ | $CH_3$ | 8 | |
| 1122 | $OC_4H_9$ | $CH_3$ | $CH_3$ | 8 | |
| 1123 | $OC_4H_9$ | $OC_3$ | CHO | 8 | |
| 1124 | $OC_4H_9$ | $CH_3$ | $CH_2OH$ | 8 | |
| 1125 | $Oi\text{-}C_4H_9$ | $CH_3$ | $CH_3$ | 8 | |
| 1126 | $Ot\text{-}C_4H_9$ | $CH_3$ | $CH_3$ | 8 | |
| 1127 | OPh | $CH_3$ | $CH_3$ | 8 | |
| 1128 | OPh | $CH_3$ | CHO | 8 | |
| 1129 | OPh | $CH_3$ | $CH_2OH$ | 8 | |
| 1130 | $OCH_2Ph$ | $CH_3$ | $CH_3$ | 8 | |
| 1131 | $OCH_2Ph$ | $CH_3$ | CHO | 8 | |
| 1132 | $OCH_2Ph$ | $CH_3$ | $CH_2OH$ | 8 | |
| 1133 | $OCOCH_3$ | $CH_3$ | $CH_3$ | 8 | |
| 1134 | $OCOCH_3$ | $CH_3$ | H | 8 | |
| 1135 | $OCOCH_3$ | $CH_3$ | $CH{=}CH_2$ | 8 | |
| 1136 | $OCOCH_3$ | $CH_3$ | $CHOHCH_2OH-(R)$ | 8 | |
| 1137 | $OCOCH_3$ | $CH_3$ | $CHOHCH_2OH-(S)$ | 8 | |
| 1138 | $OCOCH_3$ | $CH_3$ | CHO | 8 | |
| 1139 | $OCOCH_3$ | $CH_3$ | $CH_2OH$ | 8 | |
| 1140 | $OCOCH_3$ | $CH_3$ | $CO_2H$ | 8 | |
| 1141 | $OCOCH_3$ | $CH_3$ | $CO_2CH_3$ | 8 | |
| 1142 | $OCOCH_3$ | $CH_3$ | $CH{=}NOH$ | 8 | |
| 1143 | $OCOCH_3$ | $CH_3$ | $CHOHCH{=}CH_2-(R)$ | 8 | |
| 1144 | $OCOCH_3$ | $CH_3$ | $CHOHCH{=}CH_2-(S)$ | 8 | |
| 1145 | $OCOCH_3$ | $CH_3$ | $CH_2SH$ | 8 | |
| 1146 | $OCOCH_3$ | $CH_3$ | $CH_2NH_2$ | 8 | |
| 1147 | $OCOCH_3$ | $CH_3$ | $COCH_3$ | 8 | |
| 1148 | $OCOCH_3$ | $CH_3$ | $CONH_2$ | 8 | |
| 1149 | $OCOCH_3$ | $CH_3$ | $CSNH_2$ | 8 | |
| 1150 | $OCOCH_3$ | $CH_3$ | $CH_2CH_2OH$ | 8 | |
| 1151 | $OCOCH_3$ | $CH_3$ | $CH_2CHO$ | 8 | |
| 1152 | $OCOCH_3$ | $CH_3$ | $CH_2COCH_3$ | 8 | |
| 1153 | $OCOCH_3$ | $CH_3$ | $CH_2CO_2CH_3$ | 8 | |
| 1154 | $OCOCH_3$ | $CH_3$ | $CH_2CONH_2$ | 8 | |
| 1155 | $OCOCH_3$ | $CH_3$ | $CH_2Cl$ | 8 | |
| 1156 | $OCOCH_3$ | $CH_3$ | $CH_2CH_2Cl$ | 8 | |
| 1157 | $OCOCH_3$ | $CH_3$ | CN | 8 | |
| 1158 | $OCOCH_3$ | $CH_3$ | $CH-NNH_2$ | 8 | |
| 1159 | $OCOCH_3$ | $CH_3$ | $CH_2NHOH$ | 8 | |
| 1160 | $OCOCH_3$ | $CH_3$ | $CH_2NHNH_2$ | 8 | |
| 1161 | $OCOCH_3$ | $CH_3$ | $CH_2CN$ | 8 | |
| 1162 | $OCOCH_3$ | $CH_3$ | $CH_2CH{=}NOH$ | 8 | |
| 1163 | $OCOCH_3$ | $CH_3$ | $CH_2CH{=}NNH_2$ | 8 | |
| 1164 | $OCOCH_3$ | $CH_3$ | $CH_2CH_2NHOH$ | 8 | |
| 1165 | $OCOCH_3$ | $CH_3$ | $CH_2CH_2NHNH_2$ | 8 | |
| 1166 | $OCOCH_3$ | $CH_3$ | CONHOH | 8 | |
| 1167 | $OCOCH_3$ | $CH_3$ | $CH{=}CHCHO$ | 8 | |
| 1168 | $OCOCH_3$ | $CH_3$ | $CH{=}CHCOCH_3$ | 8 | |
| 1169 | $OCOCH_3$ | $CH_3$ | $CH{=}CHCH_2Cl$ | 8 | |
| 1170 | $OCOCH_3$ | $CH_3$ | $CH_2CHOHCH_2OH$ | 8 | |
| 1171 | $OCOCH_3$ | $CH_3$ | 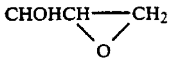 | 8 | |
| 1172 | $OCOCH_3$ | H | $CH_3$ | 8 | |
| 1173 | $OCOCH_3$ | H | H | 8 | |
| 1174 | $OCOCH_3$ | H | $CH{=}CH_2$ | 8 | |
| 1175 | $OCOCH_3$ | H | $CHOHCH_2OH-(R)$ | 8 | |
| 1176 | $OCOCH_3$ | H | $CHOHCH_2OH-(S)$ | 8 | |
| 1177 | $OCOCH_3$ | H | CHO | 8 | |

TABLE 3-continued

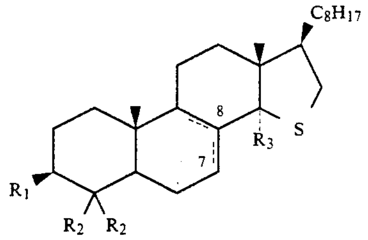

| Ex. No. | $R_1$ | $R_2$ | $R_3$ | D | No. | M.P. |
|---|---|---|---|---|---|---|
| 1178 | $OCOCH_3$ | H | $CH_2OH$ | 8 | | |
| 1179 | $OCOCH_3$ | H | $CO_2H$ | 8 | | |
| 1180 | $OCOCH_3$ | H | $CO_2CH_3$ | 8 | | |
| 1181 | $OCOCH_3$ | H | $CH{=}NOH$ | 8 | | |
| 1182 | $OCOCH_3$ | H | $CHOHCH{=}CH_2{-}(R)$ | 8 | | |
| 1183 | $OCOCH_3$ | H | $CHOHCH{=}CH_2{-}(S)$ | 8 | | |
| 1184 | $OCOC_2H_5$ | $CH_3$ | $CH_3$ | 8 | | |
| 1185 | $OCOC_2H_5$ | $CH_3$ | CHO | 8 | | |
| 1186 | $OCOC_2H_5$ | $CH_3$ | $CH_2OH$ | 8 | | |
| 1187 | $OCOC_3H_7$ | $CH_3$ | $CH_3$ | 8 | | |
| 1188 | $OCOC_3H_7$ | $CH_3$ | CHO | 8 | | |
| 1189 | $OCOC_3H_7$ | $CH_3$ | $CH_2OH$ | 8 | | |
| 1190 | $OCOi\text{-}C_4H_7$ | $CH_3$ | $CH_3$ | 8 | | |
| 1191 | $OCOC_4H_9$ | $CH_3$ | $CH_3$ | 8 | | |
| 1192 | $OCOC_4H_9$ | $CH_3$ | CHO | 8 | | |
| 1193 | $OCOC_4H_9$ | $CH_3$ | $CH_2OH$ | 8 | | |
| 1194 | $OCOi\text{-}C_4H_9$ | $CH_3$ | $CH_3$ | 8 | | |
| 1195 | $OCOt\text{-}C_4H_9$ | $CH_3$ | $CH_3$ | 8 | | |
| 1195 | $OCOC_{15}H_{31}$ | $CH_3$ | $CH_3$ | 8 | | |
| 1197 | $OCOC_{15}H_{31}$ | $CH_3$ | CHO | 8 | | |
| 1198 | $OCOC_{15}H_{31}$ | $CH_3$ | $CH_2OH$ | 8 | | |
| 1199 | $OCOC_{15}H_{29}$ | $CH_3$ | $CH_3$ | 8 | | |
| 1200 | $OCOC_{17}H_{35}$ | $CH_3$ | $CH_3$ | 8 | | |
| 1201 | $OCOC_{17}H_{33}$ | $CH_3$ | $CH_3$ | 8 | | |
| 1202 | $OCOC_{17}H_{31}$ | $CH_3$ | $CH_3$ | 8 | | |
| 1203 | $OCOC_{17}H_{29}$ | $CH_3$ | $CH_3$ | 8 | | |
| 1204 | $OCOC_{19}H_{31}$ | $CH_3$ | $CH_3$ | 8 | | |
| 1205 | OCOPh | $CH_3$ | $CH_3$ | 8 | | |
| 1206 | OCOPh | $CH_3$ | CHO | 8 | | |
| 1207 | OCOPh | $CH_3$ | $CH_2OH$ | 8 | | |
| 1208 | OH | $CH_3$ | $CH_3$ | 7 | | |
| 1209 | OH | $CH_3$ | H | 7 | | |
| 1210 | OH | $CH_3$ | $CH{=}CH_2$ | 7 | | |
| 1211 | OH | $CH_3$ | $CHOHCH_2OH{-}(R)$ | 7 | | |
| 1212 | OH | $CH_3$ | $CHOHCH_2OH{-}(S)$ | 7 | | |
| 1213 | OH | $CH_3$ | CHO | 7 | | |
| 1214 | OH | $CH_3$ | $CH_2OH$ | 7 | | |
| 1215 | OH | $CH_3$ | $CO_2H$ | 7 | | |
| 1216 | OH | $CH_3$ | $CO_2CH_3$ | 7 | | |
| 1217 | OH | $CH_3$ | $CH{=}NOH$ | 7 | | |
| 1218 | OH | $CH_3$ | $CHOHCH{=}CH_2{-}(R)$ | 7 | | |
| 1219 | OH | H | $CH_3$ | 7 | | |
| 1220 | OH | H | H | 7 | | |
| 1221 | OH | H | $CH{=}CH_2$ | 7 | | |
| 1222 | OH | H | $CHOHCH_2OH{-}(R)$ | 7 | | |
| 1223 | OH | H | $CHOHCH_2OH{-}(S)$ | 7 | | |
| 1224 | OH | H | CHO | 7 | | |
| 1225 | OH | H | $CH_2OH$ | 7 | | |
| 1226 | OH | H | $CO_2H$ | 7 | | |
| 1227 | OH | H | $CO_2CH_3$ | 7 | | |
| 1228 | OH | H | $CH{=}NOH$ | 7 | | |
| 1229 | OH | H | $CHOHCH{-}CH_2{-}(R)$ | 7 | | |
| 1230 | OH | H | $CHOHCH{-}CH_2{-}(S)$ | 7 | | |
| 1231 | =O | $CH_3$ | $CH_3$ | 7 | | |
| 1232 | =O | $CH_3$ | H | 7 | | |
| 1233 | =O | $CH_3$ | $CH{=}CH_2$ | 7 | | |
| 1234 | =O | $CH_3$ | $CHOHCH_2OH{-}(R)$ | 7 | | |
| 1235 | =O | $CH_3$ | $CHOHCH_2OH{-}(S)$ | 7 | | |
| 1236 | =O | $CH_3$ | CHO | 7 | | |
| 1237 | =O | $CH_3$ | $CH_2OH$ | 7 | | |
| 1238 | =O | $CH_3$ | $CO_2H$ | 7 | | |
| 1239 | =O | $CH_3$ | $CO_2CH_3$ | 7 | | |
| 1240 | =O | $CH_3$ | $CH{=}NOH$ | 7 | | |
| 1241 | =O | $CH_3$ | $CHOHCH{=}CH_2{-}(R)$ | 7 | | |
| 1242 | =O | $CH_3$ | $CHOHCH{=}CH_2{-}(S)$ | 7 | | |
| 1243 | =O | H | $CH_3$ | 7 | | |
| 1244 | =O | H | H | 7 | | |
| 1245 | =O | H | $CH{=}CH_2$ | 7 | | |
| 1246 | =O | H | $CHOHCH_2OH{-}(R)$ | 7 | | |

TABLE 3-continued

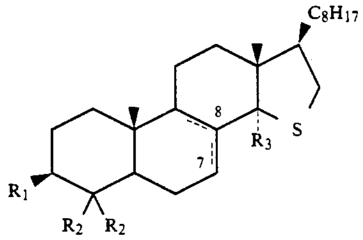

| Ex. No. | $R_1$ | $R_2$ | $R_3$ | D | No. | M.P. |
|---|---|---|---|---|---|---|
| 1247 | =O | H | $CHOHCH_2OH$—(S) | 7 | | |
| 1248 | =O | H | CHO | 7 | | |
| 1249 | =O | H | $CH_2OH$ | 7 | | |
| 1250 | =O | H | $CO_2H$ | 7 | | |
| 1251 | =O | H | $CO_2CH_3$ | 7 | | |
| 1252 | =O | H | CH=NOH | 7 | | |
| 1253 | =O | H | $CHOHCH=CH_2$—(R) | 7 | | |
| 1254 | =O | H | $CHOHCH=CH_2$—(S) | 7 | | |
| 1255 | $OCH_3$ | $CH_3$ | $CH_3$ | 7 | | |
| 1256 | $OCH_3$ | $CH_3$ | H | 7 | | |
| 1257 | $OCH_3$ | $CH_3$ | $CH=CH_2$ | 7 | | |
| 1258 | $OCH_3$ | $CH_3$ | $CHOHCH_2OH$—(R) | 7 | | |
| 1259 | $OCH_3$ | $CH_3$ | $CHOHCH_2OH$—(S) | 7 | | |
| 1260 | $OCH_3$ | $CH_3$ | CHO | 7 | | |
| 1261 | $OCH_3$ | $CH_3$ | $CH_2OH$ | 7 | | |
| 1262 | $OCH_3$ | $CH_3$ | $CO_2H$ | 7 | | |
| 1263 | $OCH_3$ | $CH_3$ | $CO_2CH_3$ | 7 | | |
| 1264 | $OCH_3$ | $CH_3$ | CH=NOH | 7 | | |
| 1265 | $OCH_3$ | $CH_3$ | $CHOHCH=CH_2$—(R) | 7 | | |
| 1266 | $OCH_3$ | $CH_3$ | $CHOHCH=CH_2$—(S) | 7 | | |
| 1267 | $OCH_3$ | H | $CH_3$ | 7 | | |
| 1268 | $OCH_3$ | H | H | 7 | | |
| 1269 | $OCH_3$ | H | $CH=CH_2$ | 7 | | |
| 1270 | $OCH_3$ | H | $CHOHCH_2OH$—(R) | 7 | | |
| 1271 | $OCH_3$ | H | $CHOHCH_2OH$—(S) | 7 | | |
| 1272 | $OCH_3$ | H | CHO | 7 | | |
| 1273 | $OCH_3$ | H | $CH_2OH$ | 7 | | |
| 1274 | $OCH_3$ | H | $CO_2H$ | 7 | | |
| 1275 | $OCH_3$ | H | $CO_2CH_3$ | 7 | | |
| 1276 | $OCH_3$ | H | CH=NOH | 7 | | |
| 1277 | $OCH_3$ | H | $CHOHCH=CH_2$—(R) | 7 | | |
| 1278 | $OCH_3$ | H | $CHOHCH=CH_2$—(S) | 7 | | |
| 1279 | $OCOCH_3$ | $CH_3$ | $CH_3$ | 7 | | |
| 1280 | $OCOCH_3$ | $CH_3$ | H | 7 | | |
| 1281 | $OCOCH_3$ | $CH_3$ | $CH=CH_2$ | 7 | | |
| 1282 | $OCOCH_3$ | $CH_3$ | $CHOHCH_2OH$—(R) | 7 | | |
| 1283 | $OCOCH_3$ | $CH_3$ | $CHOHCH_2OH$—(S) | 7 | | |
| 1284 | $OCOCH_3$ | $CH_3$ | CHO | 7 | | |
| 1285 | $OCOCH_3$ | $CH_3$ | $CH_2OH$ | 7 | | |
| 1286 | $OCOCH_3$ | $CH_3$ | $CO_2H$ | 7 | | |
| 1287 | $OCOCH_3$ | $CH_3$ | $CO_2CH_3$ | 7 | | |
| 1288 | $OCOCH_3$ | $CH_3$ | CH=NOH | 7 | | |
| 1289 | $OCOCH_3$ | $CH_3$ | $CHOHCH=CH_2$—(R) | 7 | | |
| 1290 | $OCOCH_3$ | $CH_3$ | $CHOHCH=CH_2$—(S) | 7 | | |
| 1291 | $OCOCH_3$ | H | $CH_3$ | 7 | | |
| 1292 | $OCOCH_3$ | H | H | 7 | | |
| 1293 | $OCOCH_3$ | H | $CH=CH_2$ | 7 | | |
| 1294 | $OCOCH_3$ | H | $CHOHCH_2OH$—(R) | 7 | | |
| 1295 | $OCOCH_3$ | H | $CHOHCH_2OH$—(S) | 7 | | |
| 1296 | $OCOCH_3$ | H | CHO | 7 | | |
| 1297 | $OCOCH_3$ | H | $CH_2OH$ | 7 | | |
| 1298 | $OCOCH_3$ | H | $CO_2H$ | 7 | | |
| 1299 | $OCOCH_3$ | H | $CO_2CH_3$ | 7 | | |
| 1300 | $OCOCH_3$ | H | CH=NOH | 7 | | |
| 1301 | $OCOCH_3$ | H | $CHOHCH=CH_2$—(R) | 7 | | |
| 1302 | $OCOCH_3$ | H | $CHOHCH=CH_2$—(S) | 7 | | |

*Further analytical data are available in the examples section.

TABLE 4

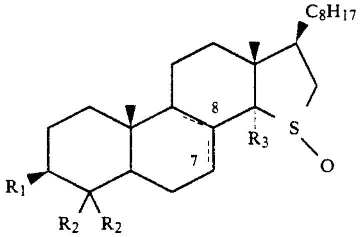

| Ex. No. | $R_1$ | $R_2$ | $R_3$ | D | No. | M.P. |
|---|---|---|---|---|---|---|
| 1303 | OH | $CH_3$ | $CH_3$ | 8 | 52 | amorphous* |
| 1304 | OH | $CH_3$ | H | 8 | 53 | amorphous* |
| 1305 | OH | $CH_3$ | $CH{=}CH_2$ | 8 | 54 | amorphous* |
| 1306 | OH | $CH_3$ | $CHOHCH_2OH$—(R) | 8 | | |
| 1307 | OH | $CH_3$ | $CHOHCH_2OH$—(S) | 8 | | |
| 1308 | OH | $CH_3$ | CHO | 8 | | |
| 1309 | OH | $CH_3$ | $CH_2OH$ | 8 | | |
| 1310 | OH | $CH_3$ | $CO_2H$ | 8 | | |
| 1311 | OH | $CH_3$ | $CO_2CH_3$ | 8 | | |
| 1312 | OH | $CH_3$ | $CH{=}NOH$ | 8 | | |
| 1313 | OH | $CH_3$ | $CHOHCH{=}CH_2$—(R) | 8 | | |
| 1314 | OH | $CH_3$ | $CHOHCH{=}CH_2$—(S) | 8 | | |
| 1315 | OH | H | $CH_3$ | 8 | | |
| 1316 | OH | H | H | 8 | | |
| 1317 | OH | H | $CH{=}CH_2$ | 8 | | |
| 1318 | OH | H | $CHOHCH_2OH$—(R) | 8 | | |
| 1319 | OH | H | $CHOHCH_2OH$—(S) | 8 | | |
| 1320 | OH | H | CHO | 8 | | |
| 1321 | OH | H | $CH_2OH$ | 8 | | |
| 1322 | OH | H | $CO_2CH_3$ | 8 | | |
| 1323 | OH | H | $CH{=}NOH$ | 8 | | |
| 1324 | OH | H | $CHOHCH{=}CH_2$—(R) | 8 | | |
| 1325 | OH | H | $CHOHCH{=}CH_2$—(S) | 8 | | |
| 1326 | OH | $CH_3$ | $CH_2SH$ | 8 | | |
| 1327 | OH | $CH_3$ | $CH_2NH_2$ | 8 | | |
| 1328 | OH | $CH_3$ | $COCH_3$ | 8 | | |
| 1329 | OH | $CH_3$ | $CONH_2$ | 8 | | |
| 1330 | OH | $CH_3$ | $CSNH_2$ | 8 | | |
| 1331 | OH | $CH_3$ | $CH_2CH_2OH$ | 8 | | |
| 1332 | OH | $CH_3$ | $CH_2CHO$ | 8 | | |
| 1333 | OH | $CH_3$ | $CH_2COCH_3$ | 8 | | |
| 1334 | OH | $CH_3$ | $CH_2CO_2CH_3$ | 8 | | |
| 1335 | OH | $CH_3$ | $CH_2CONH_2$ | 8 | | |
| 1336 | OH | $CH_3$ | $CH_2Cl$ | 8 | | |
| 1337 | OH | $CH_3$ | $CH_2CH_2Cl$ | 8 | | |
| 1338 | OH | $CH_3$ | CN | 8 | | |
| 1339 | OH | $CH_3$ | $CH{=}NNH_2$ | 8 | | |
| 1340 | OH | $CH_3$ | $CH_2NHOH$ | 8 | | |
| 1341 | OH | $CH_3$ | $CH_2NHNH_2$ | 8 | | |
| 1342 | OH | $CH_3$ | $CH_2CN$ | 8 | | |
| 1343 | OH | $CH_3$ | $CH_2CH{=}NOH$ | 8 | | |
| 1344 | OH | $CH_3$ | $CH_2CH{-}NNH_2$ | 8 | | |
| 1345 | OH | $CH_3$ | $CH_2CH_2NHOH$ | 8 | | |
| 1346 | OH | $CH_3$ | $CH_2CH_2NHNH_2$ | 8 | | |
| 1347 | OH | $CH_3$ | CONHOH | 8 | | |
| 1348 | OH | $CH_3$ | $CH{=}CHCHO$ | 8 | | |
| 1349 | OH | $CH_3$ | $CH{=}CHCOCH_3$ | 8 | | |
| 1350 | OH | $CH_3$ | $CH{=}CHCH_2Cl$ | 8 | | |
| 1351 | OH | $CH_3$ | $CH_2CHOHCH_2OH$ | 8 | | |
| 1352 | OH | $CH_3$ | 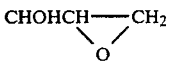 | 8 | | |
| 1353 | =O | $CH_3$ | $CH_3$ | 8 | | |
| 1354 | =O | $CH_3$ | CHO | 8 | | |
| 1355 | =O | $CH_3$ | $CH_2OH$ | 8 | | |
| 1356 | =O | H | $CH_3$ | 8 | | |
| 1357 | =O | H | CHO | 8 | | |
| 1358 | =O | H | $CH_2OH$ | 8 | | |
| 1359 | $OCH_3$ | $CH_3$ | $CH_3$ | 8 | | |
| 1360 | $OCH_3$ | $CH_3$ | CHO | 8 | | |
| 1361 | $OCH_3$ | $CH_3$ | $CH_2OH$ | 8 | | |
| 1362 | $OCH_3$ | H | $CH_3$ | 8 | | |
| 1363 | $OCH_3$ | H | CHO | 8 | | |
| 1364 | $OCH_3$ | H | $CH_2OH$ | 8 | | |
| 1365 | OPh | $CH_3$ | $CH_3$ | 8 | | |
| 1366 | OPh | $CH_3$ | CHO | 8 | | |
| 1367 | OPh | $CH_3$ | $CH_2OH$ | 8 | | |

TABLE 4-continued

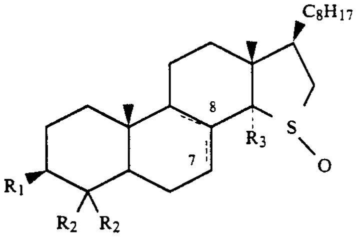

| Ex. No. | $R_1$ | $R_2$ | $R_3$ | D | No. | M.P. |
|---|---|---|---|---|---|---|
| 1368 | $OCH_2Ph$ | $CH_3$ | $CH_3$ | 8 | | |
| 1369 | $OCH_2Ph$ | $CH_3$ | CHO | 8 | | |
| 1370 | $OCH_2Ph$ | $CH_3$ | $CH_2OH$ | 8 | | |
| 1371 | $OCOCH_3$ | $CH_3$ | $CH_3$ | 8 | | |
| 1372 | $OCOCH_3$ | $CH_3$ | CHO | 8 | | |
| 1373 | $OCOCH_3$ | $CH_3$ | $CH_2OH$ | 8 | | |
| 1374 | $OCOCH_3$ | H | $CH_3$ | 8 | | |
| 1375 | $OCOCH_3$ | H | CHO | 8 | | |
| 1376 | $OCOCH_3$ | H | $CH_2OH$ | 8 | | |
| 1377 | OCOPh | $CH_3$ | $CH_3$ | 8 | | |
| 1378 | OCOPh | $CH_3$ | CHO | 8 | | |
| 1379 | OCOPh | $CH_3$ | $CH_2OH$ | 8 | | |
| 1380 | OH | $CH_3$ | $CH_3$ | 7 | | |
| 1381 | OH | $CH_3$ | CHO | 7 | | |
| 1382 | OH | $CH_3$ | $CH_2OH$ | 7 | | |
| 1383 | OH | $CH_3$ | $CO_2H$ | 7 | | |
| 1384 | OH | H | $CH_3$ | 7 | | |
| 1385 | OH | H | CHO | 7 | | |
| 1386 | OH | H | $CH_2OH$ | 7 | | |
| 1387 | =O | $CH_3$ | $CH_3$ | 7 | | |
| 1388 | =O | $CH_3$ | CHO | 7 | | |
| 1389 | =O | $CH_3$ | $CH_2OH$ | 7 | | |
| 1390 | =O | H | $CH_3$ | 7 | | |
| 1391 | =O | H | CHO | 7 | | |
| 1392 | =O | H | $CH_2OH$ | 7 | | |
| 1393 | $OCH_3$ | $CH_3$ | $CH_3$ | 7 | | |
| 1394 | $OCH_3$ | $CH_3$ | CHO | 7 | | |
| 1395 | $OCH_3$ | $CH_3$ | $CH_2OH$ | 7 | | |
| 1396 | $OCH_3$ | H | $CH_3$ | 7 | | |
| 1397 | $OCH_2$ | H | CHO | 7 | | |
| 1398 | $OCH_3$ | H | $CH_2OH$ | 7 | | |
| 1399 | $OCOCH_3$ | $CH_3$ | $CH_3$ | 7 | | |
| 1400 | $OCOCH_3$ | $CH_3$ | CHO | 7 | | |
| 1401 | $OCOCH_3$ | $CH_3$ | $CH_2OH$ | 7 | | |
| 1402 | $OCOCH_3$ | H | $CH_3$ | 7 | | |
| 1403 | $OCOCH_3$ | H | CHO | 7 | | |
| 1404 | $OCOCH_3$ | H | $CH_2OH$ | 7 | | |

*Further analytical data are availble in the examples section.

TABLE 5

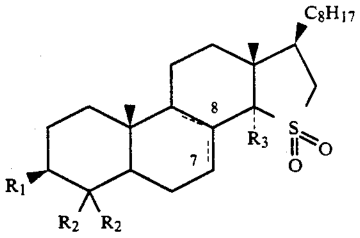

| Ex. No. | $R_1$ | $R_2$ | $R_3$ | D | No. | M.P. |
|---|---|---|---|---|---|---|
| 1405 | OH | $CH_3$ | $CH_3$ | 8 | | |
| 1406 | OH | $CH_3$ | H | 8 | | |
| 1407 | OH | $CH_3$ | $CH{=}CH_2$ | 8 | | |
| 1408 | OH | $CH_3$ | $CHOHCH_2OH$—(R) | 8 | | |
| 1409 | OH | $CH_3$ | $CHOHCH_2OH$—(S) | 8 | | |
| 1410 | OH | $CH_3$ | CHO | 8 | | |
| 1411 | OH | $CH_3$ | $CH_2OH$ | 8 | | |
| 1412 | OH | $CH_3$ | $CO_2H$ | 8 | | |
| 1413 | OH | $CH_3$ | $CO_2CH_3$ | 8 | | |
| 1414 | OH | $CH_3$ | CH=NOH | 8 | | |
| 1415 | OH | $CH_3$ | $CHOHCH{=}CH_2$—(R) | 8 | | |
| 1416 | OH | $CH_3$ | $CHOHCH{=}CH_2$—(S) | 8 | | |

TABLE 5-continued

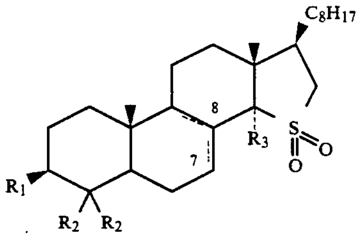

| Ex. No. | $R_1$ | $R_2$ | $R_3$ | D | No. | M.P. |
|---|---|---|---|---|---|---|
| 1417 | OH | H | $CH_3$ | 8 | | |
| 1418 | OH | H | H | 8 | | |
| 1419 | OH | H | $CH{=}CH_2$ | 8 | | |
| 1420 | OH | H | $CHOHCH_2OH$—(R) | 8 | | |
| 1421 | OH | H | $CHOHCH_2OH$—(S) | 8 | | |
| 1422 | OH | H | CHO | 8 | | |
| 1423 | OH | H | $CH_2OH$ | 8 | | |
| 1424 | OH | H | $CO_2H$ | 8 | | |
| 1425 | OH | H | $CO_2CH_3$ | 8 | | |
| 1426 | OH | H | CH=NOH | 8 | | |
| 1327 | OH | H | $CHOHCH{=}CH_2$—(R) | 8 | | |
| 1428 | OH | H | $CHOHCH{=}CH_2$—(S) | 8 | | |

TABLE 5-continued

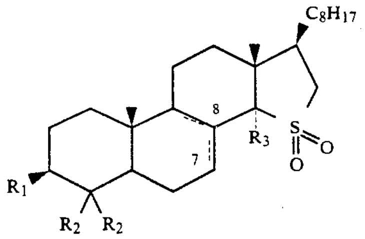

| Ex. No. | $R_1$ | $R_2$ | $R_3$ | D | No. | M.P. |
|---|---|---|---|---|---|---|
| 1429 | OH | $CH_3$ | $CH_2SH$ | 8 | | |
| 1430 | OH | $CH_3$ | $CH_2NH_2$ | 8 | | |
| 1431 | OH | $CH_3$ | $COCH_3$ | 8 | | |
| 1432 | OH | $CH_3$ | $CONH_2$ | 8 | | |
| 1433 | OH | $CH_3$ | $CSNH_2$ | 8 | | |
| 1434 | OH | $CH_3$ | $CH_2CH_2OH$ | 8 | | |
| 1435 | OH | $CH_3$ | $CH_3CHO$ | 8 | | |
| 1436 | OH | $CH_3$ | $CH_2COCH_3$ | 8 | | |
| 1437 | OH | $CH_3$ | $CH_2CO_2CH_3$ | 8 | | |
| 1438 | OH | $CH_3$ | $CH_2CONH_2$ | 8 | | |
| 1439 | OH | $CH_3$ | $CH_2Cl$ | 8 | | |
| 1440 | OH | $CH_3$ | $CH_2CH_2Cl$ | 8 | | |
| 1441 | OH | $CH_3$ | CN | 8 | | |
| 1442 | OH | $CH_3$ | $CH{=}NNH_2$ | 8 | | |
| 1443 | OH | $CH_3$ | $CH_2NHOH$ | 8 | | |
| 1444 | OH | $CH_3$ | $CH_2NHNH_2$ | 8 | | |
| 1445 | OH | $CH_3$ | $CH_2CN$ | 8 | | |
| 1446 | OH | $CH_3$ | $CH_2CH{=}NOH$ | 8 | | |
| 1447 | OH | $CH_3$ | $CH_2CH{=}NNH_2$ | 8 | | |
| 1448 | OH | $CH_3$ | $CH_2CH_2NHOH$ | 8 | | |
| 1449 | OH | $CH_3$ | $CH_2CH_2NHNH_2$ | 8 | | |
| 1450 | OH | $CH_3$ | CONHOH | 8 | | |
| 1451 | OH | $CH_3$ | $CH{=}CHCHO$ | 8 | | |
| 1452 | OH | $CH_3$ | $CH{=}CHCOCH_3$ | 8 | | |
| 1453 | OH | $CH_3$ | $CH_2CHOHCH_2OH$ | 8 | | |
| 1455 | OH | $CH_3$ | 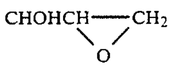 | 8 | | |
| 1456 | =O | $CH_3$ | $CH_3$ | 8 | | |
| 1457 | =O | $CH_3$ | CHO | 8 | | |
| 1458 | =O | $CH_3$ | $CH_2OH$ | 8 | | |
| 1459 | =O | H | $CH_3$ | 8 | | |
| 1460 | =O | H | CHO | 8 | | |
| 1461 | =O | H | $CH_2OH$ | 8 | | |
| 1462 | $OCH_3$ | $CH_3$ | $CH_3$ | 8 | | |
| 1463 | $OCH_3$ | $CH_3$ | CHO | 8 | | |
| 1464 | $OCH_3$ | $CH_3$ | $CH_2OH$ | 8 | | |
| 1465 | $OCH_3$ | H | $CH_3$ | 8 | | |
| 1466 | $OCH_3$ | H | CHO | 8 | | |
| 1467 | $OCH_3$ | H | $CH_2OH$ | 8 | | |
| 1468 | OPh | $CH_3$ | $CH_3$ | 8 | | |
| 1469 | OPh | $CH_3$ | CHO | 8 | | |
| 1470 | OPh | $CH_3$ | $CH_2OH$ | 8 | | |
| 1471 | $OCH_2Ph$ | $CH_3$ | $CH_3$ | 8 | | |
| 1472 | $OCH_2Ph$ | $CH_3$ | CHO | 8 | | |
| 1473 | $OCH_2Ph$ | $CH_3$ | $CH_2OH$ | 8 | | |
| 1474 | $OCOCH_3$ | $CH_3$ | $CH_3$ | 8 | | |
| 1475 | $OCOCH_3$ | $CH_3$ | CHO | 8 | | |
| 1476 | $OCOCH_3$ | $CH_3$ | $CH_2OH$ | 8 | | |
| 1477 | $OCOCH_3$ | H | $CH_3$ | 8 | | |
| 1478 | $OCOCH_3$ | H | CHO | 8 | | |
| 1479 | $OCOCH_3$ | H | $CH_2OH$ | 8 | | |
| 1480 | OCOPh | $CH_3$ | $CH_3$ | 8 | | |
| 1481 | OCOPh | $CH_3$ | CHO | 8 | | |
| 1482 | OCOPh | $CH_3$ | $CH_2OH$ | 8 | | |
| 1483 | OH | $CH_3$ | $CH_3$ | 7 | | |
| 1484 | OH | $CH_3$ | CHO | 7 | | |
| 1485 | OH | $CH_3$ | $CH_2OH$ | 7 | | |
| 1486 | OH | $CH_3$ | $CH_2H$ | 7 | | |

TABLE 5-continued

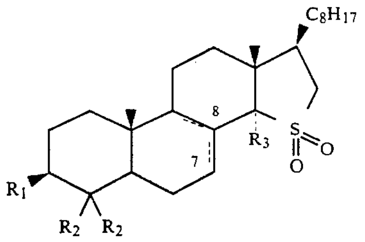

| Ex. No. | $R_1$ | $R_2$ | $R_3$ | D | No. | M.P. |
|---|---|---|---|---|---|---|
| 1487 | OH | H | $CH_3$ | 7 | | |
| 1488 | OH | H | CHO | 7 | | |
| 1489 | OH | H | $CH_2OH$ | 7 | | |
| 1490 | =O | $CH_3$ | $CH_3$ | 7 | | |
| 1491 | =O | $CH_3$ | CHO | 7 | | |
| 1492 | =O | $CH_3$ | $CH_2OH$ | 7 | | |
| 1493 | =O | H | $CH_3$ | 7 | | |
| 1494 | =O | H | CHO | 7 | | |
| 1495 | =O | H | $CH_2OH$ | 7 | | |
| 1496 | $OCH_3$ | $CH_3$ | $CH_3$ | 7 | | |
| 1497 | $OCH_3$ | $CH_3$ | CHO | 7 | | |
| 1498 | $OCH_3$ | $CH_3$ | $CH_2OH$ | 7 | | |
| 1499 | $OCH_3$ | H | $CH_3$ | 7 | | |
| 1500 | $OCH_3$ | H | CHO | 7 | | |
| 1501 | $OCH_3$ | H | $CH_2OH$ | 7 | | |
| 1502 | $OCOCH_3$ | $CH_3$ | $CH_3$ | 7 | | |
| 1503 | $OCOCH_3$ | $CH_3$ | CHO | 7 | | |
| 1504 | $OCOCH_3$ | $CH_3$ | $CH_2OH$ | 7 | | |
| 1505 | $OCOCH_3$ | H | $CH_3$ | 7 | | |
| 1506 | $OCOCH_3$ | H | CHO | 7 | | |
| 1507 | $OCOCH_3$ | H | $CH_2OH$ | 7 | | |

The six-membered 15-thia-D-homo-lanosterol derivatives have also been synthesized from the six-membered 15-thia-lanosterols synthesis. Treatment of the mixture of the cyclic acetal 7d with hydrogen sulfide and boron trifluoride etherate in methylene chloride followed by triethylsilane afforded the desired 15-thia-D-homo-dihydrolanosterl (57) in 44% yield (See, Scheme VII).

4,4-Dimethyl-15-thia-D-homo-5a-cholest-8-en-3b-ol (56) has also been prepared in the same manner from the compound 13d in 59.2% yield.

4,4-dimethyl-15-thia-14a-vinyl-D-homo-5a-cholest-8-en-3b-ol (58) may also be synthesized in the same manner from the corresponding cyclic acetal 19a or cyclic acetal 19d. Compounds 56, 57 and 58 constitute three additional examples within the scope of the present invention.

The 15-thia-D-homo-lanosterol 56 was reacted with sodium metaperiodate in 5 parts of ethanol and 1 part of water to provide the corresponding sulfoxide 59, also within the scope of the present invention. The 14-methyl and 14-vinyl derivatives 60 and 61, which are likewise within the scope of the present invention, may also be synthesized in the same manner.

As mentioned earlier in the 5-membered case, sulfones with the general structure 62, which are within the scope of the present invention may be synthesized from the corresponding sulfides or sulfoxides. Further functionalization at C-14 to prepare the compounds within the scope may also be achieved by converting the vinyl group of 58 to an aldehyde and carrying out other necessary chemistry as discussed in 15-oxa-lanosterol section, supra.

SCHEME VII

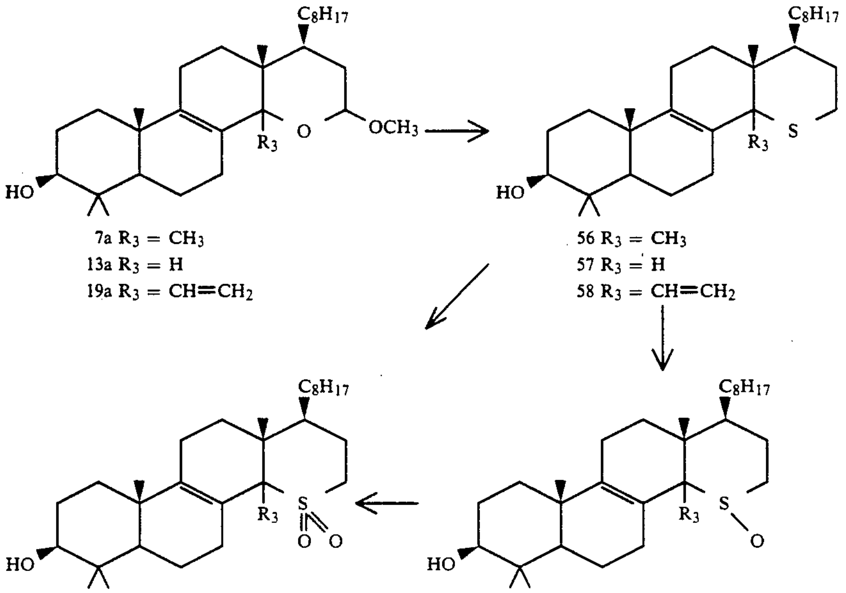

7a $R_3 = CH_3$
13a $R_3 = H$
19a $R_3 = CH{=}CH_2$

56 $R_3 = CH_3$
57 $R_3 = H$
58 $R_3 = CH{=}CH_2$

62

59 $R_3 = CH_3$
60 $R_3 = H$
61 $R_3 = CH{=}CH_2$

Tables 6, 7, and 8 set forth various thiasterols of the present invention.

TABLE 6

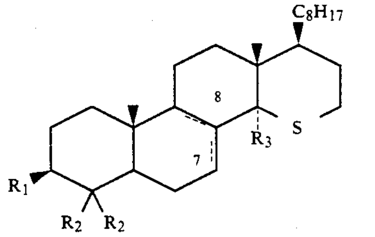

| Ex. No. | $R_1$ | $R_2$ | $R_3$ | D | No. | M.P. |
|---|---|---|---|---|---|---|
| 1508 | OH | $CH_3$ | $CH_3$ | 8 | 56 | amorphous* |
| 1509 | OH | $CH_3$ | H | 8 | 57 | amorphous* |
| 1510 | OH | $CH_3$ | $CH{=}CH_2$ | 8 | 58 | amorphous* |
| 1511 | OH | $CH_3$ | $CHOHCH_2OH{-}(R)$ | 8 | | |
| 1512 | OH | $CH_3$ | $CHOHCH_2OH{-}(S)$ | 8 | | |
| 1513 | OH | $CH_3$ | CHO | 8 | | |
| 1514 | OH | $CH_3$ | $CH_2OH$ | 8 | | |
| 1515 | OH | $CH_3$ | $CO_2H$ | 8 | | |
| 1516 | OH | $CH_3$ | $CH_2CH_3$ | 8 | | |
| 1517 | OH | $CH_3$ | $CH{=}NOH$ | 8 | | |
| 1518 | OH | $CH_3$ | $CHOHCH{-}CH_2{-}(R)$ | 8 | | |
| 1519 | OH | $CH_3$ | $CHOHCH{=}CH_2{-}(S)$ | 8 | | |
| 1520 | OH | H | $CH_3$ | 8 | | |
| 1521 | OH | H | H | 8 | | |
| 1522 | OH | H | $CH{=}CH_2$ | 8 | | |
| 1523 | OH | H | $CHOHCH_2OH{-}(R)$ | 8 | | |
| 1524 | OH | H | $CHOHCH_2OH{-}(S)$ | 8 | | |
| 1525 | OH | H | CHO | 8 | | |
| 1526 | OH | H | $CH_2OH$ | 8 | | |
| 1527 | OH | H | $CO_2H$ | 8 | | |
| 1528 | OH | H | $CO_2CH_3$ | 8 | | |
| 1529 | OH | H | $CH{=}NOH$ | 8 | | |
| 1530 | OH | H | $CHOHCH{=}CH_2{-}(R)$ | 8 | | |
| 1531 | OH | H | $CHOHCH{=}CH_2{-}(S)$ | 8 | | |
| 1532 | OH | $CH_3$ | $CH_2SH$ | 8 | | |
| 1533 | OH | $CH_3$ | $CH_2NH_2$ | 8 | | |
| 1534 | OH | $CH_3$ | $COCH_3$ | 8 | | |
| 1535 | OH | $CH_3$ | $CONH_2$ | 8 | | |
| 1536 | OH | $CH_3$ | $CSNH_2$ | 8 | | |
| 1537 | OH | $CH_3$ | $CH_2CH_2OH$ | 8 | | |

TABLE 6-continued

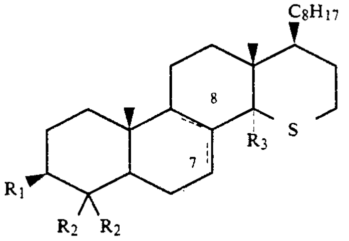

| Ex. No. | $R_1$ | $R_2$ | $R_3$ | D | No. | M.P. |
|---|---|---|---|---|---|---|
| 1538 | OH | $CH_3$ | $CH_2CHO$ | 8 | | |
| 1539 | OH | $CH_3$ | $CH_2COCH_3$ | 8 | | |
| 1540 | OH | $CH_3$ | $CH_2CO_2CH_3$ | 8 | | |
| 1541 | OH | $CH_3$ | $CH_2CONH_2$ | 8 | | |
| 1542 | OH | $CH_3$ | $CH_2Cl$ | 8 | | |
| 1543 | OH | $CH_3$ | $CH_2CH_2Cl$ | 8 | | |
| 1544 | OH | $CH_3$ | CN | 8 | | |
| 1545 | OH | $CH_3$ | $CH{=}NNH_2$ | 8 | | |
| 1546 | OH | $CH_3$ | $CH_2NHOH$ | 8 | | |
| 1547 | OH | $CH_3$ | $CH_2NHNH_2$ | 8 | | |
| 1548 | OH | $CH_3$ | $CH_2CN$ | 8 | | |
| 1549 | OH | $CH_3$ | $CH_2CH{=}NOH$ | 8 | | |
| 1550 | OH | $CH_3$ | $CH_2CH{=}NNH_2$ | 8 | | |
| 1551 | OH | $CH_3$ | $CH_2CH_2NHOH$ | 8 | | |
| 1552 | OH | $CH_3$ | $CH_2CH_2NHNH_2$ | 8 | | |
| 1553 | OH | $CH_3$ | CONHOH | 8 | | |
| 1554 | OH | $CH_3$ | $CH{=}CHCHO$ | 8 | | |
| 1555 | OH | $CH_3$ | $CH{=}CHOCH_3$ | 8 | | |
| 1556 | OH | $CH_3$ | $CH{=}CHCH_2Cl$ | 8 | | |
| 1557 | OH | $CH_3$ | $CH_2CHOHCH_2OH$ | 8 | | |
| 1558 | OH | $CH_3$ | 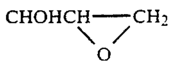 | 8 | | |
| 1560 | =O | $CH_3$ | CHO | 8 | | |
| 1561 | =O | $CH_3$ | $CH_2OH$ | 8 | | |
| 1562 | =O | H | $CH_3$ | 8 | | |
| 1563 | =O | H | CHO | 8 | | |
| 1564 | =O | H | $CH_2OH$ | 8 | | |
| 1565 | $OCH_3$ | $CH_3$ | $CH_3$ | 8 | | |
| 1566 | $OCH_3$ | $CH_3$ | CHO | 8 | | |
| 1567 | $OCH_3$ | $CH_3$ | $CH_2OH$ | 8 | | |
| 1568 | $OCH_3$ | H | $CH_3$ | 8 | | |
| 1569 | $OCH_3$ | H | CHO | 8 | | |
| 1570 | $OCH_3$ | H | $CH_2OH$ | 8 | | |
| 1571 | OPh | $CH_3$ | $CH_3$ | 8 | | |
| 1572 | OPh | $CH_3$ | CHO | 8 | | |
| 1573 | OPh | $CH_3$ | $CH_2OH$ | 8 | | |
| 1574 | $OCH_2Ph$ | $CH_3$ | $CH_3$ | 8 | | |
| 1575 | $OCH_2Ph$ | $CH_3$ | CHO | 8 | | |
| 1576 | $OCH_2Ph$ | $CH_3$ | $CH_2OH$ | 8 | | |
| 1577 | $OCOCH_3$ | $CH_3$ | $CH_3$ | 8 | | |
| 1578 | $OCOCH_3$ | $CH_3$ | CHO | 8 | | |
| 1579 | $OCOCH_3$ | $CH_3$ | $CH_2OH$ | 8 | | |
| 1580 | $OCOCH_3$ | H | $CH_3$ | 8 | | |
| 1581 | $OCOCH_3$ | H | CHO | 8 | | |
| 1582 | $OCOCH_3$ | H | $CH_2OH$ | 8 | | |
| 1583 | OCOPh | $CH_3$ | $CH_3$ | 8 | | |
| 1584 | OCOPh | $CH_3$ | CHO | 8 | | |
| 1585 | OCOPh | $CH_3$ | $CH_2OH$ | 8 | | |
| 1586 | OH | $CH_3$ | $CH_3$ | 7 | | |
| 1587 | OH | $CH_3$ | CHO | 7 | | |
| 1588 | OH | $CH_3$ | $CH_2OH$ | 7 | | |
| 1589 | OH | $CH_3$ | $CO_2H$ | 7 | | |
| 1590 | OH | H | $CH_3$ | 7 | | |
| 1591 | OH | H | CHO | 7 | | |
| 1592 | OH | H | $CH_2OH$ | 7 | | |
| 1593 | =O | $CH_3$ | $CH_3$ | 7 | | |
| 1594 | =O | $CH_3$ | CHO | 7 | | |
| 1595 | =O | $CH_3$ | $CH_2OH$ | 7 | | |
| 1596 | =O | H | $CH_3$ | 7 | | |
| 1597 | =O | H | CHO | 7 | | |
| 1598 | =O | H | $CH_2OH$ | 7 | | |
| 1599 | $OCH_3$ | $CH_3$ | $CH_3$ | 7 | | |
| 1600 | $OCH_3$ | $CH_3$ | CHO | 7 | | |
| 1601 | $OCH_3$ | $CH_3$ | $CH_2OH$ | 7 | | |
| 1602 | $OCH_3$ | H | $CH_3$ | 7 | | |

TABLE 6-continued

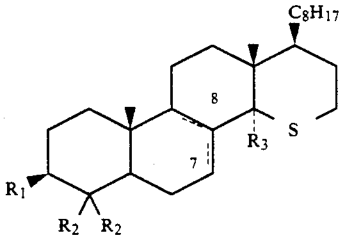

| Ex. No. | $R_1$ | $R_2$ | $R_3$ | D | No. | M.P. |
|---|---|---|---|---|---|---|
| 1603 | $OCH_3$ | H | CHO | 7 | | |
| 1604 | $OCH_3$ | H | $CH_2OH$ | 7 | | |
| 1605 | $OCOCH_3$ | $CH_3$ | $CH_3$ | 7 | | |
| 1606 | $OCOCH_3$ | $CH_3$ | CHO | 7 | | |
| 1607 | $OCOCH_3$ | $CH_3$ | $CH_2OH$ | 7 | | |
| 1608 | $OCOCH_3$ | H | $CH_3$ | 7 | | |
| 1609 | $OCOCH_3$ | H | CHO | 7 | | |
| 1610 | $OCOCH_3$ | H | $CH_2OH$ | 7 | | |

*Further analytical data are available in the examples section.

TABLE 7

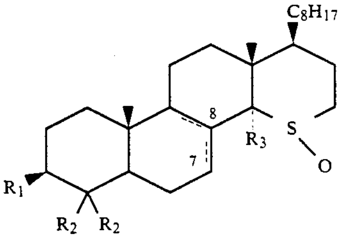

| No. | $R_1$ | $R_2$ | $R_3$ | D | No. | M. P. |
|---|---|---|---|---|---|---|
| 1611 | OH | $CH_3$ | $CH_3$ | 8 | 59 | amorphous* |
| 1612 | OH | $CH_3$ | H | 8 | 60 | amorphous* |
| 1613 | OH | $CH_3$ | $CH{=}CH_2$ | 8 | 61 | amorphous* |
| 1614 | OH | $CH_3$ | $CHOHCH_2OH$—(R) | 8 | | |
| 1615 | OH | $CH_3$ | $CHOHCH_2OH$—(S) | 8 | | |
| 1616 | OH | $CH_3$ | CHO | 8 | | |
| 1617 | OH | $CH_3$ | $CH_2OH$ | 8 | | |
| 1618 | OH | $CH_3$ | $CO_2H$ | 8 | | |
| 1619 | OH | $CH_3$ | $CO_2CH_3$ | 8 | | |
| 1620 | OH | $CH_3$ | CH=NOH | 8 | | |
| 1621 | OH | $CH_3$ | $CHOHCH{=}CH_2$—(R) | 8 | | |
| 1622 | OH | $CH_3$ | $CHOHCH{=}CH_2$—(S) | 8 | | |
| 1623 | OH | H | $CH_3$ | 8 | | |
| 1624 | OH | H | H | 8 | | |
| 1625 | OH | H | $CH{=}CH_2$ | 8 | | |
| 1626 | OH | H | $CHOHCH_2OH$—(R) | 8 | | |
| 1627 | OH | H | $CHOHCH_2OH$—(S) | 8 | | |
| 1628 | OH | H | CHO | 8 | | |
| 1629 | OH | H | $CH_2OH$ | 8 | | |
| 1630 | OH | H | $CO_2H$ | 8 | | |
| 1631 | OH | H | $CO_2CH_3$ | 8 | | |
| 1632 | OH | H | CH=NOH | 8 | | |
| 1633 | OH | H | $CHOHCH{=}CH_2$—(R) | 8 | | |
| 1634 | OH | H | $CHOHCH—CH_2$—(S) | 8 | | |
| 1635 | OH | $CH_3$ | $CH_2SH$ | 8 | | |
| 1636 | OH | $CH_3$ | $CH_2NH_2$ | 8 | | |
| 1637 | OH | $CH_3$ | $COCH_3$ | 8 | | |
| 1638 | OH | $CH_3$ | $CONH_2$ | 8 | | |
| 1639 | OH | $CH_3$ | $CSNH_2$ | 8 | | |
| 1640 | OH | $CH_3$ | $CH_2CH_2OH$ | 8 | | |
| 1641 | OH | $CH_3$ | $CH_2CHO$ | 8 | | |
| 1642 | OH | $CH_3$ | $CH_2COCH_3$ | 8 | | |
| 1643 | OH | $CH_3$ | $CH_2CO_2CH_3$ | 8 | | |
| 1644 | OH | $CH_3$ | $CH_2CONH_2$ | 8 | | |
| 1645 | OH | $CH_3$ | $CH_2Cl$ | 8 | | |
| 1646 | OH | $CH_3$ | $CH_2CH_2Cl$ | 8 | | |
| 1647 | OH | $CH_3$ | CN | 8 | | |
| 1648 | OH | $CH_3$ | $CH{=}NNH_2$ | 8 | | |
| 1649 | OH | $CH_3$ | $CH_2NHOH$ | 8 | | |
| 1650 | OH | $CH_3$ | $CH_2NHNH_2$ | 8 | | |
| 1651 | OH | $CH_3$ | $CH_2CN$ | 8 | | |
| 1652 | OH | $CH_3$ | $CH_2CH{=}NOH$ | 8 | | |

TABLE 7-continued

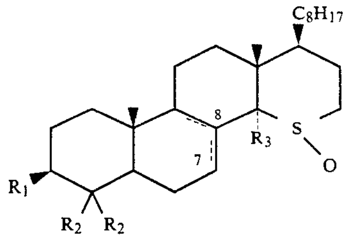

| No. | R1 | R2 | R3 | D | No. | M. P. |
|---|---|---|---|---|---|---|
| 1653 | OH | $CH_3$ | $CH_2CH{=}NNH_2$ | 8 | | |
| 1654 | OH | $CH_3$ | $CH_2CH_2NHOH$ | 8 | | |
| 1655 | OH | $CH_3$ | $CH_2CH_2NHNH_2$ | 8 | | |
| 1656 | OH | $CH_3$ | CONHOH | 8 | | |
| 1657 | OH | $CH_3$ | CH=CHCHO | 8 | | |
| 1658 | OH | $CH_3$ | $CH{=}CHCOCH_3$ | 8 | | |
| 1659 | OH | $CH_3$ | $CH{=}CHCH_2Cl$ | 8 | | |
| 1660 | OH | $CH_3$ | $CH_2CHOHCH_2OH$ | 8 | | |
| 1661 | OH | $CH_3$ | 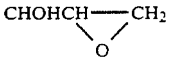 | 8 | | |
| 1662 | =O | $CH_3$ | $CH_3$ | 8 | | |
| 1663 | =O | $CH_3$ | CHO | 8 | | |
| 1664 | =O | $CH_3$ | $CH_2OH$ | 8 | | |
| 1665 | =O | H | $CH_3$ | 8 | | |
| 1666 | =O | H | CHO | 8 | | |
| 1667 | =O | H | $CH_2OH$ | 8 | | |
| 1668 | $OCH_3$ | $CH_3$ | $CH^3$ | 8 | | |
| 1669 | $OCH_3$ | $CH_3$ | CHO | 8 | | |
| 1670 | $OCH_3$ | $CH_3$ | $CH_2OH$ | 8 | | |
| 1671 | $OCH_3$ | H | $CH_3$ | 8 | | |
| 1672 | $OCH_3$ | H | CHO | 8 | | |
| 1673 | $OCH_3$ | H | $CH_2OH$ | 8 | | |
| 1674 | OPh | $CH_3$ | $CH_3$ | 8 | | |
| 1675 | OPh | $CH_3$ | CHO | 8 | | |
| 1676 | OPh | $CH_3$ | $CH_2OH$ | 8 | | |
| 1677 | $OCH_2Ph$ | $CH_3$ | $CH_3$ | 8 | | |
| 1678 | $OCH_2Ph$ | $CH_3$ | CHO | 8 | | |
| 1679 | $OCH_2Ph$ | $CH_3$ | $CH_2OH$ | 8 | | |
| 1680 | $OCOCH_3$ | $CH_3$ | $CH_3$ | 8 | | |
| 1681 | $OCOCH_3$ | $CH_3$ | CHO | 8 | | |
| 1682 | $OCOCH_3$ | $CH_3$ | $CH_2OH$ | 8 | | |
| 1683 | $OCOCH_3$ | H | $CH_3$ | 8 | | |
| 1684 | $OCOCH_3$ | H | CHO | 8 | | |
| 1685 | $OCOCH_3$ | H | $CH_2OH$ | 8 | | |
| 1686 | OCOPh | $CH_3$ | $CH_3$ | 8 | | |
| 1687 | OCOPh | $CH_3$ | CHO | 8 | | |
| 1688 | OCOPh | $CH_3$ | $CH_2OH$ | 8 | | |
| 1689 | OH | $CH_3$ | $CH_3$ | 7 | | |
| 1690 | OH | $CH_3$ | CHO | 7 | | |
| 1691 | OH | $CH_3$ | $CH_2OH$ | 7 | | |
| 1692 | OH | $CH_3$ | $CO_2H$ | 7 | | |
| 1693 | OH | H | $CH_3$ | 7 | | |
| 1694 | OH | H | CHO | 7 | | |
| 1695 | OH | H | $CH_2OH$ | 7 | | |
| 1696 | =O | $CH_3$ | $CH_3$ | 7 | | |
| 1697 | =O | $CH_3$ | CHO | 7 | | |
| 1698 | =O | $CH_3$ | $CH_2OH$ | 7 | | |
| 1699 | =O | H | $CH_3$ | 7 | | |
| 1700 | =O | H | CHO | 7 | | |
| 1701 | =O | H | $CH_2OH$ | 7 | | |
| 1702 | $OCH_3$ | $CH_3$ | $CH_3$ | 7 | | |
| 1703 | $OCH_3$ | $CH_3$ | CHO | 7 | | |
| 1704 | $OCH_3$ | $CH_3$ | $CH_2OH$ | 7 | | |
| 1705 | $OCH_3$ | H | $CH_3$ | 7 | | |
| 1706 | $OCH_3$ | H | CHO | 7 | | |
| 1707 | $OCH_3$ | H | $CH_2OH$ | 7 | | |
| 1708 | $OCOCH_3$ | $CH_3$ | $CH_3$ | 7 | | |
| 1709 | $OCOCH_3$ | $CH_3$ | CHO | 7 | | |
| 1710 | $OCOCH_3$ | $CH_3$ | $CH_2OH$ | 7 | | |
| 1711 | $OCOCH_3$ | H | $CH_3$ | 7 | | |
| 1712 | $OCOCH_3$ | H | CHO | 7 | | |
| 1713 | $OCOCH_3$ | H | $CH_2OH$ | 7 | | |

*Further analytical data are available in the examples section.

TABLE 8

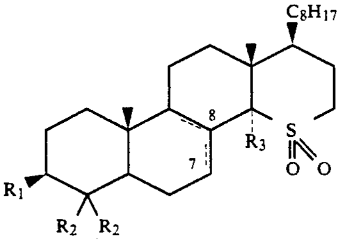

TABLE 8-continued

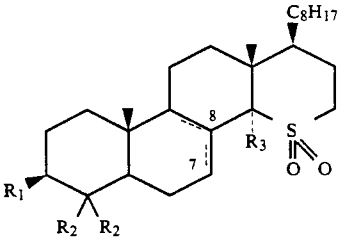

| No. | $R_1$ | $R_2$ | $R_3$ | D | No. | M.P. |
|---|---|---|---|---|---|---|
| 1714 | OH | $CH_3$ | $CH_3$ | 8 | | |
| 1715 | OH | $CH_3$ | H | 8 | | |
| 1716 | OH | $CH_3$ | $CH=CH_2$ | 8 | | |
| 1717 | OH | $CH_3$ | $CHOHCH_2OH$—(R) | 8 | | |
| 1718 | OH | $CH_3$ | $CHOHCH_2OH$—(S) | 8 | | |
| 1719 | OH | $CH_3$ | CHO | 8 | | |
| 1720 | OH | $CH_3$ | $CH_2OH$ | 8 | | |
| 1721 | OH | $CH_3$ | $CO_2H$ | 8 | | |
| 1722 | OH | $CH_3$ | $CO_2CH_3$ | 8 | | |
| 1723 | OH | $CH_3$ | $CH=NOH$ | 8 | | |
| 1724 | OH | $CH_3$ | $CHOHCH=CH_2$—(R) | 8 | | |
| 1725 | OH | $CH_3$ | $CHOHCH=CH_2$—(S) | 8 | | |
| 1726 | OH | H | $CH_3$ | 8 | | |
| 1727 | OH | H | H | 8 | | |
| 1728 | OH | H | $CH=CH_2$ | 8 | | |
| 1729 | OH | H | $CHOHCH_2OH$—(R) | 8 | | |
| 1730 | OH | H | $CHOHCH_2OH$—(S) | 8 | | |
| 1731 | OH | H | CHO | 8 | | |
| 1732 | OH | H | $CH_2OH$ | 8 | | |
| 1733 | OH | H | $CO_2H$ | 8 | | |
| 1734 | OH | H | $CO_2CH_3$ | 8 | | |
| 1735 | OH | H | $CH=NOH$ | 8 | | |
| 1736 | OH | H | $CHOHCH=CH_2$—(R) | 8 | | |
| 1737 | OH | H | $CHOHCH=CH_2$—(S) | 8 | | |
| 1738 | OH | $CH_3$ | $CH_2SH$ | 8 | | |
| 1739 | OH | $CH_3$ | $CH_2NH_2$ | 8 | | |
| 1740 | OH | $CH_3$ | $COCH_3$ | 8 | | |
| 1741 | OH | $CH_3$ | $CONH_2$ | 8 | | |
| 1742 | OH | $CH_3$ | $CSNH_2$ | 8 | | |
| 1743 | OH | $CH_3$ | $CH_2CH_2OH$ | 8 | | |
| 1744 | OH | $CH_3$ | $CH_2CHO$ | 8 | | |
| 1745 | OH | $CH_3$ | $CH_2COCH_3$ | 8 | | |
| 1746 | OH | $CH_3$ | $CH_2CO_2CH_3$ | 8 | | |
| 1747 | OH | $CH_3$ | $CH_2CONH_2$ | 8 | | |
| 1748 | OH | $CH_3$ | $CH_2Cl$ | 8 | | |
| 1749 | OH | $CH_3$ | $CH_2CH_2Cl$ | 8 | | |
| 1750 | OH | $CH_3$ | CN | 8 | | |
| 1751 | OH | $CH_3$ | $CH=NNH_2$ | 8 | | |
| 1752 | OH | $CH_3$ | $CH_2NHOH$ | 8 | | |
| 1753 | OH | $CH_3$ | $CH_2NHNH_2$ | 8 | | |
| 1754 | OH | $CH_3$ | $CH_2CN$ | 8 | | |
| 1755 | OH | $CH_3$ | $CH_2CH=NOH$ | 8 | | |
| 1756 | OH | $CH_3$ | $CH_2CH=NNH_2$ | 8 | | |
| 1757 | OH | $CH_3$ | $CH_2CH_2NHOH$ | 8 | | |
| 1758 | OH | $CH_3$ | $CH_2CH_2NHNH_2$ | 8 | | |
| 1759 | OH | $CH_3$ | CONHOH | 8 | | |
| 1760 | OH | $CH_3$ | $CH=CHCHO$ | 8 | | |
| 1761 | OH | $CH_3$ | $CH=CHCOCH_3$ | 8 | | |
| 1762 | OH | $CH_3$ | $CH=CHCH_2Cl$ | 8 | | |
| 1763 | OH | $CH_3$ | $CH_2CHOHCH_2OH$ | 8 | | |
| 1764 | OH | $CH_3$ | 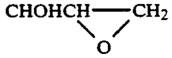 | 8 | | |
| 1765 | =O | $CH_3$ | $CH_3$ | 8 | | |
| 1766 | =O | $CH_3$ | CHO | 8 | | |
| 1767 | =O | $CH_3$ | $CH_2OH$ | 8 | | |
| 1768 | =O | H | $CH_3$ | 8 | | |
| 1769 | =O | H | CHO | 8 | | |
| 1770 | =O | H | $CH_2OH$ | 8 | | |
| 1771 | $OCH_3$ | $CH_3$ | $CH_3$ | 8 | | |
| 1772 | $OCH_3$ | $CH_3$ | CHO | 8 | | |
| 1773 | $OCH_3$ | $CH_3$ | $CH_2OH$ | 8 | | |
| 1774 | $OCH_3$ | H | $CH_3$ | 8 | | |
| 1775 | $OCH_3$ | H | CHO | 8 | | |
| 1776 | $OCH_3$ | H | $CH_2OH$ | 8 | | |
| 1777 | OPh | $CH_3$ | $CH_3$ | 8 | | |
| 1778 | OPh | $CH_3$ | CHO | 8 | | |
| 1779 | OPh | $CH_3$ | $CH_2OH$ | 8 | | |
| 1780 | $OCH_2Ph$ | $CH_3$ | $CH_3$ | 8 | | |
| 1781 | $OCH_2Ph$ | $CH_3$ | CHO | 8 | | |
| 1782 | $OCH_2Ph$ | $CH_3$ | $CH_2OH$ | 8 | | |
| 1783 | $OCOCH_3$ | $CH_3$ | $CH_3$ | 8 | | |
| 1784 | $OCOCH_3$ | $CH_3$ | CHO | 8 | | |
| 1785 | $OCOCH_3$ | $CH_3$ | $CH_2OH$ | 8 | | |
| 1786 | $OCOCH_3$ | H | $CH_3$ | 8 | | |
| 1787 | $OCOCH_3$ | H | CHO | 8 | | |
| 1788 | $OCOCH_3$ | H | $CH_2OH$ | 8 | | |
| 1789 | OCOPh | $CH_3$ | $CH_3$ | 8 | | |
| 1790 | OCOPh | $CH_3$ | CHO | 8 | | |
| 1791 | OCOPh | $CH_3$ | $CH_2OH$ | 8 | | |
| 1792 | OH | $CH_3$ | $CH_3$ | 7 | | |
| 1793 | OH | $CH_3$ | CHO | 7 | | |
| 1794 | OH | $CH_3$ | $CH_2OH$ | 7 | | |
| 1795 | OH | $CH_3$ | $CO_2H$ | 7 | | |
| 1796 | OH | H | $CH_3$ | 6 | | |
| 1797 | OH | H | CHO | 7 | | |
| 1798 | OH | H | $CH_2OH$ | 7 | | |
| 1799 | =O | $CH_3$ | $CH_3$ | 7 | | |
| 1800 | =O | $CH_3$ | CHO | 7 | | |
| 1801 | =O | $CH_3$ | $CH_2OH$ | 7 | | |
| 1802 | =O | H | $CH_3$ | 7 | | |
| 1803 | =O | H | CHO | 7 | | |
| 1804 | =O | H | $CH_2OH$ | 7 | | |
| 1805 | $OCH_3$ | $CH_3$ | $CH_3$ | 7 | | |
| 1806 | $OCH_3$ | $CH_3$ | CHO | 7 | | |
| 1807 | $OCH_3$ | $CH_3$ | $CH_2OH$ | 7 | | |
| 1808 | $OCH_3$ | H | $CH_3$ | 7 | | |
| 1809 | $OCH_3$ | H | CHO | 7 | | |
| 1810 | $OCH_3$ | H | $CH_2OH$ | 7 | | |
| 1811 | $OCOCH_3$ | $CH_3$ | $CH_3$ | 7 | | |
| 1812 | $OCOCH_3$ | $CH_3$ | CHO | 7 | | |
| 1813 | $OCOCH_3$ | $CH_3$ | $CH_2OH$ | 7 | | |
| 1814 | $OCOCH_3$ | H | $CH_3$ | 7 | | |
| 1815 | $OCOCH_3$ | H | CHO | 7 | | |
| 1816 | $OCOCH_3$ | H | $CH_2OH$ | 7 | | |

15-Azasterols

Because the same chemistry could not be utilized for 15-azasterols as was used for 15-oxasterols and 15-thiasterols, a new synthetic route, which involves a Curtis rearrangement as the key step, has been developed for 15-aza-lanosterols.

Thus the enone-aldehyde 4b was oxidized with sodium chlorite (Aldrich) in the presence of sulfamic acid (Fisher) in 4 parts of tertiary butanol and 1 part of water to afford the corresponding carboxylic acid 63 in near quantitative yield (See, Scheme VIII).

The acid 63 was converted to an acyl azide under phase transfer catalysis conditions. It was first treated with isobutyl chloroformate (Aldrich) and N-methylmorpholine (Aldrich) in dry methylene chloride and then the intermediate mixed anhydride was reacted with sodium azide (Fisher) and tetrabutylammonium bromide (Aldrich) in methylene chloride and water to give acyl azide 64 in quantitative yield.

A Curtis rearrangement of the acyl azide 64 in a refluxing mixture of ethyl acetate and methanol (1:5)

provided the corresponding carbamate 65 which was pure enough to be carried onto the next reaction. The carbamate 65 was hydrolyzed with potassium silanoate (Petrach Systems, Bristol, Pa. 19007) in refluxing tetrahydrofuran to give a five-membered cyclic imine 66b in 73% overall yield for six steps starting from the 8,14-diene 2b.

Finally the p-methoxybenzyl protecting group at C-3 was cleaved by treating with allyltrimethylsilane and boron trifluoride etherate in methylene chloride to afford the unprotected 15-azasterol 66a, a compound within the scope of this invention, in 93% yield.

SCHEME VIII

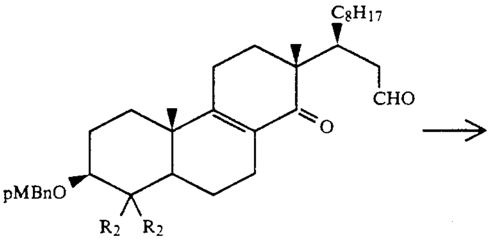

4b $R_2 = CH_3$
40 $R_2 = H$

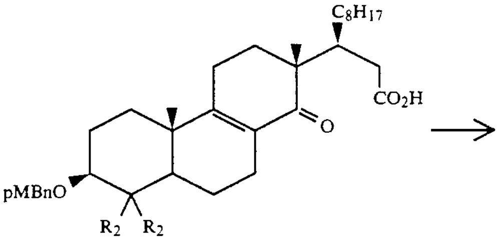

63 $R_2 = CH_3$
67 $R_2 = H$

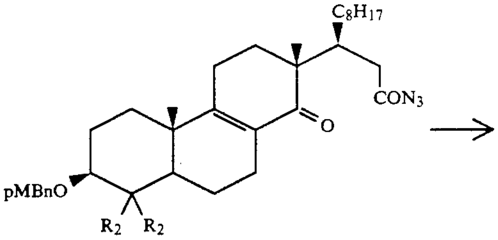

64 $R_2 = CH_3$
68 $R_2 = H$

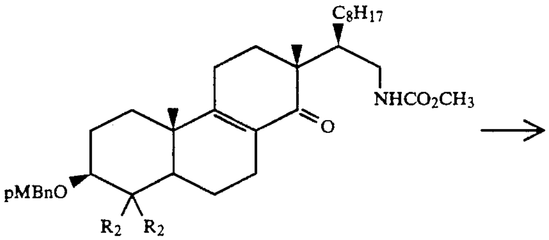

65 $R_2 = CH_3$
69 $R_2 = H$

-continued
SCHEME VIII

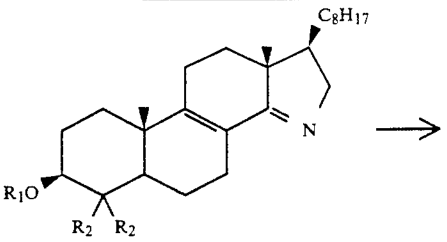

66a $R_1 = H$, $R_2 = CH_3$
66b $R_1 = pMBn$, $R_2 = CH_3$
70a $R_1 = H$, $R_2 = H$
70b $R_1 = pMBn$, $R_2 = H$

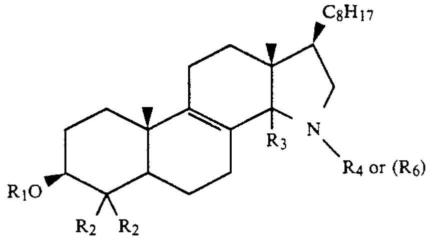

71

A bis-4,4-normethyl 15-azasterol ($R_2$ of the general structure 1 is H) has also been synthesized from the enone-aldehyde 40 by following the sequence of the reaction steps described in the synthesis of 15-azasterol 66a. Oxidation of the aldehyde 40 followed by acyl azide formation, Curtis rearrangement and hydrolysis of carbamate provided the protected 15-azasterol 70b in 61% overall yield for six steps starting from the 8,14-diene 38b. Deprotection of 70b at C-3 gave compound 70a in 96% yield based on the recovered starting material 70b. Compound 70a is another example of a 15-azalanosterol within the scope of the present invention.

Further functionalizations at the 14 and 15 positions of 15-azasterol may be achieved by a reduction or an addition to the imine followed by appropriate transformations to synthesize additional compounds within the scope, which have general structure 71 in the scheme.

Tables 9-13 set forth various azasterols of the present invention.

TABLE 9

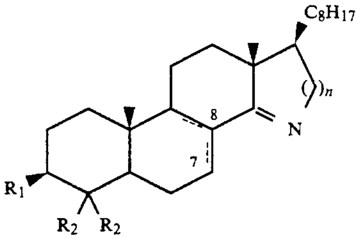

| No. | $R_1$ | $R_2$ | D | n* | No. | M.P. |
|---|---|---|---|---|---|---|
| 1817 | OH | $CH_3$ | 8 | 1 | 66a | |
| 1818 | OH | H | 8 | 1 | 70a | |
| 1819 | OH | $C_2H_5$ | 8 | 1 | | |
| 1820 | =O | $CH_3$ | 8 | 1 | | |
| 1821 | =O | H | 8 | 1 | | |
| 1822 | =O | $C_2H_5$ | 8 | 1 | | |
| 1823 | $OCH_3$ | $CH_3$ | 8 | 1 | | |
| 1824 | $OCH_3$ | H | 8 | 1 | | |
| 1825 | $OCH_3$ | $C_2H_5$ | 8 | 1 | | |
| 1826 | $OC_2H_5$ | $CH_3$ | 8 | 1 | | |
| 1827 | $OC_2H_5$ | H | 8 | 1 | | |

TABLE 9-continued

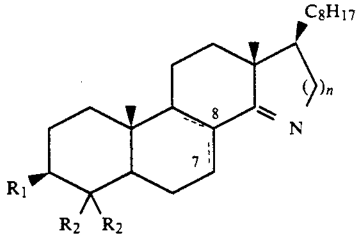

| No. | $R_1$ | $R_2$ | D | n* | No. | M.P. |
|---|---|---|---|---|---|---|
| 1828 | $OC_2H_5$ | $C_2H_5$ | 8 | 1 | | |
| 1829 | $OC_3H_7$ | $CH_3$ | 8 | 1 | | |
| 1830 | $OC_3H_7$ | H | 8 | 1 | | |
| 1831 | $OC_3H_7$ | $C_2H_5$ | 8 | 1 | | |
| 1832 | Oi-$C_3H_7$ | $CH_3$ | 8 | 1 | | |
| 1833 | Oi-$C_3H_7$ | H | 8 | 1 | | |
| 1834 | Oi-$C_3H_7$ | $C_2H_5$ | 8 | 1 | | |
| 1835 | $OC_4H_9$ | $CH_3$ | 8 | 1 | | |
| 1836 | $OC_4H_9$ | H | 8 | 1 | | |
| 1837 | $OC_4H_9$ | $C_2H_5$ | 8 | 1 | | |
| 1838 | Oi-$C_4H_9$ | $CH_3$ | 8 | 1 | | |
| 1939 | Oi-$C_4H_9$ | H | 8 | 1 | | |
| 1840 | Oi-$C_4H_9$ | $C_2H_5$ | 8 | 1 | | |
| 1841 | Ot-$C_4H_9$ | $CH_3$ | 8 | 1 | | |
| 1842 | Ot-$C_4H_9$ | H | 8 | 1 | | |
| 1843 | Ot-$C_4H_9$ | $C_2H_5$ | 8 | 1 | | |
| 1844 | OPh | $CH_3$ | 8 | 1 | | |
| 1845 | OPh | H | 8 | 1 | | |
| 1846 | OPh | $C_2H_5$ | 8 | 1 | | |
| 1847 | $OCH_2Ph$ | $CH_3$ | 8 | 1 | | |
| 1848 | $OCH_2Ph$ | H | 8 | 1 | | |
| 1849 | $OCH_2Ph$ | $C_2H_5$ | 8 | 1 | | |
| 1850 | OCOH | $CH_3$ | 8 | 1 | | |
| 1851 | OCOH | H | 8 | 1 | | |
| 1852 | OCOH | $C_2H_5$ | 8 | 1 | | |
| 1853 | $OCOCH_3$ | $CH_3$ | 8 | 1 | | |
| 1854 | $OCOCH_3$ | H | 8 | 1 | | |
| 1855 | $OCOCH_3$ | $C_2H_5$ | 8 | 1 | | |
| 1856 | $OCOC_2H_5$ | $CH_3$ | 8 | 1 | | |
| 1857 | $OCOC_2H_5$ | H | 8 | 1 | | |
| 1858 | $OCOC_2H_5$ | $C_2H_5$ | 8 | 1 | | |
| 1859 | $OCOC_3H_7$ | $CH_3$ | 8 | 1 | | |
| 1860 | $OCOC_3H_7$ | H | 8 | 1 | | |
| 1861 | $OCOC_3H_7$ | $C_2H_5$ | 8 | 1 | | |
| 1862 | OCOi-$C_3H_7$ | $CH_3$ | 8 | 1 | | |
| 1863 | OCOi-$C_3H_7$ | H | 8 | 1 | | |
| 1864 | OCOi-$C_3H_7$ | $C_2H_5$ | 8 | 1 | | |
| 1865 | $OCOC_4H_9$ | $CH_3$ | 8 | 1 | | |
| 1866 | $OCOC_4H_9$ | H | 8 | 1 | | |
| 1867 | $OCOC_4H_9$ | $C_2H_5$ | 8 | 1 | | |
| 1868 | OCOi-$C_4H_9$ | $CH_3$ | 8 | 1 | | |
| 1869 | OCOi-$C_4H_9$ | H | 8 | 1 | | |
| 1870 | OCOi-$C_4H_9$ | $C_2H_5$ | 8 | 1 | | |
| 1871 | OCOt-$C_4H_9$ | $CH_3$ | 8 | 1 | | |
| 1872 | OCOt-$C_4H_9$ | H | 8 | 1 | | |
| 1873 | OCOt-$C_4H_9$ | $C_2H_5$ | 8 | 1 | | |
| 1874 | $OCOC_{15}H_{31}$ | $CH_3$ | 8 | 1 | | |
| 1875 | $OCOC_{15}H_{31}$ | H | 8 | 1 | | |
| 1876 | $OCOC_{15}H_{31}$ | $C_2H_5$ | 8 | 1 | | |
| 1877 | $OCOC_{15}H_{29}$ | $CH_3$ | 8 | 1 | | |
| 1878 | $OCOC_{15}H_{29}$ | H | 8 | 1 | | |
| 1879 | $OCOC_{15}H_{29}$ | $C_2H_5$ | 8 | 1 | | |
| 1880 | $OCOC_{17}H_{35}$ | $CH_3$ | 8 | 1 | | |
| 1881 | $OCOC_{17}H_{35}$ | H | 8 | 1 | | |
| 1882 | $OCOC_{17}H_{35}$ | $C_2H_5$ | 8 | 1 | | |
| 1883 | $OCOC_{17}H_{33}$ | $CH_3$ | 8 | 1 | | |
| 1884 | $OCOC_{17}H_{33}$ | H | 8 | 1 | | |
| 1885 | $OCOC_{17}H_{33}$ | $C_2H_5$ | 8 | 1 | | |
| 1886 | $OCOC_{17}H_{31}$ | $CH_3$ | 8 | 1 | | |
| 1887 | $OCOC_{17}H_{31}$ | H | 8 | 1 | | |
| 1888 | $OCOC_{17}H_{31}$ | $C_2H_5$ | 8 | 1 | | |
| 1889 | $OCOC_{17}H_{29}$ | $CH_3$ | 8 | 1 | | |
| 1890 | $OCOC_{17}H_{29}$ | H | 8 | 1 | | |
| 1891 | $OCOC_{17}H_{29}$ | $C_2H_5$ | 8 | 1 | | |
| 1892 | $OCOC_{19}4_{31}$ | $CH_3$ | 8 | 1 | | |
| 1893 | $OCOC_{19}H_{31}$ | H | 8 | 1 | | |
| 1894 | $OCOC_{19}H_{31}$ | $C_2H_5$ | 8 | 1 | | |
| 1895 | OCOPh | $CH_3$ | 8 | 1 | | |
| 1896 | OCOPh | H | 8 | 1 | | |

TABLE 9-continued

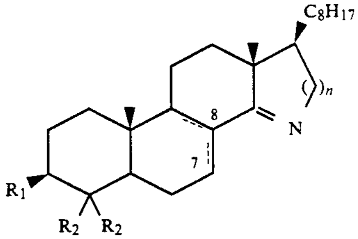

| No. | $R_1$ | $R_2$ | D | n* | No. | M.P. |
|---|---|---|---|---|---|---|
| 1897 | OCOPh | $C_2H_5$ | 8 | 1 | | |
| 1898 | OH | $CH_3$ | 8 | 1 | | |
| 1899 | OH | H | 7 | 1 | | |
| 1900 | OH | $C_2H_5$ | 7 | 1 | | |
| 1901 | =O | $CH_3$ | 7 | 1 | | |
| 1902 | =O | H | 7 | 1 | | |
| 1903 | =O | $C_2H_5$ | 7 | 1 | | |
| 1904 | $OCH_3$ | $CH_3$ | 7 | 1 | | |
| 1905 | $OCH_3$ | H | 7 | 1 | | |
| 1906 | $OCH_3$ | $C_2H_5$ | 7 | 1 | | |
| 1907 | $OC_2H_5$ | $CH_3$ | 7 | 1 | | |
| 1908 | $OC_2H_5$ | H | 7 | 1 | | |
| 1909 | $OC_2H_5$ | $C_2H_5$ | 7 | 1 | | |
| 1910 | $OC_3H_7$ | $CH_3$ | 7 | 1 | | |
| 1911 | $OC_3H_7$ | H | 7 | 1 | | |
| 1912 | $OC_3H_7$ | $C_2H_5$ | 7 | 1 | | |
| 1913 | Oi-$C_3H_7$ | $CH_3$ | 7 | 1 | | |
| 1914 | Oi-$C_3H_7$ | H | 7 | 1 | | |
| 1915 | Oi-$C_3H_7$ | $C_2H_5$ | 7 | 1 | | |
| 1916 | $OC_4H_9$ | $CH_3$ | 7 | 1 | | |
| 1917 | $OC_4H_9$ | H | 7 | 1 | | |
| 1918 | $OC_4H_9$ | $C_2H_5$ | 7 | 1 | | |
| 1919 | Oi-$C_4H_9$ | $CH_3$ | 7 | 1 | | |
| 1920 | Oi-$C_4H_9$ | H | 7 | 1 | | |
| 1921 | Oi-$C_4H_9$ | $C_2H_5$ | 7 | 1 | | |
| 1922 | Ot-$C_4H_9$ | $CH_3$ | 7 | 1 | | |
| 1923 | Ot-$C_4H_9$ | H | 7 | 1 | | |
| 1924 | Ot-$C_4H_9$ | $C_2H_5$ | 7 | 1 | | |
| 1925 | OPh | $CH_3$ | 7 | 1 | | |
| 1926 | OPh | H | 7 | 1 | | |
| 1927 | OPh | $C_2H_5$ | 7 | 1 | | |
| 1928 | $OCH_2Ph$ | $CH_3$ | 7 | 1 | | |
| 1929 | $OCH_2Ph$ | H | 7 | 1 | | |
| 1930 | $OCH_2Ph$ | $C_2H_5$ | 7 | 1 | | |
| 1931 | OCOH | $CH_3$ | 7 | 1 | | |
| 1932 | OCOH | H | 7 | 1 | | |
| 1933 | OCOH | $C_2H_5$ | 7 | 1 | | |
| 1934 | $OCOCH_3$ | $CH_3$ | 7 | 1 | | |
| 1935 | $OCOCH_3$ | H | 7 | 1 | | |
| 1936 | $OCOCH_3$ | $C_2H_5$ | 7 | 1 | | |
| 1937 | $OCOC_2H_5$ | $CH_3$ | 7 | 1 | | |
| 1938 | $OCOC_2H_5$ | H | 7 | 1 | | |
| 1939 | $OCOC_2H_5$ | $C_2H_5$ | 7 | 1 | | |
| 1940 | $OCOC_3H_7$ | $CH_3$ | 7 | 1 | | |
| 1941 | $OCOC_3H_7$ | H | 7 | 1 | | |
| 1942 | $OCOC_3H_7$ | $C_2H_5$ | 7 | 1 | | |
| 1943 | OCOi-$C_3H_7$ | $CH_3$ | 7 | 1 | | |
| 1944 | OCOi-$C_3H_7$ | H | 7 | 1 | | |
| 1945 | OCOi-$C_3H_7$ | $C_2H_5$ | 7 | 1 | | |
| 1946 | $OCOC_4H_9$ | $CH_3$ | 7 | 1 | | |
| 1947 | $OCOC_4H_9$ | H | 7 | 1 | | |
| 1948 | $OCOC_4H_9$ | $C_2H_5$ | 7 | 1 | | |
| 1949 | OCOi-$C_4H_9$ | $CH_3$ | 7 | 1 | | |
| 1950 | OCOi-$C_4H_9$ | H | 7 | 1 | | |
| 1951 | OCOi-$C_4H_9$ | $C_2H_5$ | 7 | 1 | | |
| 1952 | OCOt-$C_4H_9$ | $CH_3$ | 7 | 1 | | |
| 1953 | OCOt-$C_4H_9$ | H | 7 | 1 | | |
| 1954 | OCOt-$C_4H_9$ | $C_2H_5$ | 7 | 1 | | |
| 1955 | $OCOC_{15}H_{31}$ | $CH_3$ | 7 | 1 | | |
| 1956 | $OCOC_{15}H_{31}$ | H | 7 | 1 | | |
| 1957 | $OCOC_{15}H_{31}$ | $C_2H_5$ | 7 | 1 | | |
| 1958 | $OCOC_{15}H_{29}$ | $CH_3$ | 7 | 1 | | |
| 1959 | $OCOC_{15}H_{29}$ | H | 7 | 1 | | |
| 1960 | $OCOC_{15}H_{29}$ | $C_2H_5$ | 7 | 1 | | |
| 1961 | $OCOC_{17}H_{35}$ | $CH_3$ | 7 | 1 | | |
| 1962 | $OCOC_{17}H_{35}$ | H | 7 | 1 | | |
| 1963 | $OCOC_{17}H_{35}$ | $C_2H_5$ | 7 | 1 | | |
| 1964 | $OCOC_{17}H_{33}$ | $CH_3$ | 7 | 1 | | |
| 1965 | $OCOC_{17}H_{33}$ | H | 7 | 1 | | |

TABLE 9-continued

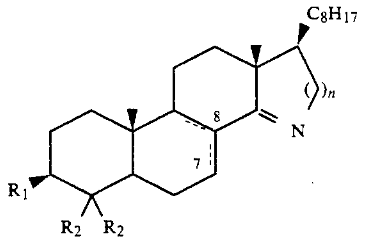

| No. | $R_1$ | $R_2$ | D | n* | No. | M.P. |
|---|---|---|---|---|---|---|
| 1966 | $OCOC_{17}H_{33}$ | $C_2H_5$ | 7 | 1 | | |
| 1967 | $OCOC_{17}H_{31}$ | $CH_3$ | 7 | 1 | | |
| 1968 | $OCOC_{17}H_{31}$ | H | 7 | 1 | | |
| 1969 | $OCOC_{17}H_{31}$ | $C_2H_5$ | 7 | 1 | | |
| 1970 | $OCOC_{17}H_{29}$ | $CH_3$ | 7 | 1 | | |
| 1971 | $OCOC_{17}H_{29}$ | H | 7 | 1 | | |
| 1972 | $OCOC_{17}H_{29}$ | $C_2H_5$ | 7 | 1 | | |
| 1973 | $OCOC_{19}H_{31}$ | $CH_3$ | 7 | 1 | | |
| 1974 | $OCOC_{19}H_{31}$ | H | 7 | 1 | | |
| 1975 | $OCOC_{19}H_{31}$ | $C_2H_5$ | 7 | 1 | | |
| 1976 | OCOPh | $CH_3$ | 7 | 1 | | |
| 1977 | OCOPh | H | 7 | 1 | | |
| 1978 | OCOPh | $C_2H_5$ | 7 | 1 | | |
| 1979 | OH | $CH_3$ | 8 | 2 | | |
| 1980 | OH | H | 8 | 2 | | |
| 1981 | OH | $C_2H_5$ | 8 | 2 | | |
| 1982 | =O | $CH_3$ | 8 | 2 | | |
| 1983 | =O | H | 8 | 2 | | |
| 1984 | =O | $C_2H_5$ | 8 | 2 | | |
| 1985 | $OCH_3$ | $CH_3$ | 8 | 2 | | |
| 1986 | $OCH_3$ | H | 8 | 2 | | |
| 1987 | $OCH_3$ | $C_2H_5$ | 8 | 2 | | |
| 1988 | $OC_2H_5$ | $CH_3$ | 8 | 2 | | |
| 1989 | $OC_2H_5$ | H | 8 | 2 | | |
| 1990 | $OC_2H_5$ | $C_2H_5$ | 8 | 2 | | |
| 1991 | $OC_3H_7$ | $CH_3$ | 8 | 2 | | |
| 1992 | $OC_3H_7$ | H | 8 | 2 | | |
| 1993 | $OC_3H_7$ | $C_2H_5$ | 8 | 2 | | |
| 1994 | $Oi-C_3H_7$ | $CH_3$ | 8 | 2 | | |
| 1995 | $Oi-C_3H_7$ | H | 8 | 2 | | |
| 1996 | $Oi-C_3H_7$ | $C_2H_5$ | 8 | 2 | | |
| 1997 | $OC_4H_9$ | $CH_3$ | 8 | 2 | | |
| 1998 | $OC_4H_9$ | H | 8 | 2 | | |
| 1999 | $OC_4H_9$ | $C_2H_5$ | 8 | 2 | | |
| 2000 | $Oi-C_4H_9$ | $CH_3$ | 8 | 2 | | |
| 2001 | $Oi-C_4H_9$ | H | 8 | 2 | | |
| 2002 | $Oi-C_4H_9$ | $C_2H_5$ | 8 | 2 | | |
| 2003 | $Ot-C_4H_9$ | $CH_3$ | 8 | 2 | | |
| 2004 | $Ot-C_4H_9$ | H | 8 | 2 | | |
| 2005 | $Ot-C_4H_9$ | $C_2H_5$ | 8 | 2 | | |
| 2006 | OPh | $CH_3$ | 8 | 2 | | |
| 2007 | OPh | H | 8 | 2 | | |
| 2008 | OPh | $C_2H_5$ | 8 | 2 | | |
| 2009 | $OCH_2Ph$ | $CH_3$ | 8 | 2 | | |
| 2010 | $OCH_2Ph$ | H | 8 | 2 | | |
| 2011 | $OCH_2Ph$ | $C_2H_5$ | 8 | 2 | | |
| 2012 | OCOH | $CH_3$ | 8 | 2 | | |
| 2013 | OCOH | H | 8 | 2 | | |
| 2014 | OCOH | $C_2H_5$ | 8 | 2 | | |
| 2015 | $OCOCH_3$ | $CH_3$ | 8 | 2 | | |
| 2016 | $OCOCH_3$ | H | 8 | 2 | | |
| 2017 | $OCOCH_3$ | $C_2H_5$ | 8 | 2 | | |
| 2018 | $OCOC_2H_5$ | $CH_3$ | 8 | 2 | | |
| 2019 | $OCOC_2H_5$ | H | 8 | 2 | | |
| 2020 | $OCOC_2H_5$ | $C_2H_5$ | 8 | 2 | | |
| 2021 | $OCOC_3H_7$ | $CH_3$ | 8 | 2 | | |
| 2022 | $OCCO_3H_7$ | H | 8 | 2 | | |
| 2023 | $OCOC_3H_7$ | $C_2H_5$ | 8 | 2 | | |
| 2024 | $OCOi-C_3H_7$ | $CH_3$ | 8 | 2 | | |
| 2025 | $OCOi-C_3H_7$ | H | 8 | 2 | | |
| 2026 | $OCOi-C_3H_7$ | $C_2H_5$ | 8 | 2 | | |
| 2027 | $OCOC_4H_9$ | $CH_3$ | 8 | 2 | | |
| 2028 | $OCOC_4H_9$ | H | 8 | 2 | | |
| 2029 | $OCOC_4H_9$ | $C_2H_5$ | 8 | 2 | | |
| 2030 | $OCOi-C_4H_9$ | $CH_3$ | 8 | 2 | | |
| 2031 | $OCOi-C_4H_9$ | H | 8 | 2 | | |
| 2032 | $OCOi-C_4H_9$ | $C_2H_5$ | 8 | 2 | | |
| 2033 | $OCOt-C_4H_9$ | $CH_3$ | 8 | 2 | | |
| 2034 | $OCOt-C_4H_9$ | H | 8 | 2 | | |

TABLE 9-continued

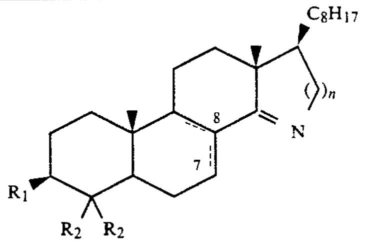

| No. | $R_1$ | $R_2$ | D | n* | No. | M.P. |
|---|---|---|---|---|---|---|
| 2035 | $OCOt-C_4H_9$ | $C_2H_5$ | 8 | 2 | | |
| 2036 | $OCOC_{15}H_{31}$ | $CH_3$ | 8 | 2 | | |
| 2037 | $OCOC_{15}H_{31}$ | H | 8 | 2 | | |
| 2038 | $OCOC_{15}H_{31}$ | $C_2H_5$ | 8 | 2 | | |
| 2039 | $OCOC_{15}H_{29}$ | $CH_3$ | 8 | 2 | | |
| 2040 | $OCOC_{15}H_{29}$ | H | 8 | 2 | | |
| 2041 | $OCOC_{15}H_{29}$ | $C_2H_5$ | 8 | 2 | | |
| 2042 | $OCOC_{17}H_{35}$ | $CH_3$ | 8 | 2 | | |
| 2043 | $OCOC_{17}H_{35}$ | H | 8 | 2 | | |
| 2044 | $OCOC_{17}H_{35}$ | $C_2H_5$ | 8 | 2 | | |
| 2045 | $OCOC_{17}H_{33}$ | $CH_3$ | 8 | 2 | | |
| 2046 | $OCOC_{17}H_{33}$ | H | 8 | 2 | | |
| 2047 | $OCOC_{17}H_{33}$ | $C_2H_5$ | 8 | 2 | | |
| 2048 | $OCOC_{17}H_{31}$ | $CH_3$ | 8 | 2 | | |
| 2049 | $OCOC_{17}H_{31}$ | H | 8 | 2 | | |
| 2050 | $OCOC_{17}H_{31}$ | $C_2H_5$ | 8 | 2 | | |
| 2051 | $OCOC_{17}H_{29}$ | $CH_3$ | 8 | 2 | | |
| 2052 | $OCOC_{17}H_{29}$ | H | 8 | 2 | | |
| 2053 | $OCOC_{17}H_{29}$ | $C_2H_5$ | 8 | 2 | | |
| 2054 | $OCOC_{19}H_{31}$ | $CH_3$ | 8 | 2 | | |
| 2055 | $OCOC_{19}H_{31}$ | H | 8 | 2 | | |
| 2056 | $OCOC_{19}H_{31}$ | $C_2H_5$ | 8 | 2 | | |
| 2057 | OCOPh | $CH_3$ | 8 | 2 | | |
| 2058 | OCOPh | H | 8 | 2 | | |
| 2059 | OCOPh | $C_2H_5$ | 8 | 2 | | |
| 2060 | OH | $CH_3$ | 7 | 2 | | |
| 2061 | OH | H | 7 | | | |
| 2062 | OH | $C_2H_5$ | 7 | 2 | | |
| 2063 | =O | $CH_3$ | 7 | 2 | | |
| 2064 | =O | H | 7 | 2 | | |
| 2065 | =O | $C_2H_5$ | 7 | 2 | | |
| 2066 | $OCH_3$ | $CH_2$ | 7 | 2 | | |
| 2067 | $OCH_3$ | H | 7 | 2 | | |
| 2068 | $OCH_3$ | $C_2H_5$ | 7 | 2 | | |
| 2069 | $OC_2H_5$ | $CH_3$ | 7 | 2 | | |
| 2070 | $OC_2H_5$ | H | 7 | 2 | | |
| 2071 | $OC_2H_5$ | $C_2H_5$ | 7 | 2 | | |
| 2072 | $OC_3H_7$ | $CH_3$ | 7 | 2 | | |
| 2073 | $OC_3H_7$ | H | 7 | 2 | | |
| 2074 | $OC_3H_7$ | $C_2H_5$ | 7 | 2 | | |
| 2075 | $Oi-C_3H_7$ | $CH_3$ | 7 | 2 | | |
| 2076 | $Oi-C_3H_7$ | H | 7 | 2 | | |
| 2077 | $Oi-C_3H_7$ | $C_2H_5$ | 7 | 2 | | |
| 2078 | $OC_4H_9$ | $CH_3$ | 7 | 2 | | |
| 2079 | $OC_4H_9$ | H | 7 | 2 | | |
| 2080 | $OC_4H_9$ | $C_2H_5$ | 7 | 2 | | |
| 2081 | $Oi-C_4H_9$ | $CH_3$ | 7 | 2 | | |
| 2082 | $Oi-C_4H_9$ | H | 7 | 2 | | |
| 2083 | $Oi-C_4H_9$ | $C_2H_5$ | 7 | 2 | | |
| 2084 | $Ot-C_4H_9$ | $CH_3$ | 7 | 2 | | |
| 2085 | $Ot-C_4H_9$ | H | 7 | 2 | | |
| 2086 | $Ot-C_4H_9$ | $C_2H_5$ | 7 | 2 | | |
| 2087 | OPh | $CH_3$ | 7 | 2 | | |
| 2088 | OPh | H | 7 | 2 | | |
| 2089 | OPh | $C_2H_5$ | 7 | 2 | | |
| 2090 | $OCH_2Ph$ | $CH_3$ | 7 | 2 | | |
| 2091 | $OCH_2Ph$ | H | 7 | 2 | | |
| 2092 | $OCH_2Ph$ | $C_2H_5$ | 7 | 2 | | |
| 2093 | OCOH | $CH_3$ | 7 | 2 | | |
| 2094 | OCOH | H | 7 | 2 | | |
| 2095 | OCOH | $C_2H_5$ | 7 | 2 | | |
| 2096 | $OCOCH_3$ | $CH_3$ | 7 | 2 | | |
| 2097 | $OCOCH_3$ | H | 7 | 2 | | |
| 2098 | $OCOCH_3$ | $C_2H_5$ | 7 | 2 | | |
| 2099 | $OCOC_2H_5$ | $CH_3$ | 7 | 2 | | |
| 2100 | $OCOC_2H_5$ | H | 7 | 2 | | |
| 2101 | $OCOC_2H_5$ | $C_2H_5$ | 7 | 2 | | |
| 2101 | $OCOC_3H_7$ | $CH_3$ | 7 | 2 | | |
| 2103 | $OCOC_3H_7$ | H | 7 | 2 | | |

TABLE 9-continued

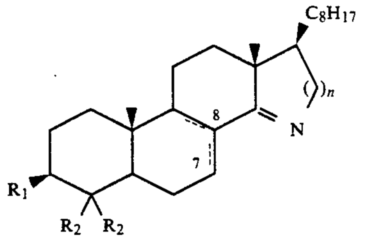

| No. | $R_1$ | $R_2$ | D | n* | No. | M.P. |
|---|---|---|---|---|---|---|
| 2104 | $OCOC_3H_7$ | $C_2H_5$ | 7 | 2 | | |
| 2105 | $OCOi\text{-}C_3H_7$ | $CH_3$ | 7 | 2 | | |
| 2106 | $OCOi\text{-}C_3H_7$ | H | 7 | 2 | | |
| 2107 | $OCOi\text{-}C_3H_7$ | $C_2H_5$ | 7 | 2 | | |
| 2108 | $OCOC_4H_9$ | $CH_3$ | 7 | 2 | | |
| 2109 | $OCOC_4H_9$ | H | 7 | 2 | | |
| 2110 | $OCOC_4H_9$ | $C_2H_5$ | 7 | 2 | | |
| 2111 | $OCOi\text{-}C_4H_9$ | $CH_3$ | 7 | 2 | | |
| 2112 | $OCOi\text{-}C_4H_9$ | H | 7 | 2 | | |
| 2113 | $OCOi\text{-}C_4H_9$ | $C_2H_5$ | 7 | 2 | | |
| 2114 | $OCOt\text{-}C_4H_9$ | $CH_3$ | 7 | 2 | | |
| 2115 | $OCOt\text{-}C_4H_9$ | H | 7 | 2 | | |
| 2116 | $OCOt\text{-}C_4H_9$ | $C_2H_5$ | 7 | 2 | | |
| 2117 | $OCOC_{15}H_{31}$ | $CH_3$ | 7 | 2 | | |
| 2118 | $OCOC_{15}H_{31}$ | H | 7 | 2 | | |
| 2119 | $OCOC_{15}H_{31}$ | $C_2H_5$ | 7 | 2 | | |
| 2120 | $OCOC_{15}H_{29}$ | $CH_3$ | 7 | 2 | | |
| 2121 | $OCOC_{15}H_{29}$ | H | 7 | 2 | | |
| 2122 | $OCOC_{15}H_{29}$ | $C_2H_5$ | 7 | 2 | | |

TABLE 9-continued

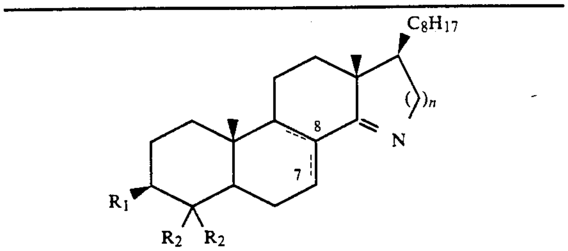

| No. | $R_1$ | $R_2$ | D | n* | No. | M.P. |
|---|---|---|---|---|---|---|
| 2123 | $OCOC_{17}H_{35}$ | $CH_3$ | 7 | 2 | | |
| 2124 | $OCOC_{17}H_{35}$ | H | 7 | 2 | | |
| 2125 | $OCOC_{17}H_{35}$ | $C_2H_5$ | 7 | 2 | | |
| 2126 | $OCOC_{17}H_{33}$ | $CH_3$ | 7 | 2 | | |
| 2127 | $OCOC_{17}H_{33}$ | H | 7 | 2 | | |
| 2128 | $OCOC_{17}H_{33}$ | $C_2H_5$ | 7 | 2 | | |
| 2129 | $OCOC_{17}H_{31}$ | $CH_3$ | 7 | 2 | | |
| 2130 | $OCOC_{17}H_{31}$ | H | 7 | 2 | | |
| 2131 | $OCOC_{17}H_{31}$ | $C_2H_5$ | 7 | 2 | | |
| 2132 | $OCOC_{17}H_{29}$ | $CH_3$ | 7 | 2 | | |
| 2133 | $OCOC_{17}H_{29}$ | H | 7 | 2 | | |
| 2134 | $OCOC_{17}H_{29}$ | $C_2H_5$ | 7 | 2 | | |
| 2135 | $OCOC_{19}H_{31}$ | $CH_3$ | 7 | 2 | | |
| 2136 | $OCOC_{19}H_{31}$ | H | 7 | 2 | | |
| 2137 | $OCOC_{19}H_{31}$ | $C_2H_5$ | 7 | 2 | | |
| 2138 | OCOPh | $CH_3$ | 7 | 2 | | |
| 2139 | OCOPh | H | 7 | 2 | | |
| 2140 | OCOPh | $C_2H_5$ | 7 | 2 | | |

*provided that when n = 2, the upper side chain (R) is not ergosterol.

TABLE 10

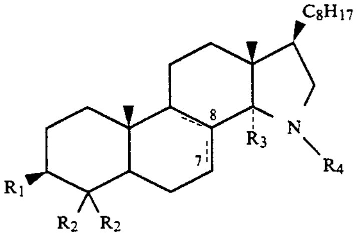

| No. | $R_1$ | $R_2$ | $R_3$ | $R_4$ | D | No. | M.P. |
|---|---|---|---|---|---|---|---|
| 2141 | OH | $CH_3$ | $CH_3$ | H | 8 | 66a | |
| 2142 | OH | $CH_3$ | H | H | 8 | | |
| 2143 | OH | $CH_3$ | $CH{=}CH_2$ | H | 8 | | |
| 2144 | OH | $CH_3$ | $CHOHCH_2OH$—(R) | H | 8 | | |
| 2145 | OH | $CH_3$ | $CHOHCH_2OH$—(S) | H | 8 | | |
| 2146 | OH | $CH_3$ | CHO | H | 8 | | |
| 2147 | OH | $CH_3$ | $CH_2OH$ | H | 8 | | |
| 2148 | OH | $CH_3$ | $CO_2H$ | H | 8 | | |
| 2149 | OH | $CH_3$ | $CO_2CH_3$ | H | 8 | | |
| 2150 | OH | $CH_3$ | $CH{=}NOH$ | H | 8 | | |
| 2151 | OH | $CH_3$ | $CHOHCH{=}CH_2$—(R) | H | 8 | | |
| 2152 | OH | $CH_3$ | $CHOHCH{=}CH_2$—(S) | H | 8 | | |
| 2153 | OH | H | $CH_3$ | H | 8 | | |
| 2154 | OH | H | H | H | 8 | 70a | |
| 2155 | OH | H | $CH{=}CH_2$ | H | 8 | | |
| 2156 | OH | H | $CHOHCH_2OH$—(R) | H | 8 | | |
| 2157 | OH | H | $CHOHCH_2OH$—(S) | H | 8 | | |
| 2158 | OH | H | CHO | H | 8 | | |
| 2159 | OH | H | $CH_2OH$ | H | 8 | | |
| 2160 | OH | H | $CO_2H$ | H | 8 | | |
| 2161 | OH | H | $CO_2CH_3$ | H | 8 | | |
| 2162 | OH | H | $CH{=}NOH$ | H | 8 | | |
| 2163 | OH | H | $CHOHCH{=}CH_2$—(R) | H | 8 | | |
| 2164 | OH | H | $CHOHCH{=}CH_2$—(S) | H | 8 | | |
| 2165 | OH | $CH_3$ | $C_2H_5$ | H | 8 | | |
| 2166 | OH | $CH_3$ | $CH_2CH{=}CH_2$ | H | 8 | | |
| 2167 | OH | $CH_3$ | $C{=}CH$ | H | 8 | | |
| 2168 | OH | $CH_3$ | $CH_2Ph$ | H | 8 | | |
| 2169 | OH | $CH_3$ | $CH_2OCH_3$ | H | 8 | | |
| 2170 | OH | $CH_3$ | $CH_2OCOCH_3$ | H | 8 | | |
| 2171 | OH | $CH_3$ | $CH_2SH$ | H | 8 | | |
| 2172 | OH | $CH_3$ | $CH_2SCH_3$ | H | 8 | | |

TABLE 10-continued

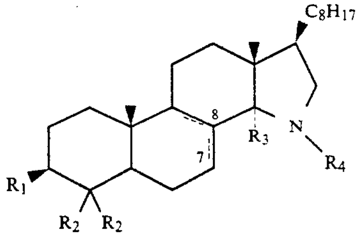

| No. | $R_1$ | $R_2$ | $R_3$ | $R_4$ | D | No. | M.P. |
|---|---|---|---|---|---|---|---|
| 2173 | OH | $CH_3$ | $CH_2SCOCH_3$ | H | 8 | | |
| 2174 | OH | $CH_3$ | $CH_2NH_2$ | H | 8 | | |
| 2175 | OH | $CH_3$ | $CH_2NHCH_3$ | H | 8 | | |
| 2176 | OH | $CH_3$ | $CH_2NHCOCH_3$ | H | 8 | | |
| 2177 | OH | $CH_3$ | $CH_2NHCSCH_3$ | H | 8 | | |
| 2178 | OH | $CH_3$ | $CH_2NHC(=NH)CH_3$ | H | 8 | | |
| 2179 | OH | $CH_3$ | $COCH_3$ | H | 8 | | |
| 2180 | OH | $CH_3$ | $COCH=CH_2$ | H | 8 | | |
| 2181 | OH | $CH_3$ | $CSCH_3$ | H | 8 | | |
| 2182 | OH | $CH_3$ | $CSCH=CH_2$ | H | 8 | | |
| 2183 | OH | $CH_3$ | $C(=NH)CH_3$ | H | 8 | | |
| 2184 | OH | $CH_3$ | $CO_2C_2H_5$ | H | 8 | | |
| 2185 | OH | $CH_3$ | $COSCH_3$ | H | 8 | | |
| 2186 | OH | $CH_3$ | $CONH_2$ | H | 8 | | |
| 2187 | OH | $CH_3$ | $CONHCH_3$ | H | 8 | | |
| 2188 | OH | $CH_3$ | $CONHCOCH_3$ | H | 8 | | |
| 2189 | OH | $CH_3$ | $CSNH_2$ | H | 8 | | |
| 2190 | OH | $CH_3$ | $CSNHCH_3$ | H | 8 | | |
| 2191 | OH | $CH_3$ | $CSNHCOCH_3$ | H | 8 | | |
| 2192 | OH | $CH_3$ | $CH_2CH_2OH$ | H | 8 | | |
| 2193 | OH | $CH_3$ | $CH_2CH_2OCH_3$ | H | 8 | | |
| 2194 | OH | $CH_3$ | $CH_2CH_2OCOCH_3$ | H | 8 | | |
| 2195 | OH | $CH_3$ | $CH_2CH_2SH$ | H | 8 | | |
| 2196 | OH | $CH_3$ | $CH_2CH_2SCH_3$ | H | 8 | | |
| 2197 | OH | $CH_3$ | $CH_2CH_2SCOCH_3$ | H | 8 | | |
| 2198 | OH | $CH_3$ | $CH_2CH_2NH_2$ | H | 8 | | |
| 2199 | OH | $CH_3$ | $CH_2CH_2NHCH_3$ | H | 8 | | |
| 2200 | OH | $CH_3$ | $CH_2CH_2NHCOCH_3$ | H | 8 | | |
| 2201 | OH | $CH_3$ | $CH_2CHO$ | H | 8 | | |
| 2202 | OH | $CH_3$ | $CH_2COCH_3$ | H | 8 | | |
| 2203 | OH | $CH_3$ | $CH_2COCH=CH_2$ | H | 8 | | |
| 2204 | OH | $CH_3$ | $CH_2CSCH_3$ | H | 8 | | |
| 2205 | OH | $CH_3$ | $CH_2CSCH=CH_2$ | H | 8 | | |
| 2206 | OH | $CH_3$ | $CH_2C(=NH)CH_3$ | H | 8 | | |
| 2207 | OH | $CH_3$ | $CH_2CO_2CH_3$ | H | 8 | | |
| 2208 | OH | $CH_3$ | $CH_2COSCH_3$ | H | 8 | | |
| 2209 | OH | $CH_3$ | $CH_2CONH_2$ | H | 8 | | |
| 2210 | OH | $CH_3$ | $CH_2CONHCH_3$ | H | 8 | | |
| 2211 | OH | $CH_3$ | $CH_2CONHCOCH_3$ | H | 8 | | |
| 2212 | OH | $CH_3$ | $CH_2CSNH_2$ | H | 8 | | |
| 2213 | OH | $CH_3$ | $CH_2C(=NH)CH_3$ | H | 8 | | |
| 2214 | OH | $CH_3$ | $CH_2CH_2Cl$ | H | 8 | | |
| 2215 | OH | $CH_3$ | CN | H | 8 | | |
| 2216 | OH | $CH_3$ | $CH=NOCH_3$ | H | 8 | | |
| 2217 | OH | $CH_3$ | $CH=NOCOCH_3$ | H | 8 | | |
| 2218 | OH | $CH_3$ | $CH=NNH_2$ | H | 8 | | |
| 2219 | OH | $CH_3$ | $CH=NNHCH_3$ | H | 8 | | |
| 2220 | OH | $CH_3$ | $CH=NHCOCH_3$ | H | 8 | | |
| 2221 | OH | $CH_3$ | $CH=NNHCSCH_3$ | H | 8 | | |
| 2222 | OH | $CH_3$ | $CH_2NHOH$ | H | 8 | | |
| 2223 | OH | $CH_3$ | $CH_2NHOCH_3$ | H | 8 | | |
| 2224 | OH | $CH_3$ | $CH_2NHOCOCH_3$ | H | 8 | | |
| 2225 | OH | $CH_3$ | $CH_2NHNH_2$ | H | 8 | | |
| 2226 | OH | $CH_3$ | $CH_2NHNHCH_3$ | H | 8 | | |
| 2227 | OH | $CH_3$ | $CH_2NHNHCOCH_3$ | H | 8 | | |
| 2228 | OH | $CH_3$ | $CH_2NHNHCSCH_3$ | H | 8 | | |
| 2229 | OH | $CH_3$ | $CH_2CN$ | H | 8 | | |
| 2230 | OH | $CH_3$ | $CH_2CH=NOH$ | H | 8 | | |
| 2231 | OH | $CH_3$ | $CH_2CH=NOCH_3$ | H | 8 | | |
| 2232 | OH | $CH_3$ | $CH_2CH=NOCOCH_3$ | H | 8 | | |
| 2233 | OH | $CH_3$ | $CH_2CH=NNH_2$ | H | 8 | | |
| 2234 | OH | $CH_3$ | $CH_2CH=NNHCH_3$ | H | 8 | | |
| 2235 | OH | $CH_3$ | $CH_2CH=NNHCOCH_3$ | H | 8 | | |
| 2236 | OH | $CH_3$ | $CH_2CH=NNHCSCH_3$ | H | 8 | | |
| 2237 | OH | $CH_3$ | $CH_2CH_2NHOH$ | H | 8 | | |
| 2238 | OH | $CH_3$ | $CH_2CH_2NHOCH_3$ | H | 8 | | |
| 2239 | OH | $CH_3$ | $CH_2CH_2NHOCOCH_3$ | H | 8 | | |
| 2240 | OH | $CH_3$ | $CH_2CH_2NHNH_2$ | H | 8 | | |
| 2241 | OH | $CH_3$ | $CH_2CH_2NHNHCH_3$ | H | 8 | | |

TABLE 10-continued

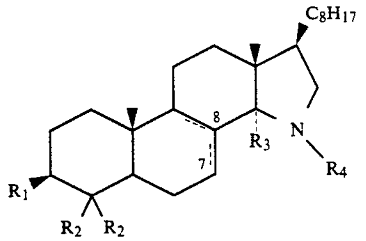

| No. | $R_1$ | $R_2$ | $R_3$ | $R_4$ | D | No. | M.P. |
|---|---|---|---|---|---|---|---|
| 2242 | OH | $CH_3$ | $CH_2CH_2NHNHCOCH_3$ | H | 8 | | |
| 2243 | OH | $CH_3$ | $CH_2CH_2NHNHCSCH_3$ | H | 8 | | |
| 2244 | OH | $CH_3$ | CONHOH | H | 8 | | |
| 2245 | OH | $CH_3$ | $CONHOCH_3$ | H | 8 | | |
| 2246 | OH | $CH_3$ | $CONHOCOCH_3$ | H | 8 | | |
| 2247 | OH | $CH_3$ | CSNHOH | H | 8 | | |
| 2248 | OH | $CH_3$ | $CSNHCOCH_3$ | H | 8 | | |
| 2249 | OH | $CH_3$ | $CSNHOCOCH_3$ | H | 8 | | |
| 2250 | OH | $CH_3$ | CH=CHCHO | H | 8 | | |
| 2251 | OH | $CH_3$ | $CH{=}CHCOCH_3$ | H | 8 | | |
| 2252 | OH | $CH_3$ | $CH{=}CHCSCH_3$ | H | 8 | | |
| 2253 | OH | $CH_3$ | CH=CHCH—NH | H | 8 | | |
| 2254 | OH | $CH_3$ | $CH{=}CHC({=}NH)CH_3$ | H | 8 | | |
| 2255 | OH | $CH_3$ | C=CCHO | H | 8 | | |
| 2256 | OH | $CH_3$ | $C{=}CCOCH_3$ | H | 8 | | |
| 2257 | OH | $CH_3$ | $C{=}CCSCH_3$ | H | 8 | | |
| 2258 | OH | $CH_3$ | C=CCH=NH | H | 8 | | |
| 2259 | OH | $CH_3$ | $C{=}CC({=}NH)CH_3$ | H | 8 | | |
| 2260 | OH | $CH_3$ | $CH{=}CHCH_2Cl$ | H | 8 | | |
| 2261 | OH | $CH_3$ | $C{=}CCH_2Cl$ | H | 8 | | |
| 2262 | OH | $CH_3$ | $CH{=}CHCH_2OCOCH_3$ | H | 8 | | |
| 2263 | OH | $CH_3$ | $C{=}CCH_2OCOCH_3$ | H | 8 | | |
| 2264 | OH | $CH_3$ | $CH_2CHOHCH_2OH$ | H | 8 | | |
| 2265 | OH | $CH_3$ | $CHOHCHOHCH_2OH$ | H | 8 | | |
| 2266 | OH | $CH_3$ | 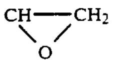 | H | 8 | | |
| 2267 | OH | $CH_3$ | 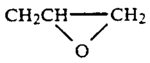 | H | 8 | | |
| 2268 | OH | $CH_3$ | 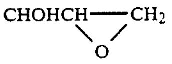 | H | 8 | | |
| 2269 | OH | H | $CH_2SH$ | H | 8 | | |
| 2270 | OH | H | $CH_2NH_2$ | H | 8 | | |
| 2271 | OH | H | $COCH_3$ | H | 8 | | |
| 2272 | OH | H | $CONH_2$ | H | 8 | | |
| 2273 | OH | H | $CSNH_2$ | H | 8 | | |
| 2274 | OH | H | $CH_2CH_2OH$ | H | 8 | | |
| 2275 | OH | H | $CH_2CHO$ | H | 8 | | |
| 2276 | OH | H | $CH_2COCH_3$ | H | 8 | | |
| 2277 | OH | H | $CH_2CO_2CH_3$ | H | 8 | | |
| 2278 | OH | H | $CH_2CONH_2$ | H | 8 | | |
| 2279 | OH | H | $CH_2CH_2Cl$ | H | 8 | | |
| 2280 | OH | H | CN | H | 8 | | |
| 2281 | OH | H | $CH{=}NNH_2$ | H | 8 | | |
| 2282 | OH | H | $CH_2NHOH$ | H | 8 | | |
| 2283 | OH | H | $CH_2NHNH_2$ | H | 8 | | |
| 2284 | OH | H | $H_2CN$ | H | 8 | | |
| 2285 | OH | H | $CH_2CH{=}NOH$ | H | 8 | | |
| 2286 | OH | H | $CH_2CH{=}NNH_2$ | H | 8 | | |
| 2287 | OH | H | $CH_2CH_2NHOH$ | H | 8 | | |
| 2288 | OH | H | $CH_2CH_2NHNH_2$ | H | 8 | | |
| 2289 | OH | H | CONHOH | H | 8 | | |
| 2290 | OH | H | CH=CHCHO | H | 8 | | |
| 2291 | OH | H | $CH{=}CHCOCH_3$ | H | 8 | | |
| 2292 | OH | H | $CH{=}CHCH_2Cl$ | H | 8 | | |
| 2293 | OH | H | $CH_2CHOHCH_2OH$ | H | 8 | | |
| 2294 | OH | H | 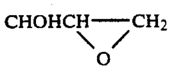 | H | 8 | | |
| 2295 | =O | $CH_3$ | $CH_3$ | H | 8 | | |

TABLE 10-continued

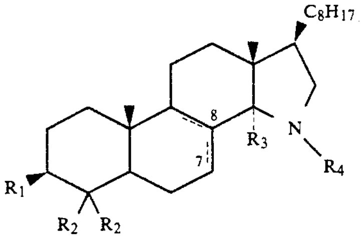

| No. | $R_1$ | $R_2$ | $R_3$ | $R_4$ | D | No. | M.P. |
|---|---|---|---|---|---|---|---|
| 2296 | =O | $CH_3$ | H | H | 8 | | |
| 2297 | =O | $CH_3$ | $CH{=}CH_2$ | H | 8 | | |
| 2298 | =O | $CH_3$ | $CHOHCH_2OH$—(R) | H | 8 | | |
| 2299 | =O | $CH_3$ | $CHOHCH_2OH$—(S) | H | 8 | | |
| 2300 | =O | $CH_3$ | CHO | H | 8 | | |
| 2301 | =O | $CH_3$ | $CH_2OH$ | H | 8 | | |
| 2302 | =O | $CH_3$ | $CO_2H$ | H | 8 | | |
| 2303 | =O | $CH_3$ | $CO_2CH_3$ | H | 8 | | |
| 2304 | =O | $CH_3$ | $CH{=}NOH$ | H | 8 | | |
| 2305 | =O | $CH_3$ | $CHOHCH{=}CH_2$—(R) | H | 8 | | |
| 2306 | =O | $CH_3$ | $CHOHCH{=}CH_2$—(S) | H | 8 | | |
| 2307 | =O | $CH_3$ | $CH_2SH$ | H | 8 | | |
| 2308 | =O | $CH_3$ | $CH_2NHCH_3$ | H | 8 | | |
| 2309 | =O | $CH_3$ | $COCH_3$ | H | 8 | | |
| 2310 | =O | $CH_3$ | $CONH_2$ | H | 8 | | |
| 2311 | =O | $CH_3$ | $CSNH_2$ | H | 8 | | |
| 2312 | =O | $CH_3$ | $CH_2CH_2OH$ | H | 8 | | |
| 2313 | =O | $CH_3$ | $CH_2CHO$ | H | 8 | | |
| 2314 | =O | $CH_3$ | $CH_2COCH_3$ | H | 8 | | |
| 2315 | =O | $CH_3$ | $CH_2CO_2CH_3$ | H | 8 | | |
| 2316 | =O | $CH_3$ | $CH_2CONH_2$ | H | 8 | | |
| 2317 | =O | $CH_3$ | $CH_2CH_2Cl$ | H | 8 | | |
| 2318 | =O | $CH_3$ | CN | H | 8 | | |
| 2319 | =O | $CH_3$ | $CH{=}NNHCH_3$ | H | 8 | | |
| 2320 | =O | $CH_3$ | $CH_2NHOH$ | H | 8 | | |
| 2321 | =O | $CH_3$ | $CH_2NHNHCH_3$ | H | 8 | | |
| 2322 | =O | $CH_3$ | $CH_2CN$ | H | 8 | | |
| 2323 | =O | $CH_3$ | $CH_2CH$—NOH | H | 8 | | |
| 2324 | =O | $CH_3$ | $CH_2CH{=}NNHCH_3$ | H | 8 | | |
| 2325 | =O | $CH_3$ | $CH_2CH_2NHOH$ | H | 8 | | |
| 2326 | =O | $CH_3$ | $CH_2CH_2NHNHCH_3$ | H | 8 | | |
| 2327 | =O | $CH_3$ | CONHOH | H | 8 | | |
| 2328 | =O | $CH_3$ | $CH{=}CHCHO$ | H | 8 | | |
| 2329 | =O | $CH_3$ | $CH{=}CHCOCH_3$ | H | 8 | | |
| 2330 | =O | $CH_3$ | $CH{=}CHCH_2Cl$ | H | 8 | | |
| 2331 | =O | $CH_3$ | $CH_2CHOHCH_2OH$ | H | 8 | | |
| 2332 | =O | $CH_3$ | 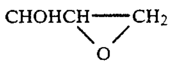 | H | 8 | | |
| 2333 | =O | H | $CH_3$ | H | 8 | | |
| 2334 | =O | H | H | H | 8 | | |
| 2335 | =O | H | $CH{=}CH_2$ | H | 8 | | |
| 2336 | =O | H | $CHOHCH_2OH$—(R) | H | 8 | | |
| 2337 | =O | H | $CHOHCH_2OH$—(S) | H | 8 | | |
| 2338 | =O | H | CHO | H | 8 | | |
| 2339 | =O | H | $CH_2OH$ | H | 8 | | |
| 2340 | =O | H | $CO_2H$ | H | 8 | | |
| 2341 | =O | H | $CO_2CH_3$ | H | 8 | | |
| 2342 | =O | H | $CH{=}NOH$ | H | 8 | | |
| 2343 | =O | H | $CHOHCH{=}CH_2$—(R) | H | 8 | | |
| 2344 | =O | H | $CHOHCH{=}CH_2$—(S) | H | 8 | | |
| 2345 | $OCH_3$ | $CH_3$ | $CH_3$ | H | 8 | | |
| 2346 | $OCH_3$ | $CH_3$ | H | H | 8 | | |
| 2347 | $OCH_3$ | $CH_3$ | $CH{=}CH_2$ | H | 8 | | |
| 2348 | $OCH_3$ | $CH_3$ | $CHOHCH_2OH$—(R) | H | 8 | | |
| 2349 | $OCH_3$ | $CH_3$ | $CHOHCH_2OH$—(S) | H | 8 | | |
| 2350 | $OCH_3$ | $CH_3$ | CHO | H | 8 | | |
| 2351 | $OCH_3$ | $CH_3$ | $CH_2OH$ | H | 8 | | |
| 2352 | $OCH_3$ | $CH_3$ | $CO_2H$ | H | 8 | | |
| 2353 | $OCH_3$ | $CH_3$ | $CO_2CH_3$ | H | 8 | | |
| 2354 | $OCH_3$ | $CH_3$ | $CH{=}NOH$ | H | 8 | | |
| 2355 | $OCH_3$ | $CH_3$ | $CHOHCH{=}CH_2$—(R) | H | 8 | | |
| 2356 | $OCH_3$ | $CH_3$ | $CHOHCH{=}CH_2$—(S) | H | 8 | | |
| 2357 | $OCH_3$ | $CH_3$ | $CH_2SH$ | H | 8 | | |
| 2358 | $OCH_3$ | $CH_3$ | $CH_2NH_2$ | H | 8 | | |
| 2359 | $OCH_3$ | $CH_3$ | $COCH_3$ | H | 8 | | |
| 2360 | $OCH_3$ | $CH_3$ | $CONH_2$ | H | 8 | | |

TABLE 10-continued

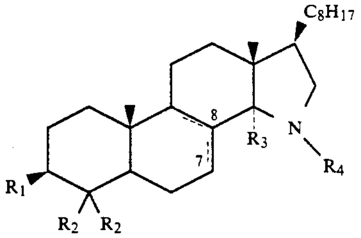

| No. | $R_1$ | $R_2$ | $R_3$ | $R_4$ | D | No. | M.P. |
|---|---|---|---|---|---|---|---|
| 2361 | $OCH_3$ | $CH_3$ | $CSNH_2$ | H | 8 | | |
| 2362 | $OCH_3$ | $CH_3$ | $CH_2CH_2OH$ | H | 8 | | |
| 2363 | $OCH_3$ | $CH_3$ | $CH_2CHO$ | H | 8 | | |
| 2364 | $OCH_3$ | $CH_3$ | $CH_2COCH_3$ | H | 8 | | |
| 2365 | $OCH_3$ | $CH_3$ | $CH_2CO_2CH_3$ | H | 8 | | |
| 2366 | $OCH_3$ | $CH_3$ | $CH_2CONH_2$ | H | 8 | | |
| 2367 | $OCH_3$ | $CH_3$ | $CH_2CH_2Cl$ | H | 8 | | |
| 2368 | $OCH_3$ | $CH_3$ | CN | H | 8 | | |
| 2369 | $OCH_3$ | $CH_3$ | $CH=NNH_2$ | H | 8 | | |
| 2370 | $OCH_3$ | $CH_3$ | $CH_2NHOH$ | H | 8 | | |
| 2371 | $OCH_3$ | $CH_3$ | $CH_2NHNH_2$ | H | 8 | | |
| 2372 | $OCH_3$ | $CH_3$ | $CH_2CN$ | H | 8 | | |
| 2373 | $OCH_3$ | $CH_3$ | $CH_2CH=NOH$ | H | 8 | | |
| 2374 | $OCH_3$ | $CH_3$ | $CH_2CH=NNH_2$ | H | 8 | | |
| 2375 | $OCH_3$ | $CH_3$ | $CH_2CH_2NHOH$ | H | 8 | | |
| 2376 | $OCH_3$ | $CH_3$ | $CH_2CH_2NHNH_2$ | H | 8 | | |
| 2377 | $OCH_3$ | $CH_3$ | CONHOH | H | 8 | | |
| 2378 | $OCH_3$ | $CH_3$ | $CH=CHCHO$ | H | 8 | | |
| 2379 | $OCH_3$ | $CH_3$ | $CH=CHCOCH_3$ | H | 8 | | |
| 2380 | $OCH_3$ | $CH_3$ | $CH=CHCH_2Cl$ | H | 8 | | |
| 2381 | $OCH_3$ | $CH_3$ | $CH_2CHOHCH_2OH$ | H | 8 | | |
| 2382 | $OCH_3$ | $CH_3$ | 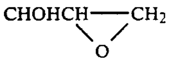 | H | 8 | | |
| 2383 | $OCH_3$ | H | $CH_3$ | H | 8 | | |
| 2384 | $OCH_3$ | H | H | H | 8 | | |
| 2385 | $OCH_3$ | H | $CH=CH_2$ | H | 8 | | |
| 2386 | $OCH_3$ | H | $CHOHCH_2OH$—(R) | H | 8 | | |
| 2387 | $OCH_3$ | H | $CHOHCH_2OH$—(S) | H | 8 | | |
| 2388 | $OCH_3$ | H | CHO | H | 8 | | |
| 2389 | $OCH_3$ | H | $CH_2OH$ | H | 8 | | |
| 2390 | $OCH_3$ | H | $CO_2H$ | H | 8 | | |
| 2391 | $OCH_3$ | H | $CO_2CH_3$ | H | 8 | | |
| 2392 | $OCH_3$ | H | $CH=NOH$ | H | 8 | | |
| 2393 | $OCH_3$ | H | $CHOHCH=CH_2$—(R) | H | 8 | | |
| 2394 | $OCH_3$ | H | $CHOHCH=CH_2$—(S) | H | 8 | | |
| 2395 | $OC_2H_5$ | $CH_3$ | $CH_3$ | H | 8 | | |
| 2396 | $OC_2H_5$ | $CH_3$ | CHO | H | 8 | | |
| 2397 | $OC_2H_5$ | $CH_3$ | $CH_2OH$ | H | 8 | | |
| 2398 | $OC_3H_7$ | $CH_3$ | $CH_3$ | H | 8 | | |
| 2399 | $OC_3H_7$ | $CH_3$ | CHO | H | 8 | | |
| 2400 | $OC_3H_7$ | $CH_3$ | $CH_2OH$ | H | 8 | | |
| 2401 | Oi-$C_3H_7$ | $CH_3$ | $CH_3$ | H | 8 | | |
| 2402 | $OC_4H_9$ | $CH_3$ | $CH_3$ | H | 8 | | |
| 2403 | $OC_4H_9$ | $CH_3$ | CHO | H | 8 | | |
| 2404 | $OC_4H_9$ | $CH_3$ | $CH_2OH$ | H | 8 | | |
| 2405 | Oi-$C_4H_9$ | $CH_3$ | $CH_3$ | H | 8 | | |
| 2406 | Ot-$C_4H_9$ | $CH_3$ | $CH_3$ | H | 8 | | |
| 2407 | OPh | $CH_3$ | $CH_3$ | H | 8 | | |
| 2408 | OPh | $CH_3$ | CHO | H | 8 | | |
| 2409 | OPh | $CH_3$ | $CH_2OH$ | H | 8 | | |
| 2410 | $OCH_2Ph$ | $CH_3$ | $CH_3$ | H | 8 | | |
| 2411 | $OCH_2Ph$ | $CH_3$ | CHO | H | 8 | | |
| 2412 | $OCH_2Ph$ | $CH_3$ | $CH_2OH$ | H | 8 | | |
| 2413 | $OCOCH_3$ | $CH_3$ | $CH_3$ | H | 8 | | |
| 2414 | $OCOCH_3$ | $CH_3$ | H | H | 8 | | |
| 2415 | $OCOCH_3$ | $CH_3$ | $CH=CH_2$ | H | 8 | | |
| 2416 | $OCOCH_3$ | $CH_3$ | $CHOHCH_2OH$—(R) | H | 8 | | |
| 2417 | $OCOCH_3$ | $CH_3$ | $CHOHCH_2OH$—(S) | H | 8 | | |
| 2418 | $OCOCH_3$ | $CH_3$ | CHO | H | 8 | | |
| 2419 | $OCOCH_3$ | $CH_3$ | $CH_2OH$ | H | 8 | | |
| 2420 | $OCOCH_3$ | $CH_3$ | $CO_2H$ | H | 8 | | |
| 2421 | $OCOCH_3$ | $CH_3$ | $CO_2CH_3$ | H | 8 | | |
| 2422 | $OCOCH_3$ | $CH_3$ | CH—NOH | H | 8 | | |
| 2423 | $OCOCH_3$ | $CH_3$ | $CHOHCH=CH_2$—(R) | H | 8 | | |
| 2424 | $OCOCH_3$ | $CH_3$ | $CHOHCH=CH_2$—(S) | H | 8 | | |
| 2425 | $OCOCH_3$ | $CH_3$ | $CH_2SH$ | H | 8 | | |

TABLE 10-continued

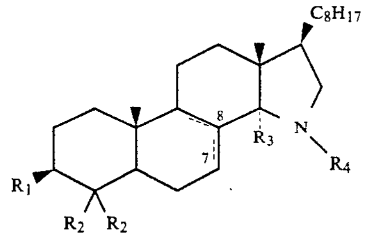

| No. | $R_1$ | $R_2$ | $R_3$ | $R_4$ | D | No. | M.P. |
|---|---|---|---|---|---|---|---|
| 2426 | $OCOCH_3$ | $CH_3$ | $CH_2NH_2$ | H | 8 | | |
| 2427 | $OCOCH_3$ | $CH_3$ | $COCH_3$ | H | 8 | | |
| 2428 | $OCOCH_3$ | $CH_3$ | $CONH_2$ | H | 8 | | |
| 2429 | $OCOCH_3$ | $CH_3$ | $CSNH_2$ | H | 8 | | |
| 2430 | $OCOCH_3$ | $CH_3$ | $CH_2CH_2OH$ | H | 8 | | |
| 2431 | $OCOCH_3$ | $CH_3$ | $CH_2CHO$ | H | 8 | | |
| 2432 | $OCOCH_3$ | $CH_3$ | $CH_2COCH_3$ | H | 8 | | |
| 2433 | $OCOCH_3$ | $CH_3$ | $CH_2CO_2CH_3$ | H | 8 | | |
| 2434 | $OCOCH_3$ | $CH_3$ | $CH_2CONH_2$ | H | 8 | | |
| 2435 | $OCOCH_3$ | $CH_3$ | $CH_2CH_2Cl$ | H | 8 | | |
| 2436 | $OCOCH_3$ | $CH_3$ | CN | H | 8 | | |
| 2437 | $OCOCH_3$ | $CH_3$ | $CH{=}NNH_2$ | H | 8 | | |
| 2438 | $OCOCH_3$ | $CH_3$ | $CH_2NHOH$ | H | 8 | | |
| 2439 | $OCOCH_3$ | $CH_3$ | $CH_2NHNH_2$ | H | 8 | | |
| 2440 | $OCOCH_3$ | $CH_3$ | $CH_2CN$ | H | 8 | | |
| 2441 | $OCOCH_3$ | $CH_3$ | $CH_2CH{=}NOH$ | H | 8 | | |
| 2442 | $OCOCH_3$ | $CH_3$ | $CH_2CH{=}NNH_2$ | H | 8 | | |
| 2443 | $OCOCH_3$ | $CH_3$ | $CH_2CH_2NHOH$ | H | 8 | | |
| 2444 | $OCOCH_3$ | $CH_3$ | $CH_2CH_2NHNH_2$ | H | 8 | | |
| 2445 | $OCOCH_3$ | $CH_3$ | CONHOH | H | 8 | | |
| 2446 | $OCOCH_3$ | $CH_3$ | $CH{=}CHCHO$ | H | 8 | | |
| 2447 | $OCOCH_3$ | $CH_3$ | $CH{=}CHCOCH_3$ | H | 8 | | |
| 2448 | $OCOCH_3$ | $CH_3$ | $CH{=}CHCH_2Cl$ | H | 8 | | |
| 2449 | $OCOCH_3$ | $CH_3$ | $CH_2CHOHCH_2OH$ | H | 8 | | |
| 2450 | $OCOCH_3$ | $CH_3$ | 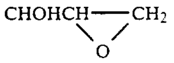 | H | 8 | | |
| 2451 | $OCOCH_3$ | H | $CH_3$ | H | 8 | | |
| 2452 | $OCOCH_3$ | H | H | H | 8 | | |
| 2453 | $OCOCH_3$ | H | $CH{=}CH_2$ | H | 8 | | |
| 2454 | $OCOCH_3$ | H | $CHOHCH_2OH$—(R) | H | 8 | | |
| 2455 | $OCOCH_3$ | H | $CHOHCH_2OH$—(S) | H | 8 | | |
| 2456 | $OCOCH_3$ | H | CHO | H | 8 | | |
| 2457 | $OCOCH_3$ | H | $CH_2OH$ | H | 8 | | |
| 2458 | $OCOCH_3$ | H | $CO_2H$ | H | 8 | | |
| 2459 | $OCOCH_3$ | H | $CO_2CH_3$ | H | 8 | | |
| 2460 | $OCOCH_3$ | H | $CH{=}NOH$ | H | 8 | | |
| 2461 | $OCOCH_3$ | H | $CHOHCH{=}CH_2$—(R) | H | 8 | | |
| 2462 | $OCOCH_3$ | H | $CHOHCH{=}CH_2$—(S) | H | 8 | | |
| 2463 | $OCOC_2H_5$ | $CH_3$ | $CH_3$ | H | 8 | | |
| 2464 | $OCOC_2H_5$ | $CH_3$ | CHO | H | 8 | | |
| 2465 | $OCOC_2H_5$ | $CH_3$ | $CH_2OH$ | H | 8 | | |
| 2466 | $OCOC_3H_7$ | $CH_3$ | $CH_3$ | H | 8 | | |
| 2467 | $OCOC_3H_7$ | $CH_3$ | CHO | H | 8 | | |
| 2468 | $OCOC_3H_7$ | $CH_3$ | $CH_2OH$ | H | 8 | | |
| 2469 | OCOi-$C_3H_7$ | $CH_3$ | $CH_3$ | H | 8 | | |
| 2470 | $OCOC_4H_9$ | $CH_3$ | $CH_3$ | H | 8 | | |
| 2471 | $OCOC_4H_9$ | $CH_3$ | CHO | H | 8 | | |
| 2472 | $OCOC_4H_9$ | $CH_3$ | $CH_2OH$ | H | 8 | | |
| 2473 | OCOi-$C_4H_9$ | $CH_3$ | $CH_3$ | H | 8 | | |
| 2474 | OCOt-$C_4H_9$ | $CH_3$ | $CH_3$ | H | 8 | | |
| 2475 | $OCOC_{15}H_{31}$ | $CH_3$ | $CH_3$ | H | 8 | | |
| 2476 | $OCOC_{15}H_{31}$ | $CH_3$ | CHO | H | 8 | | |
| 2477 | $OCOC_{15}H_{31}$ | $CH_3$ | $CH_2OH$ | H | 8 | | |
| 2478 | $OCOC_{15}H_{29}$ | $CH_3$ | $CH_3$ | H | 8 | | |
| 2479 | $OCOC_{17}H_{35}$ | $CH_3$ | $CH_3$ | H | 8 | | |
| 2480 | $OCOC_{17}H_{33}$ | $CH_3$ | $CH_3$ | H | 8 | | |
| 2481 | $OCOC_{17}H_{31}$ | $CH_3$ | $CH_3$ | H | 8 | | |
| 2482 | $OCOC_{17}H_{29}$ | $CH_3$ | $CH_3$ | H | 8 | | |
| 2483 | $OCOC_{19}H_{31}$ | $CH_3$ | $CH_3$ | H | 8 | | |
| 2484 | OCOPh | $CH_3$ | $CH_3$ | H | 8 | | |
| 2485 | OCOPh | $CH_3$ | CHO | H | 8 | | |
| 2486 | OCOPh | $CH_3$ | $CH_2OH$ | H | 8 | | |
| 2487 | OH | $CH_3$ | $CH_3$ | H | 7 | | |
| 2488 | OH | $CH_3$ | H | H | 7 | | |
| 2489 | OH | $CH_3$ | $CH{=}CH_2$ | H | 7 | | |
| 2490 | OH | $CH_3$ | $CHOHCH_2OH$—(R) | H | 7 | | |

TABLE 10-continued

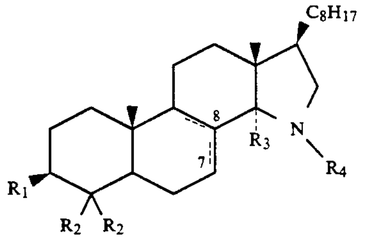

| No. | R1 | R2 | R3 | R4 | D | No. | M.P. |
|---|---|---|---|---|---|---|---|
| 2491 | OH | $CH_3$ | $CHOHCH_2OH$—(S) | H | 7 | | |
| 2492 | OH | $CH_3$ | CHO | H | 7 | | |
| 2493 | OH | $CH_3$ | $CH_2OH$ | H | 7 | | |
| 2494 | OH | $CH_3$ | $CO_2H$ | H | 7 | | |
| 2495 | OH | $CH_3$ | $CO_2CH_3$ | H | 7 | | |
| 2496 | OH | $CH_3$ | CH=NOH | H | 7 | | |
| 2497 | OH | $CH_3$ | $CHOHCH=CH_2$—(R) | H | 7 | | |
| 2498 | OH | $CH_3$ | $CHOHCH=CH_2$—(S) | H | 7 | | |
| 2499 | OH | H | $CH_3$ | H | 7 | | |
| 2500 | OH | H | H | H | 7 | | |
| 2501 | OH | H | $CH=CH_2$ | H | 7 | | |
| 2502 | OH | H | $CHOHCH_2OH$—(R) | H | 7 | | |
| 2503 | OH | H | $CHOHCH_2OH$—(S) | H | 7 | | |
| 2504 | OH | H | CHO | H | 7 | | |
| 2505 | OH | H | $CH_2OH$ | H | 7 | | |
| 2506 | OH | H | $CO_2H$ | H | 7 | | |
| 2507 | OH | H | $CO_2CH_3$ | H | 7 | | |
| 2508 | OH | H | CH=NOH | H | 7 | | |
| 2509 | OH | H | $CHOHCH=CH_2$—(R) | H | 7 | | |
| 2510 | OH | H | $CHOHCH=CH_2$—(S) | H | 7 | | |
| 2511 | =O | $CH_3$ | $CH_3$ | H | 7 | | |
| 2512 | =O | $CH_3$ | H | H | 7 | | |
| 2513 | =O | $CH_3$ | $CH=CH_2$ | H | 7 | | |
| 2514 | =O | $CH_3$ | $CHOHCH_2OH$—(R) | H | 7 | | |
| 2515 | =O | $CH_3$ | $CHOHCH_2OH$—(S) | H | 7 | | |
| 2516 | =O | $CH_3$ | CHO | H | 7 | | |
| 2517 | =O | $CH_3$ | $CH_2OH$ | H | 7 | | |
| 2518 | =O | $CH_3$ | $CO_2H$ | H | 7 | | |
| 2519 | =O | $CH_3$ | $CO_2CH_3$ | H | 7 | | |
| 2520 | =O | $CH_3$ | CH=NOH | H | 7 | | |
| 2521 | =O | $CH_3$ | $CHOHCH=CH_2$—(R) | H | 7 | | |
| 2522 | =O | $CH_3$ | $CHOHCH=CH_2$—(R) | H | 7 | | |
| 2523 | =O | H | $CH_3$ | H | 7 | | |
| 2524 | =O | H | H | H | 7 | | |
| 2525 | =O | H | $CH=CH_2$ | H | 7 | | |
| 2526 | =O | H | $CHOHCH_2OH$—(R) | H | 7 | | |
| 2527 | =O | H | $CHOHCH_2OH$—(S) | H | 7 | | |
| 2528 | =O | H | CHO | H | 7 | | |
| 2529 | =O | H | $CH_2OH$ | H | 7 | | |
| 2530 | =O | H | $CO_2H$ | H | 7 | | |
| 2531 | =O | H | $CO_2CH_3$ | H | 7 | | |
| 2532 | =O | H | CH=NOH | H | 7 | | |
| 2533 | =O | H | $CHOHCH=CH_2$—(R) | H | 7 | | |
| 2534 | =O | H | $CHOHCH=CH_2$—(S) | H | 7 | | |
| 2535 | $OCH_3$ | $CH_3$ | $CH_3$ | H | 7 | | |
| 2536 | $OCH_3$ | $CH_3$ | H | H | 7 | | |
| 2537 | $OCH_3$ | $CH_3$ | $CH=CH_2$ | H | 7 | | |
| 2538 | $OCH_3$ | $CH_3$ | $CHOHCH_2OH$—(R) | H | 7 | | |
| 2539 | $OCH_3$ | $CH_3$ | $CHOHCH_2OH$—(S) | H | 7 | | |
| 2540 | $OCH_3$ | $CH_3$ | CHO | H | 7 | | |
| 2541 | $OCH_3$ | $CH_3$ | $CH_2OH$ | H | 7 | | |
| 2542 | $OCH_3$ | $CH_3$ | $CO_2H$ | H | 7 | | |
| 2543 | $OCH_3$ | $CH_3$ | $CO_2CH_3$ | H | 7 | | |
| 2544 | $OCH_3$ | $CH_3$ | CH=NOH | H | 7 | | |
| 2545 | $OCH_3$ | $CH_3$ | $CHOHCH=CH_2$—(R) | H | 7 | | |
| 2546 | $OCH_3$ | $CH_3$ | $CHOHCH=CH_2$—(S) | H | 7 | | |
| 2547 | $OCH_3$ | H | $CH_3$ | H | 7 | | |
| 2548 | $OCH_3$ | H | H | H | 7 | | |
| 2549 | $OCH_3$ | H | $CH=CH_2$ | H | 7 | | |
| 2550 | $OCH_3$ | H | $CHOHCH_2OH$—(R) | H | 7 | | |
| 2551 | $OCH_3$ | H | $CHOHCH_2OH$—(S) | H | 7 | | |
| 2552 | $OCH_3$ | H | CHO | H | 7 | | |
| 2553 | $OCH_3$ | H | $CH_2OH$ | H | 7 | | |
| 2554 | $OCH_3$ | H | $CO_2H$ | H | 7 | | |
| 2555 | $OCH_3$ | H | $CO_2CH_3$ | H | 7 | | |
| 2556 | $OCH_3$ | H | CH=NOH | H | 7 | | |
| 2557 | $OCH_3$ | H | $CHOHCH=CH_2$—(R) | H | 7 | | |
| 2558 | $OCH_3$ | H | $CHOHCH=CH_2$—(S) | H | 7 | | |
| 2559 | $OCOCH_3$ | $CH_3$ | $CH_3$ | H | 7 | | |

TABLE 10-continued

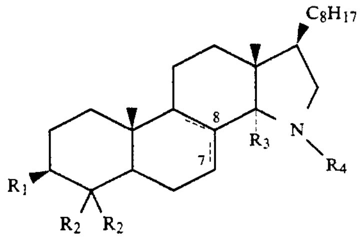

| No. | $R_1$ | $R_2$ | $R_3$ | $R_4$ | D | No. | M.P. |
|---|---|---|---|---|---|---|---|
| 2560 | $OCOCH_3$ | $CH_3$ | H | H | 7 | | |
| 2561 | $OCOCH_3$ | $CH_3$ | $CH{=}CH_2$ | H | 7 | | |
| 2562 | $OCOCH_3$ | $CH_3$ | $CHOHCH_2OH$—(R) | H | 7 | | |
| 2563 | $OCOCH_3$ | $CH_3$ | $CHOHCH_2OH$—(S) | H | 7 | | |
| 2564 | $OCOCH_3$ | $CH_3$ | CHO | H | 7 | | |
| 2565 | $OCOCH_3$ | $CH_3$ | $CH_2OH$ | H | 7 | | |
| 2566 | $OCOCH_3$ | $CH_3$ | $CO_2H$ | H | 7 | | |
| 2567 | $OCOCH_3$ | $CH_3$ | $CO_2CH_3$ | H | 7 | | |
| 2568 | $OCOCH_3$ | $CH_3$ | CH=NOH | H | 7 | | |
| 2569 | $OCOCH_3$ | $CH_3$ | $CHOHCH{=}CH_2$—(R) | H | 7 | | |
| 2570 | $OCOCH_3$ | $CH_3$ | $CHOHCH{=}CH_2$—(S) | H | 7 | | |
| 2571 | $OCOCH_3$ | H | $CH_3$ | H | 7 | | |
| 2572 | $OCOCH_3$ | H | H | H | 7 | | |
| 2573 | $OCOCH_3$ | H | $CH{=}CH_2$ | H | 7 | | |
| 2574 | $OCOCH_3$ | H | $CHOHCH_2OH$—(R) | H | 7 | | |
| 2575 | $OCOCH_3$ | H | $CHOHCH_2OH$—(S) | H | 7 | | |
| 2576 | $OCOCH_3$ | H | CHO | H | 7 | | |
| 2577 | $OCOCH_3$ | H | $CH_2OH$ | H | 7 | | |
| 2578 | $OCOCH_3$ | H | $CO_2H$ | H | 7 | | |
| 2579 | $OCOCH_3$ | H | $CO_2CH_3$ | H | 7 | | |
| 2580 | $OCOCH_3$ | H | CH=NOH | H | 7 | | |
| 2581 | $OCOCH_3$ | H | $CHOHCH{=}CH_2$—(R) | H | 7 | | |
| 2582 | $OCOCH_3$ | H | $CHOHCH{=}CH_2$—(S) | H | 7 | | |
| 2583 | OH | $CH_3$ | $CH_3$ | $CH_3$ | 8 | | |
| 2584 | OH | $CH_3$ | H | $CH_3$ | 8 | | |
| 2585 | OH | $CH_3$ | CHO | $CH_3$ | 8 | | |
| 2586 | OH | $CH_3$ | $CH_2OH$ | $CH_3$ | 8 | | |
| 2587 | OH | $CH_3$ | $CO_2H$ | $CH_3$ | 8 | | |
| 2588 | OH | H | $CH_3$ | $CH_3$ | 8 | | |
| 2589 | OH | H | H | $CH_3$ | 8 | | |
| 2590 | OH | H | CHO | $CH_3$ | 8 | | |
| 2591 | OH | H | $CH_2OH$ | $CH_3$ | 8 | | |
| 2592 | OH | H | $CO_2H$ | $CH_3$ | 8 | | |
| 2593 | =O | $CH_3$ | $CH_3$ | $CH_3$ | 8 | | |
| 2594 | =O | $CH_3$ | H | $CH_3$ | 8 | | |
| 2595 | =O | $CH_3$ | CHO | $CH_3$ | 8 | | |
| 2596 | =O | $CH_3$ | $CH_2OH$ | $CH_3$ | 8 | | |
| 2597 | =O | $CH_3$ | $CO_2H$ | $CH_3$ | 8 | | |
| 2598 | =O | H | $CH_3$ | $CH_3$ | 8 | | |
| 2599 | =O | H | H | $CH_3$ | 8 | | |
| 2600 | =O | H | CHO | $CH_3$ | 8 | | |
| 2601 | =O | H | $CH_2OH$ | $CH_3$ | 8 | | |
| 2602 | =O | H | $CO_2H$ | $CH_3$ | 8 | | |
| 2603 | $OCH_3$ | $CH_3$ | $CH_3$ | $CH_3$ | 8 | | |
| 2604 | $OCH_3$ | $CH_3$ | H | $CH_3$ | 8 | | |
| 2605 | $OCH_3$ | $CH_3$ | CHO | $CH_3$ | 8 | | |
| 2606 | $OCH_3$ | $CH_3$ | $CH_2OH$ | $CH_3$ | 8 | | |
| 2607 | $OCH_3$ | $CH_3$ | $CO_2H$ | $CH_3$ | 8 | | |
| 2608 | $OCH_3$ | H | $CH_3$ | $CH_3$ | 8 | | |
| 2609 | $OCH_3$ | H | H | $CH_3$ | 8 | | |
| 2610 | $OCH_3$ | H | CHO | $CH_3$ | 8 | | |
| 2611 | $OCH_3$ | H | $CH_2OH$ | $CH_3$ | 8 | | |
| 2612 | $OCH_3$ | H | $CH_2H$ | $CH_3$ | 8 | | |
| 2613 | $OCOCH_3$ | $CH_3$ | $CH_3$ | $CH_3$ | 8 | | |
| 2614 | $OCOCH_3$ | $CH_3$ | H | $CH_3$ | 8 | | |
| 2615 | $OCOCH_3$ | $CH_3$ | CHO | $CH_3$ | 8 | | |
| 2616 | $OCOCH_3$ | $CH_3$ | $CH_2OH$ | $CH_3$ | 8 | | |
| 2617 | $OCOCH_3$ | $CH_3$ | $CO_2H$ | $CH_3$ | 8 | | |
| 2618 | $OCOCH_3$ | H | $CH_3$ | $CH_3$ | 8 | | |
| 2619 | $OCOCH_3$ | H | H | $CH_3$ | 8 | | |
| 2620 | $OCOCH_3$ | H | CHO | $CH_3$ | 8 | | |
| 2621 | $OCOCH_3$ | H | $CH_2OH$ | $CH_3$ | 8 | | |
| 2622 | $OCOCH_3$ | H | $CO_2H$ | $CH_3$ | 8 | | |
| 2623 | OH | $CH_3$ | $CH_3$ | $CH_3$ | 7 | | |
| 2624 | OH | $CH_3$ | H | $CH_3$ | 7 | | |
| 2625 | OH | $CH_3$ | CHO | $CH_3$ | 7 | | |
| 2626 | OH | $CH_3$ | $CH_2OH$ | $CH_3$ | 7 | | |
| 2627 | OH | $CH_3$ | $CO_2H$ | $CH_3$ | 7 | | |
| 2628 | OH | H | $CH_3$ | $CH_3$ | 7 | | |

TABLE 10-continued

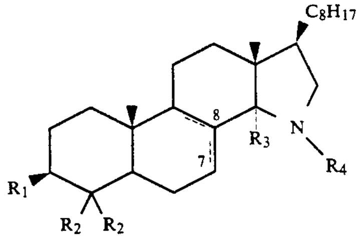

| No. | R1 | R2 | R3 | R4 | D | No. | M.P. |
|---|---|---|---|---|---|---|---|
| 2629 | OH | H | H | $CH_3$ | 7 | | |
| 2630 | OH | H | CHO | $CH_3$ | 7 | | |
| 2631 | OH | H | $CH_2OH$ | $CH_3$ | 7 | | |
| 2632 | OH | H | $CO_2H$ | $CH_3$ | 7 | | |
| 2633 | =O | $CH_3$ | $CH_3$ | $CH_3$ | 7 | | |
| 2634 | =O | $CH_3$ | H | $CH_3$ | 7 | | |
| 2635 | =O | $CH_3$ | CHO | $CH_3$ | 7 | | |
| 2636 | =O | $CH_3$ | $CH_2OH$ | $CH_3$ | 7 | | |
| 2637 | =O | $CH_3$ | $CO_2H$ | $CH_3$ | 7 | | |
| 2638 | =O | H | $CH_3$ | $CH_3$ | 7 | | |
| 2639 | =O | H | H | $CH_3$ | 7 | | |
| 2640 | =O | H | CHO | $CH_3$ | 7 | | |
| 2641 | =O | H | $CH_2OH$ | $CH_3$ | 7 | | |
| 2642 | =O | H | $CO_2H$ | $CH_3$ | 7 | | |
| 2643 | $OCH_3$ | $CH_3$ | $CH_3$ | $CH_3$ | 7 | | |
| 2644 | $OCH_3$ | $CH_3$ | H | $CH_3$ | 7 | | |
| 2645 | $OCH_3$ | $CH_3$ | CHO | $CH_3$ | 7 | | |
| 2646 | $OCH_3$ | $CH_3$ | $CH_2OH$ | $CH_3$ | 7 | | |
| 2647 | $OCH_3$ | $CH_3$ | $CO_2H$ | $CH_3$ | 7 | | |
| 2648 | $OCH_3$ | H | $CH_3$ | $CH_3$ | 7 | | |
| 2649 | $OCH_3$ | H | H | $CH_3$ | 7 | | |
| 2650 | $OCH_3$ | H | CHO | $CH_3$ | 7 | | |
| 2651 | $OCH_3$ | H | $CH_2OH$ | $CH_3$ | 7 | | |
| 2652 | $OCH_3$ | H | $CO_2H$ | $CH_3$ | 7 | | |
| 2653 | $OCOCH_3$ | $CH_3$ | $CH_3$ | $CH_3$ | 7 | | |
| 2654 | $OCOCH_3$ | $CH_3$ | H | $CH_3$ | 7 | | |
| 2655 | $OCOCH_3$ | $CH_3$ | CHO | $CH_3$ | 7 | | |
| 2656 | $OCOCH_3$ | $CH_3$ | $CH_2OH$ | $CH_3$ | 7 | | |
| 2657 | $OCOCH_3$ | $CH_3$ | $CO_2H$ | $CH_3$ | 7 | | |
| 2658 | $OCOCH_3$ | H | $CH_3$ | $CH_3$ | 7 | | |
| 2659 | $OCOCH_3$ | H | H | $CH_3$ | 7 | | |
| 2660 | $OCOCH_3$ | H | CHO | $CH_3$ | 7 | | |
| 2661 | $OCOCH_3$ | H | $CH_2OH$ | $CH_3$ | 7 | | |
| 2662 | $OCOCH_3$ | H | $CO_2H$ | $CH_3$ | 7 | | |
| 2663 | OH | $CH_3$ | $CH_3$ | CHO | 8 | | |
| 2664 | OH | $CH_3$ | H | CHO | 8 | | |
| 2665 | OH | $CH_3$ | CHO | CHO | 8 | | |
| 2666 | OH | $CH_3$ | $CH_2OH$ | CHO | 8 | | |
| 2667 | OH | $CH_3$ | $CO_2H$ | CHO | 8 | | |
| 2668 | OH | H | $CH_3$ | CHO | 8 | | |
| 2669 | OH | H | H | CHO | 8 | | |
| 2670 | OH | H | CHO | CHO | 8 | | |
| 2671 | OH | H | $CH_2OH$ | CHO | 8 | | |
| 2672 | OH | H | $CO_2OH$ | CHO | 8 | | |
| 2673 | =O | $CH_3$ | $CH_3$ | CHO | 8 | | |
| 2674 | =O | $CH_3$ | H | CHO | 8 | | |
| 2675 | =O | $CH_3$ | CHO | CHO | 8 | | |
| 2676 | =O | $CH_3$ | $CH_2OH$ | CHO | 8 | | |
| 2677 | =O | $CH_3$ | $CH_2H$ | CHO | 8 | | |
| 2678 | =O | H | $CH_3$ | CHO | 8 | | |
| 2679 | =O | H | H | CHO | 8 | | |
| 2680 | =O | H | CHO | CHO | 8 | | |
| 2681 | =O | H | $CH_2OH$ | CHO | 8 | | |
| 2682 | =O | H | $CO_2H$ | CHO | 8 | | |
| 2683 | $OCH_3$ | $CH_3$ | $CH_3$ | CHO | 8 | | |
| 2684 | $OCH_3$ | $CH_3$ | H | CHO | 8 | | |
| 2685 | $OCH_3$ | $CH_3$ | CHO | CHO | 8 | | |
| 2686 | $OCH_3$ | $CH_3$ | $CH_2OH$ | CHO | 8 | | |
| 2687 | $OCH_3$ | $CH_3$ | $CO_2H$ | CHO | 8 | | |
| 2688 | $OCH_3$ | H | $CH_3$ | CHO | 8 | | |
| 2689 | $OCH_3$ | H | H | CHO | 8 | | |
| 2690 | $OCH_3$ | H | CHO | CHO | 8 | | |
| 2691 | $OCH_3$ | H | $CH_2OH$ | CHO | 8 | | |
| 2692 | $OCH_3$ | H | $CO_2H$ | CHO | 8 | | |
| 2693 | $OCOCH_3$ | $CH_3$ | $CH_3$ | CHO | 8 | | |
| 2694 | $OCOCH_3$ | $CH_3$ | H | CHO | 8 | | |
| 2695 | $OCOCH_3$ | $CH_3$ | CHO | CHO | 8 | | |
| 2696 | $OCOCH_3$ | $CH_3$ | $CH_2OH$ | CHO | 8 | | |
| 2697 | $OCOCH_3$ | $CH_3$ | $CO_2H$ | CHO | 8 | | |

TABLE 10-continued

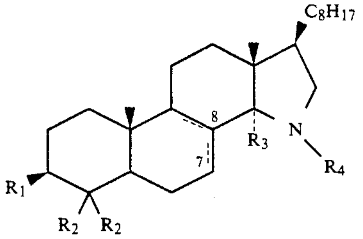

| No. | R1 | R2 | R3 | R4 | D | No. | M.P. |
|---|---|---|---|---|---|---|---|
| 2698 | $OCOCH_3$ | H | $CH_3$ | CHO | 8 | | |
| 2699 | $OCOCH_3$ | H | H | CHO | 8 | | |
| 2700 | $OCOCH_3$ | H | CHO | CHO | 8 | | |
| 2701 | $OCOCH_3$ | H | $CH_2OH$ | CHO | 8 | | |
| 2702 | $OCOCH_3$ | H | $CO_2H$ | CHO | 8 | | |
| 2703 | OH | $CH_3$ | $CH_3$ | CHO | 7 | | |
| 2704 | OH | $CH_3$ | H | CHO | 7 | | |
| 2705 | OH | $CH_3$ | CHO | CHO | 7 | | |
| 2706 | OH | $CH_3$ | $CH_2OH$ | CHO | 7 | | |
| 2707 | OH | $CH_3$ | $CO_2H$ | CHO | 7 | | |
| 2708 | OH | H | $CH_3$ | CHO | 7 | | |
| 2709 | OH | H | H | CHO | 7 | | |
| 2710 | OH | H | CHO | CHO | 7 | | |
| 2711 | OH | H | $CH_2OH$ | CHO | 7 | | |
| 2712 | OH | H | $CO_2H$ | CHO | 7 | | |
| 2713 | =O | $CH_3$ | $CH_3$ | CHO | 7 | | |
| 2714 | =O | $CH_3$ | H | CHO | 7 | | |
| 2715 | =O | $CH_3$ | CHO | CHO | 7 | | |
| 2716 | =O | $CH_3$ | $CH_2OH$ | CHO | 7 | | |
| 2717 | =O | $CH_3$ | $CO_2H$ | CHO | 7 | | |
| 2718 | =O | H | $CH_3$ | CHO | 7 | | |
| 2719 | =O | H | H | CHO | 7 | | |
| 2720 | =O | H | CHO | CHO | 7 | | |
| 2721 | =O | H | $CH_2OH$ | CHO | 7 | | |
| 2722 | =O | H | $CO_2H$ | CHO | 7 | | |
| 2723 | $OCH_3$ | $CH_3$ | $CH_3$ | CHO | 7 | | |
| 2724 | $OCH_3$ | $CH_3$ | H | CHO | 7 | | |
| 2725 | $OCH_3$ | $CH_3$ | CHO | CHO | 7 | | |
| 2726 | $OCH_3$ | $CH_3$ | $CH_2OH$ | CHO | 7 | | |
| 2727 | $OCH_3$ | $CH_3$ | $CO_2H$ | CHO | 7 | | |
| 2728 | $OCH_3$ | H | $CH_3$ | CHO | 7 | | |
| 2729 | $OCH_3$ | H | H | CHO | 7 | | |
| 2730 | $OCH_3$ | H | CHO | CHO | 7 | | |
| 2731 | $OCH_3$ | H | $CH_2OH$ | CHO | 7 | | |
| 2732 | $OCH_3$ | H | $CO_2H$ | CHO | 7 | | |
| 2733 | $OCOCH_3$ | $CH_3$ | $CH_3$ | CHO | 7 | | |
| 2734 | $OCOCH_3$ | $CH_3$ | H | CHO | 7 | | |
| 2735 | $OCOCH_3$ | $CH_3$ | CHO | CHO | 7 | | |
| 2736 | $OCOCH_3$ | $CH_3$ | $CH_2OH$ | CHO | 7 | | |
| 2737 | $OCOCH_3$ | $CH_3$ | $CO_2H$ | CHO | 7 | | |
| 2738 | $OCOCH_3$ | H | $CH_3$ | CHO | 7 | | |
| 2739 | $OCOCH_3$ | H | H | CHO | 7 | | |
| 2740 | $OCOCH_3$ | H | CHO | CHO | 7 | | |
| 2741 | $OCOCH_3$ | H | $CH_2OH$ | CHO | 7 | | |
| 2742 | $OCOCH_3$ | H | $CO_2H$ | CHO | 7 | | |
| 2743 | OH | $CH_3$ | $CH_3$ | $COCH_3$ | 8 | | |
| 2744 | OH | $CH_3$ | H | $COCH_3$ | 8 | | |
| 2745 | OH | $CH_3$ | CHO | $COCH_3$ | 8 | | |
| 2746 | OH | $CH_3$ | $CH_2OH$ | $COCH_3$ | 8 | | |
| 2747 | OH | $CH_3$ | $CO_2H$ | $COCH_3$ | 8 | | |
| 2748 | OH | H | $CH_3$ | $COCH_3$ | 8 | | |
| 2749 | OH | H | H | $COCH_3$ | 8 | | |
| 2750 | OH | H | CHO | $COCH_3$ | 8 | | |
| 2751 | OH | H | $CH_2OH$ | $COCH_3$ | 8 | | |
| 2752 | OH | H | $CO_2H$ | $COCH_3$ | 8 | | |
| 2753 | =O | $CH_3$ | $CH_3$ | $COCH_3$ | 8 | | |
| 2754 | =O | $CH_3$ | H | $COCH_3$ | 8 | | |
| 2755 | =O | $CH_3$ | CHO | $COCH_3$ | 8 | | |
| 2756 | =O | $CH_3$ | $CH_2OH$ | $COCH_3$ | 8 | | |
| 2757 | =O | $CH_3$ | $CO_2H$ | $COCH_3$ | 8 | | |
| 2758 | =O | H | $CH_3$ | $COCH_3$ | 8 | | |
| 2759 | =O | H | H | $COCH_3$ | 8 | | |
| 2760 | =O | H | CHO | $COCH_3$ | 8 | | |
| 2761 | =O | H | $CH_2OH$ | $COCH_3$ | 8 | | |
| 2762 | =O | H | $CO_2H$ | $COCH_3$ | 8 | | |
| 2763 | $OCH_3$ | $CH_3$ | $CH_3$ | $COCH_3$ | 8 | | |
| 2764 | $OCH_3$ | $CH_3$ | H | $COCH_3$ | 8 | | |
| 2765 | $OCH_3$ | $CH_3$ | CHO | $COCH_3$ | 8 | | |
| 2766 | $OCH_3$ | $CH_3$ | $CH_2OH$ | $COCH_3$ | 8 | | |

TABLE 10-continued

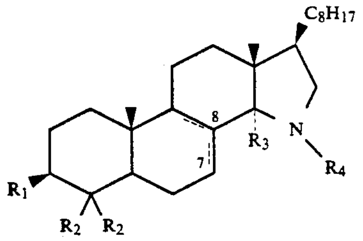

| No. | R1 | R2 | R3 | R4 | D | No. | M.P. |
|---|---|---|---|---|---|---|---|
| 2767 | $OCH_3$ | $CH_3$ | $CO_2H$ | $COCH_3$ | 8 | | |
| 2768 | $OCH_3$ | H | $CH_3$ | $COCH_3$ | 8 | | |
| 2769 | $OCH_3$ | H | H | $COCH_3$ | 8 | | |
| 2770 | $OCH_3$ | H | CHO | $COCH_3$ | 8 | | |
| 2771 | $OCH_3$ | H | $CH_2OH$ | $COCH_3$ | 8 | | |
| 2772 | $OCH_3$ | H | $CO_2H$ | $COCH_3$ | 8 | | |
| 2773 | $OCOCH_3$ | $CH_3$ | $CH_3$ | $COCH_3$ | 8 | | |
| 2774 | $OCOCH_3$ | $CH_3$ | H | $COCH_3$ | 8 | | |
| 2775 | $OCOCH_3$ | $CH_3$ | CHO | $COCH_3$ | 8 | | |
| 2776 | $OCOCH_3$ | $CH_3$ | $CH_2OH$ | $COCH_3$ | 8 | | |
| 2777 | $OCOCH_3$ | $CH_3$ | $CO_2H$ | $COCH_3$ | 8 | | |
| 2778 | $OCOCH_3$ | H | $CH_3$ | $COCH_3$ | 8 | | |
| 2779 | $OCOCH_3$ | H | H | $COCH_3$ | 8 | | |
| 2780 | $OCOCH_3$ | H | CHO | $COCH_3$ | 8 | | |
| 2781 | $OCOCH_3$ | H | $CH_2OH$ | $COCH_3$ | 8 | | |
| 2782 | $OCOCH_3$ | H | $CO_2H$ | $COCH_3$ | 8 | | |
| 2783 | OH | $CH_3$ | $CH_3$ | $COCH_3$ | 7 | | |
| 2784 | OH | $CH_3$ | H | $COCH_3$ | 7 | | |
| 2785 | OH | $CH_3$ | CHO | $COCH_3$ | 7 | | |
| 2786 | OH | $CH_3$ | $CH_2OH$ | $COCH_3$ | 7 | | |
| 2787 | OH | $CH_3$ | $CO_2H$ | $COCH_3$ | 7 | | |
| 2788 | OH | H | $CH_3$ | $COCH_3$ | 7 | | |
| 2789 | OH | H | H | $COCH_3$ | 7 | | |
| 2790 | OH | H | CHO | $COCH_3$ | 7 | | |
| 2791 | OH | H | $CH_2OH$ | $COCH_3$ | 7 | | |
| 2792 | OH | H | $CO_2H$ | $COCH_3$ | 7 | | |
| 2793 | =O | $CH_3$ | $CH_3$ | $COCH_3$ | 7 | | |
| 2794 | =O | $CH_3$ | H | $COCH_3$ | 7 | | |
| 2795 | =O | $CH_3$ | CHO | $COCH_3$ | 7 | | |
| 2796 | =O | $CH_3$ | $CH_2OH$ | $COCH_3$ | 7 | | |
| 2797 | =O | $CH_3$ | $CO_2H$ | $COCH_3$ | 7 | | |
| 2798 | =O | H | $CH_3$ | $COCH_3$ | 7 | | |
| 2799 | =O | H | H | $COCH_3$ | 7 | | |
| 2800 | =O | H | CHO | $COCH_3$ | 7 | | |
| 2801 | =O | H | $CH_2OH$ | $COCH_3$ | 7 | | |
| 2802 | =O | H | $CO_2H$ | $COCH_3$ | 7 | | |
| 2803 | $OCH_3$ | $CH_3$ | $CH_3$ | $COCH_3$ | 7 | | |
| 2804 | $OCH_3$ | $CH_3$ | H | $COCH_3$ | 7 | | |
| 2805 | $OCH_3$ | $CH_3$ | CHO | $COCH_3$ | 7 | | |
| 2806 | $OCH_3$ | $CH_3$ | $CH_2OH$ | $COCH_3$ | 7 | | |
| 2807 | $OCH_3$ | $CH_3$ | $CO_3H$ | $COCH_3$ | 7 | | |
| 2808 | $OCH_3$ | H | $CH_3$ | $COCH_3$ | 7 | | |
| 2809 | $OCH_3$ | H | H | $COCH_3$ | 7 | | |
| 2810 | $OCH_3$ | H | CHO | $COCH_3$ | 7 | | |
| 2811 | $OCH_3$ | H | $CH_3OH$ | $COCH_3$ | 7 | | |
| 2812 | $OCH_3$ | H | $CO_2OH$ | $COCH_3$ | 7 | | |
| 2813 | $OCOCH_3$ | $CH_3$ | $CH_3$ | $COCH_3$ | 7 | | |
| 2814 | $OCOCH_3$ | $CH_3$ | H | $COCH_3$ | 7 | | |
| 2815 | $OCOCH_3$ | $CH_3$ | CHO | $COCH_3$ | 7 | | |
| 2816 | $OCOCH_3$ | $CH_3$ | $CH_2OH$ | $COCH_3$ | 7 | | |
| 2817 | $OCOCH_3$ | $CH_3$ | $CO_2H$ | $COCH_3$ | 7 | | |
| 2818 | $OCOCH_3$ | H | $CH_3$ | $COCH_3$ | 7 | | |
| 2819 | $OCOCH_3$ | H | CHO | $COCH_3$ | 7 | | |
| 2821 | $OCOCH_3$ | H | $CH_2OH$ | $COCH_3$ | 7 | | |
| 2822 | $OCOCH_3$ | H | $CO_2H$ | $COCH_3$ | 7 | | |

TABLE 11

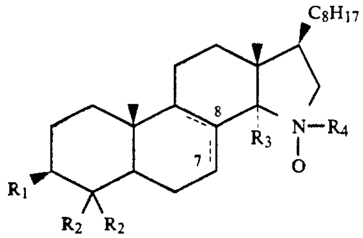

| No. | $R_1$ | $R_2$ | $R_3$ | $R_4$ | D | No. | M.P. |
|---|---|---|---|---|---|---|---|
| 2823 | OH | $CH_3$ | $CH_3$ | $CH_3$ | 8 | | |
| 2824 | OH | $CH_3$ | H | $CH_3$ | 8 | | |
| 2825 | OH | $CH_3$ | $CH{=}CH_2$ | $CH_3$ | 8 | | |
| 2826 | OH | $CH_3$ | $CHOHCH_2OH$—(R) | $CH_3$ | 8 | | |
| 2827 | OH | $CH_3$ | $CHOHCH_2OH$—(S) | $CH_3$ | 8 | | |
| 2828 | OH | $CH_3$ | CHO | $CH_3$ | 8 | | |
| 2829 | OH | $CH_3$ | $CH_2OH$ | $CH_3$ | 8 | | |
| 2830 | OH | $CH_3$ | $CO_2H$ | $CH_3$ | 8 | | |
| 2831 | OH | $CH_3$ | $CO_2CH_3$ | $CH_3$ | 8 | | |
| 2832 | OH | $CH_3$ | CH=NOH | $CH_3$ | 8 | | |
| 2833 | OH | $CH_3$ | $CHOHCH{=}CH_2$—(R) | $CH_3$ | 8 | | |
| 2834 | OH | $CH_3$ | $CHOHCH{=}CH_2$—(S) | $CH_3$ | 8 | | |
| 2835 | OH | H | $CH_3$ | $CH_3$ | 8 | | |
| 2836 | OH | H | H | $CH_3$ | 8 | | |
| 2837 | OH | H | $CH{=}CH_2$ | $CH_3$ | 8 | | |
| 2838 | OH | H | $CHOHCH_2OH$—(R) | $CH_3$ | 8 | | |
| 2839 | OH | H | $CHOHCH_2OH$—(S) | $CH_3$ | 8 | | |
| 2840 | OH | H | CHO | $CH_3$ | 8 | | |
| 2841 | OH | H | $CH_2OH$ | $CH_3$ | 8 | | |
| 2842 | OH | H | $CO_2H$ | $CH_3$ | 8 | | |
| 2843 | OH | H | $CO_2CH_3$ | $CH_3$ | 8 | | |
| 2844 | OH | H | CH=NOH | $CH_3$ | 8 | | |
| 2845 | OH | H | $CHOHCH{=}CH_2$—(R) | $CH_3$ | | | |
| 2846 | OH | H | $CHOHCH{=}CH_2$—(S) | $CH_3$ | | | |
| 2847 | =O | $CH_3$ | $CH_3$ | $CH_3$ | | | |
| 2848 | =O | $CH_3$ | H | $CH_3$ | 8 | | |
| 2849 | =O | $CH_3$ | CHO | $CH_3$ | 8 | | |
| 2850 | =O | $CH_3$ | $CH_2OH$ | $CH_3$ | 8 | | |
| 2851 | =O | $CH_3$ | $CO_2H$ | $CH_3$ | 8 | | |
| 2852 | =O | H | $CH_3$ | $CH_3$ | 8 | | |
| 2853 | =O | H | H | $CH_3$ | 8 | | |
| 2854 | =O | H | CHO | $CH_3$ | 8 | | |
| 2855 | =O | H | $CH_2OH$ | $CH_3$ | 8 | | |
| 2856 | =O | H | $CO_2H$ | $CH_3$ | 8 | | |
| 2857 | $OCH_3$ | $CH_3$ | $CH_3$ | $CH_3$ | 8 | | |
| 2858 | $OCH_3$ | $CH_3$ | H | $CH_3$ | 8 | | |
| 2859 | $OCH_3$ | $CH_3$ | $CH_2OH$ | $CH_3$ | 8 | | |
| 2860 | $OCH_3$ | $CH_3$ | $CO_2H$ | $CH_3$ | 8 | | |
| 2861 | $OCH_3$ | H | $CH_3$ | $CH_3$ | 8 | | |
| 2862 | $OCH_3$ | H | H | $CH_3$ | 8 | | |
| 2863 | $OCH_3$ | H | CHO | $CH_3$ | 8 | | |
| 2864 | $OCH_3$ | H | $CH_2OH$ | $CH_3$ | 8 | | |
| 2865 | $OCH_3$ | H | $CO_2H$ | $CH_3$ | 8 | | |
| 2866 | $OCOCH_3$ | $CH_3$ | $CH_3$ | $CH_3$ | 8 | | |
| 2867 | $OCOCH_3$ | $CH_3$ | H | $CH_3$ | 8 | | |
| 2868 | $OCOCH_3$ | $CH_3$ | CHO | $CH_3$ | 8 | | |
| 2869 | $OCOCH_3$ | $CH_3$ | $CH_2OH$ | $CH_3$ | 8 | | |
| 2870 | $OCOCH_3$ | $CH_3$ | $CO_2H$ | $CH_3$ | 8 | | |
| 2871 | $OCOCH_3$ | H | $CH_3$ | $CH_3$ | 8 | | |
| 2872 | $OCOCH_3$ | H | H | $CH_3$ | 8 | | |
| 2873 | $OCOCH_3$ | H | CHO | $CH_3$ | 8 | | |
| 2874 | $OCOCH_3$ | H | $CH_2OH$ | $CH_3$ | 8 | | |
| 2875 | $OCOCH_3$ | H | $CO_2H$ | $CH_3$ | 8 | | |
| 2876 | OH | $CH_3$ | $CH_3$ | $CH_3$ | 7 | | |
| 2877 | OH | $CH_3$ | H | $CH_3$ | 7 | | |
| 2878 | OH | $CH_3$ | CHO | $CH_3$ | 7 | | |
| 2879 | OH | $CH_3$ | $CH_2OH$ | $CH_3$ | 7 | | |
| 2880 | OH | $CH_3$ | $CO_2H$ | $CH_3$ | 7 | | |
| 2881 | OH | H | $CH_{32}$ | $CH_3$ | 7 | | |
| 2882 | OH | H | H | $CH_3$ | 7 | | |
| 2883 | OH | H | CHO | $CH_3$ | 7 | | |
| 2884 | OH | H | $CH_2OH$ | $CH_3$ | 7 | | |
| 2885 | OH | H | $CO_2H$ | $CH_3$ | 7 | | |
| 2886 | =O | $CH_3$ | $CH_3$ | $CH_3$ | 7 | | |
| 2887 | =O | $CH_3$ | H | $CH_3$ | 7 | | |
| 2888 | =O | $CH_3$ | CHO | $CH_3$ | 7 | | |
| 2889 | =O | $CH_3$ | $CH_2OH$ | $CH_3$ | 7 | | |
| 2890 | =O | $CH_3$ | $CO_2H$ | $CH_3$ | 7 | | |
| 2891 | =O | H | $CH_3$ | $CH_3$ | 7 | | |

TABLE 11-continued

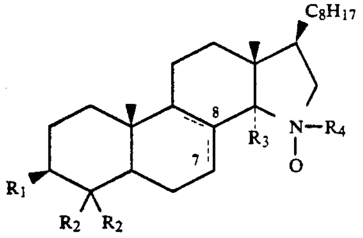

| No. | $R_1$ | $R_2$ | $R_3$ | $R_4$ | D | No. | M.P. |
|---|---|---|---|---|---|---|---|
| 2892 | =O | H | H | $CH_3$ | 7 | | |
| 2893 | =O | H | CHO | $CH_3$ | 7 | | |
| 2894 | =O | H | $CH_2OH$ | $CH_3$ | 7 | | |
| 2895 | =O | H | $CO_2H$ | $CH_3$ | 7 | | |
| 2896 | $OCH_3$ | $CH_3$ | $CH_3$ | $CH_3$ | 7 | | |
| 2897 | $OCH_3$ | $CH_3$ | H | $CH_3$ | 7 | | |
| 2898 | $OCH_3$ | $CH_3$ | CHO | $CH_3$ | 7 | | |
| 2899 | $OCH_3$ | $CH_3$ | $CH_2OH$ | $CH_3$ | 7 | | |
| 2900 | $OCH_3$ | $CH_3$ | $CO_2H$ | $CH_3$ | 7 | | |
| 2901 | $OCH_3$ | H | $CH_3$ | $CH_3$ | 7 | | |
| 2902 | $OCH_3$ | H | H | $CH_3$ | 7 | | |
| 2903 | $OCH_3$ | H | CHO | $CH_3$ | 7 | | |
| 2904 | $OCH_3$ | H | $CH_2OH$ | $CH_3$ | 7 | | |
| 2905 | $OCH_3$ | H | $CO_2H$ | $CH_3$ | 7 | | |
| 2906 | $OCOCH_3$ | $CH_3$ | $CH_3$ | $CH_3$ | 7 | | |
| 2907 | $OCOCH_3$ | $CH_3$ | H | $CH_3$ | 7 | | |
| 2908 | $OCOCH_3$ | $CH_3$ | CHO | $CH_3$ | 7 | | |
| 2909 | $OCOCH_3$ | $CH_3$ | $CH_2OH$ | $CH_3$ | 7 | | |
| 2910 | $OCOCH_3$ | $CH_3$ | $CO_2H$ | $CH_3$ | 7 | | |
| 2911 | $OCOCH_3$ | H | $CH_3$ | $CH_3$ | 7 | | |
| 2912 | $OCOCH_3$ | H | H | $CH_3$ | 7 | | |
| 2913 | $OCOCH_3$ | H | CHO | $CH_3$ | 7 | | |
| 2914 | $OCOCH_3$ | H | $CH_2OH$ | $CH_3$ | 7 | | |
| 2915 | $OCOCH_3$ | H | $CO_2H$ | $CH_3$ | 7 | | |

TABLE 12

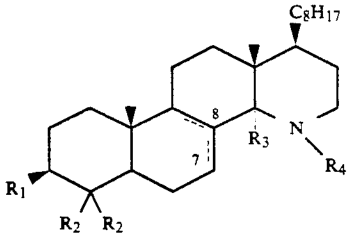

| No. | $R_1$ | $R_2$ | $R_3$ | $R_4$ | D | No. | M.P. |
|---|---|---|---|---|---|---|---|
| 2916 | OH | $CH_3$ | $CH_3$ | H | 8 | | |
| 2917 | OH | $CH_3$ | H | H | 8 | | |
| 2918 | OH | $CH_3$ | $CH{=}CH_2$ | H | 8 | | |
| 2919 | OH | $CH_3$ | $CHOHCH_2OH$—(R) | H | 8 | | |
| 2920 | OH | $CH_3$ | $CHOHCH_2OH$—(S) | H | 8 | | |
| 2921 | OH | $CH_3$ | CHO | H | 8 | | |
| 2922 | OH | $CH_3$ | $CH_2OH$ | H | 8 | | |
| 2923 | OH | $CH_3$ | $CO_2H$ | H | 8 | | |
| 2924 | OH | $CH_3$ | $CO_2CH_3$ | H | 8 | | |
| 2925 | OH | $CH_3$ | CH=NOH | H | 8 | | |
| 2926 | OH | $CH_3$ | $CHOHCH{=}CH_2$—(R) | H | 8 | | |
| 2927 | OH | $CH_3$ | $CHOHCH{=}CH_2$—(S) | H | 8 | | |
| 2928 | OH | H | $CH_3$ | H | 8 | | |
| 2929 | OH | H | H | H | 8 | | |
| 2930 | OH | H | $CH{=}CH_2$ | H | 8 | | |
| 2931 | OH | H | $CHOHCH_2OH$—(R) | H | 8 | | |
| 2932 | OH | H | $CHOHCH_2OH$—(S) | H | 8 | | |
| 2933 | OH | H | CHO | H | 8 | | |
| 2934 | OH | H | $CH_2OH$ | H | 8 | | |
| 2935 | OH | H | $CO_2H$ | H | 8 | | |
| 2936 | OH | H | $CO_2CH_3$ | H | 8 | | |
| 2937 | OH | H | CH=NOH | H | 8 | | |
| 2938 | OH | H | $CHOHCH{=}CH_2$—(R) | H | 8 | | |
| 2939 | OH | H | $CHOHCH{=}CH_2$—(S) | H | 8 | | |
| 2940 | OH | $CH_3$ | $CH_2SH$ | H | 8 | | |
| 2941 | OH | $CH_3$ | $CH_2NH_2$ | H | 8 | | |
| 2942 | OH | $CH_3$ | $COCH_3$ | H | 8 | | |

TABLE 12-continued

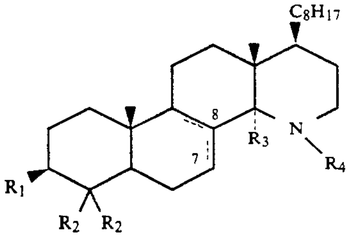

| No. | R1 | R2 | R3 | R4 | D | No. | M.P. |
|---|---|---|---|---|---|---|---|
| 2943 | OH | $CH_3$ | $CONH_2$ | H | 8 | | |
| 2944 | OH | $CH_3$ | $CSNH_2$ | H | 8 | | |
| 2945 | OH | $CH_3$ | $CH_2CH_2OH$ | H | 8 | | |
| 2946 | OH | $CH_3$ | $CH_2CHO$ | H | 8 | | |
| 2947 | OH | $CH_3$ | $CH_2COCH_3$ | H | 8 | | |
| 2948 | OH | $CH_3$ | $CH_2CO_2CH_3$ | H | 8 | | |
| 2949 | OH | $CH_3$ | $CH_2CONH_2$ | H | 8 | | |
| 2950 | OH | $CH_3$ | $CH_2CH_2Cl$ | H | 8 | | |
| 2951 | OH | $CH_3$ | CN | H | 8 | | |
| 2952 | OH | $CH_3$ | $CH{=}NNH_2$ | H | 8 | | |
| 2953 | OH | $CH_3$ | $CH_2NHOH$ | H | 8 | | |
| 2954 | OH | $CH_3$ | $CH_2NHNH_2$ | H | 8 | | |
| 2955 | OH | $CH_3$ | $CH_2CN$ | H | 8 | | |
| 2956 | OH | $CH_3$ | $CH_2CH{=}NOH$ | H | 8 | | |
| 2957 | OH | $CH_3$ | $CH_2CH{=}NNH_2$ | H | 8 | | |
| 2958 | OH | $CH_3$ | $CH_2CH_2NHOH$ | H | 8 | | |
| 2959 | OH | $CH_3$ | $CH_2CH_2NHNH_2$ | H | 8 | | |
| 2960 | OH | $CH_3$ | CONHOH | H | 8 | | |
| 2961 | OH | $CH_3$ | $CH{=}CHCHO$ | H | 8 | | |
| 2962 | OH | $CH_3$ | $CH{=}CHCOCH_3$ | H | 8 | | |
| 2963 | OH | $CH_3$ | $CH{=}CHCH_2Cl$ | H | 8 | | |
| 2964 | OH | $CH_3$ | $CH_2CHOHCH_2OH$ | H | 8 | | |
| 2965 | OH | $CH_3$ | 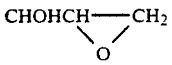 | H | 8 | | |
| 2966 | =O | $CH_3$ | $CH_3$ | H | 8 | | |
| 2967 | =O | $CH_3$ | H | H | 8 | | |
| 2968 | =O | $CH_3$ | CHO | H | 8 | | |
| 2969 | =O | $CH_3$ | $CH_2OH$ | H | 8 | | |
| 2970 | =O | $CH_3$ | $CO_2H$ | H | 8 | | |
| 2971 | =O | H | $CH_3$ | H | 8 | | |
| 2972 | =O | H | H | H | 8 | | |
| 2973 | =O | H | CHO | H | 8 | | |
| 2974 | =O | H | $CH_2OH$ | H | 8 | | |
| 2975 | =O | H | $CO_2H$ | H | 8 | | |
| 2976 | $OCH_3$ | $CH_3$ | $CH_3$ | H | 8 | | |
| 2977 | $OCH_3$ | $CH_3$ | H | H | 8 | | |
| 2978 | $OCH_3$ | $CH_3$ | $CH_2OH$ | H | 8 | | |
| 2979 | $OCH_3$ | $CH_3$ | $CO_2H$ | H | 8 | | |
| 2980 | $OCH_3$ | H | $CH_3$ | H | 8 | | |
| 2981 | $OCH_3$ | H | H | H | 8 | | |
| 2982 | $OCH_3$ | H | CHO | H | 8 | | |
| 2983 | $OCH_3$ | H | $CH_2OH$ | H | 8 | | |
| 2984 | $OCH_3$ | H | $CO_2H$ | H | 8 | | |
| 2985 | $OCOCH_3$ | $CH_3$ | $CH_3$ | H | 8 | | |
| 2986 | $OCOCH_3$ | $CH_3$ | H | H | 8 | | |
| 2987 | $OCOCH_3$ | $CH_3$ | CHO | H | 8 | | |
| 2988 | $OCOCH_3$ | $CH_3$ | $CH_2OH$ | H | 8 | | |
| 2989 | $OCOCH_3$ | $CH_3$ | $CO_2H$ | H | 8 | | |
| 2990 | $OCOCH_3$ | H | $CH_3$ | H | 8 | | |
| 2991 | $OCOCH_3$ | H | H | H | 8 | | |
| 2992 | $OCOCH_3$ | H | CHO | H | 8 | | |
| 2993 | $OCOCH_3$ | H | $CH_2OH$ | H | 8 | | |
| 2994 | $OCOCH_3$ | H | $CO_2H$ | H | 8 | | |
| 2995 | OH | $CH_3$ | $CH_3$ | H | 7 | | |
| 2996 | OH | $CH_3$ | H | H | 7 | | |
| 2997 | OH | $CH_3$ | CHO | H | 7 | | |
| 2998 | OH | $CH_3$ | $CH_2OH$ | H | 7 | | |
| 2999 | OH | $CH_3$ | $CO_2H$ | H | 7 | | |
| 3000 | OH | H | $CH_3$ | H | 7 | | |
| 3001 | OH | H | H | H | 7 | | |
| 3002 | OH | H | CHO | H | 7 | | |
| 3003 | OH | H | $CH_2OH$ | H | 7 | | |
| 3004 | OH | H | $CO_2H$ | H | 7 | | |
| 3005 | =O | $CH_3$ | $CH_3$ | H | 7 | | |
| 3006 | =O | $CH_3$ | H | H | 7 | | |

TABLE 12-continued

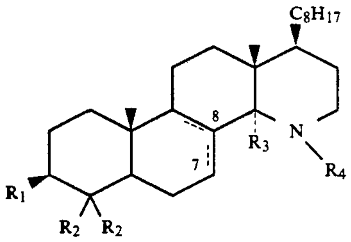

| No. | $R_1$ | $R_2$ | $R_3$ | $R_4$ | D | No. | M.P. |
|---|---|---|---|---|---|---|---|
| 3007 | =O | $CH_3$ | CHO | H | 7 | | |
| 3008 | =O | $CH_3$ | $CH_2OH$ | H | 7 | | |
| 3009 | =O | $CH_3$ | $CO_2H$ | H | 7 | | |
| 3010 | =O | H | $CH_3$ | H | 7 | | |
| 3011 | =O | H | H | H | 7 | | |
| 3012 | =O | H | CHO | H | 7 | | |
| 3013 | =O | H | $CH_2OH$ | H | 7 | | |
| 3014 | =O | H | $CO_2H$ | H | 7 | | |
| 3015 | $OCH_3$ | $CH_3$ | $CH_3$ | H | 7 | | |
| 3016 | $OCH_3$ | $CH_3$ | H | H | 7 | | |
| 3017 | $OCH_3$ | $CH_3$ | CHO | H | 7 | | |
| 3018 | $OCH_3$ | $CH_3$ | $CH_2OH$ | H | 7 | | |
| 3019 | $OCH_3$ | $CH_3$ | $CO_2$ | H | 7 | | |
| 3020 | $OCH_3$ | H | $CH_3$ | H | 7 | | |
| 3021 | $OCH_3$ | H | H | H | 7 | | |
| 3022 | $OCH_3$ | H | CHO | H | 7 | | |
| 3023 | $OCH_3$ | H | $CH_2OH$ | H | 7 | | |
| 3024 | $OCH_3$ | H | $CO_2H$ | H | 7 | | |
| 3025 | $OCOCH_3$ | $CH_3$ | $CH_3$ | H | 7 | | |
| 3026 | $OCOCH_3$ | $CH_3$ | H | H | 7 | | |
| 3027 | $OCOCH_3$ | $CH_3$ | CHO | H | 7 | | |
| 3028 | $OCOCH_3$ | $CH_3$ | $CH_2OH$ | H | 7 | | |
| 3029 | $OCOCH_3$ | $CH_3$ | $CO_2H$ | H | 7 | | |
| 3030 | $OCOCH_3$ | H | $CH_3$ | H | 7 | | |
| 3031 | $OCOCH_3$ | H | H | H | 7 | | |
| 3032 | $OCOCH_3$ | H | CHO | H | 7 | | |
| 3033 | $OCOCH_3$ | H | $CH_2OH$ | H | 7 | | |
| 3034 | $OCOCH_3$ | H | $CO_2H$ | H | 7 | | |
| 3035 | OH | $CH_3$ | $CH_3$ | $CH_3$ | 8 | | |
| 3036 | OH | $CH_3$ | H | $CH_3$ | 8 | | |
| 3037 | OH | $CH_3$ | CHO | $CH_3$ | 8 | | |
| 3038 | OH | $CH_3$ | $CH_2OH$ | $CH_3$ | 8 | | |
| 3039 | OH | $CH_3$ | $CO_2H$ | $CH_3$ | 8 | | |
| 3040 | OH | H | $CH_3$ | $CH_3$ | 8 | | |
| 3041 | OH | H | H | $CH_3$ | 8 | | |
| 3042 | OH | H | CHO | $CH_3$ | 8 | | |
| 3043 | OH | H | $CH_2OH$ | $CH_3$ | 8 | | |
| 3044 | OH | H | $CO_2H$ | $CH_3$ | 8 | | |
| 3045 | =O | $CH_3$ | $CH_3$ | $CH_3$ | 8 | | |
| 3046 | =O | $CH_3$ | H | $CH_3$ | 8 | | |
| 3047 | =O | $CH_3$ | CHO | $CH_3$ | 8 | | |
| 3048 | =O | $CH_3$ | $CH_2OH$ | $CH_3$ | 8 | | |
| 3049 | =O | $CH_3$ | $CO_2H$ | $CH_3$ | 8 | | |
| 3050 | =O | H | $CH_3$ | $CH_3$ | 8 | | |
| 3051 | =O | H | H | $CH_3$ | 8 | | |
| 3052 | =O | H | CHO | $CH_3$ | 8 | | |
| 3053 | =O | H | $CH_2OH$ | $CH_3$ | 8 | | |
| 3054 | =O | H | $CO_2H$ | $CH_3$ | 8 | | |
| 3055 | $OCH_3$ | $CH_3$ | $CH_3$ | $CH_3$ | 8 | | |
| 3056 | $OCH_3$ | $CH_3$ | H | $CH_3$ | 8 | | |
| 3057 | $OCH_3$ | $CH_3$ | CHO | $CH_3$ | 8 | | |
| 3058 | $OCH_3$ | $CH_3$ | $CH_2OH$ | $CH_3$ | 8 | | |
| 3059 | $OCH_3$ | $CO_3H$ | | $CH_3$ | 8 | | |
| 3060 | $OCH_3$ | H | $CH_3$ | $CH_3$ | 8 | | |
| 3061 | $OCH_3$ | H | H | $CH_3$ | 8 | | |
| 3062 | $OCH_3$ | H | CHO | $CH_3$ | 8 | | |
| 3063 | $OCH_3$ | H | $CH_2OH$ | $CH_3$ | 8 | | |
| 3064 | $OCH_3$ | H | $CO_2H$ | $CH_3$ | 8 | | |
| 3065 | $OCOCH_3$ | $CH_3$ | $CH_3$ | $CH_3$ | 8 | | |
| 3066 | $OCOCH_3$ | $CH_3$ | H | $CH_3$ | 8 | | |
| 3067 | $OCOCH_3$ | $CH_3$ | CHO | $CH_3$ | 8 | | |
| 3068 | $OCOCH_3$ | $CH_3$ | $CH_2OH$ | $CH_3$ | 8 | | |
| 3069 | $OCOCH_3$ | $CH_3$ | $CO_2H$ | $CH_3$ | 8 | | |
| 3070 | $OCOCH_3$ | H | $CH_3$ | $CH_3$ | 8 | | |
| 3071 | $OCOCH_3$ | H | H | $CH_3$ | 8 | | |
| 3072 | $OCOCH_3$ | H | CHO | $CH_3$ | 8 | | |
| 3073 | $OCOCH_3$ | H | $CH_2OH$ | $CH_3$ | 8 | | |
| 3074 | $OCOCH_3$ | H | $CO_2H$ | $CH_3$ | 8 | | |
| 3075 | OH | $CH_3$ | $CH_3$ | $CH_3$ | 7 | | |

TABLE 12-continued

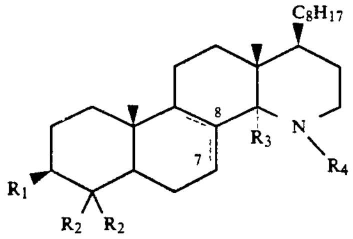

| No. | R1 | R2 | R3 | R4 | D | No. | M.P. |
|---|---|---|---|---|---|---|---|
| 3076 | OH | $CH_3$ | H | $CH_3$ | 7 | | |
| 3077 | OH | $CH_3$ | CHO | $CH_3$ | 7 | | |
| 3078 | OH | $CH_3$ | $CH_2OH$ | $CH_3$ | 7 | | |
| 3079 | OH | $CH_3$ | $CO_2H$ | $CH_3$ | 7 | | |
| 3080 | OH | H | $CH_3$ | $CH_3$ | 7 | | |
| 3081 | OH | H | H | $CH_3$ | 7 | | |
| 3082 | OH | H | CHO | $CH_3$ | 7 | | |
| 3083 | OH | H | $CH_2OH$ | $CH_3$ | 7 | | |
| 3084 | OH | H | $CO_2H$ | $CH_3$ | 7 | | |
| 3085 | =O | $CH_3$ | $CH_3$ | $CH_3$ | 7 | | |
| 3086 | =O | $CH_3$ | H | $CH_3$ | 7 | | |
| 3087 | =O | $CH_3$ | CHO | $CH_3$ | 7 | | |
| 3088 | =O | $CH_3$ | $CH_2OH$ | $CH_3$ | 7 | | |
| 3089 | =O | $CH_3$ | $CO_2H$ | $CH_3$ | 7 | | |
| 3090 | =O | H | $CH_3$ | $CH_3$ | 7 | | |
| 3091 | =O | H | H | $CH_3$ | 7 | | |
| 3092 | =O | H | CHO | $CH_3$ | 7 | | |
| 3093 | =O | H | $CH_2OH$ | $CH_3$ | 7 | | |
| 3094 | =O | H | $CO_2H$ | $CH_3$ | 7 | | |
| 3095 | $OCH_3$ | $CH_3$ | $CH_3$ | $CH_3$ | 7 | | |
| 3096 | $OCH_3$ | $CH_3$ | H | $CH_3$ | 7 | | |
| 3097 | $OCH_3$ | $CH_3$ | CHO | $CH_3$ | 7 | | |
| 3098 | $OCH_3$ | $CH_3$ | $CH_2OH$ | $CH_3$ | 7 | | |
| 3099 | $OCH_3$ | $CH_3$ | $CO_2H$ | $CH_3$ | 7 | | |
| 3100 | $OCH_3$ | H | $CH_3$ | $CH_3$ | 7 | | |
| 3101 | $OCH_3$ | H | H | $CH_3$ | 7 | | |
| 3102 | $OCH_3$ | H | CHO | $CH_3$ | 7 | | |
| 3103 | $OCH_3$ | H | $CH_2OH$ | $CH_3$ | 7 | | |
| 3104 | $OCH_3$ | H | $CO_2H$ | $CH_3$ | 7 | | |
| 3105 | $OCOCH_3$ | $CH_3$ | $CH_3$ | $CH_3$ | 7 | | |
| 3106 | $OCOCH_3$ | $CH_3$ | H | $CH_3$ | 7 | | |
| 3107 | $OCOCH_3$ | $CH_3$ | CHO | $CH_3$ | 7 | | |
| 3108 | $OCOCH_3$ | $CH_3$ | $CH_2OH$ | $CH_3$ | 7 | | |
| 3109 | $OCOCH_3$ | $CH_3$ | $CO_2H$ | $CH_3$ | 7 | | |
| 3110 | $OCOCH_3$ | H | $CH_3$ | $CH_3$ | 7 | | |
| 3111 | $OCOCH_3$ | H | H | $CH_3$ | 7 | | |
| 3112 | $OCOCH_3$ | H | CHO | $CH_3$ | 7 | | |
| 3113 | $OCOCH_3$ | H | $CH_2OH$ | $CH_3$ | 7 | | |
| 3114 | $OCOCH_3$ | H | $CO_2H$ | $CH_3$ | 7 | | |
| 3115 | OH | $CH_3$ | $CH_3$ | CHO | 8 | | |
| 3116 | OH | $CH_3$ | H | CHO | 8 | | |
| 3117 | OH | $CH_3$ | $CH_3$ | CHO | 8 | | |
| 3118 | OH | $CH_3$ | $CH_2OH$ | CHO | 8 | | |
| 3119 | OH | $CH_3$ | $CO_2H$ | CHO | 8 | | |
| 3120 | OH | H | $CH_3$ | CHO | 8 | | |
| 3121 | OH | H | H | CHO | 8 | | |
| 3122 | OH | H | CHO | CHO | 8 | | |
| 3123 | OH | H | $CH_2OH$ | CHO | 8 | | |
| 3124 | OH | H | $CO_2H$ | CHO | 8 | | |
| 3125 | =O | $CH_3$ | $CH_3$ | CHO | 8 | | |
| 3126 | =O | $CH_3$ | H | CHO | 8 | | |
| 3127 | =O | $CH_3$ | CHO | CHO | 8 | | |
| 3128 | =O | $CH_3$ | $CH_2OH$ | CHO | 8 | | |
| 3129 | =O | $CH_3$ | $CO_2H$ | CHO | 8 | | |
| 3130 | =O | H | $CH_3$ | CHO | 8 | | |
| 3131 | =O | H | H | CHO | 8 | | |
| 3132 | =O | H | CHO | CHO | 8 | | |
| 3133 | =O | H | $CH_2OH$ | CHO | 8 | | |
| 3134 | =O | H | $CO_2H$ | CHO | 8 | | |
| 3135 | $OCH_3$ | $CH_3$ | $CH_3$ | CHO | 8 | | |
| 3136 | $OCH_3$ | $CH_3$ | H | CHO | 8 | | |
| 3137 | $OCH_3$ | $CH_3$ | CHO | CHO | 8 | | |
| 3138 | $OCH_3$ | $CH_3$ | $CH_2OH$ | CHO | 8 | | |
| 3139 | $OCH_3$ | $CH_3$ | $CO_2H$ | CHO | 8 | | |
| 3140 | $OCH_3$ | H | $CH_3$ | CHO | 8 | | |
| 3141 | $OCH_3$ | H | H | CHO | 8 | | |
| 3142 | $OCH_3$ | H | CHO | CHO | 8 | | |
| 3143 | $OCH_3$ | H | $CH_2OH$ | CHO | 8 | | |
| 3144 | $OCH_3$ | H | $CO_2H$ | CHO | 8 | | |

TABLE 12-continued

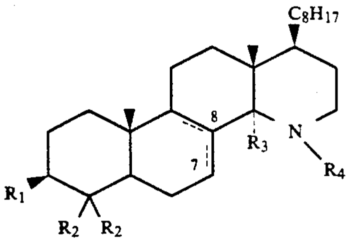

| No. | R1 | R2 | R3 | R4 | D | No. | M.P. |
|---|---|---|---|---|---|---|---|
| 3145 | $OCOCH_3$ | $CH_3$ | $CH_3$ | CHO | 8 | | |
| 3146 | $OCOCH_3$ | $CH_3$ | H | CHO | 8 | | |
| 3147 | $OCOCH_3$ | $CH_3$ | CHO | CHO | 8 | | |
| 3148 | $OCOCH_3$ | $CH_3$ | $CH_2OH$ | CHO | 8 | | |
| 3149 | $OCOCH_3$ | $CH_3$ | $CO_2H$ | CHO | 8 | | |
| 3150 | $OCOCH_3$ | H | $CH_3$ | CHO | 8 | | |
| 3151 | $OCOCH_3$ | H | H | CHO | 8 | | |
| 3152 | $OCOCH_3$ | H | CHO | CHO | 8 | | |
| 3153 | $OCOCH_3$ | H | $CH_2OH$ | CHO | 8 | | |
| 3154 | $OCOCH_3$ | H | $CO_2H$ | CHO | 8 | | |
| 3155 | OH | $CH_3$ | $CH_3$ | CHO | 7 | | |
| 3156 | OH | $CH_3$ | H | CHO | 7 | | |
| 3157 | OH | $CH_3$ | CHO | CHO | 7 | | |
| 3158 | OH | $CH_3$ | $CH_2OH$ | CHO | 7 | | |
| 3159 | OH | $CH_3$ | $CO_2H$ | CHO | 7 | | |
| 3160 | OH | H | $CH_3$ | CHO | 7 | | |
| 3161 | OH | H | H | CHO | 7 | | |
| 3162 | OH | H | CHO | CHO | 7 | | |
| 3163 | OH | H | $CH_2OH$ | CHO | 7 | | |
| 3164 | OH | H | $CO_2H$ | CHO | 7 | | |
| 3165 | =O | $CH_3$ | $CH_3$ | CHO | 7 | | |
| 3166 | =O | $CH_3$ | H | CHO | 7 | | |
| 3167 | =O | $CH_3$ | CHO | CHO | 7 | | |
| 3168 | =O | $CH_3$ | $CH_2OH$ | CHO | 7 | | |
| 3169 | =O | $CH_3$ | $CO_2H$ | CHO | 7 | | |
| 3170 | =O | H | $CH_3$ | CHO | 7 | | |
| 3171 | =O | H | H | CHO | 7 | | |
| 3172 | =O | H | CHO | CHO | 7 | | |
| 3173 | =O | H | $CH_2OH$ | CHO | 7 | | |
| 3174 | =O | H | $CO_2H$ | CHO | 7 | | |
| 3175 | $OCH_3$ | $CH_3$ | $CH_3$ | CHO | 7 | | |
| 3176 | $OCH_3$ | $CH_3$ | H | CHO | 7 | | |
| 3177 | $OCH_3$ | $CH_3$ | CHO | CHO | 7 | | |
| 3178 | $OCH_3$ | $CH_3$ | $CH_2OH$ | CHO | 7 | | |
| 3179 | $OCH_3$ | $CH_3$ | $CO_2H$ | CHO | 7 | | |
| 3180 | $OCH_3$ | H | $CH_3$ | CHO | 7 | | |
| 3181 | $OCH_3$ | H | H | CHO | 7 | | |
| 3182 | $OCH_3$ | H | CHO | CHO | 7 | | |
| 3183 | $OCH_3$ | H | $CH_2OH$ | CHO | 7 | | |
| 3184 | $OCH_3$ | H | $CO_2H$ | CHO | 7 | | |
| 3185 | $OCOCH_3$ | $CH_3$ | $CH_3$ | CHO | 7 | | |
| 3186 | $OCOCH_3$ | $CH_3$ | H | CHO | 7 | | |
| 3187 | $OCOCH_3$ | $CH_3$ | CHO | CHO | 7 | | |
| 3188 | $OCOCH_3$ | $CH_3$ | $CH_2OH$ | CHO | 7 | | |
| 3189 | $OCOCH_3$ | $CH_3$ | $CO_2H$ | CHO | 7 | | |
| 3190 | $OCOCH_3$ | H | $CH_3$ | CHO | 7 | | |
| 3191 | $OCOCH_3$ | H | H | CHO | 7 | | |
| 3192 | $OCOCH_3$ | H | CHO | CHO | 7 | | |
| 3193 | $OCOCH_3$ | H | $CH_2OH$ | CHO | 7 | | |
| 3194 | $OCOCH_3$ | H | $CO_2H$ | CHO | 7 | | |
| 3195 | OH | $CH_3$ | $CH_3$ | $COCH_3$ | 8 | | |
| 3196 | OH | $C_3$ | H | $COCH_3$ | 8 | | |
| 3197 | OH | $CH_3$ | CHO | $COCH_3$ | 8 | | |
| 3198 | OH | $CH_3$ | $CH_2OH$ | $COCH_3$ | 8 | | |
| 3199 | OH | $CH_3$ | $CO_2H$ | $COCH_3$ | 8 | | |
| 3200 | OH | H | $CH_3$ | $COCH_3$ | 8 | | |
| 3201 | OH | H | H | $COCH_3$ | 8 | | |
| 3202 | OH | H | CHO | $COCH_3$ | 8 | | |
| 3203 | OH | H | $CH_2OH$ | $COCH_3$ | 8 | | |
| 3204 | OH | H | $CO_2H$ | $COCH_3$ | 8 | | |
| 3205 | =O | $CH_3$ | $CH_3$ | $COCH_3$ | 8 | | |
| 3206 | =O | $CH_3$ | H | $COCH_3$ | 8 | | |
| 3207 | =O | $CH_3$ | CHO | $COCH_3$ | 8 | | |
| 3208 | =O | $CH_3$ | $CH_2OH$ | $COCH_3$ | 8 | | |
| 3209 | =O | $CH_3$ | $CO_2OH$ | $COCH_3$ | 8 | | |
| 3210 | =O | H | $CH_3$ | $COCH_3$ | 8 | | |
| 3211 | =O | H | H | $COCH_3$ | 8 | | |
| 3212 | =O | H | CHO | $COCH_3$ | 8 | | |
| 3213 | =O | H | $CH_2OH$ | $COCH_3$ | 8 | | |

TABLE 12-continued

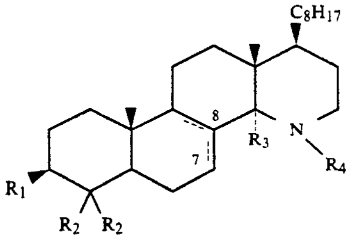

| No. | $R_1$ | $R_2$ | $R_3$ | $R_4$ | D | No. | M.P. |
|---|---|---|---|---|---|---|---|
| 3214 | =O | H | $CO_2H$ | $COCH_3$ | 8 | | |
| 3215 | $OCH_3$ | $CH_3$ | $CH_3$ | $COCH_3$ | 8 | | |
| 3216 | $OCH_3$ | $CH_3$ | H | $COCH_3$ | 8 | | |
| 3217 | $OCH_3$ | $CH_3$ | CHO | $COCH_3$ | 8 | | |
| 3218 | $OCH_3$ | $CH_3$ | $CH_2OH$ | $COCH_3$ | 8 | | |
| 3219 | $OCH_3$ | $CH_3$ | $CO_2H$ | $COCH_3$ | 8 | | |
| 3220 | $OCH_3$ | H | $CH_3$ | $COCH_3$ | 8 | | |
| 3221 | $OCH_3$ | H | H | $COCH_3$ | 8 | | |
| 3222 | $OCH_3$ | H | CHO | $COCH_3$ | 8 | | |
| 3223 | $OCH_3$ | H | CHO | $COCH_3$ | 8 | | |
| 3224 | $OCH_3$ | H | $CO_2H$ | $COCH_3$ | 8 | | |
| 3225 | $OCOCH_3$ | $CH_3$ | $COCH_3$ | $COCH_3$ | 8 | | |
| 3226 | $OCOCH_3$ | $CH_3$ | H | $COCH_3$ | 8 | | |
| 3227 | $OCOCH_3$ | $CH_3$ | CHO | $COCH_3$ | 8 | | |
| 3228 | $OCOCH_3$ | $CH_3$ | $CH_2OH$ | $COCH_3$ | 8 | | |
| 3229 | $OCOCH_3$ | $CH_3$ | $CO_2H$ | $COCH_3$ | 8 | | |
| 3230 | $OCOCH_3$ | H | H | $COCH_3$ | 8 | | |
| 3231 | $OCOCH_3$ | H | CHO | $COCH_3$ | 8 | | |
| 3232 | $OCOCH_3$ | H | $CH_2OH$ | $COCH_3$ | 8 | | |
| 3233 | $OCOCH_3$ | H | $CH_2OH$ | $COCH_3$ | 8 | | |
| 3234 | $OCOCH_3$ | H | $CO_2H$ | $COCH_3$ | 8 | | |
| 3235 | OH | $CH_3$ | $CH_3$ | $COCH_3$ | 7 | | |
| 3236 | OH | $CH_3$ | H | $COCH_3$ | 7 | | |
| 3237 | OH | $CH_3$ | CHO | $COCH_3$ | 7 | | |
| 3228 | OH | $CH_3$ | $CH_2OH$ | $COCH_3$ | 7 | | |
| 3239 | OH | $CH_3$ | $CO_2H$ | $COCH_3$ | 7 | | |
| 3240 | OH | H | $CH_3$ | $COCH_3$ | 7 | | |
| 3241 | OH | H | H | $COCH_3$ | 7 | | |
| 3242 | OH | H | CHO | $COCH_3$ | 7 | | |
| 3243 | OH | H | $CH_2OH$ | $COCH_3$ | 7 | | |
| 3244 | OH | H | $CO_2H$ | $COCH_3$ | 7 | | |
| 3245 | =O | $CH_3$ | $CH_3$ | $COCH_3$ | 7 | | |
| 3246 | =O | $CH_3$ | H | $COCH_3$ | 7 | | |
| 3247 | =O | $CH_3$ | CHO | $COCH_3$ | 7 | | |
| 3248 | =O | $CH_3$ | $CH_2OH$ | $COCH_3$ | 7 | | |
| 3249 | =O | $CH_3$ | $CO_2H$ | $COCH_3$ | 7 | | |
| 3250 | =O | H | $CH_3$ | $COCH_3$ | 7 | | |
| 3251 | =O | H | H | $COCH_3$ | 7 | | |
| 3252 | =O | H | CHO | $COCH_3$ | 7 | | |
| 3253 | =O | H | $CH_2OH$ | $COCH_3$ | 7 | | |
| 3254 | =O | H | $CO_2H$ | $COCH_3$ | 7 | | |
| 3255 | $OCH_3$ | $CH_3$ | $CH_3$ | $COCH_3$ | 7 | | |
| 3256 | $OCH_3$ | $CH_3$ | H | $COCH_3$ | 7 | | |
| 3257 | $OCH_3$ | $CH_3$ | CHO | $COCH_3$ | 7 | | |
| 3258 | $OCH_3$ | $CH_3$ | $CH_2OH$ | $COCH_3$ | 7 | | |
| 3259 | $OCH_3$ | $CH_3$ | $CO_2H$ | $COCH_3$ | 7 | | |
| 3260 | $OCH_3$ | H | $CH_3$ | $COCH_3$ | 7 | | |
| 3261 | $OCH_3$ | H | H | $COCH_3$ | 7 | | |
| 3262 | $OCH_3$ | H | CHO | $COCH_3$ | 7 | | |
| 3263 | $OCH_3$ | H | $CH_2OH$ | $COCH_3$ | 7 | | |
| 3264 | $OCH_3$ | H | $CO_2H$ | $COCH_3$ | 7 | | |
| 3265 | $OCOCH_3$ | $CH_3$ | $CH_3$ | $COCH_3$ | 7 | | |
| 3266 | $OCOCH_3$ | $CH_3$ | H | $COCH_3$ | 7 | | |
| 3267 | $OCOCH_3$ | $CH_3$ | CHO | $COCH_3$ | 7 | | |
| 3268 | $OCOCH_3$ | $CH_3$ | $CH_2OH$ | $COCH_3$ | 7 | | |
| 3269 | $OCOCH_3$ | H | $CH_3$ | $COCH_3$ | 7 | | |
| 3270 | $OCOCH_3$ | H | $CH_3$ | $COCH_3$ | 7 | | |
| 3271 | $OCOCH_3$ | H | H | $COCH_3$ | 7 | | |
| 3272 | $OCOCH_3$ | H | CHO | $COCH_3$ | 7 | | |
| 3273 | $OCOCH_3$ | H | $CH_2OH$ | $COCH_3$ | 7 | | |
| 3274 | $OCOCH_3$ | H | $CO_2H$ | $COCH_3$ | 7 | | |

TABLE 13

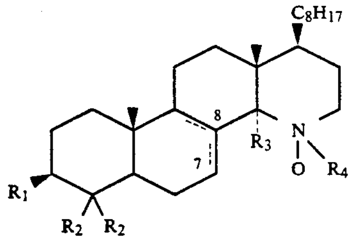

| No. | R1 | R2 | R3 | R4 | D | No. | M.P. |
|---|---|---|---|---|---|---|---|
| 3275 | OH | $CH_3$ | $CH_3$ | $CH_3$ | 8 | | |
| 3276 | OH | $CH_3$ | H | $CH_3$ | 8 | | |
| 3277 | OH | $CH_3$ | $CH{=}CH_2$ | $CH_3$ | 8 | | |
| 3278 | OH | $CH_3$ | $CHOHCH_2OH$—(R) | $CH_3$ | 8 | | |
| 3279 | OH | $CH_3$ | $CHOHCH_2OH$—(S) | $CH_3$ | 8 | | |
| 3280 | OH | $CH_3$ | CHO | $CH_3$ | 8 | | |
| 3281 | OH | $CH_3$ | $CH_2OH$ | $CH_3$ | 8 | | |
| 3282 | OH | $CH_3$ | $CH_2H$ | $CH_3$ | 8 | | |
| 3283 | OH | $CH_3$ | $CO_2H_3$ | $CH_3$ | 8 | | |
| 3284 | OH | $CH_3$ | $CH{=}NOH$ | $CH_3$ | 8 | | |
| 3285 | OH | $CH_3$ | $CHOHCH{=}CH_2$—(R) | $CH_3$ | 8 | | |
| 3286 | OH | $CH_3$ | $CHOHCH{=}CH_2$—(S) | $CH_3$ | 8 | | |
| 3287 | OH | H | $CH_3$ | $CH_3$ | 8 | | |
| 3288 | OH | H | H | $CH_3$ | 8 | | |
| 3289 | OH | H | $CH{=}CH_2$ | $CH_3$ | 8 | | |
| 3290 | OH | H | $CHOHCH_2OH$—(R) | $CH_3$ | 8 | | |
| 3291 | OH | H | $CHOHCH_2OH$—(S) | $CH_3$ | 8 | | |
| 3292 | OH | H | CHO | $CH_3$ | 8 | | |
| 3293 | OH | H | $CH_2OH$ | $CH_3$ | 8 | | |
| 3294 | OH | H | $CO_2H$ | $CH_3$ | 8 | | |
| 3295 | OH | H | $CO_2CH_3$ | $CH_3$ | 8 | | |
| 3296 | OH | H | $CH{=}NOH$ | $CH_3$ | 8 | | |
| 3297 | OH | H | $CHOHCH{=}CH_2$—(R) | $CH_3$ | 8 | | |
| 3298 | OH | H | $CHOHCH{=}CH_2$—(S) | $CH_3$ | 8 | | |
| 3299 | =O | $CH_3$ | $CH_3$ | $CH_3$ | 8 | | |
| 3300 | =O | $CH_3$ | H | $CH_3$ | 8 | | |
| 3301 | =O | $CH_3$ | CHO | $CH_3$ | 8 | | |
| 3302 | =O | $CH_3$ | $CH_2OH$ | $CH_3$ | 8 | | |
| 3303 | =O | $CH_3$ | $CO_2H$ | $CH_3$ | 8 | | |
| 3304 | =O | H | $CH_3$ | $CH_3$ | 8 | | |
| 3305 | =O | H | H | $CH_3$ | 8 | | |
| 3306 | =O | H | CHO | $CH_3$ | 8 | | |
| 3307 | =O | H | $CH_2OH$ | $CH_3$ | 8 | | |
| 3308 | =O | H | $CO_2H$ | $CH_3$ | 8 | | |
| 3309 | $OCH_3$ | $CH_3$ | $CH_3$ | $CH_3$ | 8 | | |
| 3310 | $OCH_3$ | $CH_3$ | H | $CH_3$ | 8 | | |
| 3311 | $OCH_3$ | $CH_3$ | $CH_2OH$ | $CH_3$ | 8 | | |
| 3312 | $OCH_3$ | $CH_3$ | $CO_2H$ | $CH_3$ | 8 | | |
| 3313 | $OCH_3$ | H | $CH_3$ | $CH_3$ | 8 | | |
| 3314 | $OCH_3$ | H | H | $CH_3$ | 8 | | |
| 3315 | $OCH_3$ | H | $CH_2OH$ | $CH_3$ | 8 | | |
| 3317 | $OCH_3$ | H | $CO_2H$ | $CH_3$ | 8 | | |
| 3318 | $OCOCH_3$ | $CH_3$ | $CH_3$ | $CH_3$ | 8 | | |
| 3319 | $OCOCH_3$ | $CH_3$ | H | $CH_3$ | 8 | | |
| 3320 | $OCOCH_3$ | $CH_3$ | CHO | $CH_3$ | 8 | | |
| 3321 | $OCOCH_3$ | $CH_3$ | $CH_2OH$ | $CH_3$ | 8 | | |
| 3322 | $OCOCH_3$ | $CH_3$ | $CO_2H$ | $CH_3$ | 8 | | |
| 3323 | $OCOCH_3$ | H | $CH_3$ | $CH_3$ | 8 | | |
| 3324 | $OCOCH_3$ | H | H | $CH_3$ | 8 | | |
| 3325 | $OCOCH_3$ | H | CHO | $CH_3$ | 8 | | |
| 3326 | $OCOCH_3$ | H | $CH_2OH$ | $CH_3$ | 8 | | |
| 3327 | $OCOCH_3$ | H | $CO_2H$ | $CH_3$ | 8 | | |
| 3328 | OH | $CH_3$ | $CH_3$ | $CH_3$ | 7 | | |
| 3329 | OH | $CH_3$ | H | $CH_3$ | 7 | | |
| 3330 | OH | $CH_3$ | CHO | $CH_3$ | 7 | | |
| 3331 | OH | $CH_3$ | $CH_2OH$ | $CH_3$ | 7 | | |
| 3332 | OH | $CH_3$ | $CO_2H$ | $CH_3$ | 7 | | |
| 3333 | OH | H | $CH_3$ | $CH_3$ | 7 | | |
| 3334 | OH | H | H | $CH_3$ | 7 | | |
| 3335 | OH | H | CHO | $CH_3$ | 7 | | |
| 3336 | OH | H | $CH_2OH$ | $CH_3$ | 7 | | |
| 3337 | OH | H | $CO_2H$ | $CH_3$ | 7 | | |
| 3338 | =O | $CH_3$ | $CH_3$ | $CH_3$ | 7 | | |
| 3339 | =O | $CH_3$ | H | $CH_3$ | 7 | | |
| 3340 | =O | $CH_3$ | CHO | $CH_3$ | 7 | | |
| 3341 | =O | $CH_3$ | $CH_2OH$ | $CH_3$ | 7 | | |
| 3342 | =O | $CH_3$ | $CO_2H$ | $CH_3$ | 7 | | |
| 3343 | =O | H | $CH_3$ | $CH_3$ | 7 | | |
| 3344 | =O | H | H | $CH_3$ | 7 | | |

TABLE 13-continued

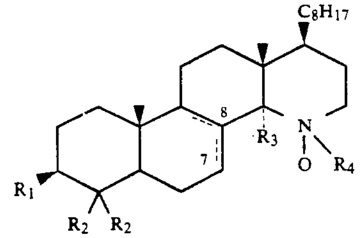

| No. | $R_1$ | $R_2$ | $R_3$ | $R_4$ | D | No. | M.P. |
|---|---|---|---|---|---|---|---|
| 3345 | =O | H | CHO | $CH_3$ | 7 | | |
| 3346 | =O | H | $CH_2OH$ | $CH_3$ | 7 | | |
| 3347 | =O | H | $CO_2H$ | $CH_3$ | 7 | | |
| 3348 | $OCH_3$ | $CH_3$ | $CH_3$ | $CH_3$ | 7 | | |
| 3349 | $OCH_3$ | $CH_3$ | H | $CH_3$ | 7 | | |
| 3350 | $OCH_3$ | $CH_3$ | CHO | $CH_3$ | 7 | | |
| 3351 | $OCH_3$ | $CH_3$ | $CH_2OH$ | $CH_3$ | 7 | | |
| 3352 | $OCH_3$ | $CH_3$ | $CO_2H$ | $CH_3$ | 7 | | |
| 3353 | $OCH_3$ | H | $CH_3$ | $CH_3$ | 7 | | |
| 3354 | $OCH_3$ | H | H | $CH_3$ | 7 | | |
| 3355 | $OCH_3$ | H | CHO | $CH_3$ | 7 | | |
| 3356 | $OCH_3$ | H | $CH_2OH$ | $CH_3$ | 7 | | |
| 3357 | $OCH_3$ | H | $CO_2H$ | $CH_3$ | 7 | | |
| 3358 | $OCOCH_3$ | $CH_3$ | $CH_3$ | $CH_3$ | 7 | | |
| 3359 | $OCOCH_3$ | $CH_3$ | H | $CH_3$ | 7 | | |
| 3360 | $OCOCH_3$ | $CH_3$ | CHO | $CH_3$ | 7 | | |
| 3361 | $OCOCH_3$ | $CH_3$ | $CH_2OH$ | $CH_3$ | 7 | | |
| 3362 | $OCOCH_3$ | $CH_3$ | $CO_2H$ | $CH_3$ | 7 | | |
| 3363 | $OCOCH_3$ | H | $CH_3$ | $CH_3$ | 7 | | |
| 3364 | $OCOCH_3$ | H | H | $CH_3$ | 7 | | |
| 3365 | $OCOCH_3$ | H | CHO | $CH_3$ | 7 | | |
| 3366 | $OCOCH_3$ | H | $CH_2OH$ | $CH_3$ | 7 | | |
| 3367 | $OCOCH_3$ | H | $CO_2H$ | $CH_3$ | 7 | | |

NOTE: When the D-ring is piperidine or the N-oxide thereof, the upper side chain (R) is not the ergosterol side chain.

SYNTHETIC EXAMPLES

The following examples describe synthetic procedures employed in production of specific compounds within the scope of the present invention. Unless otherwise indicated, all percentages in the following Examples and in the General Procedures set forth above are by weight and all temperatures are reported in degrees Celsius (°C.). All parts for reaction and chromatography solvents were determined by volume. All proton NMR spectra are referenced to tetramethylsilane (TMS) at 0.00 ppm.

The following abbreviations are employed in the examples:

NMR: nuclear magnetic resonance spectroscopy
IR: infrared spectroscopy
MS: mass spectroscopy
HRMS: high resolution mass spectroscopy
EI: electron impact
CI: chemical ionization
EA: elemental analysis
m.p.: melting point
MPLC: medium pressure liquid chromatography
Rf: retention factor on silica gel thin layer chromatography Particular intermediates or products are identified by reference to the numbered compounds in the general synthetic procedures summarized above. Physical data for various compounds produced by procedures substantially corresponding to the description contained in each example are provided following the individual examples.

EXAMPLE 1

Preparation of 15-Oxadihydrolanosterol (Compound 11a)

A. Preparation of 4,4-dimethyl-3b-[(4-methoxybenzyl)oxyl-5a-cholesta-8,14-diene (Compound 2b)

To a stirred solution of sodium hydride (50% in oil, 23.2 g, washed with 3 portions of 50 ml of dry tetrahydrofuran) in dry tetrahydrofuran (800 ml) and anhydrous N,N-dimethylformamide (200 ml) at 0° was added 4,4-dimethyl-5a-cholesta-8,14-dien-3b-ol (Compound 2a) (40 g, 96.8 mmole) and the mixture was stirred for 10 min. 4-Methoxybenzyl chloride [16.8 ml, 193.6 mmole, prepared by the method described by Schriner, et al. *J. Org. Chem.*, 10: 228 (1945)] was added and the mixture was stirred for 24 hr. at 70° under nitrogen atmosphere. After cooling to 5° water (80 ml) was added dropwise to the mixture and it was stirred for 5 min. It was poured into ether (1L) and the layers were separated and the organic phase was washed with water (3×300 ml).

The combined aqueous layers were extracted with additional diethyl ether (300 ml). The combined organic solutions were washed with brine, and dried over anhydrous magnesium sulfate and evaporated under reduced pressure to afford a crystalline solid residue.

Recrystallization from diethyl ether and methanol provided 42.5 g of purified Compound 2b. The mother liquor residue was column chromatographed on silica gel with elution by 1:9 ethyl acetate - hexane to give additional 8.2 g of Compound 2b (50.7 g total, 98% yield).

Physical Data (Compound 2b):

NMR (300 MHz, $CDCl_3$); delta 7.28 (d, J=8.7 Hz, 2H), 6.87 (d, J=8.7 Hz, 2H), 5.35 (br s, 1H), 4.60 (d, J=11.4 Hz, 1H), 4.37 (d, J=11.4 Hz, 1H), 3.80 (s, 3H), 2.92 (dd, J=3.6 Hz, 11.7 Hz, 1H), 2.40–1.00 (m, 24H), 1.04 (s, 3H), 0.99 (s, 3H), 0.93 (d, J=6.3 Hz, 3H), 0.87 (d, J=6.3 Hz, 6H), 0.86 (s, 3H), 0.80 (s, 3H);

IR (KBr): 2939, 2888, 2870, 1513, 1470, 1249, 1101, 1095 $cm^{-1}$.

B. Preparation of 4,4-dimethyl-3b-[(4-methoxybenzyl)oxy]-5a-cholest-8-ene-14a. 15a-diol (Compound 3b)

To a solution of the 8,14-diene (Compound 2b) (16 g, 30 mmole) and dry pyridine (24.4 ml, 300 mmole) in benzene (640 ml) at 0° was added a solution of osmium tetroxide (8 g, 31.4 mmole) in methylene chloride (160 ml) dropwise over a period of 1 hr.

The dark brown mixture was stirred for 2 hr. at room temperature.

At the end of this period hydrogen sulfide (Union Carbide Corp., Linde Division, Danbury, Conn. 06817) was bubbled through the solution for about 20 min. and the black precipitates that formed were filtered off through Celite (Manville Products Corp. Denver, Colo.).

The filtrate was evaporated under reduced pressure to afford a brown solid residue (17.5 g) of the diol (Compound 3b). This material was routinely used for further transformations without purification.

An analytical sample of Compound 3b was obtained in the following manner:

A solution of the compound in benzene was filtered through a plug of silica gel (Kieselgel 60, EM Science, 111 Woodcrest Rd., Cherry Hill, NJ 08034-0395) with elution by 2:8 ethyl acetate - hexane and the solvents were evaporated under reduced pressure to give a white crystalline solid. This was recrystallized from ethyl acetate and hexane to give a chromatographically homogeneous sample of Compound 3b.

Physical Data (Compound 3b):

m.p.=124°-126.5° (decomposed); NMR (300 MHz, $CDCl_3$): delta 7.28 (d, J=8.7 Hz, 2H), 6.87 (d, J=8.7 Hz, 1H), 4.66 (d, J=11.4 Hz, 1H), 4.37 (d, J=11.4 Hz, 1H), 2.45 (d, J=9.9 Hz, 1H), 2.35–0.80 (m, 26H), 1.02 (s, 3H), 0.97 (s, 3H), 0.86 (d, J=6.3 Hz, 6H), 0.86 (d, J=6.6 Hz, 3H), 0.85 (s, 3H), 0.69 (s, 3H); IR (KBr): 3406, 2949, 2869, 2841, 1615, 1514, 1465, 1376, 1360, 1346, 1245, 1117, 1031 cm-1; HRMS for $C_{37}H_{56}O_3$ ($M-H_2O$): Calcd. 548.4229; found 548.4252.

C. Preparation of 4,4-Dimethyl-3b-[(4-methoxybenzyl)ozy]-15-oxo-5a-14,15-secocholest-8-en-14-one (Compound 4b)

To a stirred solution of the diol (Compound 3b) (30 mmole in dry benzene (880 ml, distilled from calcium hydride) in the dark was added lead tetraacetate (14 g, 31.5 mmole Aldrich, recrystallized from acetic acid) in small portions over a period of 1 hr. and the mixture was stirred at room temperature for 1 hr. under nitrogen atmosphere and in the dark. The mixture was filtered through Celite and the filter cake rinsed with benzene several times. Evaporation of the solvent under reduced pressure provided an oily residue (17.1 g) of crude keto-aldehyde (Compound 4b). The crude product was routinely used for further transformations without purification.

An analytical sample of Compound 4b was obtained by column chromatography on silica gel with elution by 1:9 ethyl acetate - hexane then 2:8 ethyl acetate - hexane.

Physical Data (Compound 4b):

NMR (300 MHz, $CDCl_3$): delta 9.57 (s, 1H), 7.28 (d, J=8.4 Hz, 2H), 6.87 (d, J=8.4 Hz, 2H), 4.60 (d, J=11.4 Hz, 1H), 4.40 (d, J=11.4 Hz, 1H), 3.80 (s, 3H), 3.01 (dd, J=4 Hz, 11.7 Hz, 1H), 2.58–1.00 (m, 24H), 1.07 (s, 3H), 1.02 (s, 3H), 0.97 (s, 3H), 0.92 (d, J=6.9 Hz, 3H), 0.87 (s, 3H), 0.86 (d, J=6.6 Hz, 6H); IR (film): 2951, 2868, 2719, 1725, 1654, 1623, 1617, 1514, 1465, 1458, 1247, 1098, 1037, $cm^{-1}$; HRMS for $C_{36}H_{56}O_4$ (M+): Calcd. 564.4179; found 564.4209.

D. Preparation of 15,15-Dimethoxy-4,4-dimethyl-3b-[(4-methoxybenzyl)oxy]5a-14,15-secocoholest-8-en-14-one (Compound 5b)

To a solution of the keto-aldehyde (Compound 4b) (30 mmole) in methanol (600 ml) were added trimethyl orthoformate (Aldrich) (48 ml, 439 mmole) and camphorsulfonic acid (Aldrich) 3.2 g, 13.8 mmole) and the mixture was stirred at room temperature for 2 hr. under nitrogen atmosphere. At the end of the stirring saturated sodium bicarbonate solution (120 ml) was added and most of the methanol was evaporated under reduced pressure. The residue was extracted with diethyl ether (3×500 ml) and the combined extracts were washed with brine, dried over anhydrous magnesium sulfate, and evaporated to give an oil residue (18.12 g) of the crude keto-acetal (Compound 5b).

The crude material was normally used for the next reaction. For analytical purposes, Compound 5b was column chromatographed on silica gel with elution by 2:8 ethyl acetate - hexane affording a purified sample of the Compound 5b.

Physical Data (Compound 5b):

NMR (300 MHz, $CDCl_3$) delta 7.27 (d, J=8.4 Hz, 2H), 6.86 (d, J=8.4 Hz, 2H), 4.60 (d, J=11.4 Hz, 1H), 4.37 (d, J=11.4 Hz, 1H), 4.05 (t, J=6 Hz, 1H), 3.26 (s, 3H), 3.21 (s, 3H), 2.90 (dd, J=4 Hz, 12 Hz, 1H), 2.60 (dd, J=5 Hz, 17 Hz), 2.40–0.90 (m, 26H), 1.08 (s, 3H), 1.10 (s, 3H), 0.99 (d, J=6.5 Hz, 6H); IR (film): 2952, 2869, 1661, 1615, 1514, 1464, 1458, 1248, 1123, 1099, 1077 $cm^{-1}$; HRMS for $C_{37}H_{54}O_3$: Calcd. 546.4073; found 546.4126.

E. Preparation of 15,15-Dimethoxy-3b-[(4-methoxybenzyl)oxy]-14,15-secolanost-8-en-14-ol (Compound 6b)

To a solution of the keto-acetal (Compound 5b) (30 mmole) in dry diethyl ether (600 ml) was added a solution of methyl magnesium bromide in diethyl ether (3 ml, Aldrich) 50 ml, 150 mmole) dropwise at 0° and the mixture was stirred at 30°-40° for 2 hr. After cooling it to 0°, hydrochloric acid (0.5 ml, 400 mmole) was added slowly and it was stirred for about 1 min. The product was extracted with diethyl ether (3×500 ml), and the combined extracts washed with water and brine and dried over anhydrous magnesium sulfate).

Evaporation of the solvent afforded an oily residue of the tricyclic alcohol (Compound 6b). The crude product was routinely used for next reaction without purification.

An analytical sample of the Compound 6b was obtained by column chromatography on silica gel with elution by 2:8 ethyl acetate - hexane.

Physical Data (Compound 6b):

NMR (300 MHz, $CDCl_3$): delta 7.29 (d, J=8.4 Hz, 2H), 6.88 (d, J=8.4 Hz, 2H), 4.61 (d, J=11.4 Hz, 1H), 4.38 (d, J=11.4 Hz, 1H), 4.21 (dd, J=2.7 Hz, 9 Hz, 1H), 3.81 (s, 3H), 3.49 (s, 3H), 3.48 (s, 3H), 2.95 (dd, J=3.9 Hz, 11.7 Hz, 1H), 2.35 (dd, J=5.4 Hz, 18 Hz, 1H), 2.20–0.90 (m, 24H), 1.19 (s, 3H), 1.01 (s, 3H), 0.98 (s, 3H), 0.93 (d, J=6.9 Hz, 3H), 0.90 (s, 3H), 0.86 (d, J=6.3 Hz, 6H), 0.86 (s, 3H); HRMS for $C_{38}H_{56}O_2$ (M-2$CH_3OH$-$H_2O$): Calcd. 544.4280; found 544.4258.

F. Preparation of 3b-[(4-Methoxybenzyl)oxy]-14a-oxa-D-homo-lanost-8-en-15-ol (Compound 7b)

A solution of the tricyclic alcohol (Compound 6b) (30 mmole) in methylene chloride (160 ml) and 80% aqueous acetic acid (600 ml) was stirred at room temperature for 2 days and the solvents were evaporated under reduced pressure to give an oily residue of the cyclic hemiacetal (Compound 7b) and the cyclic acetal (Compound 7c). Compound 7b was separated from Compound 7c by column chromatography on silica gel with elution by 15:85 ethyl acetate - hexane followed by 3:7 ethyl acetate - hexane to afford 3.5 g of the Compound 7c (Rf=0.48, 2:8 ethyl acetate - hexane) and 11.6 g of the Compound 7b (Rf=0.23, 2:8 ethyl acetate - hexane) as oils.

The compound 7c was dissolved in methylene chloride (55 ml) 80% aqueous acetic acid (160 ml) and 1M hydrochloric acid (1 ml) and the solution was stirred at room temperature for 1 day. It was worked up and purified as described above to provide an additional 1.9 g of Compound 7b (total 13.5 g, 77.5% overall yield from Compound 3b) and 1.2 g of Compound 7c (6.7% overall yield from Compound 3b).

Physical Data (Compound 7b):

NMR (300 MHz, $CDCl_3$) delta 7.28 (d, J=8.7 Hz, 2H), 6.87 (d, J=8.7 Hz, 2H), 4.60 (d, J=11.5 Hz, 1H), 4.52 (t, J=7.5 Hz, 1H), 4.37 (d, J=11.5 Hz, 1H), 3.80 (s, 3H), 2.93 (dd, J=4.2 Hz, 11.7 Hz, 1H) 2.32 (dd, J=4 Hz, 11 Hz, 1H), 1.95–0.90 (m, 24H), 1.17 (s, 3H), 0.99 (s, 3H), 087 (d, J=6.6 Hz, 6H), 0.85 (s, 3H); HRMS for $C_{38}H_{56}O_2$: Calcd. 544.4280; found 544.4197.

G. Preparation of 3b-[4-Methoxybenzyl)oxy]-14a-oxa-D-homo-lanosta-8,15-diene (Compound 8b)

To a stirred solution of the cyclic hemiacetal (Compound 7b) (13.5 g, 23.2 mmole) and anhydrous triethylamine (Aldrich) (33 ml, 232 mmole, distilled from calcium hydride) in dry methylene chloride (310 ml, distilled from phosphorous pentoxide) at 0° was added methanesulfonyl chloride (Aldrich) (5.43 ml, 69.6 mmole, filtered freshly through basic alumina) dropwise over a period of 5 min. and the mixture was stirred at 0° to 20° for 1 hr. under nitrogen atmosphere. The reaction mixture was poured into diethyl ether (1L) and the solution was washed with water, saturated sodium bicarbonate solution, water and brine. After drying over anhydrous magnesium sulfate the solvents were evaporated under the reduced pressure to give an oily residue of the glycal (Compound 8b). This crude material was normally used for next reaction without purification.

The analytical sample was prepared by column chromatography on silica gel with elution by 1:9 ethyl acetate - hexane to afford a purified sample of Compound 8b.

Physical Data (Compound 8b):

NMR (300 MHz, $CDCl_3$): delta 7.28 (d, J=8 Hz, 2H), 6.88 (d, J=8 Hz, 2H), 6.21 (dd, J=2.5 Hz, 6 Hz, 1H), 4.61 (d, J=11.5 Hz, 1H), 4.52 (dd, J=1.2 Hz, 6.3 Hz, 1H), 4.38 (d, J=11.5 Hz, 1H), 3.81 (s, 3H), 2.94 (dd, J=4 Hz, 11 Hz, 1H), 2.30–0.90 (m, 22H), 1.23 (s, 3H), 1.01 (s, 3H), 0.98 (s, 3H), 0.87 (d, J=7 Hz, 6H), 0.87 (s, 3H), 0.85 (s, 3H); HRMS for $C_{38}H_{56}O_2$ (M-$H_2O$): Calcd. 544.4280; found 544.4281.

H. Preparation of 3b-[4-Methoxybenzyl)oxy]-14a-oxa-D-homo-lanost-8-ene-15,16-diol (Compound 9b)

To a stirred solution of the glycal (Compound 8b) (23.2 mmole) and pyridine (18.8 ml, 232 mmole) in benzene (600 ml) at 0° was added a solution of osmium tetroxide (6 g, 23.6 mmole) in methylene chloride (120 ml) over a period of 10 min. and the dark brown solution was stirred at room temperature for 1 hr. At the end of the stirring hydrogen sulfide gas was bubbled through the solution for about 15 min. and the resulting black precipitates were removed by filtration through Celite. The filter cake was rinsed with ethyl acetate several times and the filtrate was evaporated under reduced pressure to give a dark brown oily residue of the diol (Compound 9b) as a mixture of diastereomers.

Due to the complexity and instability of the product, analysis was carried out after the next transformation.

Physical Data (Compound 9b):

NMR (300 MHz, $CDCl_3$): delta 7.29 (d, J=8 Hz, 2H), 6.88 (d, J=8 Hz, 2H), 4.60 (d, J=12 Hz, 1H), 4.39 (d, J=12 Hz, 1H), 4.34 (d, J=7 Hz, 1H), 3.81 (s, 3H), 3.56 (dd, J=8.5 Hz, 11.5 Hz, 1H), 3.45 (brs, 1H), 2.95 (dd, J=4 Hz, 11 Hz, 1H), 2.35–0.90 (m, 23H), 1.18 (s, 3H), 1.12 (d, J=6 Hz, 3H), 0.97 (s, 3H), 0.89 (s, 3H), 0.88 (d, J=6 Hz, 6H), 0.83 (s, 3H).

I. Preparation of 16-Methoxy-3b-[(4-methoxybenzyl)oxyl-15-oxa-lanost-8-ene (Compound 10b)

To a solution of the diol (Compound 9b) (23.2 mmole) in diethyl ether (550 ml), methanol (550 ml) and water (140 ml) were added sodium metaperiodate (Aldrich) (33 g, 154 mmole) and camphorsulfonic acid (7 g, 30 mmole) and the mixture was stirred at room temperature for 20 hrs. After addition of saturated sodium bicarbonate (350 ml) the mixture was extracted with diethyl ether (3×500 ml) and the combined organic layers were washed with brine. The aqueous layers were re-extracted with diethyl ether (300 ml) and the extract was washed with brine.

The combined extracts were dried over anhydrous magnesium sulfate and evaporated under reduced pressure to give a dark brown oily residue (13 g) of crude five-membered cyclic acetal (Compound 10b). Product of this purity was routinely used for next transformation without further purification.

The analytical sample of purified Compound 10b was obtained by a preparative thin layer chromatography on silica gel with elution by 1:9 ethyl acetate - hexane.

Physical Data (Compound 10b):

NMR (300 MHz, $CDCl_3$): delta 7.29 (d, J=8.7 Hz, 2H), 6.88 (d, J=8.7 Hz, 2H), 4.59 (d, J=11.6 Hz, 1H), 4.53 (d, J=5.7 Hz, 1H), 4.38 (d, J=11.6 Hz, 1H), 3.81 (s, 3H), 3.36 (s, 3H), 2.98 (dd, J=4.2 Hz, 11.5 Hz, 1H), 2.20–0.80 (m, 22H), 1.13 (s, 3H), 0.98(s, 3H), 0.95 (d, J=5.4 Hz, 3H), 0.95 (s, 3H), 0.88 (s, 3H), 0.87 (d, J=6.3 Hz, 6H), 0.83 (s, 3H); IR (film): 2945, 2869, 1514, 1459, 1375, 1347, 1171, 1108, 1094, 1038, 1011 $cm^{-1}$; HRMS for $C_{37}H_{56}O_3$: Calcd. 548.4230; found 548.4203.

J. Preparation of 15-Oxa-dihydrolanosterol (Compound 11a)

To a solution of Compound 10b (23.2 mmole) and triethylsilane (Aldrich) (16 ml, 0.1 mmole) in dry methylene chloride (420 ml) was added boron trifluoride etherate (Aldrich) (2.7 ml, 22 mmole) dropwise and the mixture was stirred at room temperature for 3 hr. under nitrogen atmosphere. The reaction was quenched by addition of saturated sodium bicarbonate and the products were extracted with methylene chloride (3×400 ml). The combined extracts were washed with water, dried over anhydrous magnesium sulfate, and evaporated under reduced pressure to give a dark brown oily residue. The oil was purified by column chromatography on silica gel with elution by 1:9 ethyl acetate - hexane followed by 2:8 ethyl acetate - hexane to provide 15-oxa-dihydrolanosterol (Compound 11a) (4.0 g, 40% overall yield from Compound 7b.

Physical Data (Compound 11a):

NMR (300 MHz, $CDCl_3$): delta 3.76 (t, J=9 Hz, 1H), 3.44 (dd, J=8.4 Hz, 9 Hz, 1H), 3.25 (dd, J=4.8 Hz, 11.4 Hz, 1H), 2.25–0.80 (m, 23H), 1.11 (s, 3H), 1.02 (s, 3H), 0.95 (d J=6.3 Hz, 3H) 0.95 (s, 3H), 0.86 (d, J=6.6 Hz, 6H), 0.86 (s, 3H), 0.81 (s, 3H); IR (film): 3566, 2934, 1466, 1375, 1097, 1079, 1039, 1030 $cm^{-1}$; HRMS for $C_{29}H_{50}O_2$ (M+): Calcd. 430.3811; found 430.3772; for $C_{28}H_{47}O_2$ (M-$CH_3$) Calcd. 415.3576; found 415.3583.

EXAMPLE 2

Preparation of 4,4-Dimethyl-15-oxa-5a-cholest-8-en-3b-ol (Compound 17a)

K. Preparation of 15,15-Dimethoxy-4,4-dimethyl-3b-[4-methoxybenzyl-)oxyl-5a-14,15-Secoholest-8-en-14-ol (Compound 12b)

To a stirred solution of the keto-aldehyde (Compound 5b) (2.7 g, 4.42 mmole) in a dry methylene chloride (60 ml) was added a solution of diisobutyl aluminum hydride in hexane (Aldrich) 1 M/L, 8.84 ml, 8.84 mmole) dropwise at 0° and the mixture was stirred at 0° for 1 hr. at room temperature for 1 hr. The excess reagent was destroyed by dropwise addition of methanol (0.64 ml) at 0° and stirring for 10 min. Then water (1.1 ml) was added dropwise to the mixture and it was stirred at room temperature for 1 hr. The resulting precipitates were filtered off over Celite and the filtrate was evaporated under reduced pressure to give a white foamy residue of the secondary allylic alcohol (Compound 12b) as a mixture of diastereomers. The crude material was used in the next reaction without purification.

L. Preparation of 4,4-Dimethyl-3b-[(4-methoxybenzyl)oxy]-14a-oxa-D-homo-5a-cholest-8-en-15-ol (Compound 13b)

Following the method described for Compound 7b (Example 1-F) the secondary allylic alcohol (Compound 12b) (4.42 mmole) was transformed to the six-membered cyclic hemiacetal (Compound 13b) (0.81 g) and the corresponding cyclic acetal (Compound 13c) (1.34 g) as oils. The Compound 13c was resubjected to the reaction to afford an additional 0.69 g of Compound 13b (total 1.5, 60% overall yield from Compound 12b) after purification by column chromatography on silica gel with elution by 15:85 ethyl acetate - hexane.

Physical Data (Compound 13b):

NMR (300 MHz, $CDCl_3$) delta 7.28 (d, J=8.5 Hz, 2H), 6.86 (d, J=8.5 Hz, 2H), 4.69 (t, J=6 Hz, 1H), 4.59 (d, J=12 Hz, 1H), 4.37 (d, J=12 Hz, 1H), 3.80 (s, 3H), 2.92 (dd, J=4 Hz, 12 Hz, 1H), 2.20–0.90 (m, 26H), 0.99 (s, 6H), 0.97 (s, 3H), 0.93 (d, J=6.5 Hz, 3H), 0.88 (d, J=6.5 Hz, 6H), 0.86 (s, 3H); IR (film): 3413, 2952, 2930, 2870, 1654, 1636, 1465, 1457, 1376, 1365, 1087, 1065, 1036, 1013 $cm^{-1}$.

M. Preparation of 4,4-Dimethyl-3b-[(4-methoxylbenzyl)oxy]-14a-oxa-D-homo-5a-cholest-8,15-diene (Compound 14b)

Following the method described for Compound 8b (Example 1-G) the cyclic hemiacetal (Compound 13b) (0.15 g, 0.26 mmole) was transformed to the glycal (Compound 14b) in 87% yield. The crude product from the reaction was routinely used for next conversion without purification.

The analytical sample was obtained by filtering a concentrated solution of the crude Compound 14b in diethyl ether through a Florisil (Fischer Scientific) column with elution by diethyl ether.

N. Preparation of 4,4-Dimethyl-3b-[(4-methoxybenzyl)oxy]-14a-oxa-D-homo-5a-cholest-8-ene-15,16-diol (Compound 15b)

Following the method described for Compound 9b (Example 1-H) the glycal (Compound 14b) (0.126 g, 0.23 mmole) was transformed to the diol (Compound 15b). The crude product was used for next reaction without purification.

O. Preparation of 4,4-Dimethyl-16-methoxy-3b-[(4-methoxybenzyl)oxy]-15-oxa-5a-cholest-8-ene (Compound 16b)

Following the method described for Compound 10b (Example 1-I) the diol (Compound 15b) (0.23 mmole) was transformed to the five-membered cyclic acetal (Compound 16b). The crude product (0.139 mg) was used for the next reaction without purification.

P. Preparation of 4,4-Dimethyl-15-oxa-5a-cholest-8-en-3b-ol (Compound 17a)

Following the method described for Compound 11a (Example 1-J) the cyclic acetal (Compound 16b) (0.23 mmole) was converted to the 15-oxa steroid (Compound 17a) (0.04 g, 35.7% overall yield from Compound 13b).

Physical Data (Compound 17a):

NMR (300 MHz, $CDCl_3$); delta 3.96 (t, J=8.1 Hz, 1H), 3.72 (s, 1H), 3.65 (br s, 1H), 3.51 (dd, J=9.9 Hz), 8.1 Hz, 1H), 3.25 (dd, J=4.5 Hz, 11.1 Hz, 1H), 2.27 (m, 1H), 2.02–0.70 (m, 21H), 1.01 (s, 3H), 1.00 (s, 3H), 0.97 (s, 3H), 0.95 (d, J=6.6 Hz, 3H), 0.86 (d, J=6.6 Hz, 6H), 0.81 (s, 3H); IR (film): 3448, 2951, 2932, 2869, 1465, 1458, 1376, 1365, 1091, 1032 $cm^{-1}$.

EXAMPLE 3

Preparation of 4,4-Dimethyl-15-oxa-14a-vinyl-5a-cholest-8-en-3b-ol (Compound 23a)

Q. Preparation of 15,15-Dimethoxy-4-4-dimethyl-3b-[(4-methoxybenzyl-)oxy]-14-vinyl-5a-14,15-secocholest-8-en-14-ol (Compound 18b)

To a stirred solution of the keto-acetal (Compound 5b) (8.2 g, 13.4 mmole) in dry tetrahydrofuran (270 ml) was added dropwise a solution of vinyl magnesium bromide in THF (1.6 M/L, Aldrich) (82 ml, 131.2 mmole) at 0° and the mixture was stirred at 70° for 2 hr. under nitrogen atmosphere. After cooling to 0° about 300 ml of 0.5M - hydrochloric acid was added to the solution and it was stirred for 0.5 min. The product was extracted with diethyl ether (3×300 ml) and the combined extracts were washed with water and brine. The ethereal solution was dried over anhydrous magnesium sulfate and evaporated under reduced pressure to give the tricyclic alcohol (Compound 18b) as an oil. The crude product was routinely used for the next reaction without purification.

Physical Data (Compound 18b):

IR (film): 3450, 2952, 2870, 1514, 1466, 1247, 1121, 1099, 1078, 1053, 1043 $cm^{-1}$.

R. Preparation of 4,4-Dimethyl-3b-[(4-methoxybenzyl)oxy]-14a-oxa-14a-vinyl-D-homo-5a-cholest-8-en-15-ol (Compound 19b)

A solution of the tricyclic alcohol (Compound 18b) (13.4 mmole) in methylene chloride (80 ml) and 80% aqueous acetic acid (300 ml) containing 1M hydrochloric acid (0.5 ml) was stirred at room temperature for 20 hrs. The acid and water were evaporated off under reduced pressure to give an oily residue of the cyclic hemiacetal (Compound 19b) and the cyclic acetal (Compound 19c).

The two products were separated by column chromatography on silica gel with elution by 1:9 ethyl acetate - hexane followed by 2:8 ethyl acetate - hexane to afford 3.2 g of the compound 19c (Rf=0.32, 2:8 ethyl acetate-hexane) as oils.

The Compound 19c was dissolved in methylene chloride (40 ml) and 80% aqueous acetic acid (150 ml) and the solution was stirred at room temperature for 7 days. It was worked up and purified as described above to provide additional 2.31 g of Compound 19b (Total 5.81 g, 73% overall yield from Compound 18b).

Physical Data:

NMR (300 MHz, $CDCl_3$): delta 7.28 (d, J=8.5 Hz, 2H), 6.87 (d, J=8.5 Hz, 2H), 5.74 (dd, J=10.8 Hz, 174. Hz, 1H), 5.05 (dd, J=1.8 Hz, 10.8 Hz, 17.4 Hz, 1H), 4.65 (d, J=2.1 Hz, 1H), 4.61 (d, J=11.4 Hz, 1H), 4.38 (d, J=11.4 Hz, 1H), 3.80 (s, 3H), 2.95 (dd, J=4.5 Hz, 10.5 Hz, 1H), 1.95–1.00 (m, 26H), 1.03 (s, 3H), 0.99 (s, 3H), 0.94 (d, J=6.9 Hz, 3H), 0.86 (d, J=6.6 Hz, 6H), 0.84 (s, 3H), 0.82 (s, 3H); HRMS for $C_{39}H_{58}O_3$ (M-$H_2O$): Calcd. 574.4386; found 574.4316.

S. Preparation of 4,4-Dimethyl-3b-[(4-methoxybenzyl)oxy]-14a-oxa-14a-vinyl-D-homo-5a-cholesta-8,15-diene (Compound 20b)

By the method described for Compound 8b (Example 1-G) the cyclic hemiacetal (Compound 19b) (2.65 g, 4.46 mmole) was transformed to the glycal (Compound 20b) (2.412 g, 94% yield) as a foamy solid. The crude product was normally used for next reaction without purification. Analytical sample was obtained by filtering a concentrated solution of the crude product in diethyl ether through a short Florisil column with elution by diethyl ether.

T. Preparation of 4,4-Dimethyl-3b-[(4-methoxybenzyl)oxy]-14a-oxa-14a-vinyl-D-homo-5a-cholest-8-ene-15,16-diol (Compound 21b)

By the method described for Compound 9b (Example 1-H) the glycal (Compound 20b) (2.412 g, 4.19 mmole) was converted to the diol (Compound 21b) (2.31 g, 90.5% yield) as an oil. The crude product was routinely used for next reaction without purification.

U. Preparation of 4,4-Dimethyl-16-methoxy-3b-[(4-methoxybenzyl)oxy]-15-oxa-14a-vinyl-5a-cholest-8-ene (Compound 22b)

By the method described for Compound 10b (Example 1-I) the diol (Compound 21b) (2.31 g, 3.79 mmole) was transformed to five-membered cyclic acetal (Compound 22b) (2.125 g, 94.6% yield) as a foamy solid. The crude product was used for the next reaction without purification.

V. Preparation of 4,4-Dimethyl-15-oxa-14a-vinyl-5a-cholest-8-en-3b-ol (Compound 23a)

To a stirred solution of the five-membered cyclic acetal (Compound 22b) (1.17 g, 2.64 mmole) and triethylsilane (1.6 ml, 10 mmole) in dry methylene chloride (50 ml) at −30° was added boron trifluoride etherate (0.2 ml, 1.63 mmole) dropwise and the mixture was stirred at −30° to 20° for 2 hr. The reaction was quenched by addition of saturated sodium bicarbonate (20 ml) and the products were extracted with diethyl ether (2×100 ml). The ether extracts were washed with water and brine, dried over anhydrous magnesium sulfate, and evaporated under reduced pressure to give an oily residue. It was purified by column chromatography on silica gel with elution by 15:85 ethyl acetate-hexane to give the 15-oxa-sterol (Compound 23a) (0.71 g, 81% yield) as a foamy solid.

Physical Data:

NMR (300 MHz, $CDCl_3$): delta 5.73 (dd, J=10.8 Hz, 17.4 Hz, 1H), 5.12 (dd, J=1.8 Hz, 10.8 Hz, 1H), 5.00 (dd, J=1.8 Hz, 17.4 Hz, 1H), 3.88 (t, J=8.7 Hz, 1H), 3.55 (t, J=9 Hz, 1H), 3.26 (dd, J=4.8 Hz, 11.7 Hz, 1H), 2.07–0.80 (m, 23H), 1.01 (s, 6H), 0.95 (d, J=67 Hz, 3H), 0.86 (d, J=6.3 Hz, 6H), 0.81 (s, 3H), 0.78 (s, 3H); IR (film): 2933, 2868, 1512, 1467, 1375, 1095, 1040, 1029, 1033 $cm^{-1}$; HRMS for $C_{30}H_{50}O_2$ (M+): Calcd. 442.3811; found 442.3806.

EXAMPLE 4

Preparation of 3b-Acetoxy-4,4-dimethyl-15-oxa-14a-vinyl-5a-cholest-8-ene (Compound 23c)

A solution of the 15-oxa-sterol (Compound 23a) (2g, 4.52 mmole) acetic anhydride (Fischer Scientific) (2 ml, 21.2 mmole) and dimethylaminopyridine (Aldrich) (0.1 g, 0.82 mmole) in anhydrous pyridine (Aldrich) (20 ml) was stirred at room temperature for 18 hr. under nitrogen atmosphere. After addition of methanol (5 ml) the mixture was evaporated under reduced pressure, and the residue was partitioned between water and diethyl ether. The organic layer was washed with brine, dried over anhydrous magnesium sulfate and evaporated under reduced pressure to give an oily residue. It was column chromatographed on silica gel with elution by 5:95 ethyl acetate - hexane followed by 1:9 ethyl acetate - hexane to afford the 14-vinyl-15-oxa-sterol acetate (Compound 23c) (1.78 g, 81% yield).

Physical Data:

NMR (300 MHz, $CDCl_3$): delta 5.72 (dd, J=10.8 Hz, 15.9 Hz, 1H), 5.12 (dd, J=1.8 Hz, 1H), 5.00 (dd, J=1.8 Hz, 15.9 Hz, 1H) 4.52 (dd, J=4.8 Hz, 1H), 3.87 (t, J=8.7 Hz, 1H), 3.55 (t, J=8.7 Hz, 1H), 2.06 (s, 3H), 2.06–0.80 (m, 22H), 1.03 (s, 3H), 0.94 (d, J=6.3 Hz, 3H), 0.89 (s, 3H), 0.88 (s, 3H), 0.87 (d, J=6 Hz, 6H), 0.78 (s, 3H).

EXAMPLE 5

Preparation of both Diasteroemers of 3b-Acetoxy-32-hydroxymethyl-15-oxa-lanost-8-en-32-ol (Compounds 24c and 25c)

To a solution of the 14-vinyl-15-oxa-sterol acetate (Compound 23c) (1.78 g, 3.67 mmole) was added osmium tetroxide (1 g, 3.94 mmole) and the resulting dark brown solution was stirred at room temperature for 2 days. At the end of the stirring hydrogen sulfide gas was bubbled through the solution and the black precipitates were removed by filtration over Celite. After washing the filter cake with ethyl acetate several times the filtrate and the washings were evaporated to give a black oily residue. It was purified by column chromatography on silica gel with elution by 3:7 ethyl acetate - hexane to afford 0.25 g of unreacted starting Compound 23C, 0.54 g of Compound 24c (Rf=0.20, 3:7 ethyl acetate - hexane) and 0.19 g of Compound 25c (Rf=0.16, 3:7 ethyl acetate - hexane) in 44.6% combined corrected yield.

Physical Data (Compound 24c):

IR (Film): 3451, 2951, 2870, 1733, 1650, 1642, 1632, 1467, 1366, 1246, 1100, 1028 $cm^{-1}$; HRMS for $C_{30}H_{49}O_3$ (M-CHOHCH$_2$OH): Calcd. 457.3681;; found 457.3640.

Physical Data (Compound 25c):

HRMS for $C_{30}H_{49}O_3$ (M-CHOHCH$_2$OH): Calcd. 457.3681; found 457.3659.

EXAMPLE 6

Preparation of 3b-Acetoxy-15-oxa-32-oxolanost-8-ene (Compound 26c)

To a solution of the diol (Compound 24c) (492 mg, 0.95 mmole) in ethanol (34 ml) at 0° was added a solution of sodium periodate (664 mg, 2.85 mmole) in 8.5 ml of water dropwise and the mixture was stirred at 0° for 30 min. It was extracted with diethyl ether (150 ml) and the organic layer was washed with brine. After drying over anhydrous magnesium sulfate the solvents were evaporated under reduced pressure to give an oily residue of the aldehyde (Compound 26c) (460 mg, ca. 100% yield).

Physical Data:

NMR (300 MHz, $CDCl_3$): delta 9.56 (s, 1H), 4.47 (dd, J=4.5 Hz, 11.4 Hz, 1H), 3.98 (t, J=8.4 Hz, 1H), 3.66 (t, J=8.7 Hz, 1H), 2.15–0.90 (m, 22H), 2.02 (s, 3H), 1.02 (s, 3H), 1.02 (s, 3H), 0.91 (d, J=6.3 Hz, 3H), 0.88 (s, 3H), 0.84 (brs, 9H), 0.82 (s, 3H); IR (film): 2949, 2871, 2798, 2689, 1733, 1471, 1466, 1457, 1374, 1366, 1246, 1027 $cm^{-1}$.

EXAMPLE 7

Preparation of 15-Oxa 32-oxodihydrolanosterol (Compound 26a)

To a solution of the aldehyde-acetate (Compound 26c) (30 mg, 0.062 mmole) ethanol (0.7 ml) was added 3M potassium hydroxide (41 1, 0.124 mmole) and the mixture was stirred at room temperature for 20 hr. After addition of diethyl ether (15 ml) the organic solution was washed with water and brine and dried over anhydrous magnesium sulfate. Evaporation of the solvent under reduced pressure afforded a foamy solid residue of chromatographically purified free hydroxy compound (Compound 26a) (27.5 mg, 100% yield).

Physical Data:

NMR (300 MHz, $CDCl_3$): delta 9.59 (s, 1H), 4.03 (t, J=8.4 Hz, 1H), 3.70 (dd, J=8.1 Hz, 9.6 Hz, 1H), 3.26 (dd, J=4.5 Hz, 11.4 Hz, 1H), 2.20–0.90 (m, 24H), 1.04 (s, 3H), 1.01 (s, 3H), 0.95 (d, J=6.6 Hz, 3H), 0.92 (s, 3H), 0.86 (d, J=6.3 Hz, 6H), 0.81 (s, 3H); IR (film): 3446, 2946, 2933, 2870, 2691, 1731, 1468, 1383, 1378, 1365, 1064, 1042, 1027 $cm^{-1}$; HRMS for $C_{28}H_{47}O_2$ (M-CHO): Calcd. 415.3576; found 415.3600.

EXAMPLE 8

Preparation of 15-Oxa-lanost-8-ene-3b,32-diol (Compound 27)

To a stirred solution of the aldehyde (Compound 26a) (15 mg, 0.034 mmole) in ethanol (1 ml) at 0° was added sodium borohydride (Fischer Scientific) (10 mg, 0.26 mmole) and the mixture was stirred at the same temperature for 1 hr. The excess sodium borohydride was destroyed by adding several drops of saturated ammonium chloride solution and the product was extracted with diethyl ether. The organic layer was washed with brine, dried over anhydrous magnesium sulfate and evaporated to give the diol (Compound 27) (ca. 100% yield) as a white crystalline solid.

Physical Data:

HRMS for $C_{28}H_{47}O_2$ (M-CH$_2$OH): Calcd. 415.3576; found 415.3562.

EXAMPLE 9

Preparation of both Diastereomers of 15-Oxa-32-vinyl-lanost-8-ene-3b,32-diol (Compounds 28 and 29)

To a stirred solution of the aldehyde (Compound 26c) (23 mg, 0.052 mmole) in dry tetrahydrofuran (1 ml) was added 1M vinyl magnesium bromide in tetrahydrofuran (0.52 ml, 0.52 mmole) dropwise and the mixture was stirred at 70° for 0.5 hr. under nitrogen atmosphere. After cooling to 0° about 2 ml of 0.5M hydrochloric acid was added slowly and the mixture was extracted with diethyl ether. The ether layer was washed with saturated sodium bicarbonate, water and brine, dried over anhydrous magnesium sulfate and evaporated under reduced pressure to give an oily residue of Compounds 28 and 29 (1.4:1 ratio, determined by GC, ca. 100% yield).

EXAMPLE 10

Preparation of 3b-Hydroxy-15-oxa-lanost-8-en-32-aldoxime (Compound 30)

A solution of the aldehyde (Compound 26a) (17 mg, 0.038 mmole) and hydroxylamine hydrochloride (Aldrich) (20 mg, 0.29 mmole) in pyridine (0.5 ml) was stirred at 80° for 7 hr. After addition of diethyl ether the solution was washed with water and brine, dried over anhydrous magnesium sulfate and evaporated to give an oily residue. The crude product was purified by preparative thin layer chromatography to obtain purified oxime (Compound 30) as a foamy solid (ca. 100% yield).

Physical Data:

NMR (300 MHz $CDCl_3$): delta 3.93 (t J=8.1 Hz 1H) 3 62 (t J=8.1 Hz 1H) 3.26 (dd J=4.8 Hz, 11.4 Hz 1H) 2.10–0.70 (m 25H) 1.01 (s 2§3H), 0.98 (s, 3H), 0.95 (d, J=6.3 Hz 3H) 0.89 (s 3H) 0.86 (d J=6.6 Hz 6H) 0.81 (s, 3H) IR (film): 3336, 2932, 2870, 1467, 1458, 1383, 1377, 1266, 1040, 1028, 924 737 $cm^{-1}$.

EXAMPLE 11

Preparation of 14a-Oxa-D-homodihydrolanosterol (Compound 31)

W. Preparation of 4-Dimethyl-5a-cholest-8-ene-3b-,14a,15a-triol (Compound 3a)

By the method described for Compound 3b (Example 1-B) the 8,14-diene (Compound 2a) (4.64 g, 11.24 mmole) was transformed to triol (Compound 3a). The crude product was filtered through a plug of silica gel with elution by 4:6 ethyl acetate-hexane followed by 7:3 ethyl acetate-hexane and crystallized from diethyl ether and hexane to afford purified Compound 3a as white short needles (4.18 g, 83.3% yield), m.p.=133°-134° (dec.)

Physical Data:

NMR NMR (300 MHz, $CDCl_3$-$D_{2}0$ (5%)): delta 4.11 (dd, J=5 Hz, 9 Hz, 1 Hz), 3.22 (dd, J=5 Hz, 11 Hz, 1H), 2.33 (m, 1H), 2.26 (brm, 1H), 2.09 (brm, 2H), 2.00–1.05 (m, 20H), 1.01 (d, J=3 Hz, 6H), 0.87 (s, 3H), 0.86 (d, J=8 Hz, 3H), 0.85 (s, 3H), 0.82 (s, 3H), 0.69 (s, 3H); IR (film): 3422 (bs, OH), 2950 (s), 1652 (s), 1465 (m), 1036 (m) $cm^{-1}$; EA for $C_{29}H_{50}O_3$: Calcd. C 77.97%, H 11.28%; found C 78.05%, H 11.19%.

X. Preparation of 4,4-Dimethyl-3b-hydroxy-15-oxo-5a-14,15-Secocholest-8-en-14-on (Compound 4a)

By the method described for Compound 4b (Example 1-C) the triol (Compound 3a) (1 g, 2.24 mmole) was transformed to keto-aldehyde (Compound 4a) (0.97 g, 97.4% yield) the crude material was normally used for next reaction without purification.

Physical Data:

NMR (300 MHz, $CDCl_3$): delta 3.93 (t, J=8.1 Hz, 1H), 3.63 (t, J=8.1 Hz, 1H), 3.26 (dd, J=4.8 Hz, 11.4 Hz, 1H), 2.10–0.70 (m, 25H), 1.01 (s, 3H), 0.98 (s, 3H), 0.95 (d, J=6.3 Hz, 3H), 0.89 (s, 3H), 0.88 (d, J=6.6 Hz, 6H), 0.81 (s, 3H); IR (film): 3336, 2932, 2870, 1467, 1458, 1383, 1377, 1266, 1040, 1028, 924, 737 $cm^{-1}$.

Y. Preparation of 15,15-Dimethoxy-4,4-dimethyl-3b-hydroxy-15-oxo-5a-14,15-secocholest-8-en-14-one (Compound 5a)

By the method described for Compound 5b (Example 1d) the keto-aldehyde (Compound 4a) (0.97 g, 2.18 mmole) was transformed to keto-acetal (Compound 5a) (1.09 g, ca. 100% yield) as a foamy solid. The crude product was normally used for the next reaction without purification. An analytical sample of Compound 5a was obtained by column chromatography on silica gel by elution with 3:7 ethyl acetate - hexane.

Physical Data:

NMR (300 MHz, $CDCl_3$): delta 4.06 (t, J=5.8 Hz, 1H), 3.26 (s, 3H), 3.26–3.27 (m, 1H), 3.22 (s, 3H), 2.62 (dd, J=6 Hz, 17 Hz, 1H), 2.35–0.90 (m, 25H), 1.07 (s, 3H), 1.02 (s, 3H), 0.98 (d, J=7.2 Hz, 3H), 0.95 (s, 3H), 0.86 (d, J=6.6 Hz, 6H), 0.84 (s, 3H); IR (film): 3490, 2952, 2870, 1659, 1622, 1642, 1434, 1373, 1123, 1076, 1061 $cm^{-1}$; HRMS for $C_{29}H_{46}O_2$ (M-2$CH_3OH$): Calcd. 426.2498; found 426.3415.

Z. Preparation of 15,15-Dimethoxy-14,15-Secolanost-8-ene-3b,14-diol (Compound 6a)

By the method described for Compound 6b (Example 1-E) the keto-acetal (Compound 5a) (200 mg, 0.41 mmole) was transformed to tricyclic alcohol (Compound 6a) (210 mg, ca. 100% yield) as an oil. The crude material was routinely used for next reaction without purification.

Physical Data:

NMR (300 MHz, $CDCl_3$) delta 4.05 (t, J=6 Hz, 1H), 3.27–3.20 (m, 1H), 3.26 (s, 3H), 3.22 (s, 3H), 2.61 (dd, J=5.1 Hz, 17.7 Hz, 1H), 2.50–0.80 (m, 25H), 1.07 (s, 3H), 1.02 (s, 3H), 1.02 (s, 3H), 0.98 (d, J=6.9 Hz, 3H), 0.95 (s, 3H), 0.86 (d, J=6.6 Hz, 6H), 0.85 (s, 3H), 0.84 (s, 3H).

AA. Preparation of 14a-Oxa-D-homo-lanost-8-ene-3b,15-diol (Compound 7a)

A solution of the tricyclic alcohol (Compound 6a) (0.41 mmole) in methylene chloride (2 ml) and 80% aqueous acetic acid (10 ml) was stirred at room temperature for 1.5 hr. and the solvents were evaporated off under reduced pressure to give an oily residue. The residue was dissolved in diethyl ether (20 ml) and washed with saturated sodium bicarbonate and brine.

After drying over anhydrous sodium sulfate the ether solution was evaporated under reduced pressure to give an oily residue that was column chromatographed on silica gel. Elution with 25:75 ethyl acetate-hexane afforded 117 mg of cyclic hemiacetal (Compound 7a) (28% overall yield from Compound 6a) as an oil.

AB. Preparation of 14a-Oxa-D-homo dihydrolanosterol (Compound 31)

To a stirred solution of the cyclic hemiacetal (Compound 7a) (34 mg. 0.073 mmole) in dry methylene chloride (1.5 ml) at −30° were added triethylsilane (35L, 0.22 mmole) and 2 drops of boron trifluoride etherate and the mixture was stirred at −30° to 8° for 45 min. under nitrogen atmosphere. After addition of saturated sodium bicarbonate (3 ml) the reaction mixture was extracted with diethyl ether (2×15 ml). The combined extracts were washed with brine, dried over anhydrous sodium sulfate and evaporated under reduced pressure to give an oily residue of Compound 312 (30 mg, 92.4%) yield). It was purified by MPLC on silica gel with elution by 1L (ethyl acetate - hexane to give a purified sample as a white foamy solid.

Physical Data:

NMR (300 MHz, $CDCl_3$): delta 3.67 (dd, J=2.7 Hz, 1H), 3.31–3.25 (m, 2H), 2.37 (dd, J=5.5 Hz, 18 Hz, 1H), 2.20–0.909 (m, 24H), 1.12 (s, 3H), 1.04 (s, 3H), 0.98 (s, 3H), 0.94 (d, J=7.2 Hz, 3H), 0.92 (s, 3H), 0.88 (d, J=6.6 Hz, 6H), 0.83 (s, 3H); HRMS for $C_3OH_{52}O_2$ (M+), Calcd. 444.3967, found 444.3942; for $C_{29}H_{49}O_2$ (M-$CH_3$), Calcd. 429.3733, found 429.3717.

EXAMPLE 12

Preparation of 4,4-dimethyl-14a-Oxa-D-homo-5a-cholest-8-en-3b-ol (Compound 32)

AC Preparation of 15,15-Dimethyl-4,4-dimethyl-5a-14,15-Secocholest-8-ene-3b,14-diol (Compound 12)

By the method described for Compound 12b (Example 2-K) the keto-acetal (Compound 5a) (121 mg, 0.25 mmole) was transformed to tricyclic secondary alcohol (Compound 12a) as an oil. The crude product was used for next reaction without purification.

Physical Data:

NMR (300 MHz, $CDCl_3$): delta 5.30 (s, 1H), 4.41 (dd, J=3 Hz, 9 Hz, 1H), 3.91 (d, J=4.2 Hz, 1H), 3.45 (s, 3H), 3.36 (s, 3H), 3.36 (s, 3H), 3.21 (m, 1H), 2.15–0.95 (m, 25H), 0.99 (s, 6H), 0.92 (d, J=6.6 Hz, 3H), 0.87 (d, J=6.6 Hz, 6H), 0.81 (s, 3H), 0.61 (s, 3H); HRMS for $C_{30}H_{52}O_3$ (M-$CH_3OH$): Calcd. 460.3916; found 460.3891.

AD. Preparation of 4,4-Dimethyl-14a-oxa-D-homo-5a-cholest-8-ene-3b,15-diol (Compound 13a)

By the method described for Compound 7a (Example 11-AA) with exception of reaction time (4 hr.) the secondary alcohol (Compound 12a) (0.25 mmole) was transformed to the six-membered cyclic hemiacetal (Compound 13a) (70 mg, 62.7% overall yield from Compound 5a) as an oil.

Physical Data:

NMR (300 MHz, $CDCl_3$): delta 5.30 (s, 1H), 4.72 (dd, J=3.3 Hz, 8.7 Hz, 1H), 3.79 (brs, 1H), 3.25 (dd, J=4.5 Hz, 11.1 Hz, 1H), 2.20–0.080 (m, 25H), 1.01 (s, 3H), 0.98 (s, 3H), 0.96 (s, 3H), 0.93 (d, J-6.9 Hz, 3H), 0.86 (d, J=6.6 Hz, 6H), 0.81 (s, 3H);

AE. Preparation of 4,4-Dimethyl-14a-Oxa-D-homo-5a-cholest-8-en-3b-ol (Compound 32)

To a stirred solution of the cyclic hemiacetal (Compound 13a) (31.8 mg, 0.071 mmole) and triethylsilane (34 1, 0.21 mmole) in dry acetonitrile (1.5 ml) and dry methylene chloride (0.5 ml) at −15° was added a drop of boron trifluoride etherate and the mixture was stirred at −15° to −10° for 15 min. After addition of saturated sodium bicarbonate it was extracted with diethyl ether. The ether extract was washed with brine, dried over anhydrous sodium sulfate and evaporated to give an oily residue of Compound 32. It was purified by preparative thin layer chromatography on silica gel plate with elution by 3:7 ethyl acetate - hexane to afford 12 mg of purified sample (39.2% yield) as a white foamy solid.

EXAMPLE 13

Preparation of 4,4-Dimethyl-14a-oxa-14-a oxa-14a-vinyl-D-homo-5a-cholest-8-en-3b-ol (Compound 33)

AF. Preparation of 15,15-Dimethoxy-4,4-dimethyl-14-vinyl-5a-14,15-seco-cholest-8-ene-3b,14-diol (Compound 18a)

By the method described for Compound 18b the keto-acetal (Compound 5a) (230 mg, 0.47 mmole) was transformed to a tricyclic allylic alcohol (Compound 18a) as an oil. The crude material was normally used for next reaction without purification.

Physical Data:

NMR (300 MHz, $CDCl_3$): delta 5.80 (dd, J=9.9 Hz, 17.7 Hz, 1H), 5.08 (d, J=9.9 Hz, 1H), 5.05 (d, J=17.1 Hz, 1H), 4.50 (dd, J=2.7 Hz, 9 Hz, 1H), 4.20 (s, 1H), 3.42 (s, 3H), 3.28 (s, 3H), 3.24 (dd, J=4.8 Hz, 12 Hz, 1H), 2.47 (dd, J=10.8 Hz, 14.4 Hz, 1H), 2.15–0.90 (m, 24H), 1.03 (s, 3H), 1.01 (s, 3H), 0.94 (s, 3H), 0.93 (d, J=4.5 Hz, 3H), 0.87 (d, J=6.3 Hz, 6H), 0.82 (s, 3H); IR (film): 3455, 2954, 2871, 1466, 1375, 1122, 1067, 1045 $cm^{-1}$.

AG. Preparation of 4,4-Dimethyl-14a-oxa-14a-vinyl-d-homo-5a-cholest-8-ene-3b,15-diol (Compound 19a)

By the method described for Compound 7a (Example 11-AA) the allylic alcohol (Compound 18a) (0.47 mmole) was transformed to six-membered cyclic hemiacetal (Compound 19a) (140 mg, 63% overall yield from Compound 5a).

AH. Preparation of 4,4-Dimethyl-14a-oxa-14a-vinyl-D-homo-5a-cholest-8-en-3b-ol (Compound 33)

By the method described for Compound 31 (Example 11-AB) the cyclic hemiacetal (Compound 19a) (73.8 mg. 0.16 mmole) was transformed to compound 33 (70 mg, 95.8% yield). Purified sample of Compound 33 as a white foamy solid was obtained by column chromatography on silica gel with elution by 1:9 ethyl acetate - hexane.

Physical Data:

NMR (300 MHz, $CDCl_3$): delta 5.71 (dd, J=10.8 Hz, 17.4 Hz, 1H), 5.07 (dd, J=1.5 Hz, 10.8 Hz, 1H), 4.96 (dd, J=1.5 Hz, 17.4 Hz, 1H), 3.74 (dd, J=3.3 Hz, 10.5 Hz, 1H), 3.34 (t, J=11.1 Hz, 1H), 3.28 (dd, J=3.9 Hz, 11 1 Hz, 1H), 2.10–0.80 (m, 25H), 1.04 (s, 3H), 1.03 (s, 3H), 0.94 (d, J=6.6 Hz, 3H), 0.86 (d, J=6.6 Hz, 6H), 0.83 (s, 3H), 0.82 (s, 3H); IR (film): 3438, 2947, 2933, 2868, 1635, 1466, 1399, 1377, 1265, 1096, 1040, 1027, 1003, 922, 736 $cm^{-1}$; HRMS for $C_{31}H_{52}O_2$ (M+): Calcd. 456.3968; found 456.3955.

EXAMPLE 14

Preparation of both Diastereomers of 32-hydroxy-14a-oxa-lanost-8-ene-3b,32-diol (Compounds 34 and 35)

To a solution of the 14-vinyl-D-homo-oxasterol (Compound 33) (250 mg, 0.55 mmole) in anhydrous pyridine (10 ml) was added a 5% solution of osmium tetroxide in methylene chloride (3.4 ml, 0.66 mmole) and the mixture was stirred at room temperature for 7 days. At the end of that period, hydrogen sulfide gas was bubbled through the solution for about 5 min. and the resulting black precipitates were removed by filtration over Celite.

The filter cake was rinsed with ethyl acetate several times and the filtrate and washings were evaporated to give a black oily residue. It was column chromatographed on silica gel with elution by 6:4 ethyl acetate - hexane to afford 150 mg of the unreacted starting material (compound 33) and 90 mg (foamy solid) of the triols 34 and 35 as a mixture (83.8% corrected yield).

EXAMPLE 15

Preparation of 14a-Oxa-32-oxo-D-homo-dihydrolanosterol (Compound 36)

To a stirred solution of the diasteromeric mixture of triols (Compounds 34 and 35) (90 mg, 0.184 mmole) in ethanol (4 ml) was added a solution of sodium periodate (118 mg, 0.55 mmole) in water (1 ml) dropwise over a period of 3 min. The mixture was stirred at room temperature of 0.5 hr. and diethyl ether (30 ml) was added to the mixture. The ether solution was washed with water and brine, dried over anhydrous magnesium sulfate and evaporated to give an oily residue. It was purified by MPLC on silica gel with elution by 2:8 ethyl acetate-hexane to provide purified aldehyde (Compound 36) as a white foamy solid (80–90% yield).

Physical Data:

NMR (300 MHz, $CDCl_3$) delta 9.51 (s, 1H), 3.91 (dd, J=4.5H, 11.1 Hz, 1H), 3.35 (t, J-11.4 Hz, 1H), 3.27 (dd, J=4.5 Hz, 11.4 Hz, 1H), 2.04–0.80 (m, 25H), 1.05 (s, 3H), 1.02 (s, 3H), 0.94 (d, J=6.9 Hz, 3H), 0.92 (s, 3H), 0.86 (d, J=6.6 Hz, 6H), 0.81 (s, 3H); IR (film): 3481, 2951, 2868, 2725, 1734, 1466, 1459, 1378, 1365, 1098, 1043, 1027, 1004, 733 $cm^{-1}$.

EXAMPLE 16

Preparation of 14a-Methyl-15-oxa-5a-cholest-8-en-3b-ol (Compound 47)

AI. Preparation of 3b-[(4-Methoxybenzyl)oxy]5a-cholesta-8,14-diene (Compound 38b)

By the method described for the diene p-methoxybenzyl ether (Compound 2b) (Example 1-A) 5a-cholesta-8,14-dien-3b-ol (18.6 g, 48.4 mmole) was transformed to p-methoxybenzyl ether (Compound 38b) as white crystals (17.4 g, 71.2% yield), m.p.=109°–110° C.

Physical Data:

NMR (300 MHz, $CDCl_3$) delta 7.28 (d, 8.7 Hz, 2H), 6.82 (d, J=8.7 Hz, 2H), 5.36 (m, 1H), 4.52 (d, J=11 Hz, 1H), 4.47 (d, J=11 Hz, 1H), 3.80 (s, 3H), 3.35 (m, 1H), 2.40–0.80 (m, 26H), 0.99 (s, 3H), 0.94 (d, J=6.3 Hz, 3H), 0.87 (d, J=6.5 Hz, 6H), 0.81 (s, 3H); IR (KBr): 3932, 2868, 2835, 1613, 1513, 1465, 1457, 1243, 1086, 1071, 1041 $cm^{-1}$.

AJ. Preparation of 3b-[(4-Methoxybenzyl)oxyl]-5a-cholest-8-ene-14a,15a-diol (Compound 39)

By the method described for the diol (Compound 3b) (Example 1-b) the diene (Compound 38b) (3.8 g, 7.5 mmole) was transformed to the corresponding diol (Compound 39). The crude white solid product was normally used for next reaction without purification.

Physical Data:

NMR (300 MHz, $C_6D_6$); delta 7.34 (d, J=8.2 Hz, 2H), 6.86 (d, J=8.2 Hz, 2H), 4.51 (d, J=12 Hz, 1H), 4.46 (d, J=12 Hz, 12H), 4.05 (dd, J=7.5 Hz, 17 Hz, 1H), 3.30 (s, 3H), 3.30 (m, 1H), 2.45–0.80 (m, 28H), 0.95 (d, J=6.5 Hz, 3H), 0.90 (d, J=6.6 Hz, 6H), 0.84 (s, 3H), 0.62 (s, 3H); IR (film): 3500, 2933, 2889, 1615, 1587, 1514, 1457, 1374, 1302, 1247, 1171, 1109, 1083, 1035 $cm^{-1}$; HRMS (EI) for $C_{35}H_{52}O_3$ ($M-H_2O$), Calcd. 520.3917; found 520.3895.

AK. Preparation of 3b-[(4-Methoxybenzyl)oxy]-15-oxo-5a-14,15-secocholest-8-en-14-one (Compound 40)

By the method described for the keto-aldehyde (Compound 4b) (Example 1-C) the diol (Compound 39) (7.5 mmole) was transformed to the corresponding keto-aldehyde (Compound 40).

The crude oily product was used for next reaction without purification.

Physical Data:

NMR (300 MHz, $CDCl_3$): delta 9.56 (s, 1H), 7.27 (d, J=8.4 Hz, 2H), 6.87 (d, J=8.4 Hz, 2H), 4.52 (d, J=11.7 Hz, 1H), 4.47 (d, J=11.7 Hz, 1H), 3.80 (s, 3H), 3.41 (m, 1H), 2.57–0.90 (m, 26H), 1.02 (s, 3H), 0.97 (s, 3H), 0.91 (d, J=6.6 Hz, 3H), 0.87 (d, J=6.6 Hz, 6H); IR (film): 2950, 2934, 2869, 1725, 1655, 1615, 1513, 1442, 1375, 1301, 1248, 1103, 1077, 1037 $cm^{-1}$; HRMS for $C_{34}H_{50}O_3$ ($M-CH_2O$): Calcd. 506.3760; found 506.3763.

AL. Preparation of 15,15-Dimethoxy-3b-[(4-methoxybenzyl)oxy]5a-14,15-secocholest-8-en-14-one (Compound 41)

By the method described for the keto-acetal (Compound 5b) (Example 1-D) the keto-aldehyde (Compound 40) (7.5 mmole) was transformed to the corresponding keto-acetal (Compound 41). The crude oily product was used for next reaction without purification.

Physical Data:

NMR (300 MHz, $CDCl_3$): delta 7.26 (d, J-8.4 Hz, 2H), 6.87 (d, J=−8.4 Hz, 2H), 4.51 (d, J=11.4 Hz, 1H), 4.47 (d, J=11.4 Hz, 1H), 4.07 (t, J=6 Hz, 1H), 3.80 (s, 3H), 3.30 (m, 1H), 3.26 (s, 3H), 3.21 (s, 3H), 2.53 (brd, J=16.5 Hz, 1H), 2.40–1.00 (m, 25H), 1.02 (s, 3H), 0.98 (d, J=7.2 Hz, 3H), 0.96 (s, 3H), 0.86 (d, J=6.6 Hz, 6H); IR (film): 2934, 2867, 1661, 1654, 1617, 1513, 1465, 1438, 1248, 1078, 1058, 1039 $cm^{-1}$; HRMS (EI) for $C_{36}H_{54}O_4$ ($M+-CH_3OH$), Calcd. 550.4022, found 550.4021.

AM. Preparation of 15,15-Dimethoxy-3b-[(4-methoxybenzyl)oxy]-14-methyl-14,15-secocholest-8-en-14-ol (Compound 42)

By the method described for the tricyclic alcohol (Compound 6b) (Example 1-E) the keto-acetal (Compound 41) (7.5 mmole) was transformed to the corresponding tricyclic alcohol (Compound 42). The crude oily product was used for next reaction without purification.

Physical Data:

NMR (300 MHz, $CDCl_3$): delta 7.27 (d, J=8.7 Hz, 2H), 6.87 (d, J=8.7 Hz, 2H), 4.50 (brs, 1H), 4.52 (d, J=14.1 HZ, 1H), 4.49 (t, J=3 Hz, 1H), 4.46 (d, J=14.1 Hz, 1H), 3.80 (s, 3H), 3.49 (s, 6H), 3.35 (m, 1H), 2.30–0.90 (m, 26H), 1.19 (s, 3H), 0.92 (d, J=5.7 Hz, 3H), 0.90 (s, 3H), 0.86 (s, 3H), 0.86 (d, J=6.6 Hz, 6H); IR (film): 3464, 2933, 2869, 1514, 1465, 1457, 1120, 1063, 1052, 1040 $cm^{-1}$; HRMS (EI) for $C_{36}H_{54}O_3$ (M+2CH3OH), Calcd. 534.4073, found 534.4071.

AN. Preparation of 3b-[(4-Methoxybenzyl)oxy]-14a-methyl-14a-oxa-D-homo-5a-cholest-8-en-15-ol (Compound)

By the method described for the six-membered cyclic hemiacetal (Compound 7b) (Example 1-F) the tricyclic alcohol (Compound 42) (Example 1-F) the tricyclic alcohol (Compound 42) (7.5 mmole) was transformed to the corresponding cyclic hemiacetal (Compound 43a) and cyclic acetal (Compound 43b). The oily residue of the mixture was column chromatographed on silica gel with elution by 15:85 ethyl acetate - hexane followed by 3:7 ethyl acetate - hexane to afford 1.6 g of the cyclic hemiacetal (Compound 43a) and 1.19 g of the cyclic acetal (Compound 43b). The compound 43b was subjected to the reaction condition and stirred at room temperature for 4 days. It was worked up and purified as described above to provide additional 0.47 g of the compound 43a (Total 2.07 g, 50% overall yield from Compound 38b) and 0.6 g of the Compound 43b (14.1% overall yield from Compound 38b).

Physical Data:

NMR (300 MHz, $CDCl_3$) delta 7.27 (d, J=8.1 Hz, 2H), 6.87 (d, J=8.1 Hz, 2H), 4.53 (brs, 1H), 4.49 (brs, 1H), 3.80 (s, 3H), 3.34 (m, 1H), 2.23 (brd, J-17.1 Hz, 1H), 2.10-1.00 (m, 26H), 1.18 (s, 3H), 0.86 (d, J=6.3 Hz, 6H); HRMS for $C_{36}H_{54}O_3$ (M-$H_2O$): Calcd. 534.4073; found 534.4114.

AO. Preparation of 3b-[(4-Methoxybenzyl)oxy]-14a-methyl-14a-oxa-D-homo-5a-cholesta-8,15-diene (Compound 44)

By the method described for the glycal (Compound 8b) (Example 1-G) the cyclic hemiacetal (43a) (2.07 g, 3.74 mmole) was transformed to the corresponding glycal (Compound 44). The crude oily product was used for the next reaction without purification.

Physical Data:

IR (film): 2950, 2931, 2866, 1660, 1514, 1467, 1248, 1171, 1093, 1072, 1039 $cm^{-1}$.

AP. Preparation of 3b-[(4-Methoxybenzyl)oxy]-14a-methyl-14a-oxa-D-homo-5a-cholest-8-ene-15,16-diol (Compound 45)

By the method described for the diol (Compound 9b) (Example 1-H) the glycal (Compound 44) (3.74 mmole) was transformed to the corresponding diol (Compound 45). The crude black oily product was used for next reaction without purification.

AQ. Preparation of 16-Methoxy-3b-[(4-methoxybenzyl)oxy]-14a-methyl-15-oxa-5a-cholest-8-ene (Compound 46)

By the method described for the 5-membered cyclic acetal (Compound 10b) the diol (Compound 45) (3.784 mmole) was transformed to the corresponding 5-membered cyclic acetal (Compound 46). The crude oily product was used for next reaction without purification. Analytical sample of purified Compound 46 was obtained by a preparative thin layer chromatography on silica gel with elution by 1:9 ethyl acetate - hexane.

Physical Data:

NMR (300 MHz, $CDCl_3$): delta 7.27 (d, J=8.5 Hz, 2H), 6.87 (d, J=8.5 Hz, 2H), 4.52 (d, J=5.4 Hz, 1H), 4.51 (d, J=12 Hz, 1H), 4.51 (d, J=12 Hz, 1H), 4.46 (d, J=12 Hz, 1H), 3.81 (s, 3H), 3.37 (m, 1H), 3.35 (s, 3H), 2.35 (s, 3H), 2.35-1.00 (m, 24H), 1.13 (s, 3H), 0.94 (d, J=6.6 Hz, 3H), 0.90 (s, 3H), 0.88 (s, 3H), 0.86 (d, J=6.6 Hz, 6H); IR (film): 3923, 3865, 1613, 1514, 1466, 1374, 1248, 1171, 1093, 1071, 1038, 1011 $cm^{-1}$; HRMS (EI) for $C_{35}H_{52}O_3$ (M-$CH_3OH$): Calcd. 520.3916; found 520.3880.

AR. Preparation of 14a-Methyl-15-oxa-5a-cholest-8-en-3b-ol (Compound 47)

By the method described for 15-oxa-dihydrolanosterol (Compound 11a) (Example 1-J) the cyclic acetal (Compound 46) (3.74 mmole) was transformed to 15-oxasterol (Compound 47). The crude product was purified by MPLC on silica gel with elution by 2:8 ethyl acetate-hexane to provide 0.52 g of the purified compound as foamy solid (34.5% of overall yield from Compound 43a).

Physical Data:

NMR (300 MHz, $CDCl_3$): delta 3.75 (t, J=8.4 Hz, 1H), 3.62 (m, 1H), 3.44 (t, J=8.7 Hz, 1H), 2.30 (s, 1H), 2.10-1.00 (m, 24H), 1.12 (s, 3H), 0.95 (d, J=6.3 Hz, 3H), 0.91 (s, 3H), 0.87 (s, 3H), 0.86 (d, J=6 Hz, 6H); IR (KBr): 3389, 2929, 2861, 1467, 1457, 1375, 1037 $cm^{-1}$; HRMS (EI) for $C_{26}H_{46}O_2$ (M+), Calcd. 402.3498, found 4092.3524.

EXAMPLE 18

Preparation of 4,4-Dimethyl-15-thia-5a-cholest-8-en-3b-ol (Compound 49)

Hydrogen sulfide gas was bubbled through a solution of 4,4-dimethyl-16-methoxy-3b-[(4-methoxybenzyl)oxy]-15-oxa-5a-cholest-8-ene (Compound 16b) (1.426 mmole, crude material, prepared by procedures M, N, and O from Compound 13b (0.81 g, 1.426 mmole) in 40 ml of dry methylene chloride at 0° for 120 min. Boron trifluoride etherate (2.5 ml) was added to the mixture and it was stirred at 0° for 0.5 hr. and at room temperature for 1.5 hr. under nitrogen atmosphere. At the end of the stirring it was cooled to −30° and triethylsilane (2.2 ml, 13.8 mmole) was added dropwise to the solution. The mixture was stirred at room temperature for 1.5 hr. under nitrogen atmosphere and saturated aqueous sodium bicarbonate solution (50 ml) was added to quench the reaction. It was extracted with diethyl ether twice and the combined extracts were washed with brine, dried over anhydrous magnesium sulfate and evaporated under reduced pressure to give a dark brown oily residue. It was purified by column chromatography on silica gel with elution by 15:85 ethyl acetate-hexane to afford purified Compound 49 (158 mg, 26% overall yield from Compound 13b).

Rf: 0.24, 2:8 ethyl acetate - hexane.

Physical Data:

NMR (300 MHz, $CDCl_3$): delta 3.24 (dd, J=4.5 Hz, 11.1 Hz, 1H), 2.75 (t, J=8.4 Hz, 1H), 2.66 (dd, J=9.6 Hz, 11.7 Hz, 1H), 2.57 (m, 1H), 2.11-2.03 (m, 2H), 1.90-0.80 (m, 20H), 1.30 (s, 3H), 1.01 (s, 3H), 1.01 (d, J=6.6 Hz, 3H), 0.94 (s, 3H), 0.88 (s, 3H), 0.87 (d, J-6.3 Hz, 6H), 0.80 (s, 3H); IR (film): 3415, 2950, 2869, 1465, 1439, 1376, 1367, 1082, 1026, 1001, 736 $cm^{-1}$.

EXAMPLE 19

Preparation of 15-thia-dihydrolanosterol (Compound 50)

By the method described for 15-thiasterol (Compound 49) (Example 18) five-membered cyclic acetal (Compound 10b) (198 mg, 0.34 mmole) was transformed to 15-thia-dihydrolanosterol (Compound 50) (65.4 mg, 43% overall yield from Compound 7b).

Physical Data:

NMR (300 MHz, $CDCl_3$): delta 3.24 (dd, J=4.8 Hz, 11 Hz, 3H), 3.23 (s, 1H), 2.85 (t, J=10.2 Hz, 1H), 2.77 (dd, J=7.2 Hz, 10.2 Hz, 1H), 2.20-0.80 (m, 23H), 0.99 (s, 3H), 0.95 (s, 3H), 0.88 (d, J=8.7 Hz, 3H), 0.87 (d, J=6.6 Hz, 6H), 0.81 (s, 3H); IR (film): 3443, 2953, 2932, 2869, 1465, 1457, 1382, 1375, 1366, 1089, 1034, 1016, 1004, 736 $cm^{-1}$.

EXAMPLE 20

Preparation of 4,4-Dimethyl-15-thia-14a-vinyl-5a-cholest-8-en-3b-ol (Compound 51)

By the method described for 15-thiasteroid (Compound 49) (Example 18) five-membered cyclic acetal (Compound 22b) (274 mg, 0.46 mmole) was transformed to 15-thia-14-vinyl-sterol (Compound 51) (57.3 mg, 27.2% overall yield from Compound 19b).

Physical Data:

NMR (300 MHz, $CDCl_3$): delta 5.84 (dd, J=109.5 Hz, 1H), 5.12 (dd, J=1.5 Hz, 10.5 Hz, 1H), 4.94 (dd, J=1.5 Hz, 17.1 Hz, 1H), 3.26 (dd, J=4.8 Hz, 1H), 2.85 (dd, J=7.2 Hz, 9.6 Hz, 1H), 2.74 (dd, J=10.8 Hz, 11.7 Hz, 1H), 2.46 (m, 1H), 2.06 (dd, , J=3.9 Hz, 7.2 Hz, 114 Hz, 1H), 1.96–0.75 (m, 21H), 1.02 (s, 3H), 1.01 (s, 3H), 1.01 (d, J=6 Hz, 3H), 0.87 (d, J=6.6 Hz, 6H), 0.81 (s, 3H), 0.80 (s, 3H); IR (film): 3394, 2949, 2867, 1473, 1465, 1457, 1376, 1365, 1093, 1030, 1004, 918 $cm^{-1}$.

EXAMPLE 21

Preparation of sulfoxide (Compound 53)

To a stirred solution of 15-thia-dihydrolanosterol (Compound 50) (20 mg, 0.045 mmole) in ethanol (3 ml) was added a solution of sodium periodate (38 mg, 0.18 mmole) in water (1 ml) and the mixture was stirred at room temperature for 30 mins.

After addition of diethyl ether (ca. 10 ml) it was filtered to remove the precipitates and the filtrate was evaporated under reduced pressure to give an oily residue. It was purified by preparative thin layer chromatography on silica gel with elution by 5:95 methanol - methylene chloride to give 14 mg of purified sulfoxide (Compound 53) (67% yield).

Physical Data:

NMR (300 MHz, $CDCl_3$): delta 3.74 (dd, J=7.2 Hz, 13.2 Hz, 1H), 3.22 (dd, J=4.8 Hz, 11.4 Hz, 1H), 2.49 (t, J=13.2 Hz, 1H), 2.36–0.80 (m, 23H), 1.34 (s, 3H), 1.01 (d, J=6 Hz, 3H), 1.01 (s, 3H), 0.98 (s, 3H), 0.87 (d, J=6.6 Hz, 6H), 0.81 (s, 3H); IR (film): 3394, 2950, 2932, 2868, 1457, 1437, 1384, 1376, 1364, 1015, 731 $cm^{-1}$.

EXAMPLE 22

Preparation of 4,4-Dimethyl-14a-thia-D-homo-5a-cholest-8-en-eb-ol (Compound 56)

To a stirred solution of the cyclic acetal (Compound 13d) (300 mg, 0.65 mmole) in dry methylene chloride (10 ml) at 0° was bubbled hydrogen sulfide to saturate the solution and boron trifluoride etherate (0.9 ml, 7.3 mmole) was added dropwise.

After stirring at room temperature for 1.5 hr. it was cooled to 0° and triethylsilane (1.4 ml, 8.76 mmole) was added. It was stirred at the same temperature for 2.5 hr. and saturated sodium carbonate (ca. 20 ml) was added to quench the reaction. The mixture was extracted with diethyl ether (2×30 ml) and the combined extracts were washed with water and brine, dried over anhydrous magnesium sulfate, and evaporated under reduced pressure to give a foamy solid residue. It was purified by column chromatography on silica gel with elution by 15:85 ethyl acetate-hexane to afford purified Compound 56 (172 mg, 59.2% yield) as a white foamy solid.

Physical Data:

NMR (300 MHz, $CDCl_3$): delta 3.27 (dd, J=4.8 Hz, 11.4 Hz, 1H), 2.33–2.23 (m, 4H), 1.90–0.80 (m, 21H), 1.12 (s, 3H), 1.09 (s, 3H), 1.03 (s, 3H), 0.99 (s, 3H), 0.90 (d, J=6.9 Hz, 3H), 0.87 (d, J=6.6 Hz, 6H), 0.82 (s, 3H); IR (film): 3427, 2951, 2869, 2853, 1467, 1457, 1376, 1025, 1002, 734 $cm^{-1}$.

EXAMPLE 23

Preparation of 14a-thia-D-homo-dihydrolanosterol (Compound 57)

By the method described for Compound 56 (Example 22) the cyclic acetal (Compound 7d) (300 mg, 0.63 mmole) was transformed to six-membered cyclic sulfide (Compound 57) (129 mg, 44.3% yield) as a white foamy solid.

Physical Data:

NMR (300 MHz, $CDCl_3$) delta 3.26 (dd, J=4.8 Hz, 11.1 Hz, 1H), 2.75 (s, 1H), 2.50–2.25 (m, 3H), 2.05–0.90 (m, 24H), 1.13 (s, 3H), 1.01 (s, 3H), 0.99 (s, 3H), 0.89 (d, J=6.9 Hz, 3H), 0.86 (d, J=6.6 Hz, 6H), 0.81 (s, 3H).

EXAMPLE 24

Preparation of 14-Aza-4,4-dimethyl-5a-cholesta-8,14-dien-3b-ol (Compound 66a)

AS. Preparation of 4,4-dimethyl-3b-[(4-methoxybenzyl)oxy]-14-oxo-5a-14,15-secocholest-8-ene-15-carboxylic acid (Compound 63)

To a stirred solution of the enone aldehyde (Compound 4b) [15 mmole, crude material, prepared from Compound 2b (8 g, 15 mmole)] in tert-butanol (340 ml) and water (85 ml) were added sodium chlorite (Aldrich) (2.91 g, 30 mmole) and the mixture was stirred at room temperature for 1 hr. At the end of the stirring was added methylene chloride (500 ml) to the mixture and it was washed with water (2×150 ml). The combined aqueous layers were re-extracted with methylene chloride (200 ml) and washed with water once.

The methylene chloride extracts were dried over anhydrous magnesium sulfate and evaporated under reduced pressure to give a solid residue of crude acid (Compound 63) in near quantitative yield. The crude material was routinely used for next transformation without purification. The analytical sample was obtained by recrystallization from ethyl acetate and hexane, m.p.=126°–126.5° C.

Physical Data:

NMR (300 MHz, $CDCl_3$): delta 7.29 (d, J=8.4 Hz, 2H), 6.87 (d, J=8.4 Hz, 2H), 4.60 (d, J=11.4 Hz, 1H), 4.40 (d, J=11.4 Hz, 1H), 3.80 (s, 3H), 3.00 (dd, J=3.6 Hz, 11.4 Hz, 1H), 2.47 (dd, J=7 Hz, 17.5 Hz, 1H), 2.38–0.80 (m, 22H), 1.06 (s, 3H), 1.05 (s, 3H), 0.97 (s, 3H), 0.96 (d, J=6.6 Hz, 3H), 0.87 (s, 3H), 0.86 (d, J=6.9 Hz, 6H); IR (film): 3435, 2951, 2937, 2869, 1707, 1654, 1624, 1616, 1513, 1465, 1301, 1247, 1098 $cm^{-1}$; HRMS for $C_{37}H_{54}O_4$ (M-$H_2O$); Calcd. 562.4022, found 562.4054.

AT. Preparation of 4,4-dimethyl-3b-[(4-methoxybenzyl)oxy]-14-oxo-5a-14.15-secocholest-8-ene-15carboxylic acid azide (Compound 64)

To a solution of the carboxylic acid (Compound 63) (15 mmole) and N-methylmorpholine (4.96 ml, 45 mmole) in dry methylene chloride (270 ml) at 0° was added isobutyl chloroformate (2.92 ml, 22.5 mmole) dropwise over a period of 5 min. and the mixture was stirred at 0° for 1 hr. Then a solution of sodium azide (9.78 g, 75 mmole) and tetrabutylammonium bromide (1.1 g, 3.4 mmole) in water (90 ml) was added and the two phase mixture was stirred at 0° for 1.5 hrs. The methylene chloride layer was separated and the aqueous layer was extracted with methylene chloride (2×50 ml). The combined extracts were washed with water and brine, dried over anhydrous magnesium sulfate and evaporated under reduced pressure to give an oily residue of the crude acyl azide (Compound 64) (9.1 g, quantitative mass recovery). The crude product was normally used for next reaction without purification.

Physical Data:

IR (film): 3522, 2952, 2938, 2869, 2315, 1720, 1657, 1623, 1615, 1514, 1464, 1248, 1172, 1096 $cm^{-1}$.

AU. Preparation of 15-Aza-4.4-dimethyl-3b-[(4-methoxybenzyl)oxy]-15-methoxycarbonyl-5a-14,15-secocholest-8-en-14-one (Compound 65)

A solution of the acyl azide (Compound 64) (7 g, 11.6 mmole, crude material) in ethyl acetate (20 ml) and methanol (100 ml) was refluxed under nitrogen atmosphere for 5 hr. and the solvents were evaporated off.

The oily residue of the crude carbamate (Compound 65) was normally used for next reaction without purification. Analytical sample of purified Compound 65 was obtained by crystallization from diethyl ether and hexane, m p.=144°-144.5°.

Physical Data:

NMR (300 MHz, $CDCl_3$): delta 7.27 (d, J=8.4 Hz, 2H), 6.86 (d, J=8.4 Hz, 2H), 4.60 (dm J=11.4 Hz, 1H), 4.52 (t, J=6 Hz, 1H), 4.35 (d, J=11.4 Hz, 1H), 3.80 (s, 3H), 3.53 (s, 3H), 3.33 (dd, J=7.5 Hz, 13.5 Hz, 1H), 2.90 (dd, J=3.9 Hz, 11.4 Hz, 1H), 2.84 (m, 1H), 2.56 (dd, J=6 Hz, 18 Hz, 1H), 2.25-0.80 (m, 21H), 1.13 (d, J=6.6 Hz, 3H), 1.06 (s, 3H), 1.00 (s, 3H), 0.97 (s, 3H), 0.86 (d, J=6.6 Hz, 6H), 0.86 (s, 3H); IR (film): 3464, 3366, 2952, 2869, 1727, 1654, 1623, 1617, 1514, 14654, 1458, 1380, 1247, 1099, 1037 $cm^{-1}$; HRMS for $C_{38}H_{59}NO_5$ (M+): Calcd. 609.4393; found 609.4404.

AV. Preparation of 15-Aza-4,4-dimethyl-3b-[(4-methoxybenzyl)oxy]-5a-cholest-8-,14-diene (Compound 66b)

To a solution of the carbamate (Compound 65) (11.6 mmole) in dry tetrahydrofuran (150 ml) was added potassium trimethylsilanolate (12.8 g, 100 mmole) and the mixture was refluxed under nitrogen atmosphere for 2 hrs. After cooling to room temperature diethyl ether (200 ml) was added and the organic layer was washed with water and brine. The combined aqueous layers were re-extracted with diethyl ether and the extracts were washed with brine. The ether extracts were dried over anhydrous sodium sulfate and evaporated under reduced pressure to give a solid residue. It was purified by column chromatography on silica gel with elution by 2:8 ethyl acetate - hexane to give 4.5 g of purified cyclic imine (Compound 66b) as white solid (72.7% overall yield from Compound 2b). It was crystallized from methylene chloride and hexane to afford 3.6 g of crystalline product, m.p.=159°-160°.

Physical Data:

NMR (300 MHz, $CDCl_3$): delta 7.28 (d, J=8.4 Hz, 2H), 6.87 (d, J=8.4 Hz, 2H), 4.61 (d, J=11.7 Hz, 1H), 4.39 (d, J=11.7 Hz, 1H), 3.93 (dd, J=6 Hz, 14.5 Hz, 1H), 3.81 (s, 3H), 3.34 (dd, J=9.3 Hz, 14.5 Hz, 1H), 2.93 (dd, J=3.9 Hz, 11.7 Hz, 1H), 2.40-0.78 (m, 22H), 1.09 (s, 3H), 1.01 (s, 3H), 0.91 (d, J=5.1 Hz, 3H), 0.88 (s, 3H), 0.87 (d, J=5.7 Hz, 6H), 0.86 (s, 3H); IR (KBr): 2942, 2871, 2848, 1625, 1614, 1600, 1513, 1470, 1456, 1249, 1114, 1100, m 1037, 819 $cm^{-1}$; HRMS for $C_{36}H_{55}NO_2$ (M+): Calcd. 533.4232; found 533.4218.

AW. Preparation of 14-Aza-4,4-dimethyl-5a-cholesta-8,14-dien-3b-ol (Compound 66a)

To a stirred solution of Compound 66b (300 mg, 0.56 mmole) and allyltrimethylsilane (0.18 ml, 1.12 mmole) in dry methylene chloride (6 ml) was added boron trifluoride etherate (0.39 ml, 2.53 mmole) portionwise and the mixture was stirred at room temperature for 16 hr. under nitrogen atmosphere. Saturated sodium bicarbonate solution was added slowly to make the solution basic and the product was extracted with ethyl acetate. The extract was washed with water and brine, dried over anhydrous sodium sulfate and evaporated to give a solid residue. It was purified by column chromatography on silica gel with elution by 3:7 ethyl acetate-hexane followed by 7:3 ethyl acetate - hexane, to afford 217 mg of purified Compound 66a (93.3% yield).

Physical Data:

NMR (300 MHz, $CDCl_3$): delta 3.94 (dd, J=6.6 Hz, 15.6 Hz, 1H), 3.35 (dd, J=9.6 Hz, 15.3 Hz, 1H), 3.25 (dd, J=4.5 Hz, 11.4 Hz, 1H), 2.42 (d, J=6 Hz, 1H), 2.30 (dm J=7.5 Hz, 1H), 2.10-0.90 (m, 21H), 1.08 (s, 3H), 1.03 (s, 3H), 0.91 (d, J=5.7 Hz, 3H), 0.87 (d, J=6.6 Hz, 6H), 0.87 (s, 3H), 0.85 (s, 3H); IR (KBr): 3442, 3432, 2945, 2932, 2870, 1618, 1465, 1457, 1388, 1092, 1043, 1026, 1009 $cm^{-1}$; HRMS for $C_{28}H_{47}NO$ (M+): Calcd. 413.3658; found 413.3646.

EXAMPLE 25

Preparation of 14-Aza-5a-cholesta-8,14-dien-3b-ol (Compound 70a)

AX. Preparation of 3b-[(4-Methoxybenzyl)oxy]-14-oxo-5a-14,15-secocholest-8-ene-15-carboxylic acid (Compound 67)

By the method described for carboxylic acid (Compound 63) (Example 24-AS) 3b-[(4-Methoxyl-benzyl) oxy]-15-oxo-5a-14, 15-secocholest-8-ene-14-one (Compound 40) (7.5 mmole, crude material, prepared from Compound 38b) (3.8 g, 7.5 mmole)) was transformed to carboxylic acid (Compound 67) (4.08 g, foamy solid residue) The crude material was used for next transformation without purification.

Physical Data:

NMR (300 MHz, $CDCl_3$): delta 7.27 (d, J=8.1 Hz, 2H), 6.87 (d, J=8.1 Hz, 2H), 4.53 (d, J=11 Hz, 1H), 4.47 (d, J=11 Hz, 1H), 3.80 (s, 3H), 3.39 (m, 1H), 2.43-0.90 (m, 27H), 1.01 (s, 3H), 0.98 (s, 3H), 0.95 (d, J=6.9 Hz, 3H), 0.86 (d, J=6.6 Hz, 6H)); IR (film): 3150, 2935, 2867, 1706, 1657, 1614, 1514, 1466, 1459, 1377, 1302, 1249, 1172, 1036 $cm^{-1}$; HRMS for $C_{27}H_{43}O_4$ ($M-CH_3OC_6H_4CH_2$): Calcd. 431.3161; found 431.3224.

AY. Preparation of 3b-[(4-Methoxybenzyl)oxy]-14-oxo-5a-14,15-secocholest-8-ene-15-carboxylic acid azide (Compound 68)

By the method described for acyl azide (Compound 64) (Example 24-AT) carboxylic acid (Compound 67) (7.5 mmole) was transformed to acyl azide (Compound 68) as an oil. The crude material was used for next transformation without purification.

Physical Data:

NMR (300 MHz, $CDCl_3$): delta 7.27 (d, J=8.4 Hz, 2H), 6.87 (d, J=8.4 Hz, 2H), 4.52 (d, J=11.7 Hz, 1H), 4.47 (d, J=11.7 Hz, 1H), 3.80 (s, 3H), 3.39 (m, 1H), 2.42–0.90 (m, 26H), 1.02 (s, 3H), 0.96 (s, 3H), 0.93 (d, J=6.3 Hz, 3H), 0.86 (d, J=6.6 Hz, 6H); IR (film): 2953, 2935, 2868, 2135, 1720, 1658, 1620, 1614, 1513, 1467, 1377, 1248, 1180, 1172, 1087 $cm^{-1}$.

AZ. Preparation of 15-Aza-3b-[(4-methoxybenzyl)oxy]-15-methoxycarbonyl-5a-14,15-secocholest-8-en-14-one (Compound 69)

By the method described for carbamate (Compound 65) (Example 24-AU) acyl azide (Compound 68) (7.5 mmole) was transformed to carbamate (Compound 69) as an oil. The crude product was used for next reaction without purification. The analytical sample of purified Compound 69 was obtained by crystallization from diethyl ether and hexane.

Physical Data:

NMR (300 MHz, $CDCl_3$): delta 7.25 (d, J=8.2 Hz, 2H), 6.86 (d, J=8.4 Hz, 2H), 4.48 (s, 2H), 3.79 (s, 3H), 3.51 (s, 3H), 3.30 (m, 1H), 2.85 (m, 1H), 2.50–0.90 (m, 26H), 1.11 (d, J=6.6 Hz, 3H), 1.01 (s, 6H), 0.86 (dm J=6.6 Hz, 6H); IR (KBr): 3463, 3363, 2952, 2934, 2867, 1726, 1654, 1617, 1513, 1466, 1457, 1376, 1247, 1109, 1104, 1075, 1034 $cm^{-1}$; HRMS for $C_{34}H_{50}O_3$ (M-$NH_2CO_2CH_3$): Calcd. 506.3760; found 506.3769.

BA. Preparation of 14-Aza-3b-[(4-Methoxybenzyl)oxy]-5a-cholest-8,14-diene (Compound 50b)

By the method described for cyclic imine (Compound 66b) (Example 24-AV) carbamate (Compound 69) (7.5 mmole) was transformed to cyclic imine (Compound 70b). The solid residue was purified by column chromatography on silica gel with elution by 3:7 ethyl acetate-hexane to afford 2.33 g of purified Compound 70b as solid (61.4% overall yield from Compound 38b). It was crystallized from methylene chloride and hexane to give analytically purified sample.

Physical Data:

NMR (300 MHz, $CDCl_3$): delta 7.27 (d, J=8.7 Hz, 2H), 6.87 (d, J=8.7 Hz, 2H), 4.52 (d, J=11.4 Hz, 1H), 4.47 (d, J=11.4 Hz, 1H), 3.94 (dd, J=6.9 Hz, 15.3 Hz, 1H), 3.80 (s, 3H), 3.35 (s, 3H), 3.35 (m, 2H), 2.40–0.80 (m, 24H), 1.04 (s, 3H), 1.04 (s, 3H), 0.91 (d, J=6 Hz, 3H), 0.87 (s, 3H), 0.87 (d, J=6.3 Hz, 6H); IR (film): 3921, 2869, 2852, 1620, 1614, 1598, 1515, 1466, 1454, 1369, 1301, 1249, 1104, 1092, 1078, 1032, 820 $cm^{-1}$; HRMS for $C_{34}H_{51}NOI_2$ (M+): Calcd. 505.3920; found 505.3961.

BB. Preparation of 14-Aza-5a-cholesta-8,14-dien-3b-ol (Compound 70a)

By the method described for azasterol (Compound 66a) (Example 24-AW) cyclic imine (Compound 70b) (1 g, 1.98 mmole) was transformed to azasterol (Compound 70a) as a solid. It was purified by column chromatography on silica gel with elution by 3:& ethyl acetate - hexane followed by 8:2 ethyl acetate - hexane to obtain 207 mg of unreacted starting material (Compound 70b) and 673 mg of azasterol (Compound 70a) (96.3% yield based on the recovered starting material). The product was crystallized from diethyl ether and hexane, m.p.=178°–179°.

Physical Data:

NMR (300 MHz, $CDCl_3$): delta 3.94 (dd, J=6.9 Hz, 15.3 Hz, 1H), 3.60 (m, 1H, 3.34 (dd, J=9.6 Hz, 15 Hz, 1H), 2.45–0.80 (m, 25H), 1.04 (s, 3H), 0.92 (d, J=6 Hz, 3H), 0.87 (s, 3H), 0.87 (d, J=6.6 Hz, 6H); IR (film): 3304, 2931, 2867, 2858, 1620, 1597, 1467, 1453, 1371, 1056, 1025 $cm^{-1}$; HRMS for $C_{26}H_{43}BI$ (M+): Calcd. 385.3344; found 385.3344.

Bioactivity

EXAMPLE 26

3-Hydroxy-3-Methylglutaryl Coenzyme A Reductase (HMGR) Suppression Assay

The ability of the compounds of Formula I to suppress the activity of HMGR, the rate limiting enzyme of cholesterol biosynthesis, was tested as follows.

Chinese Hamster Ovary (CHO) cells were divided twice weekly and were maintained in McCoy's 5A medium supplemented with 1% carbosil delipidated Fetal Bovine System (FBS) (obtained from Gibco Laboratories, Chagrin Falls, Ohio). Cells were harvested during the logarithmic phase of growth and cell cultures were prepared by adding 0.5×10 cells to each well in a 24 well cluster dish (obtained from Costar, Data Packaging Corp., Cambridge, Mass.) employing 1 ml of the above medium per each well. The cell cultures were incubated for 48 hr. at 37° in a 5% $CO_2$, 95% air environment. The test compounds in a 2.5% suspension of bovine serum albumin (BSA) (Fatty acid free) in ethanol were then added to the cultures such that the final ethanol and BSA concentrations in the incubation medium were 0.5% and 0.25% respectively. Treated cells were incubated with the indicated compounds for 6 hr. at 37° in a 5% $CO_2$, 95% air environment. Control cells were treated in an identical fashion to those which received test compound, except they were incubated with the BSA and ethanol suspension only.

HMGR activity was then measured in digitonin-permeabilized cells by the method developed by Leonard et al., *J. Biol. Chem.*, 262: 7914–1719 (1987).

Specifically, the medium in each well was aspirated and the cells rinsed with a 50 mM solution of phosphate buffered saline (PBS). One ml of 30 mg/ml of digitonin in CSK buffer (prepared using 10 mM Pipes [piperazine-N,N'-bis (2-ethansulfonic) acid], 100 mM KCl, 2.5 mM $MgCl_2$, 300 mM sucrose, 1 mM EGTA, pH 6.8) was added to each well and incubated for 10 min. at 22° to permeabilize the cells. The buffer was carefully aspirated and the wells were rinsed twice each time with 1 ml of PBS. HMGR activity was measured directly by adding 75 ml of PIB buffer (50 mM potassium phosphate, 1 mM $Na_2EDTA$, 10 mM dithiothreitol, pH 7.4) to each well and incubating the cells for 30 minutes at 37° as described above. The enzyme assay was initiated by the addition of 83 µl of substrate/cofactor mixture such that the final assay contained the following: 0.1M potassium phosphate, 5 mM dithiothreitol, 20 mM glucose-6-phosphate, 2.5 mM NADP, 0.175 units of glucose-6-phosphate dehydrogenase, 150 mM [$^{14}$C] HMG-Coenzyme A (15 DPM/pmol), pH 7.4. The assay mixture was incubated for 30 min. at 37° and terminated by the addition of 70 ml of [$^{3}$H]-mevalonic acid (35,000 DPM/assay), 0.15 mg/ml in 3N HCl.

The reaction was left to lactonize for an additional 30 min. at 37° or overnight at room temperature.

Reaction products were separated by thin layer chromatography on silica gel G (obtained from Analtech, Newark, Del.) developed in an unsaturated environment with acetone:benzene (3:2, v:v). The band corresponding to mevalonolactone was identified by exposure to iodine vapor and was scraped into counting vials. The extent of conversion of starting substrate, HMG-CoA, to mevalonic acid was determined by liquid scintillation counting in Biofluor (obtained from New England Nuclear, Boston, Mass.). Corrections for recovery and blank values were made for each sample. Protein determinations were made by Bio-Rad (Bio-Rad, Richmond, Calif.) dye binding assay according to the manufacturer's instruction using bovine serum albumin as standard. Cellular protein was solubilized from culture dishes by the addition of 20 μl of 16N KOH and assayed directly for protein amount. Suppression values are expressed as the amount of compound required to suppress HMGR activity by 50% relative to that of the controls. The results of HMGR suppression assays are reported in Table 1.

TABLE I

3-Hydroxy-3-Methylglutaryl Coenzyme A Reductase (HMGR) Suppression Assay

| Ex. No. | $IC_{50}$ (μM) |
|---|---|
| 1 | 0.18 |
| 2 | 0.3 |
| 3 | 0.17 |
| 6 | 0.075 |
| 7 | 0.04 |
| 8 | 2.5 |
| 10 | 0.2 |
| 13 | 2.5 |
| 16 | 2.5 |
| 17 | 1.95 |
| 18 | 0.3 |
| 19 | 2.08 |
| 386 | 0.08 |
| 672 | — |
| 673 | 1.46 |
| 677 | 2.5 |
| 678 | — |
| 857 | 0.06 |
| 858 | 0.55 |
| 859 | 0.06 |
| 1303 | 0.3 |
| 1508 | 1.25 |
| 1509 | 5. |
| 1817 | 0.5 |
| 1818 | 0.16 |

The ability of compounds of this invention to effectively suppress HMGR activity is demonstrated by the data in Table I. As a comparison, it should be noted that cholesterol, lanosta-8,24-diene-3b-ol and lanost-8-en-3b-ol, when tested under these same conditions, were without effect on measured HMGR activity. Thus, the potent HMGR suppression activities of these compounds make them very attractive as hypocholesterolemic agents.

EXAMPLE 27

Lowering Blood Cholesterol Levels in Hamsters

The ability of the compounds of Formula I to lower blood cholesterol levels has been demonstrated in hamsters utilizing the following protocol.

Male Golden Syrian hamsters (50-60 grams) were obtained from Charles River, Inc. (Wilmington, Mass.).

Animals were housed in individual suspension cages and were maintained on a light cycle consisting of 12 hours of light followed by 12 hours of dark. Animals were allowed free access to water and feed (Agway ground chow, RMH 3200, Agway, Syracuse, N.Y.) containing 1% (w/w) corn oil) for a minimum of 4 weeks.

Following this stabilization period a sample of blood was collected by orbital sinus bleeding under light ether anesthesia into heparinized capillary tubes. Plasma was separated by centrifugation (600×g for 10 minutes) and plasma cholesterols were determined by an autoanalyzer (Centrifichem 600, Baker Instruments, Allentown, Pa.). Based upon measured plasma cholesterol values, the animals were randomized into two groups such that the mean plasma cholesterol values were identical for both groups.

Animals in the two groups were then placed on one of two diets: (1) Diet A, consisting of ground chow plus 1% (w/w) corn oil, as described above; or (2) Diet B, consisting of Diet A plus 0.2% (w/w) of a test compound. Animals on Diet B, the treated animals, were allowed free access to feed and water, while animals on Diet A were pair-matched with Diet B animals and served as pair-fed controls. The animals were kept on their respective diets for 7-days at which time they were bled by cardiac puncture under $CO_2$ anesthesia. Total plasma cholesterol levels were determined as described above.

The results are presented in Table II. The data is reported as means +SEM (standard error of the mean), in units of mg/dl. The value "N" represents the number of animals in each group.

TABLE II

Effect of Various Test Compounds Upon Plasma Cholesterol Levels in Hamsters

| Example No. | Plasma Cholesterol Control (mg/dl)[1] | Plasma Cholesterol Treated (mg/dl)[1] |
|---|---|---|
| 1[2] | 133.0 ± 4.0 (N = 20) | 120. ± 2.0 (N = 10) |

[1]Values represent means ±SEM for the number of animals given in parenthesis
[2]Dosed at 0.2% (w/w) in feed As the data in Table II indicate, blood cholesterol levels can be significantly lowered by administration of compounds of Formula 1.

EXAMPLES 28-31

Scheme IX generally depicts the synthetic sequence for the preparation of the compounds of Examples 28-30. In the initial reaction, Compound 72 is preferably converted to Compound 73 using catalytic osmium tetroxide. Preferred methods for the other synthetic conversions are provided in the examples which follow this scheme.

SCHEME IX

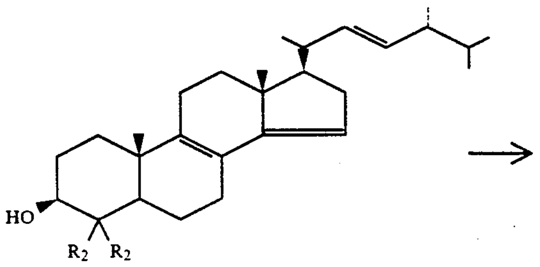

72 $R_2 = CH_3$
79 $R_2 = H$

-continued
SCHEME IX

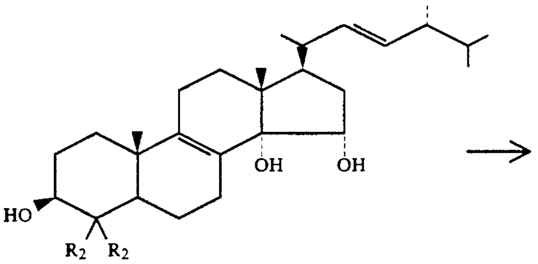

73 $R_2$ = $CH_3$

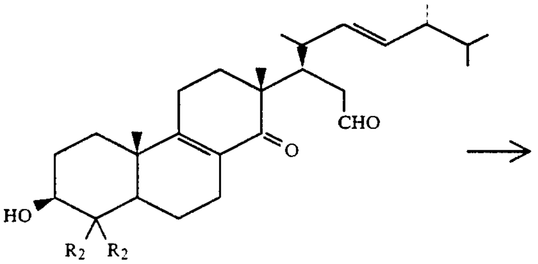

74 $R_2$ = $CH_3$

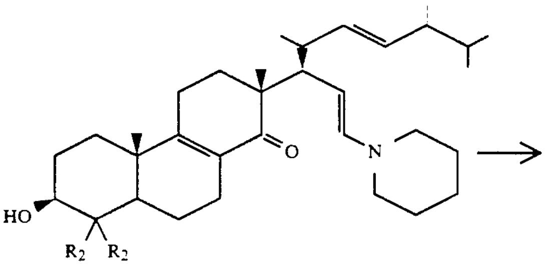

75 $R_2$ = $CH_3$

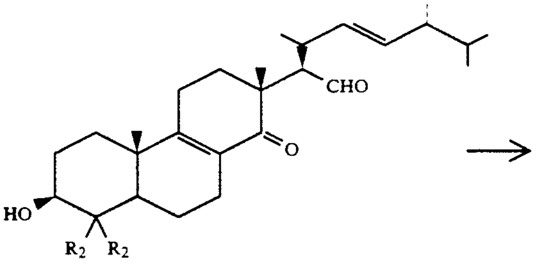

76 $R_2$ = $CH_3$

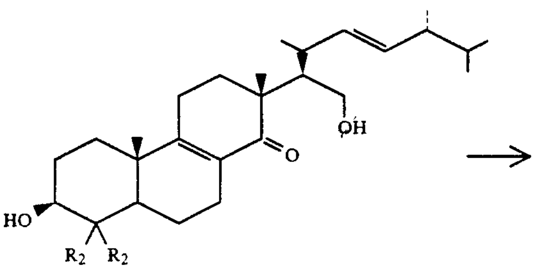

77 $R_2$ = $CH_3$

-continued
SCHEME IX

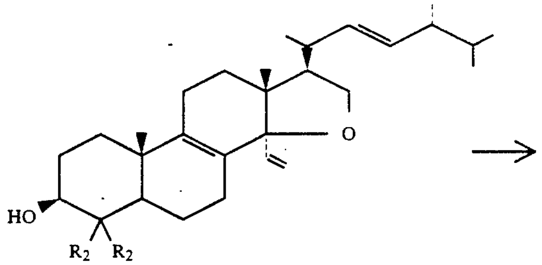

78 $R_2$ = $CH_3$
80 $R_2$ = H

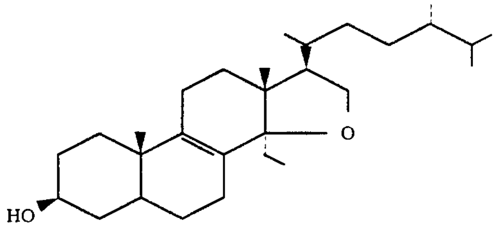

81

EXAMPLE 28

Preparation of (22E)-4,4-Dimethyl-15-oxa-14α-vinylergosta-8,22-dien-3β-ol (Compound 78)

BC. Preparation of (22E)-4,4-Dimethyl-ergosta-8,22-diene-3β,14α,15α-triol (Compound 73)

To a stirred solution of (22E)-4,4-dimethylergosta-8,14,22-trien-3β-ol (Compound 72, 10 g, 23.5 mmole) prepared by the method described by Dolle, et al. *J. Org. Chem.*, 51: 4027 (1986), in 1,4-dioxane (400 ml) were added pyridine (10 ml), 1,8-diazabicyclo[4.4.0]undec-7-ene (DBU, Aldrich Chemical Co.) (4 ml), an aqueous solution of trimethylamine N-oxide dihydrate (Aldrich Chemical Co.) (5.4 g, 47 mmole in 50 ml of water) and a 20% solution of osmium tetraoxide in methylene chloride (1.5 ml, 1.18 mmole) and the mixture was heated under reflux for 24 hr. After cooling to room temperature was added 20% solution of sodium bisulfite (50 ml) and the mixture was stirred for 0.5 hr. It was extracted with ethyl acetate (3×200 ml) and the combined extracts were washed with water and brine. The organic extract was dried over magnesium sulfate and evaporated to give a solid residue. The crude product was dissolved in a minimum amount of ether and passed through a short silica gel column with elution by ether to remove the colored impurities. The solvent was evaporated off to afford a white crystalline solid (7.47 g) of the triol (Compound 73).

Physical data:

NMR (300 MHz, $CDCl_3$): delta 5.23 (dd, J=7.3 Hz, 15.4 Hz, 1H), 5.13 (dd, J=7.3 Hz, 15.4 Hz, 1H), 4.10 (m, 1H), 3.24 (m, 1H), 2.41 (d, J=9.5 Hz, 1H), 2.38–0.80 (m, 21H), 1.02(s,3H), 1.00(s,3H), 0.97 (d, J=5.8 Hz, 3H), 0.91 (d, J=6.6 Hz, 3H), 0.84–0.81 (m, 9H), 0.71 (s, 3H).

BD. Preparation of (22E)-4,4-Dimethyl-3β-hydroxy-15-oxo-14,15-secoergosta-8,22-dien-14-one (Compound 74)

To a stirred solution of the triol (Compound 73, 13.2 g, 28.9 mmole) in dry benzene (360 ml) in the dark was added lead tetracetate (12.8 g, 28.9 mmole) in small portions over a period of 1 hr. and the mixture was stirred at room temperature for 1 hr. under nitrogen atmosphere and in the dark. The mixture was filtered through Celite and the filtercake was rinsed several times. Evaporation of the solvent provide a foamy solid of the enone aldehyde (Compound 74) in near quantitative yield.

Physical data:

NMR (300 MHz, $CDCl_3$): delta 9.55 (brs, 1H), 5.24–5.22 (m, 2H), 3.30 (dd, J=4.7 Hz, 11.3 Hz, 1H), 2.56–0.80 (m, 20H), 1.03 (s, 3H), 1.01 (s, 3H), 0.93 (d, J=6.9 Hz, 3H), 0.93 (s, 3H), 0.89 (d, J=6.9 Hz, 3H), 0.82–0.77 (m, 9H).

BE. Preparation of (22E)-4,4-Dimethyl-3β-hydroxy-15-(1'-piperidino)-14,15-secoergosta-8,15,22-trien-14-one (Compound 75)

To a solution of the enone-aldehyde (Compound 74, 11.9 g, 26 mmole) in benzene (240 ml) was added piperidine (12 ml) and the mixture was refluxed under a Dean-Stark trap until the removal of water is completed (c.a. 1 hr.). The excess piperidine and the solvent were evaporated off under reduced pressure after cooling to give a foamy solid residue of the enamine (Compound 75) in quantitative yield.

Physical data:

NMR (300 MHz, $CDCl_3$) delta 5.56 (d, J=13.5 Hz, 1H), 5.28 (dd, J=8.4 Hz, 15.4 Hz, 1H), 5.14 (dd, J=7.7 Hz, 15.4 Hz, 1H), 4.20 (br, 1H), 4.17 (dd, J=10.6 Hz, 13.5 Hz, 1H), 3.28 (dd, J=4.7 Hz, 11.3 Hz, 1H), 2.88 (m, 4H), 2.80–0.80 (m, 19H), 1.60 (m, 4H), 1.04 (s, 3H), 1.03 (s, 3H), 0.95 (s, 3H), 0.93 (d, J=6.6 Hz, 3H), 0.91 (d, J=6.6 Hz, 3H), 0.84–0.79 (m, 9H).

BG. Preparation of (22E)-4,4-Dimethyl-3β-hydroxy-16-oxo-14,16-seco-D-nor-ergosta-8,22-dien-14-one (Compound 76)

A solution of the enamine (Compound 75, 26 mmole) in dry methylene chloride (200 ml), containing c.a. 10 mg of Sudan Red 7B as an indicator, was bubbled with ozone at −78° until the color become light pink. After stirring for 5 min. dimethyl sulfide (5 ml) was added and the mixture was stirred for 30 min. at −78°. The residue after evaporation of the solvent was dissolved in a small amount of ether and passed through a plug of silica gel to remove polar impurities. Evaporation of the solvent afforded a foamy solid of the enone aldehyde (Compound 76).

Physical data:

NMR (300 MHz, $CDCl_3$): delta 9.73 (d, J=4.7 Hz, 1H), 5.33 (m, 2H), 3.28 (dd, J=4.6 Hz, 11.5 Hz, 1H), 2.32 (br, 2H), 2.18 (dd, J=6.2 Hz, 13.5 Hz, 1H), 2.60–0.8 (m, 15H), 1.21 (s, 3H), 1.07 (s, 3H), 1.04 (d, J=6.6 Hz, 3H), 1.04 (s, 3H), 0.91 (d, J=6.9 Hz, 3H), 0.84–0.81 (m, 9H).

BH. Preparation of (22E)-3β16-Dihydroxy-4,4-dimethyl-14,16-seco-D-nor-ergosta-8,22-dien-14-one (Compound 77)

To a solution of the enone-aldehyde (Compound 76, 26 mmole) in methanol (115 ml) at −40° was added sodium borohydride (0.59 g, 15.6 mmole) and the mixture was stirred for 1 hr. at from about −40°, with warming to about 10°. The excess sodium borohydride was destroyed by stirring for 5 min. with acetic acid (1 ml). It was then neutralized with saturated solution of sodium bicarbonate and concentrated under reduced pressure. The residue was extracted with ethyl acetate (3×100 ml) and the combined extracts were washed with water and brine, dried over magnesium sulfate, and evaporated to give an oily residue. The crude product was column chromatographed on silica gel with elution by ethyl acetate - hexane (2:8) to give 6 g of pure enone-alcohol (Compound 77).

Physical data:

NMR (300 MHz, $CDCl_3$): delta 5.32–5.28 (m, 2H), 3.69 (dd, J=5.3 Hz, 6.8 Hz, 1H), 3.61 (dd, J=4.4 Hz, 6.8 Hz, 1H), 2.64–0.8 (m, 19H), 1.14 (d, J=7.0 Hz, 3H), 1.07 (s, 6H), 1.03 (s, 3H), 0.92 (d, J=7.0 Hz, 3H), 0.85–0.80 (m, 9H).

BI. Preparation of (22E)-4,4-Dimethyl-15-oxa-14α-vinyl-ergosta-8,22-dien-3β-ol (Compound 78)

To a solution of the enone-alcohol (Compound 77, 1.98 g, 4.45 mmole), 2,6-lutidine (1.71 ml, 14.7 mmole) and 4-dimethylamino-pyridine (0.1 g) in dry methylene chloride (22 ml) at 0° was added chlorotrimethysilane (1.7 ml, 13.4 mmole) dropwise and the mixture was stirred for 40 min. at 0° and for 10 min. at 25°. The reaction was quenched by methanol (1 ml) and the mixture was poured into ether. The ether solution was washed with water and brine, dried over magnesium sulfate and evaporated to give a foamy solid residue.

The residue was then dissolved in dry tetrahydrofuran (25 ml) and 1 M-vinyl magnesium bromide in dry tetrahydrofuran (8.9 ml, 8.9 mmole) was added. The mixture was heat under reflux for 1 hr. and cooled to 0°. It was treated with 1N HCl (18 ml) and extracted with ethyl acetate (3×30 ml). The combined extracts were washed with water and brine, dried over magnesium sulfate, and evaporated to give an oily residue.

It was dissolved in methanol (25 ml) containing p-toluenesulfonic acid (0.5 g) and the mixture was stirred for 16 hr. at room temperature. Then the reaction mixture was made basic with saturated solution of sodium bicarbonate and extracted with ethyl acetate (3×30 ml). The combined organic solutions were washed with brine, dried over magnesium sulfate and evaporated to afford to foamy solid residue. The crude product was purified by column chromatographed on silica gel with elution by ethyl acetate - hexane (1:9) to provide 1.12 g of pure vinyl-oxasterol (Compound 78).

Physical data:

NMR (300 MHz, $CDCl_3$) delta 5.71 (dd, J=11.0 Hz, 17.6 Hz, 1H), 5.26 (dd, J=7.9 Hz, 15.2 Hz, 1H), 5.11 (d, J=11.0 Hz, 1H), 5.10 (m, 1H), 5.00 (d, J=17.4 Hz, 1H), 3.67 (t, J=8.4 Hz, 1H), 3.49 (t, J=8.6 Hz, 1H), 3.29 (brt, J=5.3 Hz, 1H), 2.12–0.8 (m, 18H), 1.02 (s, 3H), 1.01 (s, 3H), 0.90 (d, 6.5 Hz, 3H), 0.84–0.8 (m, 15H).

EXAMPLE 29

BJ. Preparation of (22E)-15-Oxa-14α-vinyl-ergosta-8,22-dien-3β-ol (Compound 80)

By the method described for 4,4-dimethyl-vinyloxasterol (Compound 79) (Example 28-BC through BI) (22E)-ergosta-8,14,22-trien-3β-ol [prepared by the method described by Dolle, et al. *J. Org. Chem.*, 51: 4027 (1986)] was transformed to the corresponding normethyl-vinyl-oxasterol (Compound 80).

Physical Data:

NMR (300 MHz, $CDCl_3$): delta 5.71 (dd, J=10.8 Hz, 7.2 Hz, 1H), 5.27 (dd, J=7.7 Hz, 15.1 Hz, 1H), 5.11 (dd, J=2.2 Hz, 10.8 Hz, 1H), 5.10 (m, 1H), 5.01 (dd, J=2.2 Hz, 17.2 Hz, 1H), 3.67 (t, J=8.10 Hz, 1H), 3.49 (t, J=8.8 Hz, 1H), 2.08–0.89 (m,21H), 1.04 (d, J=5.9 Hz, 3H), 0.97 (s, 3H), 0.90 (d, J=7.0 Hz, 3H), 0.84–0.80 (m, 9H).

EXAMPLE 30

BK. Preparation of 14α-Ethyl-15-oxa-ergost-8-en-3β-ol (Compound 81)

A solution of the vinyl-oxasterol (Compound 80, 50 mg, 0.12 mmole) and 10% palladium on carbon (10 mg) in 3 ml of ethyl acetate - acetic acid (95:5) was stirred under hydrogen atmosphere (1 atm.) for 30 min. After removal of the catalyst by filtration through Celite the solvents were evaporated to give a foamy solid of the ethyl-oxasterol (Compound 81) in quantitative yield.

Physical data:

NMR (300 MHz, $CDCl_3$): delta 3.76 (t, J=8.5 Hz, 1H), 3.66 (m, 1H), 3.43 (t, J=8.6 Hz, 1H), 2.17–0.75 (m, 26H), 0.97 (s, 3H), 0.94 (s, 3H), 0.84 (d, J=6.9 Hz, 3H), 0.81–0.73 (m, 12H).

EXAMPLE 31

Assay of $^{14}C$-Acetate Incorporation into the Biosynthesis of Cholesterol The HepG2 cells (a human hepatoma cell line) used in this example were obtained from the American Type Culture Collection (ATCC, Rockville, Md.). They were maintained in Dulbecco's Modified Eagles Medium and Ham's F12 Medium (1:1) supplemented with 10% heat inactivated Fetal Bovine serum, 10 μM Herpes, 1 mM sodium pyruvate, 1×Non-essential Amino Acids (Gibco) and 2 mM L-glutamine.

The cells were harvested by washing cultures with 10 ml Hank's Balanced Salt Solution (2×) and incubating with 0.125% Trypsin in Versene (0.02% EDTA) for approximately one minute. After the cells are visibly rounded and loosened from the flask, 9 ml of the above medium is added. The cells are transferred to a 100 mM culture dish and syringed up and down through a 20 gauge needle to break up aggregated clumps of cells. Cell cultures are plated at $0.1\times10^6$/ml and $0.075\times10^6$/ml in two 24 well plates, respectively, aliquoting 1 ml cells/well. The cells are allowed to attach for 24 hours (48 hours for the lower density plate) before washing 2× with HBSS and refed with 1 ml of the above medium with 1% Cabosil delipidated serum instead of Fetal Bovine Serum. The cells are treated with the test compounds after 24 hours of exposure to the delipidated serum media.

Chemicals are routinely prepared as a 10 mM solution in 100% ethanol or dimethyl sulfoxide (DMSO). All test compounds are added at 50 μM, 25 μM, 10 μM, 1 μM at a final concentration of 0.45% solvent, 0.25% Bovine Serum Albumin (BSA) suspension per well. The solvent BSA is sonicated for 10 seconds to ensure maximum solubilization before addition to the cells. Control wells receive solvent/BSA at the same concentrations as the drug treated cultures. After incubation for one hour at 37° C., 5% $CO^2$, 20 μCi/ml $^3H$-MVAL is added per well in ethanol/medium so the final concentration of solvent is 1.2%. After 22 hours of incubation with the test compounds 2.5 μCi of $^{14}C$-acetate is added per well for an additional 2 hours so that the final concentration of ethanol is 1.6%.

Two known cholesterol biosynthesis inhibitors are included with each assay, namely 25-hydroxycholesterol and Lovastatin, to determine the reliability and validity of each assay.

The cultures are harvested by aspirating the media and washing twice with ice cold 0.5M Tris, 0.15M NaCl, pH 7.4 to remove excess radiolabel not incorporated into the cells. Stop Reagent (1 ml of 15% potassium hydroxide, 85% methanol, 100 μg/ml butylated hydroxytoluene (BHT) is added to each well and the plate is sonicated in a mild water sonicating bath to release the cells from the bottom of the well. The digested cell extracts are transferred to 15 ml extraction tubes. Each well is rinsed with an additional 1 ml of the Tris/NaCl buffer which is added to the appropriate extraction tube. An aliquot (100 μl) is removed for protein determination at this point if desired.

The cell extracts are saponified at 80° C. for 30 minutes. After cooling 8 ml petroleum ether is added and the tubes are twirled on a rotary extractor for 5–10 minutes to extract the sterols into the organic solvent phase. The top organic phase is removed and passed through a Silica Seppak (Waters) which binds all sterols and free fatty acids. Sterols are eluted with a 5 ml diethyl ether:hexane (1:1) rinse. This sterols extraction is automated using the Millilab (Waters) to ensure reproducibility and accuracy from sample to sample.

The eluted sterols are dried under nitrogen gas and resuspended in 150 μL ethanol. A 15 μL aliquot is removed from each sample and added to a scintillation vial filled with Formula 989 (NEN). The samples are counted on the dual label $^3H$:$^{14}C$ program on the Beckman scintillation counter Model LS 7800.

The incorporation of both radiolabeled precursors into sterols is compared between the treated and nontreated (control) cultures and expressed as "% control" for each precursor. Test compounds are classified as being "active" or "inactive" from these results and $IC_{50}$ values were determined for the active compounds.

Analysis of sterol profiles is performed on the remainder of the sample by reversed phase HPLC. Analyses are done using an Ultrasphere octyl column (Altex) (0.46×25 cm), with a mobile phase consisting of acetonitrile:methanol:$H_2O$ (44.5:44.5:10). Chromatography is performed at a flow rate of 1.5 ml per minute at 45° C.

RESULTS

The following $IC_{50}$ values represent the level of inhibition of the incorporation of $^{14}C$-acetate into the cholesterol biosynthesis pathway, as determined above:

| Compound | $IC_{50}$ (μM) |
|---|---|
| Example 28 (Compound 78) | 0.05 |
| Example 29 (Compound 80) | >50.0 |
| Example 30 (Compound 81) | 0.60 |

AGRICULTURAL UTILITY

Some compounds of this invention have also shown utility as plant disease control agents. They are effective in controlling a wide range of plant diseases, including economically important diseases caused by fungi of the Ascomycetes, Basidiomycetes, and Oomycetes classes.

Plant disease control is ordinarily accomplished by applying an effective amount of the compound either pre- or post-infection to the portion of the plant to be protected, such as the roots, stems, foliage, fruit, seeds, tubers or bulbs, or to the media (soil or sand) in which the plants to be protected are growing. The compound may also be applied to the seed from which the plants to be protected are to be grown.

Rates of application for these compounds can be influenced by many factors of the environment and should be determined under actual use conditions. Foliage can normally be protected when treated at a rate of from less than 1 g/ha to 5000 g/ha of active ingredient. Plants growing in soil treated at a rate of from less than 1 g/ha to 5000 g/ha of active ingredient. Plants growing in soil treated at a concentration from 0.1 to about 20 kg/ha can be protected from disease. Seed and seedlings can normally be protected when seed is treated at a rate of from 0.06 to about 3 grams per kilogram of seed.

EXAMPLE A

The test compounds were dissolved in acetone in an amount equal to 6% of the final volume and then suspended at a concentration of 200 ppm in purified water containing 250 ppm of the surfactant TREM 014 (polyhydric alcohol esters). This suspension was sprayed to the point of run-off on apple seedlings. The following day plants were inoculated with a spore suspension of *Venturia inaequalis*, the casual agent of apple scab, and incubated in a saturated humidity chamber at 20° C. for 24 hours and then in a growth chamber at 22° C. for 11 days, when disease ratings were made.

EXAMPLE B

The test compounds were dissolved in acetone in an amount equal to 6% of the final volume and then suspended at a concentration of 200 ppm in purified water containing 250 ppm of the surfactant TREM 0124 (polyhydric alcohol esters). This suspension was sprayed to the point of run-off on peanut seedlings. The following day plants were incubated in a saturated humidity chamber at 22° C. for 24 hours, then in a high humidity chamber at 27° C. for 7 days, and then in a growth chamber at 29° C. for 7 days, when disease ratings were made.

EXAMPLE C

The test compounds were dissolved in acetone in an amount equal to 6% of the final volume and then suspended at a concentration of 200 ppm in purified water containing 250 ppm of the surfactant TREM 0914 (polyhydric alcohol esters). This suspension was sprayed to the point of run-off on broad bean seedlings. The following day plants were inoculated with a spore suspension of *Botyrtis cinerea*, the causal agent of bean grey mold, and incubated in a saturated humidity chamber at 20° C. for 24 hours when disease ratings were made.

EXAMPLE D

The test compounds were dissolved in acetone in an amount equal to 6% of the final volume and then suspended at a concentration of 200 ppm in purified water containing 250 ppm of the surfactant TREM 014 (polyhydric alcohol esters). This suspension was sprayed to the point of run-off on wheat seedlings. The following day plants were inoculated with a spore dust of *Ersiphe graminis* f. sp. tritici, the causal agent of wheat powdery mildew, and incubated in a growth chamber at 20° C. for 6 days, when disease ratings were made.

EXAMPLE E

The test compounds were dissolved in acetone in an amount equal to 6% of the final volume and then suspended at a concentration of 200 ppm in purified water containing 250 ppm of the surfactant TREM 014 (polyhydric alcohol esters). This suspension was sprayed to the point of run-off on rice seedlings. The following day plants were inoculated with a spore suspension of *Pyricularia oryzae*, the causal agent of rice blast, and incubated in a saturated humidity chamber at 27° C. for 24 hours and then in a growth chamber at 29° C. for 4 days, when disease ratings were made.

EXAMPLE F

The test compounds were dissolved in acetone in an amount equal to 6% of the final volume and then suspended at a concentration of 220 ppm in purified water containing 250 ppm of the surfactant TREM 014 (polyhydric alcohol esters). This suspension was sprayed to the point of run-off on rice seedlings. The following day plants were inoculated with a mycelial suspension of *Rhizoctonia solani*, the causal agent of rice sheath blight, and incubated in a saturated humidity chamber at 27° C. for 48 hours and then in a growth chamber at 29° C. for 4 days, when disease ratings were made.

EXAMPLE G

The test compounds were dissolved in acetone in an amount equal to 6% of the final volume and then suspended at a concentration of 220 ppm in purified water containing 250 ppm of the surfactant TREM 014 (polyhydric alcohol esters). This suspension was sprayed to the point of run-off on wheat seedlings. The following day plants were inoculated with a spore suspension of *Puccinia recondita*, the causal agent of wheat leaf rust, and incubated in a saturated humidity chamber at 20° C. for 48 hours and then in a growth chamber at 20° C. for 8 days, when disease ratings were made.

EXAMPLE H

The test compounds were dissolved in acetone in an amount equal to 6% of the final volume and then suspended at a concentration of 200 ppm in purified water containing 250 ppm of the surfactant TREM 014 (polyhydric alcohol esters). This suspension was sprayed to the point of run-off on tomato seedlings. The following day plants were inoculated with a spore suspension of *Phytophthora infestans*, the causal agent of tomato late blight, and incubated in a saturated humidity chamber at 20° C. for 48 hours and then in a growth chamber at 20° C. for 5 days, when disease ratings were made.

EXAMPLE I

The test compounds were dissolved in acetone in an amount equal to 6% of the final volume and then suspended at a concentration of 200 ppm in purified water containing 250 ppm of the surfactant TREM 014 (polyhydric alcohol esters). This suspension was sprayed to the point of run-off on grape seedlings. The following day plants were inoculated with a spore suspension of *Plasmopara victicola*, the causal agent of grape downy mildew, and incubated in a saturated humidity chamber at 20° C. for 24 hours and then in a growth chamber at 20° C. for 7 days, and then held in a saturated humidity chamber at 20° C. for 24 hours, when disease ratings were made.

EXAMPLE J

The test compounds were dissolved in acetone in an amount equal to 6% of the final volume and then suspended at a concentration of 200 ppm in purified water containing 250 ppm of the surfactant TREM 014 (polyhydric alcohol esters). This suspension was sprayed to the point of run-off on grape seedlings. The following day plants were inoculated with a spore suspension of *Botrytis cinerea*, the causal agent of grape grey mold, and incubated in a saturated humidity chamber at 20° C. for 96 hours when disease ratings were made.

EXAMPLE K

The test compounds were dissolved in acetone in an amount equal to 6% of the final volume and then suspended at a concentration of 200 ppm in purified water containing 250 ppm of the surfactant TREM 014 (polyhydric alcohol esters). This suspension was sprayed to the point of run-off on cucumber seedlings. The following day plants were inoculated with a spore suspension of *Botrytis cinerea*, the causal agent of cucumber grey mold, and incubated in a saturated humidity chamber at 20° C. for 4 days when disease ratings were made.

Results of Examples A-K for two compounds of the invention are presented in Table III. In this table, a rating of 100 indicated 100% disease control, and a rating of 0 indicates no disease control relative to untreated plants that were inoculated and incubated as described in each Example. A dashed entry indicates the specified test was not performed.

TABLE III

| Example | A | B | C | D | E | F | G | H | I | J | K |
|---|---|---|---|---|---|---|---|---|---|---|---|
| 1817 | 90 | 25 | 97 | 92 | 1 | 0 | 62 | — | — | 97 | 99 |
| 1818 | 99 | 95 | 95 | 98 | 6 | 0 | 100 | 94 | 100 | 78 | 100 |

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. Compounds having the formula:

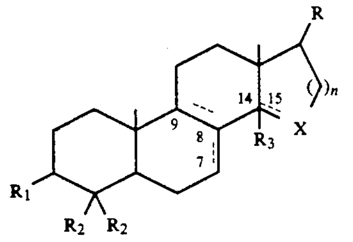

wherein

R is a side chain having either 8 or 9 carbon atoms and from 15 to 20 hydrogen atoms, optionally with one site of unsaturation; and the substituents $R_1$, independently each of $R_2$, and $R_3$, are selected from the groups defined as follows:

$R_1$ is =O, $OR_7$, or $OCOR_7$;

$R_2$ is H, $C_1$-$C_6$ alkyl, $C_2$-$C_6$ alkenyl, $C_2$-$C_6$ alkynyl, or benzyl;

$R_3$ is H, $C_1$-$C_6$ alkyl, $C_2$-$C_6$ alkenyl, $C_2$-$C_6$ alkynyl, benzyl, $C(R_4)_2R_5$, $COR_4$, $CSR_4$, $C(=NR_4)R_4$, $COR_5$, $CSR_5$, $C(R_4)_2C(R_4)_2R_5$, $C(R_4)_2COR_4$, $C(R_4)_2CSR_4$, $C(R_4)_2C(=NR_4)R_4$, $C(R_4)_2COR_5$, $C(R_4)_2CRS_5$, $C(R_4)_2Z$, $C(R_4)_2C(R_4)_2Z$, CN, $CR_4NOR_4$, $CR_4NOR_6$, $CR_4NN(R_4)_2$, $CR_4NNR_4R_6$, $CHR_4NHOR_4$, $CHR_4NHOR_6$, $CHR_4NHN(R_4)_2$, $CHR_4NHNR_4R_6$, $CHR_4CR_4NOR_4$, $CHR_4CR_4NOR_6$, $CHR_4CR_4NN(R_4)_2$, $CHR_4CR_4NNR_4R_6$, $CHR_4CHR_4NHOR_4$, $CHR_4CHR_4NHOR_6$, $CHR_4CHR_4NHN(R_4)_2$, $C(O)NH_4OR_4$, $C(O)NR_4OR_6$, $C(S)NR_4OR_4$, $C(S)NR_4OR_6$, $CR_4=CR_4R_6$, $C\equiv CR_6$, $CR_4=CR_4C(R_4)_2Z$, $C\equiv CC(R_4)_2Z$, $CR_4=CR_4C(R_4)_2OR_6$, $C\equiv CC(R_4)_2OR_6$, or poly-($OR_4$, $OR_6$, epoxy)-$C_1$-$C_6$ alkyl;

$R_4$ is H, $C_1$-$C_6$ alkyl, $C_2$-$C_6$ alkenyl, $C_2$-$C_6$ alkynyl, phenyl or phenyl substituted with $C_1$-$C_3$ alkyl, $OR_2$, Z, $N(R_2)_2$, or $CF_3$; or benzyl;

$R_5$ is $OR_4$, $SR_4$, $N(R_4)_2$, or $NR_4R_6$;

$R_6$ is $COR_4$, $CSR_4$, or $C(=NR_4)R_4$;

$R_7$ is H, $C_1$-$C_{20}$ alkyl, $C_2$-$C_{20}$ alkenyl, $C_2$-$C_{20}$ alkynyl, phenyl or phenyl substituted with $C_1$-$C_3$ alkyl, $OR_2$, Z, $N(R_2)_2$, or $CF_3$; or benzyl;

X is O or s;

Z is halogen; and n is 1;

and their physiologically acceptable salts.

2. The compounds of claim 1 wherein:

$R_3$ is H, $C_1$-$C_6$ alkyl, $C_2$-$C_6$ alkenyl, $C_2$-$C_6$ alkynyl, benzyl, $C(R_4)_2R_5$, $COR_4$, $COR_5$, $C(R_4)_2C(R_4)_2R_5$, $C(R_4)_2COR_4$, $C(R_4)_2COR_5$, $C(R_4)_2Z$, $C(R_4)_2C(R_4)_2Z$, CN, $CR_4NOR_4$, $CR_4NOR_6$, $CHR_4NHOR_4$, $CHR_4NHOR_6$, $CHR_4CR_4NOR_4$, $CHR_4CR_4NOR_6$, $CHR_4CHR_4NHOR_4$, $CHR_4CHR_4NHOR_6$, $C(O)NR_4OR_4$, $C(O)NR_4OR_6$, $CR_4=CR_4R_6$, $C\equiv CR_6$, $CR_4=CR_4C(R_4)_2OR_6$, $C\equiv CC(R_4)_2OR_6$, or poly-($OR_4$, $OR_6$, epoxy)-$C_1$-$C_6$ alkyl.

3. The compounds of claim 1, wherein:

$R_3$ is H, $C_1$-$C_6$ alkyl, $C_2$-$C_6$ alkenyl, $C_2$-$C_6$ alkynyl, $C(R_4)_2R_5$, $COR_4$, $COR_5$, $C(R_4)_2C(R_4)_2R_5$, $C(R_4)_2COR_4$, $C(R_4)_2COR_5$, CN, $CR_4NOR_4$, $CR_4NOR_6$, $C(O)NR_4OR_4$, $C(O)NR_4OR_6$, $CR_4=CR_4R_6$, $CR_4=CR_4C(R_4)_2OR_6$, or poly-($OR_4$, $OR_6$, epoxy)-$C_1$-$C_6$ alkyl.

4. The compounds of claim 1, wherein X is O or S.

5. The compounds of claim 1, wherein n is 1.

6. The compounds of claim 1, wherein:

$R_3$ is H, $C_1$-$C_6$ alkyl, $C_2$-$C_6$ alkenyl, $C_2$-$C_6$ alkynyl, benzyl, $C(R_4)_2R_5$, $COR_4$, $COR_5$, $C(R_4)_2C(R_4)_2R_5$, $C(R_4)_2COR_4$, $C(R_2)_4COR_5$, $C(R_4)_2Z$, $C(R_4)_2C(R_4)_2Z$, CN, $CR_4NOR_4$, $CR_4NOR_6$, $CHR_4NHOR_4$, $CHR_4NHOR_6$, $CHR_4CR_4NOR_4$, $CHR_4CR_4NOR_6$, $CHR_4CHR_4NHOR_4$, $CHR_4CHR_4NHOR_6$, $C(O)NR_4OR_4$, $C(O)NR_4OR_6$, $CR_4=CR_4R_6$, $C\equiv CR_6$, $CR_4=CR_4C(R_4)_2OR_6$, $C\equiv CC(R_4)_2OR_6$, or poly-($OR_4$, $OR_6$, epoxy)-$C_1$-$C_6$ alkyl;

X is O or S; and n is 1.

7. The compounds of claim 1, wherein:

$R_3$ is H, $C_1$-$C_6$ alkyl, $C_2$-$C_6$ alkenyl, $C_2$-$C_6$ alkynyl, $C(R_4)_2R_4$, $COR_4$, $COR_5$, $C(R_4)_2C(R_4)_2R_5$, $C(R_4)_2COR_4$, $C(R_4)_2COR_5$, CN, $CR_4NOR_4$, $CR_4NOR_6$, $C(O)NR_4OR_4$, $C(O)NR_4OR_6$, $CR_4{=}CR_4R_6$, $CR_4{=}CR_4C(R_4)_2OR_6$, or poly-($OR_5$, $OR_6$, epoxy)-$C_1$-$C_4$ alkyl;
X is O or S; and
n is 1.

8. The compounds of claim 1, wherein:
$R_2$ is H, $C_1$-$C_3$ alkyl, $C_2$-$C_3$ alkenyl, $C_2$-$C_3$ alkynyl, or benzyl;
$R_3$ is H, $C_1$-$C_4$ alkyl, $C_2$-$C_4$ alkenyl, $C_2$-$C_4$ alkynyl, $C(R_4)_2R_5$, $COR_4$, $COR_5$, $C(R_4)_2C(R_4)_2R_5$, $C(R_4)_2COR_4$, $C(R_4)_2COR_5$, CN, $CR_4NOR_4$, $CR_4NOR_6$, $C(O)NR_4OR_4$, $C(O)NR_4OR_6$, $CR_4{=}CR_4R_6$, $CR_4{=}CR_4C(R_4)_2OR_6$, or poly-($OR_4$, $OR_6$, epoxy-$C_1$-$C_4$ alkyl;
$R_4$ is H, $C_1$-$C_4$ alkyl, $C_2$-$C_4$ alkenyl, $C_2$-$C_4$ alkynyl, phenyl or phenyl substituted with $C_1$-$C_3$ alkyl, $OR_2$, Z, $N(R_2)_2$, or $CF_3$; or benzyl; and
$R_6$ is $COR_4$.

9. The compounds of claim 1, wherein:
$R_2$ is H, $C_1$-$C_3$ alkyl, $C_2$-$C_3$ alkenyl, $C_2$-$C_3$ alkynyl, or benzyl;
$R_3$ is H, $C_1$-$C_4$ alkyl, $C_2$-$C_4$ alkenyl, $C_2$-$C_4$ alkynyl, $C(R_4)_2R_5$, $COR_4$, $COR_5$, $C(R_4)_2C(R_4)_2R_5$, $C(R_4)_2COR_4$, $C(R_4)_2COR_5$, CN, $CR_4NOR_4$, $CR_4NOR_6$, $C(O)NR_4OR_4$, $C(O)NR_4OR_6$, $CR_4{=}CR_4R_6$, $CR_4{=}CR_4C(R_4)_2OR_6$, or poly-($OR_4$, $OR_6$, epoxy)-$C_1$-$C_4$ alkyl;
$R_4$ is H, $C_1$-$C_4$ alkyl, $C_2$-$C_4$ alkenyl, $C_2$-$C_4$ alkynyl, phenyl or phenyl substituted with $C_1$-$C_3$ alkyl, $OR_2$, Z, $N(R_2)_2$, or $CF_3$; or benzyl;
$R_6$ is $COR_4$;
X is O or S; and
n is 1.

10. The compounds of claim 1, wherein:
$R_2$ is H, $C_1$-$C_3$ alkyl, or $C_2$-$C_3$ alkenyl;
$R_3$ is H, $C_1$-$C_4$ alkyl, $C_2$-$C_4$ alkenyl, $C(R_4)_2R_5$, $COR_4$, $COR_5$, $C(R_4)_2C(R_4)_2R_5$, $C(R_4)_2COR_4$, $C(R_4)_2COR_5$, CN, $CR_4NOR_4$, $CR_4NOR_6$, $C(O)NR_4OR_4$, $C(O)NR_4OR_6$, $CR_4{=}CR_4R_6$, $CR_4{=}CR_4C(R_4)_2OR_6$, or poly-($OR_4$, $OR_6$, epoxy)-$C_1$-$C_4$ alkyl;
$R_4$ is H, $C_1$-$C_4$ alkyl, $C_2$-$C_4$ alkenyl, $C_2$-$C_4$ alkynyl, phenyl or phenyl substituted with $C_1$-$C_3$ alkyl, $OR_2$, Z, $N(R_2)_2$, or $CF_3$; or benzyl;
$R_6$ is $COR_4$;
X is O or S; and
n is 1.

11. The compounds of claim 1, wherein:
$R_2$ is H, $C_1$-$C_3$ alkyl, $C_2$-$C_3$ alkenyl;
$R_3$ is H, $C_1$-$C_4$ alkyl, $C_2$-$C_4$ alkenyl, $CH_2R_5$, $CHOHCH{=}CH_2$, $COR_4$, $COR_5$, $CH_2CH_2R_5$, $CH_2COR_4$, CN, $CH{=}NOR_4$, $CH{=}NOR_6$, $CONHOR_4$, $CONHOR_6$, $CH{=}CHR_6$, $CHOHCH_2OH$, $CHOHCHOHCH_2OH$,

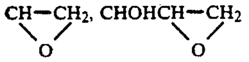

$R_4$ is H, $C_1$-$C_4$ alkyl, $C_2$-$C_4$ alkenyl, $C_2$-$C_4$ alkynyl, phenyl or phenyl substituted with $C_1$-$C_3$ alkyl, $OR_2$, Z, $N(R_2)_2$, or $CF_3$; or benzyl;
$R_6$ is $COR_4$; and
X is O or S.

12. The compounds of claim 1, wherein:
$R_2$ is H, $C_1$-$C_3$ alkyl, $C_2$-$C_3$ alkenyl;
$R_3$ is H, $C_1$-$C_4$ alkyl, $C_2$-$C_4$ alkenyl, $CH_2R_5$, $CHOHCH{=}CH_2$, $COR_4$, $COR_5$, $CH_2CH_2R_5$, $CH_2COR_4$, CN, $CH{=}NOR_4$, $CH{=}NOR_6$, $CONHOR_4$, $CONHOR_6$, $CH{=}CHR_6$, $CHOHCH_2OH$, $CHOHCHOHCH_2OH$

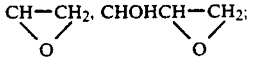

$R_4$ is H, $C_1$-$C_4$ alkyl, $C_2$-$C_4$ alkenyl, $C_2$-$C_4$ alkynyl, phenyl or phenyl substituted with $C_1$-$C_4$ alkyl, $OR_2$, Z, $N(R_2)_2$, or $CF_3$; or benzyl;
$R_6$ is $COR_4$;
X is O or S; and
n is 1.

13. The compounds of claim 1, wherein:
$R_2$ is H or $CH_3$,
$R_3$ is H, $CH_3$, $CH{=}CH_2$, $CH_2OH$, $CHOHCH{=}CH_2$, $CH_2OCOCH_3$, CHO, $COCH_3$, $CO_2H$, $CONH_2$, $CO_2CH_3$, $CH_2CH_2OH$, $CH_2CHO$, $CH_2CO_2H$, $CH_2CO_2CH_3$, CN, $CH{=}NOH$,$CH{=}NOCOCH_3$, CONHOH, $CONHOCOCH_3$, $CH{=}CHCO_2CH_3$, $CHOHCH_2OH$, $CHOHCHOHCH_2OH$,

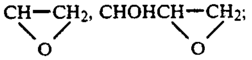

and
X is O or S.

14. The compounds of claim 1, wherein:
$R_2$ is H or $CH_3$,
$R_3$ IS H, $CH_3$, $CH{=}CH_2$, $CH_2OH$, $CHOHCH{=}CH_2$, $CH_2OCOCH_3$, CHO, $COCH_3$, $CO_2H$, $CONH_2$, $CO_2CH_3$, $CH_2CH_2OH$, $CH_2CHO$, $CH_2CO_2H$, $CH_2CO_2CH_3$, CN, $CH{=}NOH$, $CH{=}NOCOCH_3$, CONHOH, $CONHOCOCH_3$, $CH{=}CHCO_2CH_3$, $CHOHCH_2OH$, $CHOHCHOHCH_2OH$,

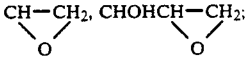

X is O or S; and
n is 1.

15. The compounds of claim 1, wherein:
$R_2$ is H, $CH_3$;
$R_3$ is H, $CH_3$, $CH{=}CH_2$, $CH_2OH$, $CHOHCH{=}CH_2$, CHO, $CO_2H$, $CONH_2$, $COCH_3$, $CH{=}NOH$, $CHOHCH_2OH$, $CHOHCHOHCH_2OH$; and
X is O or S.

16. The compounds of claim 1, wherein:
$R_2$ is H, $CH_3$;
$R_3$ is H, $CH_3$, $CH{=}CH_2$, $CH_2OH$, $CHOHCH{=}CH_2$, CHO, $CO_2H$, $CONH_2$, $COCH_3$, $CH{=}NOH$, $CHOHCH_2OH$, $CHOHCHOHCH_2OH$;
X is O or S; and
$n=1$.

17. A compound of claim 1 which is selected from the group consisting of:
15-Oxa-dihydrolanosterol,
4,4-Dimethyl-15-oxa-5α-cholest-8-en-3β-ol,
4,4-Dimethyl-15-oxa-14α-vinyl-5α-cholest8-en-3β-ol,
3β-Acetoxy-4,4-dimethyl-15-oxa-14α-vinyl-5α-cholest-8-ene,
3β-Acetoxy-32-hydroxymethyl-15-oxa-lanost-8-en-32-ol,
3β-Acetoxy-15-oxa-32-oxo-lanost-8-ene,
15-Oxa-32-oxo-dihydrolanosterol,
15-Oxa-lanost-8-ene-3β,32-diol, 15-Oxa-32-vinyl-lanost-8-ene-3β,32-diol,
3β-Hydroxy-15-oxa-lanost-8-en-32-aldoxime,
3β-Hydroxy-15-oxa-lanost-8-en-32-carboxylic acid,
14α-Methyl-15-oxa-5α-cholest-8-en-3β-ol,
15-Oxa-14α-vinyl-5α-cholest-8-en-3β-ol,
14α-(1',2'-Dihydroxy-ethyl)-15-oxa-5α-cholest-8-en-3β-ol,
14α-Formyl-15-oxa-5α-cholest-8-en-3β-ol,
14α-Hydroxymethyl-15-oxa-5α-cholest-8-en-3β-ol,
4,4-Dimethyl-15-thia-5β-cholest-8-en-3β-ol,
15-Thia-dihydrolanosterol,
4,4-Dimethyl-15-thia-14a-vinyl-5β-cholest-8-en 3β-ol,
3β-Hydroxy-15-thia-lanost-8-en-15-oxide.

18. A compound of claim 1 which is selected from the group consisting of:
15-Oxa-dihydrolanosterol,
4,4-Dimethyl-15-oxa-5α-cholest-8-en-3β-ol,
4,4-Dimethyl-15-oxa-14α-vinyl-5α-cholest8-en-3β-ol,
3β-Acetoxy-4,4-dimethyl-15-oxa-14α-vinyl-5αcholest-8-ene,
3β-Acetoxy-32-hydroxymethyl-15-oxa-lanost-8-en-32-ol,
3β-Acetoxy-15-oxa-32-oxo-lanost-8-ene,
15-Oxa-32-oxo-dihydrolanosterol,
15-Oxa-lanost-8-ene-3β,32-diol,
15-Oxa-32-vinyl-lanost-8-ene-3β,32-diol,
3β-Hydroxy-15-oxa-lanost-8-en-32-aldoxime,
3β-Hydroxy-15-oxa-lanost-8-en-32-carboxylic acid,
14α-Methyl-15-oxa-5α-cholest-8-en-3β-ol,
15-Oxa-14α-vinyl-5α-cholest-8-en-3β-ol,
14α-(1',2'-Dihydroxy-ethyl)-15-oxa-5αcholest-8-en-3β-ol,
14α-Formyl-15-oxa-5α-cholest-8-en-3β-ol,
14α-Hydroxymethyl-15-oxa-5α-cholest-8-en-3β-ol,
4,4-Dimethyl-15-thia-5α-cholest-8-en-3β-ol,
15-Thia-dihydrolanosterol,
4,4-Dimethyl-15-thia-14α-vinyl-5αcholest-8-en-3β-ol,
3β-Hydroxy-15-thia-lanost-8-en-15-oxide.

19. A composition suitable for decreasing cholesterol formation in mammals, said composition comprising (i) an effective amount of an active compound of the formula:

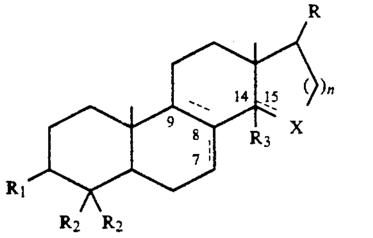

wherein
R is a side chain having either 8 or 9 carbon atoms and from 15 to 20 hydrogen atoms, optionally with one site of unsaturation; and
wherein the substituents $R_1$, independently each of $R_2$, and $R_3$, are selected from the groups defined as follows:
$R_1$ is =O, $OR_7$, or $OCOR_7$;
$R_2$ is H, $C_1$–$C_6$ alkyl, $C_2$–$C_6$ alkenyl, $C_2$–$C_6$ alkynyl, or benzyl;
$R_3$ is H, $C_1$–$C_6$ alkyl, $C_2$–$C_6$ alkenyl, $C_2$–$C_6$ alkynyl, benzyl, $C(R_4)_2R_5$, $COR_4$, $CSR_4$, $C(=NR_4)R_4$, $COR_5$, $CSR_5$, $C(R_4)_2C(R_4)_2R_5$, $C(R_4)_2COR_4$, $C(R_4)_2CSR_4$, $C(R_4)_2C(=NR_4)R_4$, $C(R_4)_2COR_5$, $C(R_4)_2CRS_5$, $C(R_4)_2Z$, $C(R_4)_2C(R_4)_2Z$, CN, $CR_4NOR_4$, $CR_4NOR_6$, $CR_4NN(R_4)_2$, $CR_4NNR_4R_6$, $CHR_4NHOR_4$, $CHR_4NHOR_6$, $CHR_4NHN(R_4)_2$, $CHR_4NHNR_4R_6$, $CHR_4CR_4NOR_4$, $CHR_4CR_4NOR_6$, $CHR_4CR_4NN(R_4)_2$, $CHR_4CR_4NNR_4R_6$, $CHR_4CHR_4NHOR_4$, $CHR_4CHR_4NHOR_6$, $CHR_4CHR_4NHN(R_4)_2$, $C(O)NR_4OR_4$, $C(O)NR_4OR_6$, $C(S)NR_4OR_4$, $C(S)NR_4OR_6$, $CR_4{=}CR_4R_6$, $C{\equiv}CR_6$, $CR_4{=}CR_4C(R_4)_2Z$, $C{\equiv}CC(R_4)_2Z$, $CR_4{=}CR_4C(R_4)_2OR_6$, $C{\equiv}CC(R_4)_2OR_6$, or poly-($OR_4$, $OR_6$, epoxy)-$C_1$–$C_6$ alkyl;
$R_4$ is H, $C_1$–$C_6$ alkyl, $C_2$–$C_6$ alkenyl, $C_2$–$C_6$ alkynyl, phenyl or phenyl substituted with $C_1$–$C_3$ alkyl, $OR_2$, Z, $N(R_2)_2$, or $CF_3$; or benzyl;
$R_5$ is $OR_4$, $SR_4$, $N(R_4)_2$, or $NR_4R_6$;
$R_6$ is $COR_4$, $CSR_4$, or $C(=NR_4)R_4$;
$R_7$ is H, $C_1$–$C_{20}$ alkyl, $C_2$–$C_{20}$ alkenyl, $C_2$–$C_{20}$ alkynyl, phenyl or phenyl substituted with $C_1$–$C_3$ alkyl, $OR_2$, Z, $N(R_2)_2$, or $CF_3$; or benzyl;
X is O or S;
Z is halogen; and
n is 1;
and their physiologically acceptable salts; and (ii) an acceptable pharmaceutical or veterinary carrier or diluent.

20. The composition of claim 19, wherein:
$R_3$ is H, $C_1$–$C_6$ alkyl, $C_2$–$C_6$ alkenyl, $C_2$–$C_6$ alkynyl, benzyl, $C(R_4)_2R_5$, $COR_4$, $COR_5$, $C(R_4)_2C(R_4)_2R_5$, $C(R_4)_2COR_4$, $C(R_4)_2COR_5$, $C(R_4)_2Z$, $C(R_4)_2C(R_4)_2Z$, CN, $CR_4NOR_4$, $CR_4NOR_6$, $CHR_4NHOR_4$, $CHR_4NHOR_6$, $CHR_4CR_4NOR_4$, $CHR_4CR_4NOR_6$, $CHR_4CHR_4NHOR_4$, $CHR_4CHR_4NHOR_6$, $C(O)NR_4OR_4$, $C(O)NR_4OR_6$, $CR_4{=}CR_4R_6$, $C{\equiv}CR_6$, $CR_4{=}CR_4C(R_4)_2OR_6$, $C{\equiv}CC(R_4)_2OR_6$, or poly-($OR_4$, $OR_6$, epoxy)-$C_1$–$C_6$ alkyl.

21. The composition of claim 19, wherein:
$R_3$ is H, $C_1$–$C_6$ alkyl, $C_2$–$C_6$ alkenyl, $C_2$–$C_6$ alkynyl, $C(R_4)_2R_5$, $COR_4$, $COR_5$, $C(R_4)_2C(R_4)_2R_5$, $C(R_4)_2COR_4$, $C(R_4)_2COR_5$, CN, $CR_4NOR_4$, $CR_4NOR$, $C(O)NR_4OR_4$, $C(O)NR_4OR_6$, $CR_4{=}CR_4R_6$,$CR_4{=}CR_4C(R_4)_2OR_6$, or poly-($OR_4$,$OR_6$, epoxy)-$C_1$–$C_6$ alkyl.

22. The composition of claim 19, wherein X is O or S.

23. The composition of claim 19, wherein n is 1.

24. The composition of claim 19, wherein:
$R_3$ is H, $C_1$–$C_6$ alkyl, $C_2$–$C_6$ alkenyl, $C_2$–$C_6$ alkynyl, benzyl, $C(R_4)_2R_5$, $COR_4$, $COR_5$, $C(R_4)_2C(R_4)_2R_5$, $C(R_4)_2COR_4$, $C(R_4)_2COR_5$, $C(R_4)_2Z$, $C(R_4)_2C(R_4)_2Z$, CN, $CR_4NOR_4$, $CR_4NOR_6$, $CHR_4NHOR_4$, $CHR_4NHOR_6$, $CHR_4CR_4NOR_4$, $CHR_4CR_4NOR_6$, $CHR_4CHR_4NHOR_4$, $CHR_4CHR_4NHOR_6$, $C(O)NR_4OR_4$, $C(O)NR_4OR_6$, $CR_4{=}CR_4R_6$, $C{\equiv}CR_6$, $CR_4{=}CR_4C(R_4)_2OR_6$, $C{\equiv}CC(R_4)_2OR_6$, or poly-($OR_4$, $OR_6$, epoxy)-$C_1$–$C_6$ alkyl;
X is O or S; and
n is 1.

25. The composition of claim 19, wherein:
$R_3$ is H, $C_1$–$C_6$ alkyl, $C_2$–$C_6$ alkenyl, $C_2$–$C_6$ alkynyl, $C(R_4)_2R_5$, $COR_4$, $COR_5$, $C(R_4)_2C(R_4)_2R_5$, $C(R_4)_2COR_4$, $C(R_4)_2COR_5$, CN, $CR_4NOR_4$, $CR_4NOR_6$, $C(O)NR_4OR_4$, $C(O)NR_4OR_6$, $CR_4{=}CR_4R_6$, $CR_4{=}CR_4C(R_4)_2OR_6$, or poly-($OR_4$, $OR_6$, epoxy)-$C_1$–$C_4$ alkyl;
X is O or S; and
n is 1.

26. The composition of claim 19, wherein:

$R_2$ is H, $C_1$-$C_3$ alkyl, $C_2$-$C_3$ alkenyl, $C_2$-$C_3$ alkynyl, or benzyl;

$R_3$ is H, $C_1$-$C_4$ alkyl, $C_2$-$C_4$ alkenyl, $C_2$-$C_4$ alkynyl, $C(R_4)_2R_5$, $COR_4$, $COR_5$, $C(R_4)_2C(R_4)_2R_5$, $C(R_4)_2COR_4$, $C(R_4)_2COR_5$, CN, $CR_4NOR_4$, $CR_4NOR_6$, $C(O)NR_4OR_4$, $C(O)NR_4OR_6$, $CR_4{=}CR_4R_6$, $CR_4{=}CR_4C(R_4)_2OR_6$, or poly-($OR_4$, $OR_6$, epoxy)-$C_1$-$C_4$ alkyl;

$R_4$ is H, $C_1$-$C_4$ alkyl, $C_2$-$C_4$ alkenyl, $C_2$-$C_4$ alkynyl, phenyl or phenyl substituted with $C_1$-$C_3$ alkyl, $OR_2$, Z, $N(R_2)_2$, or $CF_3$; or benzyl; and $R_6$ is $COR_4$.

27. The composition of claim 19, wherein:

$R_2$ is H, $C_1$-$C_3$ alkyl, $C_2$-$C_3$ alkenyl, $C_2$-$C_3$ alkynyl, or benzyl;

$R_3$ is H, $C_1$-$C_4$ alkyl, $C_2$-$C_4$ alkenyl, $C_2$-$C_4$ alkynyl, $C(R_4)_2R_5$, $COR_4$, $COR_5$, $C(R_4)_2C(R_4)_2R_5$, $C(R_4)_2COR_4$, $C(R_4)_2COR_5$, CN, $CR_4NOR_4$, $CR_4NOR_6$, $C(O)NR_4OR_4$, $C(O)NR_4OR_6$, $CR_4{=}CR_5R_6$, $CR_4{=}CR_4C(R_4)_2OR_6$, or poly-($OR_4$, $OR_6$, epoxy)-$C_1$-$C_4$ alkyl;

$R_4$ is H, $C_1$-$C_4$ alkyl, $C_2$-$C_4$ alkenyl, $C_2$-$C_4$ alkynyl, phenyl or phenyl substituted with $C_1$-$C_3$ alkyl, $OR_2$, Z, $N(R_2)_2$, or $CF_3$; or benzyl;

$R_6$ is $COR_4$;

X is O or S; and n is 1.

28. The composition of claim 19, wherein:

$R_2$ is H, $C_1$-$C_3$ alkyl, or $C_2$-$C_3$ alkenyl;

$R_3$ is H, $C_1$-$C_4$ alkyl, $C_2$-$C_4$ alkenyl, $C(R_4)_2R_5$, $COR_4$, $COR_5$, $C(R_4)_2C(R_4)_2R_5$, $C(R_4)_2COR_4$, $C(R_4)_2COR_5$, CN, $CR_4NOR_4$, $CR_4NOR_6$, $C(O)NR_4OR_4$, $C(O)NR_4OR_6$, $CR_4{=}CR_4R_6$, $CR_4{=}CR_4C(R_4)_2OR_6$, or poly-($R_4$, $OR_6$, epoxy)-$C_1$-$C_4$ alkyl;

$R_4$ is H, $C_1$-$C_4$ alkyl, $C_2$-$C_4$ alkenyl, or phenyl or phenyl substituted by $C_1$-$C_3$ alkyl, $OR_2$, Z, $N(R_2)_2$, or $CF_3$; or benzyl;

$R_6$ is $COR_4$;

X is O or S; and n is 1.

29. The composition of claim 19, wherein:

$R_2$ is H, $C_1$-$C_3$ alkyl, $C_2$-$C_3$ alkenyl;

$R_3$ is H, $C_1$-$C_4$ alkyl, $C_2$-$C_4$ alkenyl, $CH_2R_5$, $CHOHCH{=}CH_2$, $COR_4$, $COR_5$, $CH_2CH_2R_5$, $CH_2COR_4$, CN, $CH{=}NOR_4$, $CH{=}NOR_6$, $CONHOR_4$, $CONHOR_6$, $CH{=}CHR_6$, $CHOHCH_2OH$, $CHOHCHOHCH_2OH$,

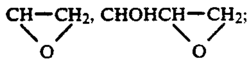

$R_4$ is H, $C_1$-$C_4$ alkyl, $C_2$-$C_4$ alkenyl, $C_2$-$C_4$ alkynyl, phenyl or phenyl substituted by $C_1$-$C_3$ alkyl, $OR_2$, Z, $N(R_2)_2$, or $CF_3$, or benzyl;

$R_6$ is $COR_4$; and

X is O or S.

30. The composition of claim 19, wherein:

$R_2$ is H, $C_1$-$C_3$ alkyl, $C_2$-$C_3$ alkenyl;

$R_3$ is H, $C_1$-$C_4$ alkyl, $C_2$-$C_4$ alkenyl, $CH_2R_5$, $CHOHCH{=}CH_2$, $COR_4$, $COR_5$, $CH_2CH_2R_5$, $CH_2COR_4$, CN, $CH{=}NOR_4$, $CH{=}NOR_6$, $CONHOR_4$, $CONHOR_6$, $CH{=}CHR_6$, $CHOHCH_2OH$, $CHOHCHOHCH_2OH$,

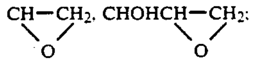

is H, $C_1$-$C_4$ alkyl, $C_2$-$C_4$ alkenyl, $C_2$-$C_4$ alkenyl, phenyl or phenyl substituted by $C_1$-$C_3$ alkyl, $OR_2$, Z, $N(R_2)_2$, or $CF_3$; or benzyl;

$R_6$ is $COR_4$;

X is O or S; and n is 1.

31. The composition of claim 19, wherein:

$R_2$ is H or $CH_3$, $R_3$ is H, $CH_3$, $CH{=}CH_2$, $CH_2OH$, $CHOHCH{=}CH_2$, $CH_2OCOCH_3$, CHO, $COCH_3$, $CO_2H$, $CONH_2$, $CO_2CH_3$, $CH_2CH_2OH$, $CH_2CHO$, $CH_2CO_2H$, $CH_2CO_2CH_3$, CN, $CH{=}NOH$, $CH{=}NOCOCH_3$, CONHOH, $CONHOCOCH_3$, $CH{=}CHCO_2CH_3$, $CHOHCH_2OH$, $CHOHCHOHCH_2OH$,

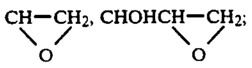

and

X is O or S.

32. The composition of claim 19, wherein:

$R_2$ is H or $CH_3$, $R_3$ is H, $CH_3$, $CH{=}CH_2$, $CH_2OH$, $CHOHCH{=}CH_2$, $CH_2OCOCH_3$, CHO, $COCH_3$, $CO_2H$, $CONH_2$, $CO_2CH_3$, $CH_2CH_2OH$, $CH_2CHO$, $CH_2CO_2H$, $CH_2CO_2CH_3$, CN, $CH{=}NOH$, $CH{=}NOCOCH_3$, CONHOH, $CONHOCOCH_3$, $CH{=}CHCO_2CH_3$, $CHOHCH_2OH$, $CHOHCHOHCH_2OH$,

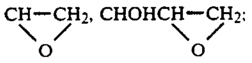

and

X is O or S; and n is 1.

33. The composition of claim 19, wherein:

$R_2$ is H, $CH_3$;

$R_3$ is H, $CH_3$, $CH{=}CH_2$, $CH_2OH$, $CHOHCH{=}CH_2$, CHO, $CO_2H$, $CONH_2$, $COCH_3$, $CH{=}NOH$, $CHOHCH_2OH$, $CHOHCHOHCH_2OH$; and X is O or S.

34. The composition of claim 19, wherein:

$R_2$ is H, $CH_3$;

$R_3$ is H, $CH_3$, $CH{=}CH_2$, $CH_2OH$, $CHOHCH{=}CH_2$, CHO, $CO_2H$, $CONH_2$, $COCH_3$, $CH{=}NOH$, $CHOHCH_2OH$, $CHOHCHOHCH_2OH$;

X is O or S; and n is 1.

35. A composition of claim 19, wherein the preferred compound is selected from the group consisting of:

15-Oxa-dihydrolanosterol, 4,4-Dimethyl-15-oxa-5α-cholest-8-en-3β-ol, 4,4-Dimethyl-15-oxa-14α-vinyl-5α-cholest8-en-3β-ol, 3β-Acetoxy-4,4-dimethyl-15-oxa-14α-vinyl-5αcholest-8-ene, 3β-Acetoxy-32-hydroxymethyl-15-oxa-lanost-8-en-32-ol, 3β-Acetoxy-15-oxa-32-oxo-lanost-8-ene, 15-Oxa-32-oxo-dihydrolanosterol, 15-Oxa-lanost-8-ene-3β,32-diol, 15-Oxa-32-vinyl-lanost-8-ene-3β,32-diol, 3β-Hydroxy-15-oxa-lanost-8-en-32-aldoxime,
3β-Hydroxy-15-oxa-lanost-8-en-32-carboxylic acid,
14α-Methyl-15-oxa-5α-cholest-8-en-3β-ol,
15-Oxa-14α-vinyl-5α-cholest-8-en-3β-ol,
14α-(1',2'-Dihydroxy-ethyl)-15-oxa-5αcholest-8-en-3β-ol,
14α-Formyl-15-oxa-5α-cholest-8-en-3β-ol,
14β-Hydroxymethyl-15-oxa-5α-cholest-8-en-3β-ol,
4,4-Dimethyl-15-thia-5α-cholest-8-en-3β-ol,
15-Thia-dihydrolanosterol,
4,4-Dimethyl-15-thia-14α-vinyl-5αcholest-8-en-3β-ol,
3β-Hydroxy-15-thia-lanost-8-en-15-oxide.

36. The composition of claim 19, wherein the preferred compound is selected from the group consisting of:
15-Oxa-dihydrolanosterol,
4,4-Dimethyl-15-oxa-5α-cholest-8-en-3β-ol,
4,4-Dimethyl-15-oxa-14β-vinyl-5β-cholest8-en-3β-ol,
3β-Acetoxy-4,4-dimethyl-15-oxa-14α-vinyl-5αcholest-8-ene,
3β-Acetoxy-32-hydroxymethyl-15-oxa-lanost-8-en-32-ol,
3β-Acetoxy-15-oxa-32-oxo-lanost-8-ene,
15-Oxa-32-oxo-dihydrolanosterol,
15-Oxa-lanost-8-ene-3β,32-diol,
15-Oxa-32-vinyl-lanost-8-ene-3β,32-diol,
3β-Hydroxy-15-oxa-lanost-8-en-32-aldoxime,
3β-Hydroxy-15-oxa-lanost-8-en-32-carboxylic acid,
14α-Oxa-D-homo-dihydrolanosterol,
4,4-Dimethyl-14α-oxa-D-homo-5α-cholest-8-en-3β-ol,
4,4-Dimethyl-14α-oxa-14α-vinyl-D-homo-5α-cholest-8en-3β-ol,
32-Hydroxymethyl-14α-oxa-D-homo-lanost-8-ene-3β,32-diol,
14α-Oxa-32-oxo-D-homo-dinhydrolanosterol,
14α-Methyl-15-oxa-5α-cholest-8-en-3β-ol,
15-Oxa-14α-vinyl-5α-cholest-8-en-3β-ol,
14α-(1',2'-Dihydroxy-ethyl)-15-oxa-5-cholest-8-,en-3β-ol,
14α-Formyl-15-oxa-5α-cholest-8-en-3β-ol,
14α-Hydroxymethyl-15-oxa-5α-cholest-8-en-3β-ol,
4,4-Dimethyl-15-thia-5α-cholest-8-en-3β-ol,
15-Thia-dihydrolanosterol,
4,4-Dimethyl-15-thia-14α-vinyl-5α-cholest-8-en-,3β-ol,
3β-Hydroxy-15-thia-lanost-8-en-15-oxide,
4,4-Dimethyl-14α-thia-D-homo-5α-cholest-8-en-,3β-ol,
14α-Thia-D-homo-dihydrolanosterol.

37. A method of decreasing cholesterol formation in mammals in need of such therapy, said method comprising administering an effective amount of an active compound of the formula:

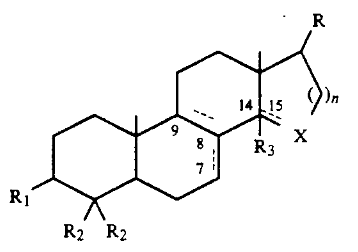

wherein
R is a side chain having either 8 or 9 carbon atoms and from 15 to 20 hydrogen atoms, optionally with one site of unsaturation; and
wherein the substituents $R_1$, independently each of $R_2$, and $R_3$, are selected from the groups defined as follows:
$R_1$ is =O, $OR_7$, or $OCOR_7$;
$R_2$ is H, $C_1$–$C_6$ alkyl, $C_2$–$C_6$ alkenyl, $C_2$–$C_6$ alkynyl, or benzyl;
$R_3$ is H, $C_1$–$C_6$ alkyl, $C_2$–$C_6$ alkenyl, $C_2$–$C_6$ alkynyl, benzyl, $C(R_4)_2R_5$, $COR_4$, $CSR_4$, $C(=NR_4)R_4$, $COR_5$, $CSR_5$, $C(R_4)_2C(R_4)_2R_5$, $C(R_4)_2COR_4$, $C(R_4)_2CSR_4$, $C(R_4)_2C(=NR_4)R_4$, $C(R_4)_2COR_5$, $C(R_4)_2CRS_5$, $C(R_4)_2Z$, $C(R_4)_2C(R_4)_2Z$, CN, $CR_4NOR_4$, $CR_4NOR_6$, $CR_4NN(R_4)_2$, $CR_4NNR_4R_6$, $CHR_4NHOR_4$, $CHR_4NHOR_6$, $CHR_4NHN(R_4)_2$, $CHR_4NHNR_4R_6$, $CHR_4CR_4NOR_4$, $CHR_4CR_4NOR_6$, $CHR_4CR_4NN(R_4)_2$, $CHR_4CR_4NNR_4R_6$, $CHR_4CHR_4NHOR_4$, $CHR_4CHR_4NHOR_6$, $CHR_4CHR_4NHN(R_4)_2$, $C(O)NR_4OR_4$, $C(O)NR_4OR_6$, $C(S)NR_4OR_4$, $C(S)NR_4OR_6$, $CR_4{=}CR_4R_6$, $C{\equiv}CR_6$, $CR_4{=}CR_4C(R_4)_2Z$, $C{\equiv}CC(R_4)_2Z$, $CR_4{=}CR_4C(R_4)_2OR_6$, $C{\equiv}CC(R_4)_2OR_6$, or poly-$OR_4$, $OR_6$, epoxy)-$C_1$–$C_6$ alkyl;
$R_4$ is H, $C_1$–$C_6$ alkyl, $C_2$–$C_6$ alkenyl, $C_2$–$C_6$ alkynyl, phenyl or phenyl substituted with $C_1$–$C_3$ alkyl, $OR_2$, Z, $N(R_2)_2$, or $CF_3$; or benzyl;
$R_5$ is $OR_4$, $SR_4$, $N(R_4)_2$, or $NR_4R_6$;
$R_6$ is $COR_4$, $CSR_4$, or $C(=NR_4)R_4$;
$R_7$ is H, $C_1$–$C_{20}$ alkyl, $C_2$–$C_{20}$ alkenyl, $C_2$–$C_{20}$ alkynyl, phenyl or phenyl substituted with $C_1$–$C_3$ alkyl, $OR_2$, Z, $N(R_2)_2$, or $CF_3$; or benzyl;
X is O or S;
Z is halogen; and
n is 1;
and their physiologically acceptable salts in an acceptable pharmaceutical or veterinary carrier or diluent to said mammal.

38. The method of claim 37, wherein:
$R_3$ is H, $C_1$–$C_6$ alkyl, $C_2$–$C_6$ alkenyl, $C_2$–$C_6$ alkynyl, benzyl, $C(R_4)_2R_5$, $COR_4$, $COR_5$, $C(R_4)_2C(R_4)_2R_5$, $C(R_4)_2COR_4$, $C(R_4)_2COR_5$, $C(R_4)_2Z$, $C(R_4)_2C(R_4)_2Z$, CN, $CR_4NOR_4$, $CR_4NOR_6$, $CHR_4NHOR_4$, $CHR_4NHOR_6$, $CHR_4CR_4NOR_4$, $CHR_4CR_4NOR_6$, $CHR_4CHR_4NHOR_4$, $CHR_4CHR_4NHOR_6$, $C(O)NR_4OR_4$, $C(O)NR_4OR_6$, $CR_4{=}CR_4R_6$, $C{\equiv}CR_6$, $CR_4{=}CR_4C(R_4)_2OR_6$-,$C{\equiv}CC(R_4)_2OR_6$, or poly-($R_4$, $OR_6$, epoxy)-$C_1$–$C_6$ alkyl.

39. The method of claim 37, wherein:
$R_3$ is H, $C_1$–$C_6$ alkyl, $C_2$–$C_6$ alkenyl, $C_2$–$C_6$ alkynyl, $C(R_4)_2R_5$, $COR_4$, $COR_5$, $C(R_4)_2C(R_4)_2R_5$, $C(R_4)_2COR_4$, $C(R_4)_2COR_5$, CN, $CR_4NOR_4$, $CR_4NOR_6$, $C(O)NR_4OR_4$, $C(O)NR_4OR_6$, $CR_4{=}CR_4R_6$, $CR_4{=}CR_4C(R_4)_2OR_6$, or poly-($OR_4$, $OR_6$, epoxy)-$C_1$–$C_6$ alkyl.

40. The method of claim 37, wherein x is O or S.

41. The method of claim 37, wherein n is 1.

42. The method of claim 37, wherein:
$R_3$ is H, $C_1$–$C_6$ alkyl, $C_2$–$C_6$ alkenyl, $C_2$–$C_6$ alkynyl, benzyl, $C(R_4)_2R_5$, $COR_4$, $COR_5$, $C(R_4)_2C(R_4)_2R_5$, $C(R_4)_2COR_4$, $C(R_4)_2COR_5$, $C(R_4)_2Z$, $C(R_4)_2C(R_4)_2Z$, CN, $CR_4NOR_4$, $CR_4NOR_6$, $CHR_4NHOR_4$, $CHR_4NHOR_6$, $CHR_4CR_4NOR_4$, $CHR_4CR_4NOR_6$, $CHR_4CHR_4NHOR_4$, $CHR_4CHR_4NHOR_6$, $C(O)NR_4OR_4$, $C(O)NR_4OR_6$, $CR_4{=}CR_4R_6$, $C{\equiv}CR_6$, $CR_4{=}CR_4C(R_4)_2OR_6$, $C{\equiv}CC(R_4)_2OR_6$, or poly-($OR_4$, $OR_6$, epoxy)-$C_1$–$C_6$ alkyl;
X is O or S; and
n is 1.

43. The method of claim 37, wherein:
$R_3$ is H, $C_1$–$C_6$ alkyl, $C_2$–$C_6$ alkenyl, $C_2$–$C_6$ alkynyl, $C(R_4)_2R_5$, $COR_4$, $COR_5$, $C(R_4)_2C(R_4)_2R_5$, $C(R_4)_2COR_4$, $C(R_4)_2COR_5$, CN, $CR_4NOR_4$, $CR_4NOR_6$, $C(O)NR_4OR_4$, $C(O)NR_4OR_6$, $CR_4{=}CR_4R_6$, $CR_4{=}CR_4C(R_4)_2OR_6$, or poly-($OR_4$, $OR_6$, epoxy)-$C_1$–$C_4$ alkyl;
X is O or S; and
n is 1.

44. The method of claim 37, wherein:
$R_2$ is H, $C_1$–$C_3$ alkyl, $C_2$–$C_3$ alkenyl, $C_2$–$C_3$ alkynyl, or benzyl;
$R_3$ is H, $C_1$–$C_4$ alkyl, $C_2$–$C_4$ alkenyl, $C_2$–$C_4$ alkynyl, $C(R_4)_2R_5$, $COR_4$, $COR_5$, $C(R_4)_2C(R_4)_2R_5$, $C(R_4)_2COR_4$, $C(R_4)_2COR_5$, CN, $CR_4NOR_4$, $CR_4NOR_6$, $C(O)NR_4OR_4$, $C(O)NR_4OR_6$, $CR_4{=}CR_4R_6$, $CR_4{=}CR_4C(R_4)_2OR_6$, or poly-($OR_4$, $OR_6$, epoxy)-$C_1$–$C_4$ alkyl;
$R_4$ is H, $C_1$–$C_4$ alkyl, $C_2$–$C_4$ alkenyl, $C_2$–$C_4$ alkynyl, phenyl or phenyl substituted with $C_1$–$C_3$ alkyl, $OR_2$, Z, $N(R_2)_2$, or $CF_3$; or benzyl; and
$R_6$ is $COR_4$.

45. The method of claim 37, wherein:
$R_2$ is H, $C_1$–$C_3$ alkyl, $C_2$–$C_3$ alkenyl, $C_2$–$C_3$ alkynyl, or benzyl;
$R_3$ is H, $C_1$–$C_4$ alkyl, $C_2$–$C_4$ alkenyl, $C_2$–$C_4$ alkynyl, $C(R_4)_2R_5$, $COR_4$, $COR_5$, $C(R_4)_2C(R_4)_2R_5$, $C(R_4)_2COR_4$, $C(R_4)_2COR_5$, CN, $CR_4NOR_4$, $CR_4NOR_6$, $C(O)NR_4OR_4$, $C(O)NR_4OR_6$, $CR_4{=}CR_4R_6$, $CR_4{=}CR_4C(R_4)_2OR_6$, or poly-($OR_4$, $OR_6$, epoxy)-$C_1$–$C_4$ alkyl;
$R_4$ is H, $C_1$–$C_4$ alkyl, $C_2$–$C_4$ alkenyl, $C_2$–$C_4$ alkynyl, phenyl or phenyl substituted with $C_1$–$C_3$ alkyl, $OR_2$, Z, $N(R_2)_2$, or $CF_3$; or benzyl;
$R_6$ is $COR_4$;
X is O or S; and
n is 1.

46. The method of claim 37, wherein:
$R_2$ is H, $C_1$–$C_3$ alkyl, or $C_2$–$C_3$ alkenyl;
$R_3$ is H, $C_1$–$C_4$ alkyl, $C_2$–$C_4$ alkenyl, $C(R_4)_2R_5$, $COR_4$, $COR_5$, $C(R_4)_2C(R_4)_2R_5$, $C(R_4)_2COR_4$, $C(R_4)_2COR_5$, CN, $CR_4NOR_4$, $CR_4NOR_6$, $C(O)NR_4OR_4$, $C(O)NR_4OR_6$, $CR_4{=}CR_4R_6$, $CR_4{=}CR_4C(R_4)_2OR_6$, or poly-($OR_4$, $OR_6$, epoxy)-$C_1$–$C_4$ alkyl;
$R_4$ is H, $C_1$–$C_4$ alkyl, $C_2$–$C_4$ alkenyl, $C_2$–$C_4$ alkynyl, phenyl or phenyl substituted by $C_1$–$C_3$ alkyl, $OR_2$, Z, $N(R_2)_2$, or $CF_3$, or benzyl;
$R_6$ is $COR_4$;
X is O or S; and
n is 1.

47. The method of claim 37, wherein:
$R_2$ is H, $C_1$–$C_3$ alkyl, $C_2$–$C_3$ alkenyl;
$R_3$ is H, $C_1$–$C_4$ alkyl, $C_2$–$C_4$ alkenyl, $CH_2R_5$, $CHOHCH{=}CH_2$, $COR_4$, $COR_5$, $CH_2CH_2R_5$, $CH_2COR_4$, CN, $CH{=}NOR_6$, $CH{=}NOR_5$, $CONHOR_4$, $CONHOR_6$, $CH{=}CHR_6$, $CHOHCH_2OH$, $CHOHCHOHCH_2OH$,

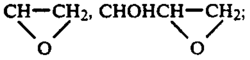

$R_4$ is H, $C_1$–$C_4$ alkyl, $C_2$–$C_4$ alkenyl, phenyl or phenyl substituted by $C_1$–$C_3$ alkyl, $OR_2$, Z, $N(R_2)_2$, or $CF_3$, or benzyl;
$R_6$ is $COR_4$; and
X is O or S.

48. The method of claim 37, wherein:
$R_2$ is H, $C_1$–$C_3$ alkyl, $C_2$–$C_3$ alkenyl;
$R_3$ is H, $C_1$–$C_4$ alkyl, $C_2$–$C_4$ alkenyl, $CH_2R_5$, $CHOHCH{=}CH_2$, $COR_4$, $COR_6$, $CH_2COR_4$, CN, $CH{=}NOR_4$, $CH{=}NOR_6$, $CONHOR_4$, $CONHOR_6$, $CH{=}CHR_6$, $CHOHCH_2OH$, $CHOHCHOHCH_2OH$,

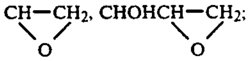

$R_4$ is H, $C_1$–$C_4$ alkyl, $C_2$–$C_4$ alkenyl, $C_2$–$C_4$ alkynyl, phenyl or phenyl substituted by $C_1$–$C_3$ alkyl, $OR_2$, Z, $N(R_2)_2$, or $CF_3$, or benzyl;
$R_6$ is $COR_4$;
X is O or S; and
n is 1.

49. The method of claim 37, wherein:
$R_2$ is H or $CH_3$,
$R_3$ is H, $CH_3$, $CH{=}CH_2$, $CH_2OH$, $CHOHCH{=}CH_2$, $CH_2OCOCH_3$, CHO, $COCH_3$, $CO_2H$, $CONH_2$, $CO_2CH_3$, $CH_2CH_2OH$, $CH_2CHO$, $CH_2CO_2H$, $CH_2CO_2CH_3$, CN, $CH{=}NOH$, $CH{=}NOCOCH_3$, CONHOH, $CONHOCOCH_3$, $CH{=}CHCO_2CH_3$, $CHOHCH_2OH$, $CHOHCHOHCH_2OH$,

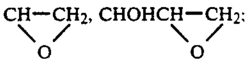

and
X is O or S.

50. The method of claim 37, wherein:
$R_2$ is H or $CH_3$,
$R_3$ is H, $CH_3$, $CH{=}CH_2$, $CH_2OH$, $CHOHCH{\equiv}CH_2$, $CH_2OCOCH_3$, CHO, $COCH_3$, $CO_2H$, $CONH_2$, $CO_2CH_3$, $CH_2CH_2OH$, $CH_2CHO$, $CH_2CO_2H$, $CH_2CO_2CH_3$, CN, $CH{=}NOH$, $CH{=}NOCOCH_3$, CONHOH, $CONHOCOCH_3$, $CH{=}CHCO_2CH_3$, $CHOHCH_2OH$, $CHOHCHOHCH_2OH$,

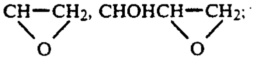

and
X is O or S; and
n is 1.

51. The method of claim 37, wherein:
$R_2$ is H, $CH_3$;
$R_3$ is H, $CH_3$, $CH{=}CH_2$, $CH_2OH$, $CHOHCH{=}CH_2$, CHO, $CO_2H$, $CONH_2$, $COCH_3$, $CH{=}NOH$, $CHOHCH_2OH$, $CHOHCHOHCH_2OH$; and
X is O or S.

52. The method of claim 37, wherein:
$R_2$ is H, $CH_3$;
$R_3$ is H, $CH_3$, $CH{=}CH_2$, $CH_2OH$, $CHOHCH{=}CH_2$, CHO, $CO_2H$, $CONH_2$, $COCH_3$, $CH{=}NOH$, $CHOHCH_2OH$, $CHOHCHOHCH_2OH$;
X is O or S; and
n is 1.

53. The method of claim 37, wherein the preferred compound is selected from the group consisting of:
15-Oxa-dihydrolanosterol,
4,4-Dimethyl-15-oxa-5α-cholest-8-en-3β-ol,
4,4-Dimethyl-15-oxa-14α-vinyl-5α-cholest8-en-3β-ol,
3β-Acetoxy-4,4-dimethyl-15-oxa-14α-vinyl-5-cholest-8-ene, 3$\beta$-Acetoxy-32-hydroxymethyl-15-oxa-lanost-8-en-32-ol,
3$\beta$-Acetoxy-15-oxa-32-oxo-lanost-8-ene,
15-Oxa-32-oxo-dihydrolanosterol,
15-Oxa-lanost-8-ene-3$\beta$,32-diol,
15-Oxa-32-vinyl-lanost-8-ene-3$\beta$,32-diol,
3$\beta$-Hydroxy-15-oxa-lanost-8-en-32-aldoxime,
3$\beta$-Hydroxy-15-oxa-lanost-8-en-32-carboxylic acid,
14$\alpha$-Oxa-32-oxo-D-homo-dihydrolanosterol,
14$\alpha$-Methyl-15-oxa-5$\alpha$-cholest-8-en-3$\beta$-ol,
15-Oxa-14$\alpha$-vinyl-5$\alpha$-cholest-8-en-3$\beta$-ol,
14$\alpha$-(1',2'-Dihydroxy-ethyl)-15-oxa-5$\alpha$-cholest-8en-$\beta$-ol,
14$\alpha$-Formyl-15-oxa-5$\alpha$-cholest-8-en-3$\beta$-ol,
14$\alpha$-Hydroxymethyl-15-oxa-5$\alpha$-cholest-8-en-3$\beta$-ol,
4,4-Dimethyl-15-thia-5$\alpha$-cholest-8-en-3$\beta$-ol,
15-Thia-dihydrolanosterol,
4,4-Dimethyl-15-thia-14-vinyl-5$\alpha$-cholest-8-en-,3$\beta$-ol,
3$\beta$-Hydroxy-15-thia-lanost-8-en-15-oxide,
4,4-Dimethyl-14$\alpha$-thia-D-homo-5$\alpha$-cholest-8-en3$\beta$-ol.

54. The method of claim 37, wherein the preferred compound is selected from the group consisting of:
15-Oxa-dihydrolanosterol,
4,4-Dimethyl-15-oxa-5$\alpha$-cholest-8-en-3$\beta$-ol,
4,4-Dimethyl-15-oxa-14$\alpha$-vinyl-5$\alpha$-cholest8-en-3$\beta$-ol,
3$\beta$-Acetoxy-4,4-dimethyl-15-oxa-14$\alpha$-vinyl-5$\alpha$cholest-8-ene,
3$\beta$-Acetoxy-32-hydroxymethyl-15-oxa-lanost-8-en-32-ol,
3$\beta$-Acetoxy-15-oxa-32-oxo-lanost-8-ene,
15-Oxa-32-oxo-dihydrolanosterol,
15-Oxa-lanost-8-ene-3$\beta$,32-diol,
15-Oxa-32-vinyl-lanost-8-ene-3$\beta$,32-diol,
3$\beta$-Hydroxy-15-oxa-lanost-8-en-32-aldoxime,
3$\beta$-Hydroxy-15-oxa-lanost-8-en-32-carboxylic acid,
14$\alpha$-Oxa-32-D-homo-dihydrolanosterol,
14$\alpha$-Methyl-15-oxa-5$\alpha$-cholest-8-en-3$\beta$-ol,
15-Oxa-14$\alpha$-vinyl-5$\alpha$-cholest-8-en-3$\beta$-ol,
14$\alpha$-(1',2'-Dihydroxy-ethyl)-15-oxa-5$\alpha$-cholest-8-, en-3$\beta$-ol,
14$\alpha$-Formyl-15-oxa-5$\alpha$-cholest-8-en-3$\beta$-ol,
14$\alpha$-Hydroxymethyl-15-oxa-5$\alpha$-cholest-8-en-3$\beta$-ol,
4,4-Dimethyl-15-thia-5$\alpha$-cholest-8-en-3$\beta$-ol,
15-Thia-dihydrolanosterol,
4,4-Dimethyl-15-thia-14$\alpha$-vinyl-5$\alpha$-cholest-8-en-, 3$\beta$-ol,
3$\beta$-Hydroxy-15-thia-lanost-8-en-15-oxide.

55. A process for the formation of 15-thia-lanosterols having the formula:

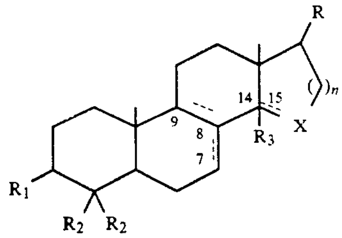

wherein

R is a side chain having either 8 or 9 carbon atoms and from 15 to 20 hydrogen atoms, optionally with one site of unsaturation; and wherein the substituents $R_1$, independently each of $R_2$, and $R_3$, are selected from the groups defined as follows:

$R_1$ is $OR_7$ or $OCOR_7$;

$R_2$ is H, $C_1$–$C_6$ alkyl, $C_2$–$C_6$ alkenyl, $C_2$–$C_6$ alkynyl, or benzyl;

$R_3$ is H, $C_1$–$C_6$ alkyl, $C_2$–$C_6$ alkenyl, $C_2$–$C_6$ alkynyl, benzyl, $C(R_4)_2R_5$, $C(R_4)_2C(R_4)_2R_5$, $CR_4{=}CR_4R_6$, $C{\equiv}CR_6$;

$R_4$ is H, $C_1$–$C_6$ alkyl, $C_2$–$C_6$ alkenyl, $C_2$–$C_6$ alkynyl, phenyl or phenyl substituted with $C_1$–$C_3$ alkyl, $OR_2$, Z, $N(R_2)_2$, or $CF_3$; or benzyl;

$R_5$ is $OR_4$, $SR_4$, $N(R_4)_2$, or $NR_4R_6$;

$R_6$ is $COR_4$, $CSR_4$, or $C({=}NR_4)R_4$;

$R_7$ is H, $C_1$–$C_{20}$ alkyl, $C_2$–$C_{20}$ alkenyl, $C_2$–$C_{20}$ alkynyl, phenyl or phenyl substituted with $C_1$–$C_3$ alkyl, $OR_2$, Z, $N(R_2)_2$, or $CF_3$; or benzyl;

X is S;

Z is halogen; and n is 1;

which process comprises treating a cyclic hemiacetal of the corresponding 15-oxa-dihydrolanosterol (X=O) with hydrogen sulfide and boron trifluoride etherate in a suitable reaction medium, under suitable reaction conditions, followed by reaction of the unisolated cyclic thioacetal intermediate with a trialkylsilane to yield the desired 15-thiadihydrolanosterol.

56. The process of claim 55, wherein 15-thiadihydrolanesterol ($R_3$=$CH_3$) is formed.

57. The process of claim 55, wherein 4,4-Dimethyl-15-thia-5$\alpha$-cholest-8-en-3$\beta$-ol ($R_3$=H) is formed.

58. The process of claim 55, wherein 4,4-dimethyl-15-thia-14$\alpha$-vinyl-5$\alpha$-cholest-8-en-3$\beta$-ol ($R_3$=CH=$CH_2$) is formed.

* * * * *